United States Patent
Benjamin et al.

(10) Patent No.: US 12,060,426 B2
(45) Date of Patent: Aug. 13, 2024

(54) ANTI-ULBP6 ANTIBODIES

(71) Applicants: 23andMe, Inc., Sunnyvale, CA (US); GLAXOSMITHKLINE INTELLECTUAL PROPERTY (No.3) LIMITED, Middlesex (GB)

(72) Inventors: Joel Benjamin, Foster City, CA (US); Shashank Bharill, South San Francisco, CA (US); I-Ling Chen, San Mateo, CA (US); Yu Chen, Foster City, CA (US); Wei-Jen Chung, Belmont, CA (US); Zahra Bahrami Dizicheh, San Mateo, CA (US); Germaine Fuh, Pacifica, CA (US); Patrick Koenig, San Francisco, CA (US); Yujie Liu, Collegeville, PA (US); Mauro Poggio, San Francisco, CA (US); Shruti Yadav, San Mateo, CA (US); Ping-Chiao Tsai, Collegeville, PA (US); Claus Spitzfaden, Knebworth (GB)

(73) Assignee: 23andMe, Inc., Sunnyvale, CA (US)

( * ) Notice: Subject to any disclaimer, the term of this patent is extended or adjusted under 35 U.S.C. 154(b) by 0 days.

(21) Appl. No.: 18/309,272

(22) Filed: Apr. 28, 2023

(65) Prior Publication Data
US 2023/0348604 A1 Nov. 2, 2023

Related U.S. Application Data

(60) Provisional application No. 63/336,336, filed on Apr. 29, 2022.

(51) Int. Cl.
*C07K 16/28* (2006.01)
*A61P 35/00* (2006.01)

(52) U.S. Cl.
CPC ......... *C07K 16/2833* (2013.01); *A61P 35/00* (2018.01); *C07K 2317/76* (2013.01); *C07K 2317/92* (2013.01)

(58) Field of Classification Search
None
See application file for complete search history.

(56) References Cited

FOREIGN PATENT DOCUMENTS

WO 2014/140884 A2 9/2014

OTHER PUBLICATIONS

Zuo, Jianmin, et al., "A disease-linked ULBP6 polymorphism inhibits NKG2D-mediated target cell killing by enhancing the stability of NKG2D-ligand binding"; Science Signaling, vol. 10, issue 481 May 30, 2017, DOI: 10.1126/scisignal.aai8904.
Eagle, Robert, et al., "ULBP6/RAET1L is an additional human NKG2D ligand", Eur. J. Immunol. 2009. 39: 3207-3216, DOI 10.1002/eji.200939502; Molecular immunology.
Paczulla, Anna M., et al., "Absence of NKG2D ligands defines leukaemia stem cells and mediates their immune evasion"; 254 Nature vol. 572; Aug. 8, 2019.
International Search Report and Written Opinion for PCT/US2023/020381; mailed Jul. 24, 2023.

*Primary Examiner* — Daniel E Kolker
*Assistant Examiner* — Lea S O'Brien
(74) *Attorney, Agent, or Firm* — FisherBroyles, LLP; Adam K. Whiting

(57) ABSTRACT

The present disclosure relates to a ULBP6 binding protein that inhibits the interaction between ULBP6 and NKG2D, and methods of treating cancer with said ULBP6 binding protein.

17 Claims, 35 Drawing Sheets
Specification includes a Sequence Listing.

| Validation Tool Antibodies | | |
|---|---|---|
| Antibody Clone | Biacore binding ULBP6_02 $K_D$ (nM) | Blocking ELISA $IC_{50}$ (nM), NKG2D/ULBP6_02 |
| h7B3 | 0.2 ± 0.03 | 0.028 |
| h8E8 | 1.56 | Non-blocker |
| Phage antibody | 17.1 (100x weaker) | 5.1 (4x weaker) |

ANTI-ULBP6 ANTIBODIES

CROSS REFERENCE TO RELATED APPLICATIONS

This application claims priority benefit to U.S. Provisional Application No. 63/336,336, filed Apr. 29, 2022, which is hereby incorporated by reference herein.

REFERENCE TO SEQUENCE LISTING

The official copy of the Sequence Listing is submitted concurrently with the specification as an ST26 formatted xml file with filename "09402-014WO1.xml" a creation date of Apr. 27, 2023, and a size of 171,756 bytes. The Sequence Listing filed via EFS-Web is part of the specification and is incorporated in its entirety by reference herein.

NAMES OF PARTIES TO A JOINT RESEARCH AGREEMENT

The claimed subject matter of the present application was made by or on behalf of parties to a joint research agreement that was in effect on or before the date the claimed subject matter was made; the claimed subject matter was made as a result of activities undertaken within the scope of the joint research agreement; and the parties to the joint research agreement include: GlaxoSmithKline Intellectual Property (No. 3) Limited and 23andMe, Inc.

The joint research agreement was a written contract, grant or cooperative agreement entered into by the above-mentioned parties for the performance of experimental, developmental or research work in the field of the claimed subject matter.

FIELD OF THE INVENTION

The invention relates to the treatment of cancer. In particular, the invention relates to ULBP6 binding proteins including anti-ULBP6 antibodies and their uses in the treatment of cancer.

BACKGROUND TO THE INVENTION

Effective treatment of cancer is an ongoing goal of the oncology field. Immunotherapies which enhance anti-tumor immune responses are a powerful approach for treatment of cancer. Multiple immuno-oncology antibodies are currently marketed, including monoclonal antibodies targeting PD-1 (e.g., OPDIVO/nivolumab and KEYTRUDA/pembrolizumab), PD-L1 (e.g., TECENTRIQ/atezolizumab, BAVENCIO/avelumab, IMFINZI/durvalumab), CTLA-4 (e.g. YERVOY/ipilimumab) and CD20 (e.g., RITUXAN/rituximab, ARZERRA/ofatumumab). These antibody-based cancer immunotherapies may each act through different mechanisms, such as increasing immune responsiveness of T cells, relieving inhibitory checkpoints on tumor-specific T cells, induction of apoptosis, induction of enhanced antibody-dependent cellular cytotoxicity (ADCC) and/or induction of complement-dependent cytotoxicity (CDC).

Although recent advances in the immunotherapy field have improved the treatment of cancer, many patients do not respond to conventional therapies. Thus, there remains a need for alternative or improved immunotherapeutic compositions and methods for more effectively treating cancer.

SUMMARY OF THE INVENTION

Provided herein are ULBP6 binding proteins comprising: a) (i) any one or a combination of CDRs selected from CDRH1, CDRH2, CDRH3 from SEQ ID NOs: 16-19, and/or CDRL1, CDRL2, CDRL3 from SEQ ID NOs: 26-29; or (ii) a CDR variant of (i) wherein the variant has 1, 2, or 3 amino acid modifications; or b) a VH region comprising a sequence at least 80% identical to the sequence of any one of SEQ ID NOs: 21-24; and/or a VL region comprising a sequence at least 80% identical to the sequence of any one of SEQ ID NOs: 31-34. A ULBP6 binding protein can comprise a CDRH1 of SEQ ID NOs: 36, 39, 42 or 45; a CDRH2 of SEQ ID NOs: 37, 40, 43 or 46; a CDRH3 of SEQ ID NOs: 38, 41, 44 or 47; a CDRL1 of SEQ ID NOs: 51, 54, 57 or 60; a CDRL2 of SEQ ID NOs: 52, 55, 58 or 61; and/or a CDRL3 of SEQ ID NOs: 53, 56, 59 or 62, or a variant thereof.

Also provided herein are ULBP6 binding proteins comprising 6 CDRs selected from the group consisting of: CDRH1 of SEQ ID NO: 36, CDRH2 of SEQ ID NO: 37, CDRH3 of SEQ ID NO: 38, CDRL1 of SEQ ID NO: 51, CDRL2 of SEQ ID NO: 52 and CDRL3 of SEQ ID NO: 53; CDRH1 of SEQ ID NO: 39, CDRH2 of SEQ ID NO: 40, CDRH3 of SEQ ID NO: 41, CDRL1 of SEQ ID NO: 54, CDRL2 of SEQ ID NO: 55 and CDRL3 of SEQ ID NO: 56; CDRH1 of SEQ ID NO: 42, CDRH2 of SEQ ID NO: 43, CDRH3 of SEQ ID NO: 44, CDRL1 of SEQ ID NO: 57, CDRL2 of SEQ ID NO: 58 and CDRL3 of SEQ ID NO: 59; or CDRH1 of SEQ ID NO: 45, CDRH2 of SEQ ID NO: 46, CDRH3 of SEQ ID NO: 47, CDRL1 of SEQ ID NO: 60, CDRL2 of SEQ ID NO: 61 and CDRL3 of SEQ ID NO: 62.

Also provided herein are ULBP6 binding proteins that bind to ULBP6 and ULBP2 with a KD less than or equal to 1 nM and binds to ULBP5 with a KD greater than or equal to 1 nM.

Also provided herein are ULBP6 binding proteins that binds to human ULBP6, and competes for binding to said ULBP6 with a reference ULBP6 binding protein comprising: a VH region sequence of SEQ ID NO: 21 and a VL region sequence of SEQ ID NO: 31; a VH region sequence of SEQ ID NO: 22 and a VL region sequence of SEQ ID NO: 32; a VH region sequence of SEQ ID NO: 16 and a VL region sequence of SEQ ID NO: 26; or a VH region sequence of SEQ ID NO: 17 and a VL region sequence of SEQ ID NO: 27.

Also provided herein are nucleic acid sequences which encodes one or both of HC and LC of a ULBP6 binding protein provided herein. Also provided herein are expression vectors comprising a nucleic acid sequence provided herein. Also provided herein are recombinant host cells comprising a nucleic acid sequence(s) or an expression vector(s) provided herein. Also provided herein are methods for the production of a ULBP6 binding protein, comprising culturing a recombinant host cell provided herein under conditions suitable for expression of said nucleic acid sequence(s) or vector(s), whereby a polypeptide comprising a ULBP6 binding protein provided herein is produced. Also provided herein are cell lines engineered to express a ULBP6 binding protein provided herein. Also provided herein are pharmaceutical compositions comprising a ULBP6 binding protein as defined herein and a pharmaceutically acceptable excipient Also provided herein are methods for the treatment of cancer in a subject in need thereof comprising administering to said subject a therapeutically effective amount of a ULBP6 binding protein or a pharmaceutical composition as defined herein. Also provided herein are ULBP6 binding proteins and pharmaceutical compositions provided herein for use in therapy. Also provided herein are ULBP6 binding proteins and pharmaceutical compositions provided herein for use in the treatment of cancer. Also provided herein are ULBP6 antagonists for use in the treatment of basal cell carcinoma.

Also provided herein are ULBP6 antibodies and fragments thereof, which: a) bind to one or more residues of SEQ ID NO: 125 and SEQ ID NO: 127; b) bind to one or more residues of SEQ ID NO: 126 and SEQ ID NO: 127; c) bind to a conformational epitope of SEQ ID NO: 125 and/or a conformational epitope of SEQ ID NO: 127; d) bind to a conformational epitope of SEQ ID NO: 126 and/or a conformational epitope of SEQ ID NO: 127; e) protect one or more residues of SEQ ID NO: 125, SEQ ID NO: 126, or SEQ ID NO: 127 from deuterium exchange in HDX-MS analysis of SEQ ID NO: 124; f) bind to human ULBP6 and results in peptides derived from SEQ ID NO: 125, SEQ ID NO: 126, or SEQ ID NO: 127 of human ULBP6 being more resistant to deuterium incorporation compared to corresponding peptides derived from uncomplexed human ULBP6; g) bind to the NKG2D-binding interface of human ULBP6; and/or h) disrupt the interaction of human ULBP6 to NKG2D by binding to one or more residues selected from E96, E154, Y184, and D189 of SEQ ID NO: 124.

Also provided herein are ULBP6 antibodies and fragments thereof which: a) bind to one or more residues of SEQ ID NO: 128; b) bind to a conformational epitope of SEQ ID NO: 128; c) protect one or more residues of SEQ ID NO: 128 from deuterium exchange in HDX-MS analysis of SEQ ID NO: 128; and/or bind to binds to human ULBP6 and results in peptides derived from SEQ ID NO: 128 of human ULBP6 being more resistant to deuterium incorporation compared to corresponding peptides derived from uncomplexed human ULBP6.

BRIEF DESCRIPTION OF THE FIGURES

FIG. 3B depicts a summary of the properties of the tool antibodies used.

FIG. 21 depicts amino acids of ULBP6 determined by HDX experiments to be significantly protected by mAb1298, h7B3, h8E8, h1D4, h8E11, and h6E1, as underlined bold text.

DETAILED DESCRIPTION OF THE INVENTION

Figure 1:
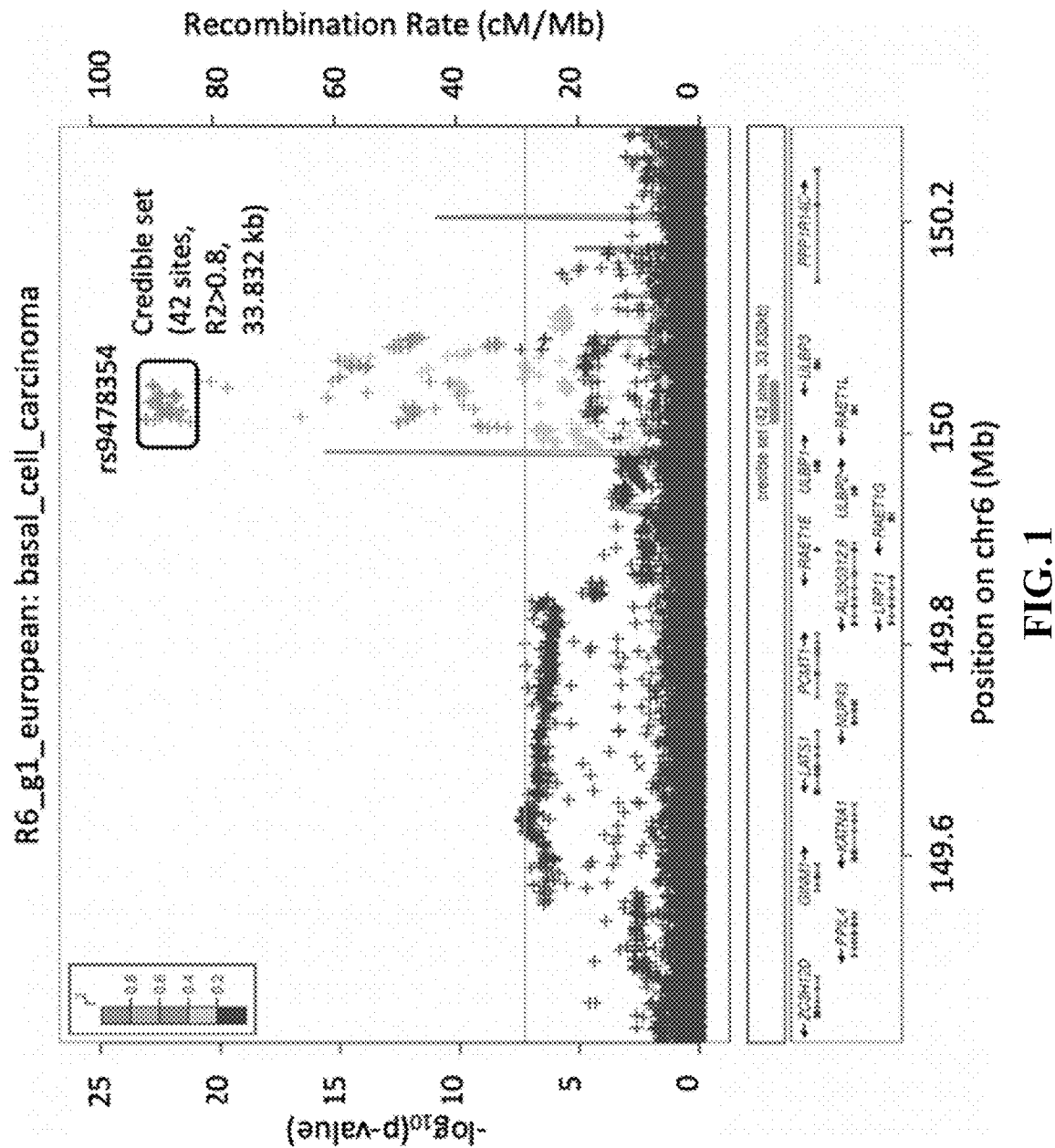
FIG. 1 depicts a regional association plot of the ULBP6 locus on chromosome 6 for basal cell carcinoma. The x-axis displays position on chromosome 6 using GRCh38/hg38 as the human reference genome build. The left hand y-axis is the $-\log_{10}$(P value) from a logistic regression testing for an association between the phenotype of interest and genotype. Plus symbols (+) denote variants for which genotype was imputed; circle symbols (○) denote variants for which genotyped calls were used; x symbols (x) denote imputed coding variants; diamond symbols (◊) denote genotyped coding variants. Color reflects the linkage disequilibrium (calculated as $r^2$) between the index SNP (shown in grey) and other nearby SNPs. The grey horizontal line represents the genome-wide significance threshold of $5\times10^{-8}$. The credible set track displays the number and location of variants in the 99% credible set, which is likely to contain the causal variant. The gene track displays genes in the locus with thick bars representing exons and thin lines representing introns.

As used herein "ULBP6" means any UL16-binding protein 6. Pseudonyms for ULBP6 include RAET1 L, Retinoic Acid Early Transcript 1 L, Retinoic Acid Early Transcript 1

L Protein and UL16 binding protein 6. ULBP6 is encoded by the RAET1L gene and is a UL16-binding protein family molecule. ULBP6 specifically binds to the activating receptor Natural Killer Group 2D receptor (NKG2D). Like other NKG2D ligands, ULBP6 functions as a stress-inducible modulator of the NKG2D pathway. ULBP6 can be expressed as a cell surface membrane bound form. ULBP6 can be a soluble molecule, which can be or shed from a cell surface. As used herein "sULBP6" refers to non-surface bound, soluble or shed ULBP6. As used herein "human ULBP6" refers to cell surface membrane bound human ULBP6 or human sULBP6. Human ULBP6 is highly polymorphic, with two haplotypes (ULBP6_01 and ULBP6_02) being the most common haplotypes observed in the population (Antoun et al, 2010, Hum Immunol, 71:610-20; Eagle et al, 2009, Eur J Immunol, 39:3207-3216). The amino acid sequences of the human sULBP6 haplotypes ULBP6_01 and ULBP6_02 are shown in Table 6.

As used herein "NKG2D" refers to the Natural Killer Group 2D receptor for ULBP6 and other NKG2DLs. NKG2D is encoded by the KLRK1 (killer cell lectin like receptor K1) gene and is an activating receptor expressed by natural killer (NK) cells, and T cells. It plays an important role in anti-pathogen and anti-tumor responses, as engagement of NKG2D leads to cellular activation, production of cytokines and cytotoxic activity. In some instances, NKG2D is human NKG2D (hNKG2D).

As used herein "NKG2DL" and "NKG2D ligand" are used interchangeably and refer to the protein ligands of NKG2D. Human NKG2DLs (hNKG2DLs) include MICA, MICB, ULBP1 (RAET1), ULBP2 (RAET1H), ULBP3 (RAET1 N), ULBP4 (RAET1 E), ULBP5 (RAET1 G), and ULBP6 (RAET1 L). Some NKG2DLs may be a soluble molecule or shed from the cell surface. As used herein "sNKG2DLs" refers to non-surface bound, soluble, or shed NKG2DLs.

ULBP6 and other NKG2DLs bind to the activating receptor NKG2D expressed on NK cells and T cells (e.g., CD8 T cells). Expression of these NKG2D ligands is typically low under homeostatic conditions but can be highly induced under conditions of cellular stress (e.g. by pathogen-infected or malignant cells). When expressed on the cell surface of stressed cells, ULBP6 can engage NKG2D, thereby enhancing NK cell/T cell activation immune surveillance. When ULBP6 is in shed/soluble form, sULBP6 can act to block the interaction between NKG2D and other NKG2DLs, thus acting in an immunosuppressive manner by inhibiting NKG2D-mediated activation of immune cells. Therefore, blockade of the interaction of sULBP6 with NKG2D using ULBP6 binding proteins is expected to increase NKG2D-mediated activation of immune cells. ULBP6 binding protein induced NKG2D-mediated activation of immune cells can offer a treatment for disorders such as cancer.

The term "ULBP6 binding protein" as used herein refers to antibodies and other protein constructs, such as domains, that are capable of binding to ULBP6. In some instances, ULBP6 is human ULBP6. The terms "ULBP6 binding protein" and "antigen binding protein" are used interchangeably herein. This does not include the natural cognate ligand or receptor (i.e., NKG2D).

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanised, multispecific antibodies, including bispecific antibodies, and heteroconjugate antibodies; a single variable domain (such as but not limited to a domain antibody (DAB)), Fab, F(ab')$_2$, Fv, disulphide linked Fv, single chain Fv, disulphide-linked scFv, diabodies, TANDABS, etc. and modified versions or antigen binding fragments of any of the foregoing.

The terms full, whole or intact antibody, used interchangeably herein, refer to a heterotetrameric glycoprotein with an approximate molecular weight of 150,000 daltons. An intact antibody is composed of two identical heavy chains (HCs) and two identical light chains (LCs) linked by covalent disulphide bonds. This H2L2 structure folds to form three functional domains comprising two antigen-binding fragments, known as Fab' fragments, and a Fc' crystallisable fragment. The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences, which are called µ, α, γ, ε and δ respectively, each heavy chain can pair with either a K or λ light chain. The majority of antibodies in the serum belong to the IgG class, there are four isotypes of human IgG (IgG1, IgG2, IgG3 and IgG4), the sequences of which differ mainly in their hinge region.

Fully human antibodies can be obtained using a variety of methods, for example using yeast-based libraries or transgenic animals (e.g. mice) that are capable of producing repertoires of human antibodies. Yeast presenting human antibodies on their surface that bind to an antigen of interest can be selected using FACS (Fluorescence-Activated Cell Sorting) based methods or by capture on beads using labelled antigens. Transgenic animals that have been modified to express human immunoglobulin genes can be immunised with an antigen of interest and antigen-specific human antibodies isolated using B-cell sorting techniques. Human antibodies produced using these techniques can then be characterised for desired properties such as affinity, developability and selectivity.

Alternative antibody formats include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer or an EGF domain.

A "humanized antibody" refers to a type of engineered antibody having its CDRs derived from a non-human donor immunoglobulin, the remaining immunoglobulin-derived parts of the molecule being derived from one or more human immunoglobulin(s). In addition, framework support residues may be altered to preserve binding affinity. A suitable human acceptor antibody may be one selected from a conventional database, e.g., the KABAT database, Los Alamos database, and Swiss Protein database, by homology to the nucleotide and amino acid sequences of a donor antibody. The acceptor antibody can be heterologous to the donor antibody, and in some embodiments can be a human antibody. The donor antibody can contribute the amino acid sequences of its variable regions, CDRs, or other functional fragments or analogs thereof to a first immunoglobulin partner. A donor can provide the altered immunoglobulin coding region and resulting expressed altered antibody with the antigenic specificity. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating heavy and/or light chain constant or variable framework regions may be selected in a similar manner. It should be noted that the acceptor antibody heavy and light chains are not required to originate from the same acceptor antibody.

The ULBP6 binding protein described herein may be an antibody or an antigen binding fragment thereof. The ULBP6 binding protein may be a humanized antibody or an antigen binding fragment thereof. The ULBP6 binding protein may comprise: a humanized VH region, or a humanized Heavy Chain (HC) sequence; and/or a humanized VL region, or a humanized Light Chain (LC) sequence. The humanized HC may be humanized using the human germline sequences IGHV3-48, IGHV7-4-1 or IGHV1-2. The humanized HC may be humanized using the human germline sequence IGHV3-48. The humanized LC may be humanized using the human germline sequences IGKV1-33, IGKV3-11 or IGKV1-16. The humanized LC may be humanized using the human germline sequences IGKV1-33. The humanized LC may be humanized using the human germline sequences IGKV3-11.

The term "single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences that are not characteristic of antibody variable domains, or antibody variable domains that have been truncated or comprise N- or C-terminal extensions, as well as folded fragments of variable domains that retain at least the binding activity and specificity of the full-length domain. A single variable domain as defined herein is capable of binding an antigen or epitope independently of a different variable region or domain. A "domain antibody" or "DAB" may be considered the same as a human "single variable domain". A single variable domain may be a human single variable domain, but also includes single variable domains from other species such as rodent (for example, as disclosed in WO 00/29004), nurse shark and Camelid VHHs Camelid VHHs are immunoglobulin single variable domain polypeptides that are derived from species including camel, llama, alpaca, dromedary, and guanaco, which produce heavy chain only antibodies naturally devoid of light chains. Such VHH domains may be humanised according to standard techniques available in the art, and such domains are considered to be "single variable domains".

An antigen binding fragment may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions.

The protein scaffold may be an Ig scaffold, for example an IgG, or IgA scaffold. The IgG scaffold may comprise some or all the domains of an intact antibody (i.e. CH1, CH2, CH3, VH, VL). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof.

The protein scaffold may be a derivative of a scaffold selected from the group consisting of CTLA-4, lipocalin, Protein A derived molecules such as Z-domain of Protein A (Affibody, SpA), A-domain (Avimer/Maxibody); heat shock proteins such as GroEl and GroES; transferrin (trans-body); ankyrin repeat protein (DARPin); peptide aptamer; C-type lectin domain (Tetranectin); human g-crystallin and human ubiquitin (affilins); PDZ domains; scorpion toxin kunitz type domains of human protease inhibitors; and fibronectin/adnectin; which has been subjected to protein engineering in order to obtain binding to an antigen, such as ULBP6, other than the natural ligand.

The term multi-specific antigen binding protein refers to an antigen binding protein that comprises at least two different antigen binding sites. Each of these antigen-binding sites is capable of binding to a different epitope, which may be present on the same antigen or different antigens. The multi-specific antigen binding protein may have specificity for more than one antigen, for example two antigens, or three antigens, or four antigens.

Bispecifics may be generally classified as having a symmetric or asymmetric architecture. Bispecifics may have an Fc or may be fragment-based (lacking an Fc). Fragment based bispecifics combine multiple antigen-binding antibody fragments in one molecule without an Fc region e.g. Fab-scFv, Fab-scFv$_2$, orthogonal Fab-Fab, Fab-Fv, tandem scFc (e.g. BiTE and BiKE molecules), Diabody, DART, TandAb, scDiabody, tandem dAb etc.

Symmetric formats combine multiple binding specificities in a single polypeptide chain or single HL pair including Fc-fusion proteins of fragment-based formats and formats whereby antibody fragments are fused to regular antibody molecules. Examples of symmetric formats may include DVD-Ig, TVD-Ig, CODV-Ig, (scFv)4-Fc, IgG-(scFv)2, Tetravalent DART-Fc, F(ab)$_4$CrossMab, IgG-HC-scFv, IgG-LC-scFv, mAb-dAb etc.

Asymmetric formats retain as closely as possible the native architecture of natural antibodies by forcing correct HL chain pairing and/or promoting H chain heterodimerization during the co-expression of three (if common heavy or light chains are used) or four polypeptide chains e.g. Triomab, asymmetric reengineering technology immunoglobulin (ART-Ig), CrossMab, Biclonics common light chain, ZW1 common light chain, DuoBody and knobs into holes (KiH), DuetMab, κλ body, Xmab, YBODY, HET-mAb, HET-Fab, DART-Fc, SEEDbody, mouse/rat chimeric IgG.

Bispecific formats can also include an antibody fused to a non-Ig scaffold such as Affimabs, Fynomabs, Zybodies, and Anticalin-IgG fusions, ImmTAC.

The term "chimeric antigen receptor" ("CAR") as used herein, refers to an engineered receptor that consists of an extracellular antigen binding domain (usually derived from a monoclonal antibody, or fragment thereof, e.g. a VH domain and a VL domain in the form of a scFv), optionally a spacer region, a transmembrane region, and one or more intracellular effector domains. CARs have also been referred to as chimeric T cell receptors or chimeric immunoreceptors (CIRs). CARs are genetically introduced into hematopoietic cells, such as T cells, to redirect T cell specificity for a desired cell-surface antigen, resulting in a CAR-T therapeutic.

The term "spacer region" as used herein, refers to an oligo- or polypeptide that functions to link the transmembrane domain to the target binding domain. This region may also be referred to as a "hinge region" or "stalk region". The size of the spacer can be varied depending on the position of the target epitope in order to maintain a set distance (e.g. 14 nm) upon CAR:target binding.

The term "transmembrane domain" as used herein, refers to the part of the CAR molecule that traverses the cell membrane.

The term "intracellular effector domain" (also referred to as the "signalling domain") as used herein refers to the domain in the CAR that is responsible for intracellular signalling following the binding of the antigen binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines.

It will be appreciated by a person skilled in the art that VH and/or VL domains disclosed herein may be incorporated, e.g. in the form of a scFv, into CAR-T therapeutics.

The antigen binding proteins described herein may show cross-reactivity between human ULBP6 and ULBP6 from another species, such as cynomolgus ULBP2/6. It should be noted that cynomolgus ULBP2/6 is named as such because it is unclear whether the single cynomolgus orthologue is evolutionarily related to human ULBP2 or ULBP6. Therefore the cynomolgus orthologue is referred to herein as cynomolgus ULBP2/6 or cULBP2/6. The antigen binding proteins described herein may specifically bind human ULBP6 and cynomolgus ULBP2/6. This is particularly useful, since drug development typically requires testing of lead drug candidates in non-human primate systems before the drug is tested in humans. The provision of a drug that can bind human and monkey species allows one to test results in these systems and make side-by-side comparisons of data using the same drug. This avoids the complication of needing to find a drug that works against a cynomolgus ULBP6 and a separate drug that works against human ULBP6, and also avoids the need to compare results in humans and cynomolgus using non-identical drugs. Cross reactivity between other species used in disease models such as dog or monkey, in particular monkey, is also envisaged. Optionally, the binding affinity of the antigen binding protein for at least cynomolgus ULBP2/6 and the binding affinity for human ULBP6 differ by no more than a factor of 2, 5, 10, 50 or 100.

Affinity, also referred to as "binding affinity", is the strength of binding at a single interaction site, i.e. of one molecule, e.g. an antigen binding protein of the invention, to another molecule, e.g. ULBP6, at a single binding site. The binding affinity of an antigen binding protein to its target may be determined by equilibrium methods (e.g. enzyme-linked immunosorbent assay (ELISA) or radioimmunoassay (RIA)), or kinetics (e.g. BIACORE analysis). For example, the BIACORE methods described in Example 7 may be used to measure binding affinity.

The equilibrium dissociation constant (KD) of the antigen binding protein-ULBP6 interaction may be 100 nM or less, 10 nM or less, 5 nM or less, 2 nM or less or 1 nM or less. Alternatively, the KD may be between 5 and 10 nM; or between 1 and 2 nM. The KD may be between 1 pM and 500 pM; or between 500 pM and 1 nM. The KD may be between 100 pM and 500 pM; or between 100 pM and 1 nM. The KD may be between 100 pM and 2 nM; or between 100 pM and 5 nM. A skilled person will appreciate that the smaller the KD numerical value, the stronger the binding. The reciprocal of KD (i.e. 1/KD) is the equilibrium association constant (KA) having units $M^{-1}$. A skilled person will appreciate that the larger the KA numerical value, the stronger the binding.

Human ULBP6 shows high sequence similarity to human ULBP2 and a lower level of sequence similarity to ULBP5. The ULBP6 binding protein described herein may bind to human ULBP6 and ULBP2 with a KD less than or equal to 1 nM. Alternatively, the ULBP6 binding protein described herein may bind to human ULBP6 with a KD less than or equal to 500 pM and bind to ULBP2 with a KD greater than or equal to 500 pM. Alternatively, the ULBP6 binding protein described herein may bind to human ULBP6 with a KD less than or equal to 300 pM and bind to ULBP2 with a KD greater than or equal to 500 pM. The ULBP6 binding protein described herein may bind to human ULBP6 with a KD less than or equal to 1 nM and bind to ULBP5 with a KD greater than or equal to 1 nM. Alternatively, the ULBP6 binding protein may bind to ULBP6 with a KD less than or equal to 500 pM and bind to ULBP5 with a KD greater than or equal to 1 nM. Alternatively, the ULBP6 binding protein may bind to ULBP6 with a KD less than or equal to 400 pM and bind to ULBP5 with a KD greater than or equal to 1 nM. Alternatively, the ULBP6 binding protein may bind to ULBP6 with a KD less than or equal to 300 pM and bind to ULBP5 with a KD greater than or equal to 1 nM. Alternatively, the ULBP6 binding protein may bind to ULBP6 with a KD less than or equal to 300 pM and bind to ULBP5 with a KD greater than or equal to 2 nM.

The dissociation rate constant (kd) or "off-rate" describes the stability of the antigen binding protein-ULBP6 complex, i.e. the fraction of complexes that decay per second. For example, a kd of 0.01 $s^{-1}$ equates to 1% of the complexes decaying per second. The dissociation rate constant (kd) of the antigen binding protein-ULBP6 interaction may be $1\times10^{-3}$ $s^{-1}$ or less, $1\times10^{-4}$ $s^{-1}$ or less, $1\times10^{-5}$ $s^{-1}$ or less, or $1\times10^{-6}$ $s^{-1}$ or less. Alternatively, the kd may be between $1\times10^{-5}$ $s^{-1}$ and $1\times10^{-4}$ $s^{-1}$; or between $1\times10^{-4}$ $s^{-1}$ and $1\times10^{-3}$ $s^{-1}$. Alternatively, the kd may be between $1\times10^{-3}$ $s^{-1}$ and $1\times10^{-2}$ $s^{-1}$.

The association rate constant (ka) or "on-rate" describes the rate of antigen binding protein-ULBP6 complex formation. The ka of the antigen binding protein-ULBP6 interaction may be about $1.5\times10^{6}$ $M^{-1}s^{-1}$. Alternatively, the ka may be between $1\times10^{6}$ $M^{-1}s^{-1}$ and $1\times10^{5}$ $M^{-1}s^{-1}$. Alternatively, the ka may be between $1\times10^{6}$ $M^{-1}s^{-1}$ and $5\times10^{6}$ $M^{-1}s^{-1}$; or between $1\times10^{6}$ $M^{-1}s^{-1}$ and $2\times10^{6}$ $M^{-1}s^{-1}$.

By "isolated" it is intended that the molecule, such as an antigen binding protein or nucleic acid, is removed from a previous environment. For example, the molecule may be purified away from substances with which it would normally exist in nature. For example, the mass of the molecule in a sample may be 95% of the total mass.

The ULBP6 binding proteins described herein may be encoded by nucleic acids, which may be isolated. Production of ULBP6 binding proteins such as antibodies, may be achieved in a cell or living organism by delivering exogenous isolated nucleic acids encoding a heavy chain and a light chain of the antibody. A subject in need may be delivered one or more nucleic acids encoding a heavy chain and a light chain of a ULBP6 binding protein. The heavy chain and the light chain of the antibody may be delivered by the same or separate nucleic acids. The nucleic acids may be DNA or RNA. The nucleic acids may be mRNA. The nucleic acid coding for the ULBP6 binding proteins may be modified or unmodified. The nucleic acids coding for the ULBP6 binding proteins may comprise at least one chemical modification. The nucleic acids encoding the ULBP6 binding protein may be delivered to the subject naked (i.e.

without an encapsulating particle) or packaged (i.e. encapsulated in liposomes or polymer based vehicles).

Also provided herein is a method of producing a ULBP6 binding protein in a cell, tissue or organism comprising contacting said cell, tissue or organism with a composition comprising an isolated nucleic acid comprising at least one chemical modification and which encodes a ULBP6 binding protein. Also provided herein is a method of producing a ULBP6 binding protein in a cell, tissue or organism comprising contacting said cell, tissue or organism with a composition comprising a polynucleotide comprising at least one chemical modification and which encodes a ULBP6 binding protein.

The term "expression vector" as used herein means an isolated nucleic acid which can be used to introduce a nucleic acid of interest into a cell, such as a eukaryotic cell or prokaryotic cell, or a cell free expression system where the nucleic acid sequence of interest is expressed as a peptide chain such as a protein. Such expression vectors may be, for example, cosmids, plasmids, viral sequences, transposons, and linear nucleic acids comprising a nucleic acid of interest. Once the expression vector is introduced into a cell or cell free expression system (e.g., reticulocyte lysate) the protein encoded by the nucleic acid of interest is produced by the transcription/translation machinery. Expression vectors within the scope of the disclosure may provide necessary elements for eukaryotic or prokaryotic expression and include viral promoter driven vectors, such as CMV promoter driven vectors, e.g., pcDNA3.1, pCEP4, and their derivatives, Baculovirus expression vectors, *Drosophila* expression vectors and expression vectors that are driven by mammalian gene promoters such as human Ig gene promoters. Other examples include prokaryotic expression vectors, such as T7 promoter driven vectors, e.g., pET41, lactose promoter driven vectors and arabinose gene promoter driven vectors. Those of ordinary skill in the art will recognise many other suitable expression vectors and expression systems.

The term "recombinant host cell" as used herein means a cell that comprises a nucleic acid sequence of interest that was isolated prior to its introduction into the cell. For example, the nucleic acid sequence of interest may be in an expression vector while the cell may be prokaryotic or eukaryotic. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells or any derivative thereof. The eukaryotic cell may be HEK293, NS0, SP2/0, or CHO cell. *E. coli* is an exemplary prokaryotic cell. A recombinant cell according to the disclosure may be generated by transfection, cell fusion, immortalization, or other procedures well known in the art. A nucleic acid of interest, such as an expression vector, transfected into a cell may be extrachromosomal or stably integrated into the chromosome of the cell.

"CDRs" are defined as the complementarity determining region amino acid sequences of an antigen binding protein. These can be the same as or overlapping with hypervariable regions (HVRs) of immunoglobulin heavy and light chains, depending on the method(s) used of determining the CDRs and HDRs. There are three heavy chain and three light chain CDRs (or CDR regions) in the variable portion of an immunoglobulin. Thus, "CDRs" as used herein generally refers to all three heavy chain CDRs, all three light chain CDRs, all heavy and light chain CDRs, or at least two CDRs.

Hypervariable regions, as used herein, may include extended or alternative hypervariable regions as follows: 24-36 or 24-34 (L1), 46-56 or 50-56 (L2) and 89-97 or 89-96 (L3) in the $V_L$ domain and 26-35 or 30-35 (H1), 50-61, 50-65 or 49-65 (H2) and 93-102, 94-102, or 95-102 (H3) in the $V_H$ domain. The variable domain residues are numbered according to Kabat et al., supra, for each of these definitions.

Throughout this specification, amino acid residues in variable domain sequences and variable domain regions within full-length antigen binding sequences, e.g. within an antibody heavy chain sequence or antibody light chain sequence, are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full-length antibody sequences. There are also alternative numbering conventions for CDR sequences, for example those set out in Chothia et al. (1989) Nature 342: 877-883. The structure and protein folding of the antigen binding protein may mean that other residues are considered part of the CDR sequence and would be understood to be so by a skilled person.

Other numbering conventions for CDR sequences available to a skilled person include "AbM" (University of Bath) and "contact" (University College London) methods. The CDR regions for SEQ ID NOs: 16-19 and SEQ ID NOs: 26-29 can be defined by any numbering convention, for example the Kabat, Chothia, AbM and contact conventions.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

CDR numbering conventions

| | Kabat CDR | Chothia CDR | AbM CDR | Contact CDR |
|---|---|---|---|---|
| H1 | 31-35/35A/35B | 26-32/33/34 | 26-35/35A/35B | 30-35/35A/35B |
| H2 | 50-65 | 52-56 | 50-58 | 47-58 |
| H3 | 95-102 | 95-102 | 95-102 | 93-101 |
| L1 | 24-34 | 24-34 | 24-34 | 30-36 |
| L2 | 50-56 | 50-56 | 50-56 | 46-55 |
| L3 | 89-97 | 89-97 | 89-97 | 89-96 |

ULBP6 binding proteins are provided. herein, which comprise any one or a combination of CDRs selected from: a) CDRH1 of SEQ ID NO: 16 or 21; CDRH2 of SEQ ID NO: 16 or 21; CDRH3 of SEQ ID NO: 16 or 21; CDRL1 of SEQ ID NO: 26 or 31; CDRL2 of SEQ ID NO: 26 or 31; CDRL3 of SEQ ID NO: 26 or 31 or b) CDRH1 of SEQ ID NO: 17 or 22; CDRH2 of SEQ ID NO: 17 or 22; CDRH3 of SEQ ID NO: 17 or 22; CDRL1 of SEQ ID NO: 27 or 32; CDRL2 of SEQ ID NO: 27 or 32; CDRL3 of SEQ ID NO: 27 or 32 or c) CDRH1 of SEQ ID NO: 18 or 23; CDRH2 of SEQ ID NO: 18 or 23; CDRH3 of SEQ ID NO: 18 or 23; CDRL1 of SEQ ID NO: 28 or 33; CDRL2 of SEQ ID NO: 28 or 33; CDRL3 of SEQ ID NO: 28 or 33 or d) CDRH1 of SEQ ID NO: 19 or 24; CDRH2 of SEQ ID NO: 19 or 24; CDRH3 of SEQ ID NO: 19 or 24; CDRL1 of SEQ ID NO: 29 or 34; CDRL2 of SEQ ID NO: 29 or 34; CDRL3 of SEQ ID NO: 29 or 34.

Alternatively, a ULBP6 binding protein described herein may comprise all 6 CDRs selected from: a) CDRH1 of SEQ ID NO: 36, CDRH2 of SEQ ID NO: 37, CDRH3 of SEQ ID NO: 38, CDRL1 of SEQ ID NO: 51, CDRL2 of SEQ ID NO: 52 and CDRL3 of SEQ ID NO: 53; b) CDRH1 of SEQ ID NO: 39, CDRH2 of SEQ ID NO: 40, CDRH3 of SEQ ID NO: 41, CDRL1 of SEQ ID NO: 54, CDRL2 of SEQ ID NO: 55 and CDRL3 of SEQ ID NO: 56; c) CDRH1 of SEQ ID NO: 42, CDRH2 of SEQ ID NO: 43, CDRH3 of SEQ ID NO: 44, CDRL1 of SEQ ID NO: 57, CDRL2 of SEQ ID NO: 58 and CDRL3 of SEQ ID NO: 59; or d) CDRH1 of SEQ ID NO: 45, CDRH2 of SEQ ID NO: 46, CDRH3 of SEQ ID NO: 47, CDRL1 of SEQ ID NO: 60, CDRL2 of SEQ ID NO: 61 and CDRL3 of SEQ ID NO: 62.

CDRs can be modified by at least one amino acid substitution, deletion or addition, wherein the variant ULBP6 binding protein substantially retains one or more the biological characteristics of the unmodified binding protein, which can be biological characteristics provided herein, such as inhibiting the binding of soluble ULBP6 to NKG2D.

It will be appreciated that each CDR H1, H2, H3, L1, L2, L3 may be modified alone or in combination with any other CDR, in any permutation or combination. A CDR may be modified by the substitution, deletion or addition of up to 3 amino acids, for example 1 or 2 amino acids, for example 1 amino acid. Each modification of a CDR, VH, VL, or other protein provided herein can be a conservative substitution. Typically, the modification is a substitution, particularly a conservative substitution, for example as shown in Table 2 below.

TABLE 2

Conservative substitutions

| Side chain | Members |
|---|---|
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

For example, in a variant CDR, the flanking residues that comprise the CDR as part of alternative definition(s) e.g. Kabat or Chothia, may be substituted with a conservative amino acid residue.

Such antigen binding proteins comprising variant CDRs as described above may be referred to herein as "functional CDR variants".

The ULBP6 binding proteins described herein may comprise (i) any one or a combination of CDRs selected from CDRH1, CDRH2, CDRH3 from SEQ ID NO: 16, and/or CDRL1, CDRL2, CDRL3 from SEQ ID NOs: 26; or (ii) a CDR variant of (i) wherein the variant has 1, 2, or 3 amino acid modifications; or a VH region comprising a sequence at least 80% identical to the sequence of SEQ ID NO: 21; and/or a VL region comprising a sequence at least 80% identical to the sequence of SEQ ID NO: 31.

Alternatively, the ULBP6 binding proteins described herein may comprise (i) any one or a combination of CDRs selected from CDRH1, CDRH2, CDRH3 from SEQ ID NO: 17, and/or CDRL1, CDRL2, CDRL3 from SEQ ID NOs: 27; or (ii) a CDR variant of (i) wherein the variant has 1, 2, or 3 amino acid modifications; or a VH region comprising a sequence at least 80% identical to the sequence of SEQ ID NO: 22; and/or a VL region comprising a sequence at least 80% identical to the sequence of SEQ ID NO: 32.

Alternatively, the ULBP6 binding proteins described herein may comprise (i) any one or a combination of CDRs selected from CDRH1, CDRH2, CDRH3 from SEQ ID NO: 18, and/or CDRL1, CDRL2, CDRL3 from SEQ ID NOs: 28; or (ii) a CDR variant of (i) wherein the variant has 1, 2, or 3 amino acid modifications; or a VH region comprising a sequence at least 80% identical to the sequence of SEQ ID NO: 23; and/or a VL region comprising a sequence at least 80% identical to the sequence of SEQ ID NO: 33.

Alternatively, the ULBP6 binding proteins described herein may comprise (i) any one or a combination of CDRs selected from CDRH1, CDRH2, CDRH3 from SEQ ID NO: 19, and/or CDRL1, CDRL2, CDRL3 from SEQ ID NOs: 29; or (ii) a CDR variant of (i) wherein the variant has 1, 2, or 3 amino acid modifications; or a VH region comprising a sequence at least 80% identical to the sequence of SEQ ID NO: 24; and/or a VL region comprising a sequence at least 80% identical to the sequence of SEQ ID NO: 34.

The ULBP6 binding proteins described herein may comprise any one or a combination of CDRs selected from CDRH1 of SEQ ID NO: 36, CDRH2 of SEQ ID NO: 37; and/or CDRH3 of SEQ ID NO: 38; CDRL1 of SEQ ID NOs: 51; CDRL2 of SEQ ID NOs: 52; and/or CDRL3 of SEQ ID NOs: 53. Alternatively, the ULBP6 binding proteins described herein may comprise any one or a combination of CDRs selected from CDRH1 of SEQ ID NO: 39, CDRH2 of SEQ ID NO: 40; and/or CDRH3 of SEQ ID NO: 41; CDRL1 of SEQ ID NOs: 54; CDRL2 of SEQ ID NOs: 55; and/or CDRL3 of SEQ ID NOs: 56. Alternatively, the ULBP6 binding proteins described herein may comprise any one or a combination of CDRs selected from CDRH1 of SEQ ID NO: 42, CDRH2 of SEQ ID NO: 43; and/or CDRH3 of SEQ ID NO: 44; CDRL1 of SEQ ID NOs: 57; CDRL2 of SEQ ID NOs: 58; and/or CDRL3 of SEQ ID NOs: 59. Alternatively, the ULBP6 binding proteins described herein may comprise any one or a combination of CDRs selected from CDRH1 of SEQ ID NO: 45, CDRH2 of SEQ ID NO: 46; and/or CDRH3 of SEQ ID NO: 47; CDRL1 of SEQ ID NOs: 60; CDRL2 of SEQ ID NOs: 61; and/or CDRL3 of SEQ ID NOs: 62.

The CDRs L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

Examples of CDR canonicals are given in Table 3 below. The amino acid numbering used is Kabat.

TABLE 3

CDR canonicals

| Antibody | CDR | CDR Definition | | |
|---|---|---|---|---|
| | | North | IMGT | Chothia |
| 7B3 | H1 | H1-13-A | H1-8-A | H1-7-A |
| | H2 | H2-10-B | H2-8-B | H2-6-B |
| | L1 | L1-10-A | L1-5-A | L1-10-A |
| | L2 | L2-8-A | L2-3-A | L2-7-A |
| | L3 | None | None | None |
| 8E11 | H1 | H1-13-A | H1-8-A | H1-7-A |
| | H2 | H2-10-B | H2-8-B | H2-6-E |
| | L1 | None | None | None |
| | L2 | L2-8-A | L2-3-A | L2-7-A |
| | L3 | None | None | None |
| 6E1 | H1 | H1-13-A | H1-8-C | H1-7-C |
| | H2 | H2-10-A | H2-8-A | H2-6-A |
| | L1 | None | None | None |
| | L2 | L2-8-A | L2-3-A | L2-7-A |
| | L3 | None | None | None |
| 1D4 | H1 | H1-13-A | H1-8-A | H1-7-A |
| | H2 | H2-10-A | H2-8-A | H2-6-A |
| | L1 | L1-11-A | L1-6-A | L1-11-A |
| | L2 | L2-8-A | L2-3-A | L2-7-A |
| | L3 | None | None | None |

Canonical nomenclature [xx-yy-zz]: xx = CDR; yy = length; zz = cluster size rank There may be multiple variant CDR canonical positions per CDR, per corresponding CDR, per binding unit, per heavy or light chain variable region, per heavy or light chain, and per antigen binding protein, and therefore any combination of substitution may be present in the antigen binding protein herein described, provided that the canonical structure of the CDR is maintained such that the antigen binding protein is capable of specifically binding ULBP6.

As discussed above, the particular canonical structure class of a CDR is defined by both the length of the CDR and by the loop packing, determined by residues located at key positions in both the CDRs and the framework regions.

The term "epitope" as used herein refers to that portion of the antigen that makes contact with a particular binding domain of the antigen binding protein, also known as the paratope. An epitope may be linear or conformational/discontinuous. A conformational or discontinuous epitope comprises amino acid residues that are separated by other sequences, i.e. not in a continuous sequence in the antigen's primary sequence assembled by tertiary folding of the polypeptide chain. Although the residues may be from different regions of the polypeptide chain, they are in close proximity in the three-dimensional structure of the antigen.

In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography. Epitope mapping can be carried out using various techniques known to persons skilled in the art. Exemplary methods include peptide-based approaches such as pepscan whereby a series of overlapping peptides are screened for binding using techniques such as ELISA or by in vitro display of large libraries of peptides or protein mutants, e.g. on phage. Detailed epitope information can be determined by structural techniques including X-ray crystallography, solution nuclear magnetic resonance (NMR) spectroscopy and cryogenic-electron microscopy (cryo-EM). Mutagenesis, such as alanine scanning, is an effective approach whereby loss of binding analysis is used for epitope mapping. Another method is hydrogen/deuterium exchange (HDX) combined with proteolysis and liquid-chromatography mass spectrometry (LC-MS) analysis to characterize discontinuous or conformational epitopes.

The term "antigen binding site" refers to a site on an antigen binding protein that is capable of specifically binding to an antigen, this may be a single variable domain, for example a folded polypeptide domain comprising sequences characteristic of antibody variable domains, or it may be paired VH/VL domains as can be found on a standard antibody. Single-chain Fv (ScFv) domains can also provide antigen-binding sites.

Competition between the ULBP6 binding protein described herein and a reference ULBP6 binding protein, e.g. a reference antibody, may be determined by one or more techniques known to the skilled person such as ELISA, FMAT, Surface Plasmon Resonance (SPR) or FORTEBIO OCTET Bio-Layer Interferometry (BLI). Such techniques may also be referred to as epitope binning. The competition assay may be carried out by BLI. There are several possible reasons for this competition: the two proteins may bind to the same or overlapping epitopes, there may be steric inhibition of binding, or binding of the first protein may induce a conformational change in the antigen that prevents or reduces binding of the second protein. The ULBP6 binding protein may bind to human ULBP6 and compete for binding to human ULBP6 with a reference ULBP6 binding protein. The reference ULBP6 binding protein may comprise (a) a VH region sequence of SEQ ID NO: 21 and a VL region sequence of SEQ ID NO: 31; or (b) a VH region sequence of SEQ ID NO: 22 and a VL region sequence of SEQ ID NO: 32; or (c) a VH region sequence of SEQ ID NO: 16 and a VL region sequence of SEQ ID NO: 26; or (d) a VH region sequence of SEQ ID NO: 17 and a VL region sequence of SEQ ID NO: 27.

The ULBP6 binding proteins described herein may share an overlapping epitope with a reference ULBP6 binding protein comprising a VH region comprising SEQ ID NO: 21 and a VL region comprising SEQ ID NO: 31; or a VH region comprising SEQ ID NO: 22 and a VL region comprising SEQ ID NO: 32. Alternatively, the ULBP6 binding proteins described herein may share an overlapping epitope with a reference ULBP6 binding protein comprising a HC sequence comprising SEQ ID NO: 75 and LC sequence comprising SEQ ID NO: 105; or a HC sequence comprising SEQ ID NO: 76 and a LC sequence comprising SEQ ID NO: 106. Alternatively, the ULBP6 binding proteins described herein may not share an overlapping epitope with a reference ULBP6 binding protein comprising a VH region comprising SEQ ID NO: 25 and a VL region comprising SEQ ID NO: 35; or a HC sequence comprising SEQ ID NO: 79 and a LC sequence comprising SEQ ID NO: 109.

The term "neutralizes" as used throughout the present specification means that the biological activity of ULBP6 is reduced in the presence of a ULBP6 binding protein as described herein in comparison to the biological activity of ULBP6 in the absence of the ULBP6 binding protein, in vitro or in vivo. Neutralisation may be due to one or more of blocking ULBP6 binding to its receptor, preventing ULBP6 from activating its receptor, down regulating ULBP6 or its receptor, or affecting effector functionality. Neutralisation may be determined or measured using one or more assays known to the skilled person or as described herein. For example, the blocking assay methods described in Example 7 may be used to assess the neutralising capability of a ULBP6 binding protein.

The effect of a ULBP6 binding protein on the interaction between ULBP6 and NKG2D may be partial or total. A neutralising ULBP6 binding protein may neutralize the activity of ULBP6 by at least 20%, 30%, 40%, 50%, 55%, 60%, 65%, 70%, 75%, 80%, 82%, 84%, 86%, 88%, 90%, 92%, 94%, 95%, 96%, 97%, 98%, 99% or 100% relative to ULBP6-NKG2D interactions in the absence of the ULBP6 binding protein. The ULBP6 binding proteins described herein may inhibit the interaction of human ULBP6 and human NKG2D by 70% or more, 75% or more, 80% or more, 85% or more, 90% or more, or 95% or more.

The ULBP6 binding proteins described herein may inhibit the binding of sULBP6 to NKG2D. The ULBP6 binding proteins may inhibit the binding of sULBP6 to NKG2D by 70% or more, 75% or more, 80% or more, 85% or more, 90% or more, or 95% or more. The ULBP6 binding proteins described herein may block the binding of sULBP6 to NKG2D. In some instances, the ULBP6 binding proteins may block the binding of sULBP6 to NKG2D by 70% or more, 75% or more, 80% or more, 90% or more, or 95% or more.

"Percent identity" or "% identity" between a query nucleic acid sequence and a subject nucleic acid sequence is the "Identities" value, expressed as a percentage, that is calculated using a suitable algorithm (e.g. BLASTN, FASTA, Needleman-Wunsch, Smith-Waterman, LALIGN, or GenePAST/KERR) or software (e.g. DNASTAR Lasergene, GenomeQuest, EMBOSS needle or EMBOSS infoalign), over the entire length of the query sequence after a pair-wise global sequence alignment has been performed using a suitable algorithm (e.g. Needleman-Wunsch or GenePAST/KERR) or software (e.g. DNASTAR Lasergene or GenePAST/KERR). Importantly, a query nucleic acid sequence may be described by a nucleic acid sequence disclosed herein, in particular in one or more of the claims.

"Percent identity" or "% identity" between a query amino acid sequence and a subject amino acid sequence is the "Identities" value, expressed as a percentage, that is calculated using a suitable algorithm (e.g. BLASTP, FASTA, Needleman-Wunsch, Smith-Waterman, LALIGN, or GenePAST/KERR) or software (e.g. DNASTAR Lasergene, GenomeQuest, EMBOSS needle or EMBOSS infoalign), over the entire length of the query sequence after a pair-wise global sequence alignment has been performed using a suitable algorithm (e.g. Needleman-Wunsch or GenePAST/KERR) or software (e.g. DNASTAR Lasergene or GenePAST/KERR). Importantly, a query amino acid sequence may be described by an amino acid sequence disclosed herein, in particular in one or more of the claims.

The query sequence may be 100% identical to the subject sequence, or it may include up to a certain integer number of amino acid or nucleotide alterations as compared to the subject sequence such that the % identity is less than 100%. For example, the query sequence is at least 50, 60, 70, 75, 80, 85, 90, 95, 96, 97, 98, or 99% identical to the subject sequence. In the case of nucleic acid sequences, such alterations include at least one nucleotide residue deletion, substitution or insertion, wherein said alterations may occur at the 5'- or 3'-terminal positions of the query sequence or anywhere between those terminal positions, interspersed either individually among the nucleotide residues in the query sequence or in one or more contiguous groups within the query sequence. In the case of amino acid sequences, such alterations include at least one amino acid residue deletion, substitution (including conservative and non-conservative substitutions), or insertion, wherein said alterations may occur at the amino- or carboxy-terminal positions of the query sequence or anywhere between those terminal positions, interspersed either individually among the amino acid residues in the query sequence or in one or more contiguous groups within the query sequence.

For antibody sequences, the % identity may be determined across the entire length of the query sequence, including the CDRs. Alternatively, the % identity may exclude one or more or all of the CDRs. For example, all of the CDRs may be 100% identical to the subject sequence and the % identity variation can be in the remaining portion of the query sequence, e.g. the framework sequence, such that the CDR sequences are fixed and intact.

The ULBP6 binding protein described herein may comprise a CDRH3 that is 100% identical to any one of SEQ ID NOs: 38, 41, 44 or 47. The ULBP6 binding protein described herein may comprise a CDRH3 that is 100% identical to SEQ ID NO: 38. The ULBP6 binding protein described herein may comprises a CDRH3 that is 100% identical to SEQ ID NO: 41. The ULBP6 binding protein described herein may comprises a CDRH3 that is 100% identical to SEQ ID NO: 44. The ULBP6 binding protein described herein may comprises a CDRH3 that is 100% identical to SEQ ID NO: 47.

The ULBP6 binding protein described herein may comprise CDRH1 that is 100% identical to SEQ ID NO: 36; CDRH2 that is 100% identical to SEQ ID NO: 37; and/or CDRH3 that is 100% identical to SEQ ID NO: 38; CDRL1 that is 100% identical to SEQ ID NO: 51; CDRL2 that is 100% identical to SEQ ID NO: 52; and/or CDRL3 that is 100% identical to SEQ ID NO: 53. Alternatively, the ULBP6 binding protein described herein may comprise CDRH1 that is 100% identical to SEQ ID NO: 39; CDRH2 that is 100% identical to SEQ ID NO: 40; and/or CDRH3 that is 100% identical to SEQ ID NO: 41; CDRL1 that is 100% identical to SEQ ID NO: 54; CDRL2 that is 100% identical to SEQ ID NO: 55; and/or CDRL3 that is 100% identical to SEQ ID NO: 56. Alternatively, the ULBP6 binding protein described herein may comprise CDRH1 that is 100% identical to SEQ ID NO: 42; CDRH2 that is 100% identical to SEQ ID NO: 43; and/or CDRH3 that is 100% identical to SEQ ID NO: 44; CDRL1 that is 100% identical to SEQ ID NO: 57; CDRL2 that is 100% identical to SEQ ID NO: 58; and/or CDRL3 that is 100% identical to SEQ ID NO: 59. Alternatively, the ULBP6 binding protein described herein may comprise CDRH1 that is 100% identical to SEQ ID NO: 45; CDRH2 that is 100% identical to SEQ ID NO: 46; and/or CDRH3 that is 100% identical to SEQ ID NO: 47; CDRL1 that is 100% identical to SEQ ID NO: 60; CDRL2 that is 100% identical to SEQ ID NO: 61; and/or CDRL3 that is 100% identical to SEQ ID NO: 62.

The ULBP6 binding protein described herein may comprise CDRH1 that is 100% identical to SEQ ID NO: 36; CDRH2 that is 100% identical to SEQ ID NO: 37; CDRH3 that is 100% identical to SEQ ID NO: 38; CDRL1 that is 100% identical to SEQ ID NO: 51; CDRL2 that is 100% identical to SEQ ID NO: 52; and CDRL3 that is 100% identical to SEQ ID NO: 53. Alternatively, the ULBP6 binding protein described herein may comprise CDRH1 that is 100% identical to SEQ ID NO: 39; CDRH2 that is 100% identical to SEQ ID NO: 40; CDRH3 that is 100% identical to SEQ ID NO: 41; CDRL1 that is 100% identical to SEQ ID NO: 54; CDRL2 that is 100% identical to SEQ ID NO: 55; and CDRL3 that is 100% identical to SEQ ID NO: 56. Alternatively, the ULBP6 binding protein described herein may comprise CDRH1 that is 100% identical to SEQ ID NO: 42; CDRH2 that is 100% identical to SEQ ID NO: 43; CDRH3 that is 100% identical to SEQ ID NO: 44; CDRL1 that is 100% identical to SEQ ID NO: 57; CDRL2 that is 100% identical to SEQ ID NO: 58; and CDRL3 that is 100% identical to SEQ ID NO: 59. Alternatively, the ULBP6 binding protein described herein may comprise CDRH1 that is 100% identical to SEQ ID NO: 45; CDRH2 that is 100% identical to SEQ ID NO: 46; CDRH3 that is 100% identical to SEQ ID NO: 47; CDRL1 that is 100% identical to SEQ ID NO: 60; CDRL2 that is 100% identical to SEQ ID NO: 61; and CDRL3 that is 100% identical to SEQ ID NO: 62.

The ULBP6 binding protein described herein may comprise a VH region that is at least 90% identical to SEQ ID NO: 21 and a VL region that is at least 90% identical to SEQ ID NO: 31. The ULBP6 binding protein described herein may comprise a VH region that is at least 95% identical to SEQ ID NO: 21 and a VL region that is 95% identical to SEQ ID NO: 31. The ULBP6 binding protein described herein may comprise a VH region that is at least 90% identical to SEQ ID NO: 22 and a VL region that is at least 90% identical to SEQ ID NO: 32. The ULBP6 binding protein described herein may comprise a VH region that is at least 95% identical to SEQ ID NO: 22 and a VL region that is 95% identical to SEQ ID NO: 32. The ULBP6 binding protein described herein may comprise a VH region that is at least 90% identical to SEQ ID NO: 23 and a VL region that is at least 90% identical to SEQ ID NO: 33. The ULBP6 binding protein described herein may comprise a VH region that is at least 95% identical to SEQ ID NO: 23 and a VL region that is 95% identical to SEQ ID NO: 33. The ULBP6 binding protein described herein may comprise a VH region that is at least 90% identical to SEQ ID NO: 24 and a VL region that is at least 90% identical to SEQ ID NO: 34. The ULBP6 binding protein described herein may comprise a VH region that is at least 95% identical to SEQ ID NO: 24 and a VL region that is 95% identical to SEQ ID NO: 34.

The ULBP6 binding protein described herein may comprise a VH region that is 100% identical to SEQ ID NO: 21 and a VL region that is 100% identical to SEQ ID NO: 31; a VH region that is 100% identical to SEQ ID NO: 22 and a VL region that is 100% identical to SEQ ID NO: 32; a VH region that is 100% identical to SEQ ID NO: 23 and a VL region that is 100% identical to SEQ ID NO: 33; or a VH region that is 100% identical to SEQ ID NO: 24 and a VL region that is 100% identical to SEQ ID NO: 34.

The ULBP6 binding protein described herein may comprise a Heavy Chain (HC) sequence that is at least 90% identical to SEQ ID NO: 75 and/or a Light Chain (LC) sequence that is at least 90% identical to SEQ ID NO: 105. Alternatively, the ULBP6 binding protein described herein may comprise a Heavy Chain (HC) sequence that is at least 95% identical to SEQ ID NO: 75 and/or a Light Chain (LC) sequence that is at least 95% identical to SEQ ID NO: 105. Alternatively, the ULBP6 binding protein described herein may comprise a Heavy Chain (HC) sequence that is at least 90% identical to SEQ ID NO: 76 and/or a Light Chain (LC) sequence that is at least 90% identical to SEQ ID NO: 106. Alternatively, the ULBP6 binding protein described herein may comprise a Heavy Chain (HC) sequence that is at least 95% identical to SEQ ID NO: 76 and/or a Light Chain (LC) sequence that is at least 95% identical to SEQ ID NO: 106.

The ULBP6 binding protein described herein may comprise a Heavy Chain (HC) sequence that is 100% identical to SEQ ID NO: 75 and/or a Light Chain (LC) sequence that is 100% identical to SEQ ID NO: 105; a Heavy Chain (HC) sequence that is 100% identical to SEQ ID NO: 76 and/or a Light Chain (LC) sequence that is 100% identical to SEQ ID NO: 106; a Heavy Chain (HC) sequence that is 100% identical to SEQ ID NO: 77 and/or a Light Chain (LC) sequence that is 100% identical to SEQ ID NO: 107; or a Heavy Chain (HC) sequence that is 100% identical to SEQ ID NO: 78 and/or a Light Chain (LC) sequence that is 100% identical to SEQ ID NO: 108. The ULBP6 binding protein described herein may comprise a Heavy Chain (HC) sequence that is 100% identical to SEQ ID NO: 75 and a Light Chain (LC) sequence that is 100% identical to SEQ ID NO: 105. Alternatively, the ULBP6 binding protein described herein may comprise a Heavy Chain (HC) sequence that is 100% identical to SEQ ID NO: 76 and a Light Chain (LC) sequence that is 100% identical to SEQ ID NO: 106. Alternatively, the ULBP6 binding protein described herein may comprise a Heavy Chain (HC) sequence that is 100% identical to SEQ ID NO: 77 and a Light Chain (LC) sequence that is 100% identical to SEQ ID NO: 107. Alternatively, the ULBP6 binding protein described herein may comprise a Heavy Chain (HC) sequence that is 100% identical to SEQ ID NO: 78 and a Light Chain (LC) sequence that is 100% identical to SEQ ID NO: 108.

The VH or VL (or HC or LC) sequence may be a variant sequence with up to 10 amino acid substitutions, additions or deletions. For example, the variant sequence may have up to 9, 8, 7, 6, 5, 4, 3, 2 or 1 amino acid substitution(s), addition(s) or deletion(s).

The HC sequence may be a variant sequence with up to 40 amino acid substitutions, additions or deletions. For example the variant sequence may have up to 35, 30, 25, 20, 15 or 10 amino acid substitutions, additions or deletions.

The LC sequence may be a variant sequence with up to 20 amino acid substitutions, additions or deletions. For example the variant sequence may have up to 15, 10 or 5 amino acid substitutions, additions or deletions.

The sequence variation may exclude one or more or all of the CDRs, for example the CDRs are the same as the VH or VL (or HC or LC) sequence and the variation is in the remaining portion of the VH or VL (or HC or LC) sequence, so that the CDR sequences are fixed and intact.

Typically, the variation is a substitution, particularly a conservative substitution, for example as shown in Table 2.

The variant sequence substantially retains the biological characteristics of the unmodified protein, such as inhibiting binding of ULBP6 to NKG2D.

The skilled person will appreciate that, upon production of an antigen binding protein, such as an antibody in a host cell, post-translational modifications may occur. For example, this may include the cleavage of certain leader sequences, the addition of various sugar moieties in various glycosylation patterns, non-enzymatic glycation, deamidation, oxidation, disulfide bond scrambling and other cysteine variants such as free sulfhydryls, racemized disulfides, thioethers and trisulfide bonds, isomerisation, C-terminal lysine clipping, and N-terminal glutamine cyclisation. The disclosure herein encompasses the use of antigen binding proteins that have been subjected to, or have undergone, one or more post-translational modifications. Thus an "antigen binding protein" or "antibody" of the invention includes an "antigen binding protein" or "antibody", respectively, as defined earlier that has undergone a post-translational modification such as described herein.

Glycation is a post-translational non-enzymatic chemical reaction between a reducing sugar, such as glucose, and a free amine group in the protein, and is typically observed at the epsilon amine of lysine side chains or at the N-Terminus of the protein. Glycation can occur during production and storage only in the presence of reducing sugars.

Deamidation can occur during production and storage, is an enzymatic reaction primarily converting asparagine (N) to iso-aspartic acid (iso-aspartate) and aspartic acid (aspartate) (D) at approximately 3:1 ratio. This deamidation reaction is therefore related to isomerization of aspartate (D) to iso-aspartate. The deamidation of asparagine and the isomerisation of aspartate, both involve the intermediate succinimide. To a much lesser degree, deamidation can occur with glutamine residues in a similar manner. Deamidation can occur in a CDR, in a Fab (non-CDR region), or in the Fc region.

Oxidation can occur during production and storage (i.e., in the presence of oxidizing conditions) and results in a covalent modification of a protein, induced either directly by reactive oxygen species or indirectly by reaction with secondary by-products of oxidative stress.

Oxidation happens primarily with methionine residues, but may occur at tryptophan and free cysteine residues. Oxidation can occur in a CDR, in a Fab (non-CDR) region, or in the Fc region.

Disulfide bond scrambling can occur during production and basic storage conditions.

Under certain circumstances, disulfide bonds can break or form incorrectly, resulting in unpaired cysteine residues (—SH). These free (unpaired) sulfhydryls (—SH) can promote shuffling.

The formation of a thioether and racemization of a disulphide bond can occur under basic conditions, in production or storage, through a beta elimination of disulphide bridges back to cysteine residues via a dehydroalanine and persulfide intermediate. Subsequent crosslinking of dehydroalanine and cysteine results in the formation of a thioether bond or the free cysteine residues can reform a disulphide bond with a mixture of D- and L-cysteine.

Trisulfides result from insertion of a sulfur atom into a disulphide bond (Cys-S—S—S-Cys) and are formed due to the presence of hydrogen sulphide in production cell culture.

N-terminal glutamine (Q) and glutamate (glutamic acid) (E) in the heavy chain and/or light chain is likely to form pyroglutamate (pGlu) via cyclization. Most pGlu formation happens in the production bioreactor, but it can be formed non-enzymatically, depending on pH and temperature of processing and storage conditions. Cyclization of N-terminal Q or E is commonly observed in natural human antibodies.

C-terminal lysine clipping is an enzymatic reaction catalyzed by carboxypeptidases, and is commonly observed in recombinant and natural human antibodies. Variants of this process include removal of lysine from one or both heavy chains due to cellular enzymes from the recombinant host cell. Upon administration to the human subject/patient is likely to result in the removal of any remaining C-terminal lysines.

Pharmaceutical Compositions

An antigen binding protein as described herein may be incorporated into a pharmaceutical composition for use in the treatment of the human diseases described herein. The pharmaceutical composition may comprise an antigen binding protein optionally in combination with one or more pharmaceutically acceptable carriers and/or excipients.

Such compositions can comprise a pharmaceutically acceptable carrier as known and called for by acceptable pharmaceutical practice.

Pharmaceutical compositions may be administered by injection or continuous infusion (examples include, but are not limited to, intravenous, intraperitoneal, intradermal, subcutaneous, intramuscular, intraocular, and intraportal). The pharmaceutical composition may be suitable for intravenous administration. The pharmaceutical composition may be suitable for subcutaneous administration. Pharmaceutical compositions may be suitable for topical administration (which includes, but is not limited to, epicutaneous, inhaled, intranasal or ocular administration) or enteral administration (which includes, but is not limited to, oral, vaginal, or rectal administration).

Pharmaceutical compositions may comprise between 0.5 mg to 10 g of ULBP6 binding protein, for example between 5 mg and 1 g of ULBP6 binding protein. Alternatively, the composition may comprise between 5 mg and 500 mg of ULBP6 binding protein, for example between 5 mg and 50 mg of ULBP6 binding protein.

Methods for the preparation of such pharmaceutical compositions are well known to those skilled in the art. Other excipients may be added to the composition as appropriate for the mode of administration and the particular protein used.

Effective doses and treatment regimes for administering the antigen binding protein may be dependent on factors such as the age, weight and health status of the patient and disease to be treated. Such factors are within the purview of the attending physician.

The pharmaceutical composition may be included in a kit containing the antigen binding protein together with other medicaments, and/or with instructions for use. For convenience, the kit may comprise the reagents in predetermined amounts with instructions for use. The kit may also include devices used for administration of the pharmaceutical composition.

The terms "individual", "subject" and "patient" are used herein. Typically, an individual of interest can be a subject, and a subject in need of treatment can be a patient. An individual, subject, or patient may be an animal. An individual, subject, or patient may be a mammal, such as a primate, for example a marmoset or monkey. An individual, subject, or patient may be a human.

The antigen binding protein described herein may also be used in methods of treatment. It will be appreciated by those skilled in the art that references herein to treatment refer to the treatment of established conditions. However, antigen binding proteins disclosed herein may, depending on the condition, also be useful in the prevention of certain diseases. The antigen binding protein described herein is used in an effective amount for therapeutic, prophylactic or preventative treatment. A therapeutically effective amount of the antigen binding protein described herein is an amount effective to ameliorate or reduce one or more symptoms of, or to prevent or cure, the disease.

Antigen binding proteins may be prepared by any of a number of conventional techniques. For example, antigen binding proteins may be purified from cells that naturally express them (e.g., an antibody can be purified from a hybridoma that produces it) or produced in recombinant expression systems.

The ULBP6 binding proteins described herein are provided for use in therapy. ULBP6 binding proteins are provided for use in the treatment of cancer. Also provided is the use of a ULBP6 binding protein in the manufacture of a medicament for the treatment of cancer. Also provided is the use of a ULBP6 binding protein in the manufacture of a medicament for the treatment of cancer, wherein the ULBP6 binding protein comprises a VH region comprising SEQ ID NO: 21 and a VL region comprising SEQ ID NO: 31. Also provided is the use of a ULBP6 binding protein in the manufacture of a medicament for the treatment of cancer, wherein the ULBP6 binding protein comprises a VH region comprising SEQ ID NO: 22 and a VL region comprising SEQ ID NO: 32. Also provided is a pharmaceutical composition comprising 100-1400 mg of a ULBP6 binding protein. Also provided is a pharmaceutical composition comprising 100-1400 mg of a ULBP6 binding protein comprising a VH region comprising SEQ ID NO: 21 and a VL region comprising SEQ ID NO: 31. Also provided herein is a pharmaceutical composition comprising 100-1400 mg of a ULBP6 binding protein comprising a HC sequence comprising SEQ ID NO: 75 and a LC sequence comprising SEQ ID NO: 105.

Also provided herein are isolated ULBP6 binding proteins or the pharmaceutical compositions comprising said isolated ULBP6 binding proteins for use in the treatment of cancer.

Production Methods

A number of different expression systems and purification regimes can be used to generate an antigen binding protein. Generally, host cells are transformed with a recombinant expression vector encoding the desired antigen binding protein. The expression vector may be maintained by the host as a separate genetic element or integrated into the host chromosome depending on the expression system. A wide range of host cells can be employed, including Prokaryotes (including Gram negative or Gram positive bacteria, for example *Escherichia coli*, Bacilli sp., *Pseudomonas* sp., *Corynebacterium* sp.), Eukaryotes including yeast (for example *Saccharomyces cerevisiae*, *Pichia pastoris*), fungi (for example *Aspergillus* sp.), or higher Eukaryotes including insect cells and cell lines of mammalian origin (for example, CHO, NS0, PER.C6, HEK293, HeLa).

A host cell may be an isolated host cell. The host cell is usually not part of a multicellular organism (e.g., plant or animal). The host cell may be a non-human host cell.

Appropriate cloning and expression vectors for use with bacterial, fungal, yeast, and mammalian host cells are known in the art.

Cells can be cultured under conditions that promote expression of the antigen binding protein using a variety of equipment such as shake flasks, spinner flasks, and bioreactors.

Polypeptide can be recovered by conventional protein purification procedures. Protein purification procedures can typically consist of a series of unit operations comprising, for example, one or more filtration and/or chromatographic processes developed to selectively concentrate and isolate the antigen binding protein. Purified antigen binding protein may be formulated in a pharmaceutically acceptable composition.

Fc engineering methods can be applied to modify the functional or pharmacokinetics properties of an antibody. Effector function may be altered by making mutations in the Fc region that increase or decrease binding to C1q or Fcγ receptors and modify CDC or ADCC activity respectively. Modifications to the glycosylation pattern of an antibody can also be made to change the effector function. The in vivo half-life of an antibody can be altered by making mutations that affect binding of the Fc to the FcRn (Neonatal Fc Receptor).

The term "Effector Function" as used herein refers to one or more of antibody-mediated effects including antibody-dependent cell-mediated cytotoxicity (ADCC), antibody-mediated complement activation including complement-dependent cytotoxicity (CDC), complement-dependent cell-mediated phagocytosis (CDCP), antibody dependent complement-mediated cell lysis (ADCML), and Fc-mediated phagocytosis or antibody-dependent cellular phagocytosis (ADCP).

The interaction between the Fc region of an antigen binding protein or antibody and various Fc receptors (FcR), including FcγRI (CD64), FcγRII (CD32), FcγRIII (CD16), FcRn, C1q, and type II Fc receptors is believed to mediate the effector functions of the antigen binding protein or antibody. Significant biological effects can be a consequence of effector functionality. Usually, the ability to mediate effector function requires binding of the antigen binding protein or antibody to an antigen and not all antigen binding proteins or antibodies will mediate every effector function.

Effector function can be assessed in a number of ways including, for example, evaluating ADCC effector function of antibody coated to target cells mediated by Natural Killer (NK) cells via FcγRIII, or monocytes/macrophages via FcγRI, or evaluating CDC effector function of antibody coated to target cells mediated by complement cascade via C1q. For example, an antigen binding protein described herein can be assessed for ADCC effector function in a Natural Killer cell assay.

The effects of mutations on effector functions (e.g., FcRn binding, FcγRs and C1q binding, CDC, ADCML, ADCC, ADCP) can be assessed.

Throughout this specification, amino acid residues in Fc regions, in antibody sequences or full-length antigen binding protein sequences, are numbered according to the EU index numbering convention.

Human IgG1 constant regions containing specific mutations have been shown to enhance binding to Fc receptors. In some cases these mutations have also been shown to enhance effector functions, such as ADCC and CDC, as described below. Antigen binding proteins described herein may include any of the following mutations.

Enhanced CDC: Fc engineering can be used to enhance complement-based effector function. For example (with reference to IgG1), K326W/E333S; S267E/H268F/S324T; and IgG1/IgG3 cross subclass can increase C1q binding; E345R and E345R/E430G/S440Y results in preformed IgG hexamers.

Enhanced ADCC: Fc engineering can be used to enhance ADCC. For example (with reference to IgG1), F243L/R292P/Y300L/V305I/P396L; S239D/I332E; and S298A/E333A/K334A increase FcγRIIIa binding; S239D/I332E/A330L increases FcγRIIIa binding and decreases FcγRIIb binding; G236A/S239D/I332E improves binding to FcγRIIa, improves the FcγRIIa/FcγRIIb binding ratio (activating/inhibitory ratio), and enhances phagocytosis of antibody-coated target cells by macrophages. The ULBP6 binding protein herein described is mutated at positions 239 and 332, for example S239D and I332E. The ULBP6 binding protein herein described may be mutated at three or more positions selected from 239 and 332 and 330, for example S239D and I332E and A330L (EU index numbering).

The ULBP6 binding proteins described herein may be an antibody or an antigen binding fragment thereof, wherein the antibody or antigen binding fragment thereof comprises a modified Fc region comprising amino acid substitutions selected from S239D/A330L/I332E, G236A/S239D/A330L/I332E, L235V/F243L/R292P/Y300L/P396L or F243L/R292P/Y300L/V305I/P396L. An asymmetric Fc in which one heavy chain contains L234Y/L235Q/G236W/S239M/H268D/D270E/S298A mutations and D270E/K326D/A330M/K334E in the opposing heavy chain, increases affinity for FcγRIIIa F158 (a lower-affinity allele) and FcγRIIIa V158 (a higher-affinity allele) with no increased binding affinity to inhibitory FcγRIIb.

Enhanced ADCP: Fc engineering can be used to enhance ADCP. For example (with reference to IgG1), G236A/S239D/I332E increases FcγRIIa binding and increases FcγRIIIa binding.

Increased co-engagement: Fc engineering can be used to increase co-engagement with FcRs. For example (with reference to IgG1), S267E/L328F increases FcγRIIb binding; N325S/L328F increases FcγRIIa binding and decreases FcγRIIIa binding.

An antigen binding protein described herein may comprise a heavy chain constant region with an altered glycosylation profile, such that the antigen binding protein has an enhanced effector function, e.g. enhanced ADCC, enhanced CDC, or both enhanced ADCC and CDC. Examples of suitable methodologies to produce antigen binding proteins with an altered glycosylation profile are described in WO2003011878, WO2006014679 and EP1229125, all of which can be applied to the antigen binding proteins herein described.

The absence of the α1,6 innermost fucose residues on the Fc glycan moiety on N297 of IgG1 antibodies can enhance affinity for FcγRIIIA. As such, afucosylated or low fucosylated monoclonal antibodies may have increased therapeutic efficacy compared with a monoclonal antibody having standard fucosylation or higher fucosylation.

Herein provided is an antigen binding protein comprising a chimeric heavy chain constant region. The antigen binding protein may comprise an IgG1/IgG3 chimeric heavy chain constant region, such that the antigen binding protein has an enhanced effector function, for example enhanced ADCC or enhanced CDC, or enhanced ADCC and CDC functions. For example, a chimeric antigen binding protein of the invention may comprise at least one CH2 domain from IgG3. The antigen binding protein may comprise one CH2 domain from IgG3 or both CH2 domains may be from IgG3. The chimeric antigen binding protein may comprise an IgG1 CH1 domain, an IgG3 CH2 domain, and an IgG3 CH3 domain. The chimeric antigen binding protein may comprise an IgG1 CH1 domain, an IgG3 CH2 domain, and an IgG3 CH3 domain except for position 435 that is a H (histidine).

The antigen binding protein may comprise an IgG1 CH1 domain and at least one CH2 domain from IgG3. The chimeric antigen binding protein may comprise an IgG1 CH1 domain and the following residues, which correspond to IgG3 residues, in a CH2 domain: 274Q, 276K, 296F, 300F and 339T. The chimeric antigen binding protein may also comprise 356E, which corresponds to an IgG3 residue, within a CH3 domain. The antigen binding protein may also comprise one or more of the following residues, which correspond to IgG3 residues within a CH3 domain: 358M, 384S, 392N, 397M, 422I, 435R, and 436F.

Also provided are methods of producing an antigen binding protein comprising: a) culturing a recombinant host cell comprising an expression vector comprising an isolated nucleic acid as described herein wherein the expression vector comprises a nucleic acid sequence encoding a chimeric Fc region having both IgG1 and IgG3 Fc region amino acid residues (e.g. as described above); and b) recovering the antigen binding protein.

Such methods for the production of antigen binding proteins with chimeric heavy chain constant regions can be performed, for example, using the COMPLEGENT technology system available from BioWa, Inc. (Princeton, NJ) and Kyowa Hakko Kirin Co., Ltd. The COMPLEGENT system comprises a recombinant host cell comprising an expression vector in which a nucleic acid sequence encoding a chimeric Fc region having both IgG1 and IgG3 Fc region amino acid residues is expressed to produce an antigen binding protein having enhanced CDC activity, i.e. CDC activity is increased relative to an otherwise identical antigen binding protein lacking such a chimeric Fc region, as described in WO2007011041 and US20070148165, each of which are incorporated herein by reference. Alternatively, CDC activity may be increased by introducing sequence specific mutations into the Fc region of an IgG chain. Those of ordinary skill in the art will also recognize other appropriate systems.

Also provided are methods of producing an antigen binding protein described herein comprising: a) culturing a recombinant host cell comprising an expression vector comprising the isolated nucleic acid as described herein, wherein the FUT8 gene encoding alpha-1,6-fucosyltransferase has been inactivated in the recombinant host cell; and b) recovering the antigen binding protein.

Such methods for the production of antigen binding proteins can be performed, for example, using the POTELLIGENT technology system available from BioWa, Inc. (Princeton, NJ) in which CHOK1SV cells lacking a functional copy of the FUT8 gene produce monoclonal antibodies having enhanced ADCC activity that is increased relative to an identical monoclonal antibody produced in a cell with a functional FUT8 gene as described in U.S. Pat. Nos. 7,214,775, 6,946,292, WO0061739 and WO0231240, all of which are incorporated herein by reference. Those of ordinary skill in the art will also recognize other appropriate systems.

An antigen binding protein described herein may be produced in a host cell in which the FUT8 gene has been inactivated. The antigen binding protein may be produced in a −/− FUT8 host cell. An antigen binding protein may be afucosylated at Asn297 (IgG1). ULBP6 binding proteins described herein may be afucosylated. The ULBP6 binding protein may be an antibody comprising a heavy chain (HC) of SEQ ID NO: 75 and a light chain (LC) of SEQ ID NO: 105, wherein the antibody is afucosylated. A ULBP6 binding protein may be an antibody comprising a heavy chain (HC) of SEQ ID NO: 76 and a light chain (LC) of SEQ ID NO: 106, wherein the antibody is afucosylated.

Some isotypes of human constant regions, in particular IgG4 and IgG2 isotypes, can essentially lack the functions of a) activation of complement by the classical pathway and/or b) ADCC. Various modifications to the heavy chain constant region of antigen binding proteins may be carried out to alter effector function depending on a desired effector property. IgG1 constant regions containing specific mutations that reduce binding to Fc receptors and reduce an effector function, such as ADCC and CDC, have been described. Such modifications can be used alone but can be used alone or in combination with each other in order to alter effector function.

Provided herein is an antigen binding protein comprising a heavy chain constant region that comprises a both a mutated and chimeric heavy chain constant region, individually described above. For example, an antigen binding protein comprising at least one CH2 domain from IgG3 and one CH2 domain from IgG1, and wherein the IgG1 CH2 domain has one or more mutations at positions selected from 239, 332 and 330 (for example the mutations may be selected from S239D, I332E and A330L), such that the antigen binding protein has enhanced effector function, e.g. enhanced ADCC or enhanced CDC, or enhanced ADCC and enhanced CDC in comparison to an equivalent antigen binding protein with an IgG1 heavy chain constant region lacking said mutations. The IgG1 CH2 domain may have the mutations S239D and I332E. The IgG1 CH2 domain may have the mutations S239D, A330L, and I332E.

The ULBP6 binding protein described herein may comprise a Heavy Chain (HC) sequence that is at least 90% identical to SEQ ID NO: 95 and/or a Light Chain (LC) sequence that is at least 90% identical to SEQ ID NO: 105. Alternatively, the ULBP6 binding protein described herein may comprise a Heavy Chain (HC) sequence that is at least 95% identical to SEQ ID NO: 95 and/or a Light Chain (LC) sequence that is at least 95% identical to SEQ ID NO: 105. Alternatively, the ULBP6 binding protein described herein may comprise a Heavy Chain (HC) sequence that is at least 90% identical to SEQ ID NO: 96 and/or a Light Chain (LC) sequence that is at least 90% identical to SEQ ID NO: 106. Alternatively, the ULBP6 binding protein described herein may comprise a Heavy Chain (HC) sequence that is at least 95% identical to SEQ ID NO: 96 and/or a Light Chain (LC) sequence that is at least 95% identical to SEQ ID NO: 106.

The ULBP6 binding protein described herein may comprise a Heavy Chain (HC) sequence that is 100% identical to SEQ ID NO: 95 and/or a Light Chain (LC) sequence that is 100% identical to SEQ ID NO: 105; a Heavy Chain (HC) sequence that is 100% identical to SEQ ID NO: 96 and/or a Light Chain (LC) sequence that is 100% identical to SEQ ID NO: 106; a Heavy Chain (HC) sequence that is 100% identical to SEQ ID NO: 97 and/or a Light Chain (LC) sequence that is 100% identical to SEQ ID NO: 107; or a Heavy Chain (HC) sequence that is 100% identical to SEQ ID NO: 98 and/or a Light Chain (LC) sequence that is 100% identical to SEQ ID NO: 108. The ULBP6 binding protein described herein may comprise a Heavy Chain (HC) sequence that is 100% identical to SEQ ID NO: 95 and a Light Chain (LC) sequence that is 100% identical to SEQ ID NO: 105. The ULBP6 binding protein described herein may comprise a Heavy Chain (HC) sequence that is 100% identical to SEQ ID NO: 96 and a Light Chain (LC) sequence that is 100% identical to SEQ ID NO: 106.

Alternatively, there is provided an antigen binding protein comprising both a chimeric heavy chain constant region and an altered glycosylation profile, as individually described above. The antigen binding protein may comprise an altered glycosylation profile such that the ratio of fucose to mannose is 0.8:3 or less. The heavy chain constant region may comprise at least one CH2 domain from IgG3 and one CH2 domain from IgG1 and has an altered glycosylation profile such that the ratio of fucose to mannose is 0.8:3 or less, for example wherein the antigen binding protein is defucosylated. Said antigen binding protein can have an enhanced effector function, e.g. enhanced ADCC or enhanced CDC, or enhanced ADCC and enhanced CDC, in comparison to an equivalent antigen binding protein with an IgG1 heavy chain constant region lacking said glycosylation profile.

Alternatively, the antigen binding protein has at least one IgG3 heavy chain CH2 domain and at least one heavy chain constant domain from IgG1 wherein both IgG CH2 domains are mutated in accordance with the limitations described herein.

Provided herein are methods of producing an antigen binding protein described herein, comprising: a) culturing a recombinant host cell containing an expression vector comprising an isolated nucleic acid as described herein wherein the expression vector comprises a nucleic acid sequence encoding a chimeric Fc domain having both IgG1 and IgG3 Fc domain amino acid residues (e.g. as described above); and wherein the FUT8 gene encoding alpha-1,6-fucosyltransferase has been inactivated in the recombinant host cell; and b) recovering the antigen binding protein.

Such methods for the production of antigen binding proteins can be performed, for example, using the ACCRETAMAB technology system available from BioWa, Inc. (Princeton, NJ) that combines the POTELLIGENT and COMPLEGENT technology systems to produce an antigen binding protein having both enhanced ADCC and CDC activity relative to an otherwise identical monoclonal antibody that lacks a chimeric Fc domain and that is fucosylated.

Also provided are antigen binding proteins comprising a mutated and chimeric heavy chain constant region wherein said antigen binding protein has an altered glycosylation profile such that the antigen binding protein has enhanced effector function, e.g. enhanced ADCC or enhanced CDC, or both enhanced ADCC and CDC. The mutations may be selected from positions 239, 332 and 330, e.g. S239D, I332E and A330L. The heavy chain constant region may comprise at least one CH2 domain from IgG3 and one CH1 domain from IgG1. The heavy chain constant region may have an altered glycosylation profile such that the ratio of fucose to mannose is 0.8:3 or less, e.g. the antigen binding protein is defucosylated, such that said antigen binding protein has an enhanced effector function in comparison with an equivalent non-chimeric antigen binding protein, lacking said mutations and lacking said altered glycosylation profile.

Provided herein are antigen binding proteins comprising a constant region such that the antigen binding protein has reduced effector function, such as reduced ADCC and/or CDC. The heavy chain constant region may comprise a naturally disabled constant region of an IgG2 or IgG4 isotype or a mutated IgG1 constant region. Examples of suitable modifications are described in EP0307434. One example comprises substitution with alanine at positions 235 and 237 (EU index numbering), i.e. L235A and G237A (commonly referred to as "LAGA" mutations). Another example comprises substitution with alanine at positions 234 and 235 (EU index numbering), i.e. L234A and L235A (commonly referred to as "LALA" mutations). Further examples, described in EP2691417 and U.S. Pat. No. 8,969,526, comprise P329G or P329R, in combination with the LALA mutations (EU index numbering) for IgG1 Fcs and P329G or P329R in combination with S228P and L235E for IgG4 Fcs (EU index numbering).

Additional alterations and mutations to decrease effector function can include: (with reference to IgG1 unless otherwise noted): aglycosylated N297A or N297Q or N297G; L235E; IgG4:F234A/L235A; and chimeric IgG2/IgG4. IgG2: H268Q/V309L/A330S/P331S, and IgG2: V234A/G237A/P238S/H268A/V309L/A330S/P331S can reduce FcγR and C1q binding (U.S. Pat. No. 8,961,967). The ULBP6 binding protein described herein may comprise a modified Fc region, wherein the modified Fc region comprises the amino acid substitution N297A, N297Q or N297G.

Other mutations that decrease effector function include L234F/L235E/P331S; a chimeric antibody created using the CH1 and hinge region from human IgG2 and the CH2 and CH3 regions from human IgG4; IgG2m4, based on the IgG2 isotype with four key amino acid residue changes derived from IgG4 (H268Q, V309L, A330S and P331S); IgG2-that contains V234A/G237A/P238S/H268A/V309L/A330S/P331S substitutions to eliminate affinity for Fcγ receptors and C1q complement protein; IgG2m4 (H268Q/V309L/A330S/P331S, changes to IgG4); IgG4 (S228P/L234A/L235A); huIgG1 L234A/L235A (AA); huIgG4 S228P/L234A/L235A; IgG1s (L234A/L235A/G237A/P238S/H268A/A330S/P331S); IgG4s1 (S228P/F234A/L235A/G237A/P238S); and IgG4s2 (S228P/F234A/L235A/DG236/G237A/P238S, wherein D denotes a deletion).

A ULBP6 binding protein described herein may comprise a Heavy Chain (HC) sequence that is at least 90% identical to SEQ ID NO: 85 and/or a Light Chain (LC) sequence that is at least 90% identical to SEQ ID NO: 105. Alternatively, the ULBP6 binding protein described herein may comprise a Heavy Chain (HC) sequence that is at least 95% identical to SEQ ID NO: 85 and/or a Light Chain (LC) sequence that is at least 95% identical to SEQ ID NO: 105. The ULBP6 binding protein described herein may comprise a Heavy Chain (HC) sequence that is at least 90% identical to SEQ ID NO: 86 and/or a Light Chain (LC) sequence that is at least 90% identical to SEQ ID NO: 106. Alternatively, the ULBP6 binding protein described herein may comprise a Heavy Chain (HC) sequence that is at least 95% identical to SEQ ID NO: 86 and/or a Light Chain (LC) sequence that is at least 95% identical to SEQ ID NO: 106.

A ULBP6 binding protein described herein may comprise a Heavy Chain (HC) sequence that is 100% identical to SEQ ID NO: 85 and/or a Light Chain (LC) sequence that is 100% identical to SEQ ID NO: 105; a Heavy Chain (HC) sequence that is 100% identical to SEQ ID NO: 86 and/or a Light Chain (LC) sequence that is 100% identical to SEQ ID NO: 106; a Heavy Chain (HC) sequence that is 100% identical to SEQ ID NO: 87 and/or a Light Chain (LC) sequence that is 100% identical to SEQ ID NO: 107; or a Heavy Chain (HC) sequence that is 100% identical to SEQ ID NO: 88 and/or a Light Chain (LC) sequence that is 100% identical to SEQ ID NO: 108. The ULBP6 binding protein described herein may comprise a Heavy Chain (HC) sequence that is 100% identical to SEQ ID NO: 85 and a Light Chain (LC) sequence that is 100% identical to SEQ ID NO: 105. The ULBP6 binding protein described herein may comprise a Heavy Chain (HC) sequence that is 100% identical to SEQ ID NO: 86 and a Light Chain (LC) sequence that is 100% identical to SEQ ID NO: 106.

Half-life ($t_{1/2}$) refers to the time required for the serum concentration of an antigen binding protein to reach half of its original value. The serum half-life of proteins can be measured by pharmacokinetic studies according to a method wherein radio-labelled protein is injected intravenously into mice and its plasma concentration is periodically measured as a function of time, for example, at about 3 minutes to about 72 hours after the injection. Other methods for pharmacokinetic analysis and determination of the half-life of a molecule will be familiar to those skilled in the art.

The long half-life of IgG antibodies is reported to be dependent on their binding to FcRn. Therefore, substitutions that increase the binding affinity of IgG to FcRn at pH 6.0 while maintaining the pH dependence of the interaction with target, by engineering the constant region, have been extensively studied. The in-vivo half-life of antigen binding proteins described herein may be altered by modification of a heavy chain constant domain or an FcRn binding domain therein.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells and, if they bind to FcRn, are recycled out of the cells back into circulation. In contrast, IgG molecules that enter the cells and do not bind to FcRn and are targeted to the lysosomal pathway where they are degraded.

FcRn may be involved in both antibody clearance and the transcytosis across tissues. Human IgG1 residues determined to interact directly with human FcRn include Ile253, Ser254, Lys288, Thr307, Gln311, Asn434 and His435. Mutations at any of these positions may enable increased serum half-life and/or altered effector properties of antigen binding proteins of the invention.

Antigen binding proteins described herein may have amino acid modifications that increase the affinity of the constant domain or fragment thereof for FcRn. Increasing the half-life (i.e., serum half-life) of therapeutic and diagnostic IgG antibodies and other bioactive molecules has many benefits including reducing the amount and/or frequency of dosing of these molecules. An antigen binding protein may comprise all or a portion (an FcRn binding portion) of an IgG constant domain having one or more of the following amino acid modifications.

For example, with reference to IgG1, M252Y/S254T/T256E (commonly referred to as "YTE" mutations) and/or M428L/N434S (commonly referred to as "LS" mutations) can increase FcRn binding at pH 6.0.

Half-life can also be enhanced by T250Q/M428L, V259I/V308F/M428L, N434A, and T307A/E380A/N434A mutations (for example, with reference to IgG1 and Kabat numbering).

Half-life and FcRn binding can also be extended by introducing H433K and N434F mutations (commonly referred to as "HN" or "NHance" mutations) (with reference to IgG1) (WO2006/130834).

WO00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386,388, 400, 413, 415, 424, 433, 434, 435, 436, 439, and 447 of the Fc region (EU index numbering).

WO02/060919 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435.

Shields et al. (2001, J Biol Chem; 276:6591-604) used alanine scanning mutagenesis to alter residues in the Fc region of a human IgG1 antibody and then assessed the binding to human FcRn. Positions that effectively abrogated binding to FcRn when changed to alanine include I253, S254, H435, and Y436. Other positions showed a less pronounced reduction in binding as follows: E233-G236, R255, K288, L309, S415, and H433. Several amino acid positions exhibited an improvement in FcRn binding when changed to alanine; notable among these are P238, T256, E272, V305, T307, Q311, D312, K317, D376, E380, E382, S424, and N434. Many other amino acid positions exhibited a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

The most pronounced effect with respect to improved FcRn binding was found for combination variants. At pH 6.0, the E380A/N434A variant showed over 8-fold better binding to FcRn, relative to native IgG1, compared with 2-fold for E380A and 3.5-fold for N434A. Adding T307A to this resulted in a 12-fold improvement in binding relative to native IgG1. The antigen binding protein described herein may comprise the E380A/N434A mutations and have increased binding to FcRn.

Dall'Acqua et al. (2002, J Immunol.; 169:5171-80) describes random mutagenesis and screening of human IgG1 hinge-Fc fragment phage display libraries against mouse FcRn. They disclosed random mutagenesis of positions 251, 252, 254-256, 308, 309, 311, 312, 314, 385-387, 389, 428, 433, 434, and 436. The major improvements in IgG1-human FcRn complex stability occur when substituting residues located in a band across the Fc-FcRn interface (M252, S254, T256, H433, N434, and Y436) and to lesser extent substitutions of residues at the periphery, such as V308, L309, Q311, G385, Q386, P387, and N389. The variant with the highest affinity to human FcRn was obtained by combining the M252Y/S254T/T256E ("YTE") and H433K/N434F/Y436H mutations and exhibited a 57-fold increase in affinity relative to the wild-type IgG1. The in vivo behaviour of such a mutated human IgG1 exhibited a nearly 4-fold increase in serum half-life in cynomolgus monkey as compared to wild-type IgG1.

Therefore, also provided is an antigen binding protein with optimized binding to FcRn. The antigen binding protein may comprise at least one amino acid modification in the Fc region of said antigen binding protein, wherein said modification is at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region.

Additionally, various publications describe methods for obtaining physiologically active molecules with modified half-lives, either by introducing an FcRn-binding polypeptide into the molecules (WO97/43316, U.S. Pat. Nos. 5,869, 046, 5,747,035, WO96/32478 and WO91/14438) or by fusing the molecules with antibodies whose FcRn-binding affinities are preserved, but affinities for other Fc receptors have been greatly reduced (WO99/43713), or fusing with FcRn binding domains of antibodies (WO00/09560, U.S. Pat. No. 4,703,039).

FcRn affinity enhanced Fc variants to improve both antibody cytotoxicity and half-life were identified in screens at pH 6.0. The selected IgG variants can be produced as low fucosylated molecules. The resulting variants show increased serum persistence in hFcRn mice, as well as conserved enhanced ADCC. Exemplary variants can include (with reference to IgG1 and Kabat numbering): P230T/V303A/K322R/N389T/F404L/N434S; P228R/N434S; Q311R/K334R/Q342E/N434Y; C226G/Q386R/N434Y; T307P/N389T/N434Y; P230S/N434S; P230T/V305A/T307A/A378V/L398P/N434S; P230T/P387S/N434S; P230Q/E269D/N434S; N276S/A378V/N434S; T307A/N315D/A330V/382V/N389T/N434Y; T256N/A378V/S383N/N434Y; N315D/A330V/N361 D/A387V/N434Y; V2591/N315D/M428L/N434Y; P230S/N315D/M428L/N434Y; F241L/V264E/T307P/A378V/H433R; T250A/N389K/N434Y; V305A/N315D/A330V/P395A/N434Y; V264E/Q386R/P396L/N434S/K439R; and E294del/T307P/N434Y (wherein 'del' indicates a deletion).

Although substitutions in the constant region are able to significantly improve the functions of therapeutic IgG antibodies, substitutions in the strictly conserved constant region have the risk of immunogenicity in humans and substitution in the highly diverse variable region sequence might be less immunogenic. Reports concerned with the variable region include engineering the CDR residues to improve binding affinity to the antigen and engineering the CDR and framework residues to improve stability and decrease immunogenicity risk. Improved affinity to the antigen can be achieved by affinity maturation using the phage or ribosome display of a randomized library.

Improved stability can be rationally obtained from sequence- and structure-based rational design. Decreased immunogenicity risk (deimmunization) can be accomplished by various humanization methodologies and the removal of potential T-cell epitopes, which can be predicted using in silico technologies or anticipated by in vitro assays. Additionally, variable regions have been engineered to lower pI. A longer half-life was observed for these antibodies as compared to wild type antibodies despite comparable FcRn binding. Engineering or selecting antibodies with pH-dependent antigen binding can be used to modify antibody and/or antigen half-life e.g. IgG2 antibody half-life can be shortened if antigen-mediated clearance mechanisms normally degrade the antibody when bound to the antigen. Similarly, the antigen:antibody complex can impact the half-life of the antigen, either by extending half-life by protecting the antigen from the typical degradation processes, or by shortening the half-life via antibody-mediated degradation (target-mediated drug disposition). Antibodies may have higher affinity for antigen at pH 7.4 as compared to endosomal pH (i.e., pH 5.5-6.0) such that the KD ratio at pH 5.5/pH 7.4 or at pH 6.0/pH 7.4 is 2 or more. For example, to enhance the pharmacokinetic (PK) and pharmacodynamic (PD) properties of the antibody, it is possible to engineer pH-sensitive binding to the antibody by introducing histidine residues into the CDRs.

A recycling antibody is engineered so that a single recycling antibody molecule can bind to an antigen multiple times (e.g., two or more times). The recycling antibody can dissociate from an antigen under acidic conditions within the cell. For example, a recycling antibody bound to a membrane-bound antigen dissociates from the antigen in a pH-dependent manner. The dissociated recycling antibody would be recycled by FcRn while the antigen is transferred to lysosome and degraded. This mechanism enables the recycling antibody to bind to antigens repeatedly in plasma and can reduce the antibody clearance.

A sweeping antibody incorporates two antibody engineering technologies: one is variable region engineering (as described above "pH switch") to enable the antibody to bind to an antigen in plasma and dissociate from the antigen in endosome (after which the antigen undergoes lysosomal degradation), and the other is by engineering the constant region to increase the cellular uptake of the antibody-antigen complex into endosome mediated, e.g. through FcRn, FcγRIIb or potentially other surface receptors. Sweeping antibodies can therapeutically target soluble antigens and enhance their elimination from the circulation (Igawa T et al., Sweeping antibody as a novel therapeutic antibody modality capable of eliminating soluble antigens from circulation. Immunol Rev. 2016 March; 270(1):132-51). Igawa et al. developed a panel of Fc variants with enhanced binding to FcRn, including M252Y, V308P, N434Y, with enhanced binding to FcRn that, in combination with pH-dependent binding to target soluble IL-6 receptor, enhanced clearance of target antigen in comparison with the wild-type Fc antibody variant (PLoS One. 8(5):e63236, 2013). FcγRIIb can be used to accelerate the uptake rate of antibody-antigen complexes into cells. Igawa et al. developed an FcγRIIIb sweeping antibody, in which the Fc region of a pH-dependent antibody was engineered to have selectively increased human FcγRIIb binding, to enhance the uptake rate of antibody-antigen complexes. An important role of this inhibitory receptor is the uptake of antibody-antigen complexes into liver endothelial cells (LSEC), therefore if the uptake of antibody-antigen complexes into cells was mediated by human FcγRIIb, it could reduce antigen concentration in the circulation. Comprehensive mutagenesis of the Fc domain of human IgG was used to identify an Fc variant (v12) that contained the following mutations: E233D/G237D/P238D/H268D/P271G/A330R, with selectively increased binding affinity to human FcγRIIb. Studies in human FcγRIIb transgenic mice revealed that the v12 variant accelerated the clearance of hsIL-6R over that of the pH-dependent sweeping antibody with wildtype hIgG1 while maintaining comparable pharmacokinetics.

Also provided are immunoconjugates (interchangeably referred to as an "antibody-drug conjugate", "ADC" or "antigen binding protein-drug conjugate") comprising an antigen binding protein described herein conjugated to one or more drugs, such as a cytotoxic agent, a chemotherapeutic agent, an immunotherapeutic agent, a growth inhibitory agent, a toxin (e.g., a protein toxin, such as an enzymatically active toxin of bacterial, fungal, plant, or animal origin, or fragments thereof), an antiviral agent, a radioactive isotope (e.g., a radioconjugate), an antibiotic, or a small interfering RNA (siRNA).

Immunoconjugates have been used for the local delivery of cytotoxic agents, i.e., drugs that kill or inhibit the growth or proliferation of cells, in the treatment of cancer. Immunoconjugates allow for, inter alia, the targeted delivery of a drug moiety to a tumor, and intracellular accumulation therein, where systemic administration of unconjugated drugs may result in unacceptable levels of toxicity to normal cells. Immunoconjugates can enable selective delivery of a potent cytotoxic payload to target cancer cells, resulting in improved efficacy, reduced systemic toxicity, and preferable pharmacokinetics (PK)/pharmacodynamics (PD) and biodistribution compared to traditional chemotherapy.

Both polyclonal antibodies and monoclonal antibodies can be useful in these strategies. Drugs used in these methods include daunomycin, doxorubicin, methotrexate, and vindesine. Toxins used in antibody-toxin conjugates can include bacterial toxins such as diphtheria toxin, plant toxins such as ricin, small molecule toxins such as geldanamycin, maytansinoids (EP 1391213), and calicheamicin.

An immunoconjugate may comprise an antigen binding protein, such as an antibody, and a drug, such as toxin, such as a chemotherapeutic agent. The drug can be modified (e.g., via standard synthetic chemistry) to allow its chemical attachment (e.g., to contain a reaction handle to allow its chemical attachment) to a reactive end of a linker that joins the drug to the antigen binding protein.

Also provided are methods of treating cancer in a subject in need of treatment thereof comprising administering to said subject a therapeutically effective amount of the ULBP6 binding protein or pharmaceutical composition as defined herein. The subject may be an animal or a human. The subject may be a human. In some embodiments, the subject can be a patient.

Cancers that may be treated include: adenocarcinoma, basal cell carcinoma, squamous cell carcinoma, adenosquamous carcinoma, carcinosarcoma, melanoma, adrenal gland cancer, adrenocortical carcinoma, pheochromocytoma, breast cancer, ductal carcinoma in situ, lobular carcinoma, inflammatory breast cancer, invasive ductal carcinoma, Paget disease of the nipple, papillary breast cancer, medullary carcinoma, mammary carcinoma, anal cancer, cloacogenic carcinoma, anorectal melanoma, appendiceal cancer, appendiceal neuroendocrine tumour, appendiceal mucinous cystadenocarcinomas, colonic-type adenocarcinoma, signet-ring cell adenocarcinoma, goblet cell carcinomas/adenoneuroendocrine carcinomas, bile duct cancer, intrahepatic cholangiocarcinoma, extrahepatic cholangiocarcinoma, perihilar cholangiocarcinoma, distal extrahepatic cholangiocarcinoma, colorectal cancer, mucinous adenocarcinoma, gastrointestinal carcinoid tumours, gastrointestinal stromal tumours, primary colorectal lymphomas, leiomyosarcoma, esophageal cancer, esophageal squamous cell carcinoma, small cell carcinoma, leiomyoma, gallbladder cancer, non-papillary adenocarcinoma, papillary adenocarcinoma, stomach cancer, gastric adenocarcinoma, liver cancer, hepatocellular carcinoma, fibrolamellar carcinoma, angiosarcoma, lymphangiosarcoma, hemangiosarcoma, hepatoblastoma, pancreatic cancer, pancreatic adenocarcinoma, ductal adenocarcinoma, acinar adenocarcinoma, acinar cell carcinoma, colloid carcinoma, giant cell tumour, hepatoid carcinoma, mucinous cystic neoplasms, pancreatoblastoma, serous cystadenoma, intraductal papillary mucinous neoplasm, pancreatic neuroendocrine tumour, gastrinoma, insulinoma, glucagonoma, VIPoma, somatostatinoma, PPoma, small intestine cancer, eye cancer, intraocular melanoma, intraocular lymphoma, intraocular retinoblastoma, conjunctival melanoma, eyelid carcinoma, sebaceous carcinoma, lacrimal gland tumour, malignant mixed epithelial tumour, adenoid cystic carcinoma, bladder cancer, urothelial carcinoma, kidney cancer, renal cell carcinoma (RCC), clear cell RCC, papillary RCC, chromophobe RCC, collecting duct RCC, multilocular cystic RCC, renal mucinous tubular and spindle cell carcinoma, tubulocystic RCC, thyroid-like follicular RCC, acquired cystic kidney disease-associated RCC, RCC with t(6;11) translocation (TFEB), hybrid oncocytoma/chromophobe RCC, Wilms tumor, penile cancer, prostate cancer, castration-resistant prostate cancer, transitional cell carcinoma, testicular cancer, seminoma, classical seminoma, spermatocytic seminoma, non-seminoma, embryonal carcinoma, yolk sac carcinoma, choriocarcinoma, teratoma, Leydig cell tumours, Sertoli cell tumours, carcinoma of the rete testis, urethral cancer, extracranial germ cell tumour, germinoma, gonadoblastoma, mixed germ cell tumour, extragonadal germ cell tumour, endodermal sinus tumours, cervical cancer, cervical squamous cell carcinoma, endometrial cancer, ovarian cancer, fallopian tube cancer, epithelial carcinoma, dysgerminoma, sex cord stromal tumours, gestational trophoblastic tumour, primary peritoneal cancer, uterine sarcoma, uterine papillary serous carcinoma, vaginal cancer, clear cell adenocarcinoma, vulvar cancer, verrucous carcinoma, head and neck cancer, head and neck squamous cell carcinoma, pharyngeal cancer, hypopharyngeal cancer, nasopharyngeal cancer, oropharyngeal cancer, non-keratinising squamous cell carcinoma, undifferentiated carcinoma, laryngeal cancer, oral cavity cancer, mouth cancer, mucoepidermoid carcinoma, paranasal sinus and nasal cavity cancer, esthesioneuroblastoma, salivary gland cancer, epithelial-myoepithelial carcinoma, parathyroid cancer, thyroid cancer, papillary thyroid carcinoma, follicular thyroid carcinoma, Hurthle cell carcinoma, medullary thyroid carcinoma, anaplastic thyroid carcinoma, paraganglioma, carotid paraganglioma, jugulotympanic paraganglioma, vagal paraganglioma, leukemia, acute lymphoblastic leukemia, T-lymphoblastic leukemia, precursor B-cell lymphoblastic leukemia, acute myelogenous leukemia, acute promyelocytic leukemia, acute myelomonocytic leukemia, acute monocytic leukemia, acute megakaryoblastic leukemia, erythroleukemia, chronic lymphocytic leukemia, B-cell chronic lymphocytic leukemia, B-cell prolymphocytic leukemia, T-cell prolymphocytic leukemia, large granular lymphocytic leukemia, T-cell large granular lymphocytic leukemia, NK-cell granular lymphocytic leukemia, hairy cell leukemia, chronic myelogenous leukemia, chronic myelomonocytic leukemia, chronic neutrophilic leukemia, chronic eosinophilic leukemia, plasma cell leukemia, lymphoma, Hodgkin's lymphoma, classical Hodgkin's lymphoma, nodular sclerosing classical Hodgkin's lymphoma, mixed cellularity classical Hodgkin's lymphoma, lymphocyte-rich classical Hodgkin's lymphoma, lymphocyte-depleted classical Hodgkin's lymphoma, nodular lymphocyte-predominant Hodgkin's lymphoma, non-Hodgkin's lymphoma, diffuse large B-cell lymphoma, primary mediastinal B-cell lymphoma, primary effusion lymphoma, T-cell/histiocyte-rich large B-cell lymphoma, lymphoplasmacytic lymphoma, lymphoblastic lymphoma, small lymphocytic lymphoma, double hit/triple hit lymphoma, Burkitt lymphoma, Burkitt-like lymphoma, small non-cleaved cell lymphoma, follicular lymphoma, follicular large-cell lymphoma, immunoblastic lymphoma, intravascular large-cell lymphoma, primary splenic lymphoma, anaplastic large-cell lymphoma, mantle cell lymphoma, marginal zone lymphoma (MZL), extranodal MZL, nodal MZL, splenic MZL, splenic MZL with villous lymphocytes, peripheral T-cell lymphoma, angioimmunoblastic T-cell lymphoma, adult T-cell lymphoma/leukemia, extranodal NK/T-cell lymphoma, enteropathy-associated T-cell lymphoma, hepatosplenic T-cell lymphoma, subcutaneous panniculitis-like T-cell lymphoma, T-cell non-Hodgkin's lymphoma not otherwise specified, gamma/delta T-cell lymphoma, mucosa-associated-lymphoid tissue lymphoma, post-transplant lymphoproliferative disorder, HIV-associated lymphoma, Langerhans cell histiocytosis, multiple myeloma, smoldering multiple myeloma, active multiple myeloma, plasmacytoma, solitary plasmacytoma of bone, extramedullary plasmacytoma, primary amyloidosis, myelodysplastic syndromes, refractory anaemia, refractory anaemia with ring sideroblasts, refractory anaemia with excess blasts, refractory anaemia with excess blasts in transformation, myeloproliferative neoplasms, polycythemia vera, essential thrombocythemia, myelofibrosis, systemic mastocytosis, bone cancer, Ewing sarcoma, osteosarcoma, intramedullary osteosarcoma, juxtacortical osteosarcoma, extraskeletal osteosarcoma, malignant fibrous histiocytoma of bone, chordoma, classic chordoma, chondroid chordoma, dedifferentiated chordoma, chondrosarcoma, conventional chondrosarcoma, clear cell chondrosarcoma, myxoid chondrosarcoma, mesenchymal chondrosarcoma, dedifferentiated chondrosarcoma, rhabdomyosarcoma, embryonal rhabdomyosarcoma, alveolar rhabdomyosarcoma, botryoid rhabdomyosarcoma, pleomorphic rhabdomyosarcoma, soft tissue sarcoma, extraosseus sarcoma, dermatofibrosarcoma protuberans, epithelioid sarcoma, Kaposi's sarcoma, liposarcoma, malignant peripheral nerve sheath tumour, fibrosarcoma, myxosarcoma, synovioma, brain cancer, anaplastic astrocytoma, glioblastoma, glioblastoma multiforme, meningioma, pituitary carcinoma, schwannoma, oligodendroglioma, ependymoma, medulloblastoma, astrocytoma, brainstem glioma, atypical teratoid/rhabdoid tumour, pinealoma, neuroblastoma, primary CNS lymphoma, primitive neuroectodermal tumour, diffuse intrinsic pontine glioma, lung cancer, non-small cell lung cancer (NSCLC), NSCLC undifferentiated, small cell lung cancer, lung squamous cell carcinoma, pleuropulmonary blastoma, bronchogenic carcinoma, malignant mesothelioma, malignant pleural mesothelioma, malignant peritoneal mesothelioma, thymoma, thymic carcinoma, skin cancer, keratoacanthoma, sebaceous gland carcinoma, sweat gland adenocarcinoma, apocrine carcinoma, eccrine carcinoma, clear cell eccrine carcinoma, Merkel cell carcinoma, cutaneous T cell lymphoma, mycosis fungoides, Sézary syndrome, chondroid syringoma, HPV-associated cancers, tumours containing transformed cells, tumours containing cells in precancerous states, precancerous hyperplasia, precancerous metaplasia, precancerous dysplasia, carcinoma in situ, mixed tumour, malignant mixed tumour, and complex carcinoma.

Cancers that may be treated include cancers having a high tumour mutational burden (TMB), a defective DNA mismatch repair system (dMMR), a high microsatellite instability status (MSI-H), low microsatellite instability status (MSI-L), elevated microsatellite alterations at selected tetranucleotide repeats (EMAST), microsatellite stable (MSS) cancers, cancers comprising mutations in polymerase delta (POLD), cancers comprising mutations in polymerase epsilon (POLE), or cancers with homologous recombination repair deficiency (HRD).

Cancers that may be treated include breast cancers defined by expression profiling (triple-negative breast cancer, HER2 positive breast cancer, luminal A breast cancer, luminal B breast cancer, normal-like breast cancer) or breast cancers with BRCA1 or BRCA2 mutations.

The cancers to be treated may express cell surface ULBP6 or sULBP6. The sULBP6 shed from the cancer cell may create an immunosuppressive environment. Therefore, the ULBP6 binding proteins described herein may be effective in treating cancers expressing sULBP6. Therefore, cancers that may be treated include cancers shown to express sULBP6.

Cancers that may be treated include head and neck cancer, cervical cancer, bladder cancer, lung cancer, colorectal cancer, pancreatic cancer or glioblastoma. Cancers that may be treated include squamous cell carcinoma. The cancer to be treated may be head and neck squamous cell carcinoma (HNSCC). The cancer to be treated may be lung cancer. The cancer to be treated may be lung cancer. The lung cancer may be NSCLC.

The genetic data described in Example 1 shows that single nucleotide polymorphisms at the ULBP6 locus are associated with susceptibility to basal cell carcinoma diagnosis in humans. Thus, ULBP6 antagonists may be useful in the treatment of basal cell carcinoma. The ULBP6 binding proteins described herein may be useful in the treatment of basal cell carcinoma.

The ULBP6 binding proteins described herein may bind to cell surface ULBP6. For example, the ULBP6 binding proteins may bind to ULBP6 expressed (endogenously or otherwise) on the surface of tumor cells or cell lines such as CHO UBLP6 expressing cells, COV644 cells or PANC02.13 cells. The half maximal effective concentration (EC50) of ULBP6 binding protein binding to cell surface ULBP6 may be determined using the FACS binding assay described in Example 7. The ULBP6 binding proteins may bind to PANC02.13 cells and COV644 cells with an EC50 of less than or equal to 2 nM, or less than or equal to 1 nM.

The ULBP6 binding proteins described herein may inhibit the binding of NKG2D-Fc to cell surface ULBP6. In some instances, the ULBP6 binding proteins may inhibit the binding of NKG2D-Fc to cell surface ULBP6 with an IC50 of less than or equal to 1 nM, less than or equal to 0.5 nM, less than or equal to 0.25 nM or less than or equal to 0.2 nM.

Soluble ULBP6 may reduce NKG2D-mediated cell activation by binding to NKG2D, thereby inhibiting binding of other NKG2DLs to NKG2D. sULBP6 may reduce NKG2D-mediated cell activation by binding to NKG2D, thereby inducing NKG2D internalization or blocking NKG2D mediated activation. sULBP6 may reduce NKG2D-mediated cell activation by binding to NKG2D, thereby inducing NKG2D downregulation or blocking NKG2D mediated activation. The ULBP6 binding proteins described herein may increase NKG2D-mediated cell activation by inhibiting sULBP6-induced NKG2D blocking. Alternatively, the ULBP6 binding proteins may increase NKG2D-mediated cell activation by inhibiting sULBP6-induced NKG2D internalization. Alternatively, the ULBP6 binding proteins may increase NKG2D-mediated cell activation by inhibiting sULBP6-induced NKG2D downregulation.

In some embodiments, a ULBP6 binding protein provided herein can target a tumor immune response escape mechanism. Immune escape through MHC loss can lead to vulnerability to NK mediated killing. This can be driven by antigen immunogenicity, such as viral and/or tumor genetic alteration derived new-antigens. Immune escape can thus occur through soluble NKG2D ligand (e.g., ULBP6). In some embodiments, a ULBP6 binding protein provided herein can interfere with such immune escape. In some instances, tumor expression of ULBP2/5/6 plus a second NKG2D ligand can elicit drug activity (e.g., MICA/B prioritized by affinity) in NK infiltrated tumors. In some embodiments, soluble ULBP can be a read out of ULBP2/5/6+ tumor burden, and hence in some cases an alternative to IHC.

The ULBP6 binding proteins described herein may inhibit the binding of sULBP6 to NKG2D, thereby increasing NKG2D activation through interaction with other NKG2DLs such as MICA. The assay described in Example 9 may be used to determine MICA-mediated cell activation.

In addition to inhibiting the binding of sULBP6 to NKG2D, the ULBP6 binding proteins described herein may also comprise a modified Fc region to enhance ADCC. The dual mechanisms of 1) inhibition of binding of sULBP6 to NKG2D and 2) Fc receptor-mediated killing of ULBP6-expressing tumor cells may synergise to effectively treat cancer. The ADCC-enhanced ULBP6 binding proteins may synergistically increase the levels of cytokines (e.g. IFNγ) secreted by Peripheral Blood Mononuclear Cells (PBMCs) co-cultured with ULBP6-expressing tumor cells, compared to ULBP6 binding proteins lacking Fc effector function. The ULBP6 binding proteins may inhibit the binding of sULBP6 to NKG2D, thereby increasing the killing of tumor cells in vitro.

The ULBP6 binding proteins described herein may bind to human ULBP6 and disrupt the interaction of ULBP6 and NKG2D. The NKG2D-binding interface of ULBP6 includes residues of ULBP6 which can interact with residues from NKG2D. By interacting with residues comprised within, or proximal to, the NKG2D-binding interface of ULBP6, ULBP6 binding proteins may disrupt the interaction of ULBP6 and NKG2D. The HDX assay described in Example 17 may be used to characterize the interaction between ULBP6 and anti-ULBP6 antibodies. The ULBP6 binding proteins may bind to one or more residues comprised within alpha helix 1 (SEQ ID NO: 125) and/or one or more residues comprised within alpha helix 2 (SEQ ID NO: 126) of human ULBP6. The ULBP6 binding proteins may bind to one or more residues comprised within SEQ ID NO: 128 and/or SEQ ID NO: 129 of human ULBP6. The ULBP6 binding proteins may bind to a conformational epitope comprised within alpha helix 1 (SEQ ID NO: 125) and/or alpha helix 2 (SEQ ID NO: 126) of human ULBP6. The ULBP6 binding proteins may bind to a conformational epitope comprised within SEQ ID NO: 128 and/or SEQ ID NO: 129 of human ULBP6. The ULBP6 binding proteins may protect one or more residues comprised within alpha helix 1 (SEQ ID NO: 125) and/or alpha helix 2 (SEQ ID NO: 126) of human ULBP6 from deuterium exchange in HDX-MS analysis. The ULBP6 binding proteins may protect one or more residues comprised within SEQ ID NO: 128 and/or SEQ ID NO: 129 of human ULBP6 from deuterium exchange in HDX-MS analysis. The ULBP6 binding proteins may bind to human ULBP6 and result in peptides derived from alpha helix 1 (SEQ ID NO: 125) and/or alpha helix 2 (SEQ ID NO: 126) of human ULBP6 being more resistant to deuterium incorporation compared to corresponding peptides derived from uncomplexed human ULBP6. The ULBP6 binding proteins may bind to human ULBP6 and result in peptides derived from SEQ ID NO: 128 and/or SEQ ID NO: 129 of human ULBP6 being more resistant to deuterium incorporation compared to corresponding peptides derived from uncomplexed human ULBP6. The ULBP6 binding proteins may bind to the NKG2D-binding interface of human ULBP6. The ULBP6 binding proteins may disrupt the interaction of human ULBP6 to NKG2D by binding to one or more residues selected from E96, E154, Y184 and D189 located within the NKG2D-binding interface of human ULBP6.

The ULBP6 binding proteins described herein may bind to one or more residues comprised within alpha helix 1 (SEQ ID NO:125), one or more residues comprised within alpha helix 2 (SEQ ID NO: 126) and/or one or more residues comprised within SEQ ID NO: 127 of human ULBP6. The ULBP6 binding proteins may bind to one or more residues comprised within SEQ ID NO: 128, SEQ ID NO: 129 and/or SEQ ID NO: 127 of human ULBP6. The ULBP6 binding proteins may bind to a conformational epitope comprised within alpha helix 1 (SEQ ID NO: 125), alpha helix 2 (SEQ ID NO: 126) and/or SEQ ID NO: 127 of human ULBP6.

The ULBP6 binding proteins may bind to a conformational epitope comprised within SEQ ID NO: 128, SEQ ID NO: 129 and/or SEQ ID NO: 127 of human ULBP6. The ULBP6 binding proteins may protect one or more residues comprised within alpha helix 1 (SEQ ID NO: 125), alpha helix 2 (SEQ ID NO: 126) and/or SEQ ID NO: 127 of human ULBP6 from deuterium exchange in HDX-MS analysis. The ULBP6 binding proteins may protect one or more residues comprised within SEQ ID NO: 128, SEQ ID NO: 129 and/or SEQ ID NO: 127 of human ULBP6 from deuterium exchange in HDX-MS analysis. The ULBP6 binding proteins may bind to human ULBP6 and result in peptides derived from alpha helix 1 (SEQ ID NO: 125), alpha helix 2 (SEQ ID NO: 126) and/or SEQ ID NO: 127 of human ULBP6 being more resistant to deuterium incorporation compared to corresponding peptides derived from uncomplexed human ULBP6. The ULBP6 binding proteins may bind to human ULBP6 and result in peptides derived from SEQ ID NO: 128, SEQ ID NO: 129, and/or SEQ ID NO: 127 of human ULBP6 being more resistant to deuterium incorporation compared to corresponding peptides derived from uncomplexed human ULBP6.

Also provided herein are antibodies and antigen binding fragments thereof that binds to UL-16 binding protein 6 (ULBP6) comprising: a variable heavy chain (VH) sequence having a heavy chain complementarity determining region 1 (CDRH1) sequence, a heavy chain complementarity determining region 2 (CDRH2) sequence, and a heavy chain complementarity determining region 3 (CDRH3) sequence; and a variable light chain (VL) sequence having a light chain complementarity determining region 1 (CDRL1) sequence, a light chain complementarity determining region 2 (CDRL2) sequence, and a light chain complementarity determining region 3 (CDRL3) sequence; wherein: CDRH1 is selected from the group consisting of SEQ ID NOs: 36, 39, 42 and 45; CDRH2 is selected from the group consisting of SEQ ID NOs: 37, 40, 43 and 46; CDRH3 is selected from the group consisting of SEQ ID NOs: 38, 41, 44 and 47; CDRL1 is selected from the group consisting of SEQ ID NOs: 51, 54, 57 and 60; CDRL2 is selected from the group consisting of SEQ ID NOs: 52, 55, 58 and 61; or CDRL3 is Selected from the group consisting of SEQ ID NOs: 53, 56, 59 or 62.

Also provided herein are antibodies and antigen binding fragments thereof, wherein CDRH1 is SEQ ID NO: 36, CDRH2 is SEQ ID NO: 37, CDRH3 is SEQ ID NO: 38, CDRL1 is SEQ ID NO: 51, CDRL2 is SEQ ID NO: 52 and CDRL3 is SEQ ID NO: 53; CDRH1 is SEQ ID NO: 39, CDRH2 is SEQ ID NO: 40, CDRH3 is SEQ ID NO: 41, CDRL1 is SEQ ID NO: 54, CDRL2 is SEQ ID NO: 55 and CDRL3 is SEQ ID NO: 56; CDRH1 is SEQ ID NO: 42, CDRH2 is SEQ ID NO: 43, CDRH3 is SEQ ID NO: 44, CDRL1 is SEQ ID NO: 57, CDRL2 is SEQ ID NO: 58 and CDRL3 is SEQ ID NO: 59; or CDRH1 is SEQ ID NO: 45, CDRH2 is SEQ ID NO: 46, CDRH3 is SEQ ID NO: 47, CDRL1 is SEQ ID NO: 60, CDRL2 is SEQ ID NO: 61 and CDRL3 is SEQ ID NO: 62.

Also provided herein are antibodies and antigen binding fragments thereof wherein: a VH region that is at least 80% identical to SEQ ID NO: 21 and a VL region that is at least 80% identical to SEQ ID NO: 31; a VH region that is at least 80% identical to SEQ ID NO: 22 and a VL region that is at least 80% identical to SEQ ID NO: 32; a VH region that is at least 80% identical to SEQ ID NO: 23 and a VL region that is at least 80% identical to SEQ ID NO: 33; or a VH region that is at least 80% identical to SEQ ID NO: 24 and a VL region that is at least 80% identical to SEQ ID NO: 34.

Also provided herein are antibodies and antigen binding fragments thereof wherein: a VH region that is at least 80% identical to SEQ ID NO: 16 and a VL region that is at least 80% identical to SEQ ID NO: 26; a VH region that is at least 80% identical to SEQ ID NO: 17 and a VL region that is at least 80% identical to SEQ ID NO: 27; a VH region that is at least 80% identical to SEQ ID NO: 18 and a VL region that is at least 80% identical to SEQ ID NO: 28; or a VH region that is at least 80% identical to SEQ ID NO: 19 and a VL region that is at least 80% identical to SEQ ID NO: 29.

Also provided herein are antibodies and antigen binding fragments thereof, wherein the binding protein comprises: a Heavy Chain (HC) sequence at least 80% identical to any one of SEQ ID NOs: 75-78, 85-88 or 95-98; and/or a Light Chain (LC) sequence at least 80% identical to any one of SEQ ID NOs: 105-108.

Also provided herein are antibodies and antigen binding fragments thereof, wherein the antibody or antigen binding fragment thereof binds to ULBP6 and ULBP2 with a KD less than or equal to 1 nM and binds to ULBP5 with a KD greater than or equal to 1 nM.

Also provided herein are antibodies and antigen binding fragments thereof, which inhibit the interaction of human ULBP6 and human NKG2D by 80% or more.

Also provided herein are antibodies and antigen binding fragments thereof that bind to a human ULBP6 protein or fragment thereof, and compete for binding to the human ULBP6 protein fragment thereof with a reference ULBP6 binding protein or fragment thereof comprising: a VH region sequence of SEQ ID NO: 21 and a VL region sequence of SEQ ID NO: 31; or a VH region sequence of SEQ ID NO: 22 and a VL region sequence of SEQ ID NO: 32

Also provided herein are antibodies and antigen binding fragments thereof, which inhibit the binding of soluble ULBP6 to NKG2D.

Also provided herein are antibodies and antigen binding fragments thereof, which inhibit the binding of soluble ULBP6 to NKG2D by 80% or more.

Also provided herein are antibodies and antigen binding fragments thereof comprising a modified Fc region.

Also provided herein are antibodies and antigen binding fragments thereof, comprising a modified Fc region, which comprises the amino acid substitutions S239D and I332E (as numbered according to the EU index).

Also provided herein are antibodies and antigen binding fragments thereof, which are afucosylated.

Also provided herein are antibodies and antigen binding fragments thereof, wherein a modified Fc region comprises a set of amino acid substitution selected from the group consisting of S239D/A330L/I332E, G236A/S239D/A330L/I332E, L235V/F243L/R292P/Y300L/P396L and F243L/R292P/Y300L/V305I/P396L (as numbered according to the EU index).

Also provided herein are nucleic acid sequences which encodes one or both of a heavy chain (HC) and a light chain (LC) of the antibody or antigen binding fragment thereof provided herein.

Also provided herein are expression vectors comprising a nucleic acid of antibodies and antigen binding fragments thereof provided herein.

Also provided herein are recombinant host cells comprising a nucleic acid sequence of antibodies and antigen binding fragments thereof provided herein.

Also provided herein are methods for the production of an antibody or antigen binding fragment thereof provided herein, comprising culturing the recombinant host cell under conditions suitable for expression of a nucleic acid sequence or vector comprised within, whereby a polypeptide comprising an antibody or antigen binding fragment thereof is produced.

Also provided herein are cell lines engineered to express antibodies and/or antigen binding fragments thereof provided herein.

Also provided herein are pharmaceutical compositions comprising one or more antibodies or antigen binding fragment thereof provided herein, and a pharmaceutically acceptable excipient.

Also provided herein are method for the treatment of cancer in a subject in need thereof comprising administering to the subject a therapeutically effective amount of an antibody or antigen binding fragment thereof provided herein or a pharmaceutical composition provided herein.

Also provided herein are methods for the treatment of cancer, wherein the cancer is basal cell carcinoma, head and neck cancer, cervical cancer, bladder cancer, lung cancer, colorectal cancer, pancreatic cancer or glioblastoma. In some such methods, the subject is a human.

Some methods provided herein can further comprise determining that the subject expresses soluble ULBP6

Also provided herein are kits comprising one or more antibodies or antigen binding fragments thereof provided herein and instructions said administering one or more antibodies or antigen binding fragments thereof to a subject having cancer.

Some such kits can be for a subject having head and neck cancer, cervical cancer, bladder cancer, lung cancer, colorectal cancer, pancreatic cancer or glioblastoma.

Also provided herein are ULBP6 antagonists for use in the treatment of basal cell carcinoma.

Also provided herein are ULBP6 binding proteins and fragments thereof comprising a) HVRH1 of SEQ ID NO: 130, HVRH2 of SEQ ID NO: 131, HVRH3 of SEQ ID NO: 132, HVRL1 of SEQ ID NO: 145, HVRL2 of SEQ ID NO: 146, and HVRL3 of SEQ ID NO: 147; b) HVRH1 of SEQ ID NO: 133, HVRH2 of SEQ ID NO: 134, HVRH3 of SEQ ID NO: 135, HVRL1 of SEQ ID NO: 148, HVRL2 of SEQ ID NO: 149, and HVRL3 of SEQ ID NO: 150; c) HVRH1 of SEQ ID NO: 136, HVRH2 of SEQ ID NO: 137, HVRH3 of SEQ ID NO: 138, HVRL1 of SEQ ID NO: 151, HVRL2 of SEQ ID NO: 152, and HVRL3 of SEQ ID NO: 153; d) HVRH1 of SEQ ID NO: 139, HVRH2 of SEQ ID NO: 140, HVRH3 of SEQ ID NO: 141, HVRL1 of SEQ ID NO: 154, HVRL2 of SEQ ID NO: 155, and HVRL3 of SEQ ID NO: 156; or HVRH1 of SEQ ID NO: 142, HVRH2 of SEQ ID NO: 143, HVRH3 of SEQ ID NO: 144, HVRL1 of SEQ ID NO: 157, HVRL2 of SEQ ID NO: 158, and HVRL3 of SEQ ID NO: 159;

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Embodiments and features described in the application should be understood to be interchangeable and combinable at least with other such embodiments and features contained within.

Example 1: Genome-wide Association Study in Individuals with Basal Cell Carcinoma A Genome-wide association (GWAS) study of individuals diagnosed with basal cell carcinoma was performed. A genetic region in the ULBP6 locus (6q25.1) was identified that reached the accepted genome-wide statistical threshold of $P<5.0E10^{-8}$.

We identified a shared genetic association between basal cell carcinoma and immune-related disease diagnosis in the 6q25.1 region, where multiple NKG2D ligands, ULBP6 (also known as RAET1 L), ULBP1, ULBP2, ULBP3, ULBP4 (RAET1 E), and ULBP5 (RAET1G) are located. The index variants were rs9478354 (dbSNP build 153 identifier), located at chromosome 6 at position 150013230 (of the human genome build GRCh38/hg38) (basal cell carcinoma; A/G, AF [allele frequency for allele G]=0.55, OR=0.965, P value=7.2E-24), rs10666240 (dbSNP build 153 identifier), located at chromosome 6 at position 150036968 (of the human genome build GRCH38/hg38) (alopecia areata; C/CAA, AF [allele frequency for allele CAA]=0.45, OR=0.930, P value=9.9E-16), and rs5006620 (dbSNP build 153 identifier), located at chromosome 6 at position 150015529 (of the human genome build GRCH38/hg38) (alopecia universalis; C/T, AF [allele frequency for allele T]=0.45, OR=0.790, P value=1.3E- 21) (FIG. 1). These variants are located in the intergenic region at the end of ULBP6.

FIG. 1 is the regional association plots of the ULBP6 locus on chromosome 6 for basal cell carcinoma. The trait analyzed was basal cell carcinoma diagnosis where "the cases" are individuals with a basal cell carcinoma diagnosis and "the controls" are individuals who did not report a basal cell carcinoma diagnosis. The x-axis shows physical positions on human genome build (GRCh38/hg38 and the left y-axis shows the −log 10 of the P value for association with the phenotype of interest. Each point in the depicted plots represents a genetic variant tested for association in the region. The grey horizontal line represents the genome-wide significance threshold of $5\times10^{-8}$. Human genes in the region are depicted on the lower panel. These GWAS data indicate that the locus (genetic region) shown is implicated in susceptibility to basal cell carcinoma diagnosis in humans.

Example 2: ULBP6 Expression in Cancer Patients

To determine whether human ULBP6 and other NKG2DLs are expressed by tumor cells and may therefore represent a therapeutic target in cancer, two complementary approaches were taken. The first approach explored transcript expression by analysis of The Cancer Genome Atlas (TCGA) and single cell RNA sequencing data, and the second approach measured levels of NKG2DL protein in the serum of patients having various cancer types.

NKG2D Ligand Expression in Tumor Cells

Expression data from multiple tumor types from the TCGA program was analyzed for the expression of ULBP2 and ULBP6. Generally, while ULBP2 appears broadly expressed across the analyzed cancer types, ULBP6 was found to be most highly expressed among squamous cell carcinomas, including HNSC, CESC, LUSC, and ESCA (squamous cell carcinoma pathology) compared with non-squamous cell carcinoma cancers. Both ULBP6_01 and ULBP6_02 haplotypes of ULBP6 were found to be expressed in tumor samples.

Furthermore, single cell RNA seq data from Puram et al. (PMID: 29198524) was analyzed for expression of ULBP2 and ULBP6. This data suggests that these ligands are specifically expressed on tumor cells.

Detection of NKG2DLs in Patient Serum

To determine the level of NKG2DL shedding into the serum (i.e., shed/soluble NKG2DLs, "sNKG2DLs"), ELISA and Luminex assays were performed to measure the presence of NKG2DLs in patient serum samples.

Materials and Methods sNKG2DLs in the sera of 158 patients and 9 cancer types was determined. Serum samples from individuals having, cervical cancer, colorectal cancer, bladder cancer, lung cancer, melanoma, pancreatic cancer, head and neck cancer, esophageal cancer, and glioblastoma and cancer-free individuals (healthy donors) were obtained. ULBP1, ULBP2/ULBP6, ULBP3, and MICB levels for the serum samples were determined using ELISA kits from R&D systems according to the manufacturer's instructions. The ELISA does not differentiate between ULBP2 and ULBP6 because the detection antibody binds to both ULBP6 and ULBP2. MICA levels for the serum samples were determined using a Luminex MICA assay according to the manufacturer's instructions. Each serum sample was screened twice (i.e. technical replicates).

The sNKG2DL concentration from healthy donors was averaged and used to calculate a cutoff for determination of elevated sNKG2DLs in serum samples from cancer patients. The cutoff for each tested sNKG2DL was set as the average of sNKG2DL concentration from healthy donors+3 standard deviations. Each sNKG2DL level from the tumor sample was compared to the cutoff. An elevated sNKG2DL level was defined when the value in both technical replicates of the tested serum sample was higher than the calculated cutoff for that sNKG2DL.

Results

As described in Table 4, 22.2% of patients had elevated shed ULBP2/6 (sULBP2/6) in serum compared to healthy donor control samples, whereas other sNKG2DLs (including ULBP1 and ULBP3 and MICA/B) were elevated in <5.2% patients compared to healthy donor control samples. These results indicate that sULBP2/6 is the most upregulated sNKG2DL in the tested serum from cancer patients.

TABLE 4 sNKG2DLs in serum from cancer patients

| sNKG2DL Hits | sULBP1 | sULBP2/6 | sULBP3 | sMICA | sMICB |
|---|---|---|---|---|---|
| HNSCC | 1/20 | 9/20 | 2/20 | 0/20 | 1/20 |
| CESC | 1/10 | 1/10 | 0/10 | 0/10 | 0/10 |
| BLCA | 2/20 | 4/20 | 2/20 | 0/20 | 0/20 |
| LUSC | 1/20 | 1/20 | 0/20 | 0/20 | 1/20 |
| CRC | 1/20 | 2/20 | 1/20 | 0/20 | 0/20 |
| Melanoma | 1/17 | 6/17 | 1/17 | 0/17 | 0/17 |
| PAAD | 1/20 | 7/20 | 0/19 | 1/20 | 0/14 |
| GBM | 0/20 | 5/20 | 1/20 | 0/20 | 1/20 |
| ESCC | 0/11 | 0/11 | 0/11 | 0/11 | 0/11 |
| % in total cancers | 5.1% | 22.2% | 4.4% | 0.6% | 1.9% |

HNSCC (head and neck squamous cell carcinoma) = head and neck cancer; CESC (cervical squamous cell carcinoma) = cervical cancer; BLCA (bladder urothelial carcinoma) = bladder cancer; LUCS (lung squamous cell carcinoma) = lung cancer; CRC (colorectal cancer) = colorectal cancer; PAAD (pancreatic adenocarcinoma) = pancreatic cancer; GBM (glioblastoma multiforme) = glioblastoma; ESCC (esophageal squamous carcinoma) = esophageal cancer.

Example 3: Binding of Human sNKG2DLs to NKG21D

NKG2DLs show variability in primary amino acid sequence, structure, expression profile and binding affinity to NKG21D, which may lead to functional differences between membrane-bound and soluble forms when interacting with NKG21D. Example 2 demonstrated that increased sULBP2 and/or sULBP6 protein are commonly observed in the serum of cancer patients. To rank the relative binding affinities of sULBP2, sULBP6 and other human sNKG2D ligands to the hNKG2D receptor, a surface plasmon resonance (SPR) assay was performed with a BIACORE 8K (Cytiva) instrument as described below.

Materials and Methods

To illustrate the binding of human sNKG2D ligands to hNKG2D, a SPR assay was performed at 37° C. with various human sNKG2D ligands, including sMICA, sMICB, sULBP1, sULBP2, sULBP3, sULBP4, sULBP5, sULBP6_01 and sULBP6_02. Briefly, 0.5 pg/ml hNKG2D-Fc in HBS-P buffer (0.01M HEPES pH 7.4, 0.15M NaCl, 0.005% surfactant P20) was applied to CYTIVA sensor chip Protein A at 30 μL/min flow rate to achieve ~50 response units in second flow cell (FC2). FC1 was used for referencing. For kinetics measurements, 3-fold serial dilutions of hNKG2D ligands in HBS-P buffer (0.01M HEPES pH 7.4, 0.15M NaCl, 0.005% surfactant P20) from high (50 nM for ULBP6_02 and 2 pM for the other sNKG2DLs) to low concentration (0.07 nM for ULBP6_02 and 2.74 nM for the other sNKG2DLs) were injected (flow rate: 30 μL/min) at 37° C. The sensorgram was recorded and subject to reference and buffer subtraction before evaluation by BIACORE 8K Evaluation Software (version 1.1.1.7442). Association rates ($k_{on}$) and dissociation rates ($k_{off}$) were calculated using a simple one-to-one Langmuir binding model. The equilibrium dissociation constant (KD) was calculated as the ratio of $k_{off}/k_{on}$ summarized in Table 5.

TABLE 5

Soluble ligand binding affinity to hNKG2D-Fc fusion on BIACORE chip

| hNKG2D Ligand | Affinity KD (nM) to hNKG2D @37° C. |
|---|---|
| ULBP6_02 | 4.8 |
| ULBP6_01 | 41 |
| MICA | 79 |
| MICB | 118 |
| ULBP1 | 125 |
| ULBP5 | 207 |
| ULBP2 | 220 |
| ULBP3 | 594 |
| ULBP4 | No Binding |

Results

No binding of sULBP4 to NKG2D was observed, while binding affinity of the remaining sNKG2D ligands ranged from 594 nM to 4.8 nM. The strongest binding affinity to NKG2D was observed for sULBP6. Haplotype 02 (sULBP6_02) had a binding affinity of 4.8 nM and haplotype 01 (sULBP6_01) had a binding affinity of 41 nM (Table 5). A far lower affinity for NKG2D of 220 nM was observed for sULBP2.

The relatively higher affinity of the soluble forms of ULBP6 for NKG2D shown herein and the prevalence of sULBP2/ULBP6 in serum of cancer patients (Example 2) indicated that disruption of the sULBP6-NKG2D interaction using anti-ULBP6 binding proteins may offer opportunities for the development of cancer therapies.

Example 4: Generation of Polypeptides

This example illustrates the preparation of the ULBP6 antigen for generation of the anti-ULBP6 antibodies. The example also includes the generation of other sNKG2DL, including human sULBP1, sULBP2, sULBP3, sULBP4, sULBP5, sMICA and sMICB, used as antigens in screening the anti-ULBP6 antibodies of the present disclosure. Also included in the example is the preparation of NKG2D and Fc tag polypeptides. Note that cULBP5 and cULBP2/6 refer to the cynomolgus soluble orthologues. Due to the high level of sequence similarity between human ULBP2 and ULBP6, it is unclear whether the single cynomolgus orthologue is evolutionarily related to human ULBP2 or ULBP6. Therefore, the cynomolgus orthologue is referred to herein as cULBP2/6.

The sequences of the human sULBP1-6, cULBP5 and cULBP2/6 polypeptide forms are provided in Table 6, and the sequences of human NKG2D (hNKG2D) or cynomolgus NKG2D (cNKG2D), additional sNKG2DLs (sMICA and sMICB), and Fc polypeptide forms are provided in Table 7.

TABLE 6

Human or cynomolgus sULBP1-6 polypeptide sequences

| Name | Domain boundary | SEQ ID NO: | Sequence |
|---|---|---|---|
| hULBP1 (Uniprot: Q9BZM6) | 21-215 | 1 | GWVDTHCLCYDFIITPKSRPEPQWCEVQGLVDERPFLHYDC VNHKAKAFASLGKKVNVTKTWEEQTETLRDVVDFLKGQLLD IQVENLIPIEPLTLQARMSCEHEAHGHGRGSWQFLFNGQKF LLFDSNNRKWTALHPGAKKMTEKWEKNRDVTMFFQKISLGD CKMWLEEFLMYWEQMLDPTKPPSLAP |
| hULBP2 (Uniporot: Q9BZM5) | 26-216 | 2 | GRADPHSLCYDITVIPKFRPGPRWCAVQGQVDEKTFLHYDC GNKTVTPVSPLGKKLNVTTAWKAQNPVLREVVDILTEQLRD IQLENYTPKEPLTLQARMSCEQKAEGHSSGSWQFSFDGQIF LLFDSEKRMWTTVHPGARKMKEKWENDKVVAMSFHYFSMGD CIGWLEDFLMGMDSTLEPSAGAPLAMS |
| hULBP3 (Uniprot: Q9BZM4) | 30-216 | 3 | DAHSLWYNFTIIHLPRHGQQWCEVQSQVDQKNFLSYDCGSD KVLSMGHLEEQLYATDAWGKQLEMLREVGQRLRLELADTEL EDFTPSGPLTLQVRMSCECEADGYIRGSWQFSFDGRKFLLF DSNNRKWTVVHAGARRMKEKWEKDSGLTTFFKMVSMRDCKS WLRDFLMHRKKRLEPTAPPTMAP |
| hULBP4 (Uniprot: Q8TD07) | 31-225 | 4 | HSLCFNFTIKSLSRPGQPWCEAQVFLNKNLFLQYNSDNNMV KPLGLLGKKVYATSTWGELTQTLGEVGRDLRMLLCDIKPQI KTSDPSTLQVEMFCQREAERCTGASWQFATNGEKSLLFDAM NMTWTVINHEASKIKETWKKDRGLEKYFRKLSKGDCDHWLR EFLGHWEAMPEPTVSPVNASDIHWSSSSLPD |
| hULBP5 (Q6H3X3) | 26-218 | 5 | GLADPHSLCYDITVIPKFRPGPRWCAVQGQVDEKTFLHYDC GSKTVTPVSPLGKKLNVTTAWKAQNPVLREVVDILTEQLLD IQLENYIPKEPLTLQARMSCEQKAEGHGSGSWQLSFDGQIF LLFDSENRMWTTVHPGARKMKEKWENDKDMTMSFHYISMGD CTGWLEDFLMGMDSTLEPSAGAPPTMSSG |
| hULBP6_01 (Uniprot: Q5VY80, 6*01) | 26-218 | 6 | GRDDPHSLCYDITVIPKFRPGPRWCAVQGQVDEKTFLHYDC GNKTVTPVSPLGKKLNVTTAWKAQNPVLREVVDILTEQLRD IQLENYTPKEPLTLQARMSCEQKAEGHSSGSWQFSIDGQIF LLFDSEKRMWTTVHPGARKMKEKWENDKDVAMSFHYISMGD CIGWLEDFLMGMDSTLEPSAGAPLAMSSG |
| hULBP6_02 (Uniprot: Q5VY80, 6*02) | 26-218 | 7 | RRDDPHSLCYDITVIPKFRPGPRWCAVQGQVDEKTFLHYDC GNKTVTPVSPLGKKLNVTTAWKAQNPVLREVVDILTEQLLD IQLENYTPKEPLTLQARMSCEQKAEGHSSGSWQFSIDGQTF LLFDSEKRMWTTVHPGARKMKEKWENDKDVAMSFHYISMGD CIGWLEDFLMGMDSTLEPSAGAPLAMSSG |
| cULBP5 (ENSMBL: ENSMFAG00000062093) | 27-216 | 8 | ADPHSLCYDITIIPKFRPGPRWCAVQGQVDKKTFLHYDCGN KTVTPVSTLGKKLNVTKAWKAQNPVLREVVDMLTEQLLDIE LENYTPREPLTLQTRMSCEQKAEGHSSGSWQLGFDGQVFLL FDSENRMWATVHPGARKMKEKWQNDKDVTMSFHYISMGDCT KWLKDFLTGMDSTLEPSAGAPLTMSS |
| cULBP2/6 (Uniprot: A0A2K5X4N3) | 27-216 | 9 | DDLHSLCYDITIIPKFRPGPRWCAVQGQVDKKTFLHYDCGN KTVTSVSTLGKKLNVTKAWKAQNPVLREVVDMLTEQLLDIQ LENYTPREPLTLQARMSCEQKAEGHSSGSWQFGFDGQVFLL FDSENRMWTTVHPGARKMKEKWENDKDVTMSFHYISMGDCT RWLGDFLMDMDSTLEPSAGAPLTMSS |

TABLE 7

Other polypeptide sequences

| Name | Domain boundary | SEQ ID NO: | Sequence |
|---|---|---|---|
| hMICA (Uniprot: Q29983) | 1-308 | 10 | MGLGPVFLLLAGIFPFAPPGAAAEPHSLRYNLTVLSWDGSV QSGFLTEVHLDGQPFLRCDRQKCRAKPQGQWAEDVLGNKTW DRETRDLTGNGKDLRMTLAHIKDQKEGLHSLQEIRVCEIHE DNSTRSSQHFYYDGELFLSQNLETKEWTMPQSSRAQTLAMN VRNFLKEDAMKTKTHYHAMHADCLQELRRYLKSGVVLRRTV PPMVNVTRSEASEGNITVTCRASGFYPWNITLSWRQDGVSL SHDTQQWGDVLPDGNGTYQTWVATRICQGEEQRFTCYMEHS GNHSTHPVPSGKVLVLQSHWQGGGSGLNDIFEAQ |

TABLE 7-continued

Other polypeptide sequences

| Name | Domain boundary | SEQ ID NO: | Sequence |
|---|---|---|---|
| hMICB (Uniprot: 29983) | 1-383 | 11 | MGLGRVLLFLAVAFPFAPPAAAAEPHSLRYNLMVLSQDESV QSGFLAEGHLDGQPFLRYDRQKRRAKPQGQWAEDVLGAKTW DTETEDLTENGQDLRRTLTHIKDQKGGLHSLQEIRVCEIHE DSSTRGSRHFYYDGELFLSQNLETQESTVPQSSRAQTLAMN VTNFWKEDAMKTKTHYRAMQADCLQKLQRYLKSGVAIRRTV PPMVNVTCSEVSEGNITVTCRASSFYPRNITLTWRQDGVSL SHNTQQWGDVLPDGNGTYQTWVATRIRQGEEQRFTCYMEHS GNHGTHPVPSGKVLVLQSQRTDFPYVSAAMPCFVIIIILCV PCCKKKTSAAEGPELVSLQVLDQHPVGTGDHRDAAQLGFQP LMSATGSTGSTEGAGGGSGLNDIFEA |
| hNKG2D (Uniprot ID: P26718) with C-terminal long huFc-Flag tag | 78-216 | 12 | FLNSLFNQEVQIPLTESYCGPCPKNWICYKNNCYQFFDESK NWYESQASCMSQNASLLKVYSKEDQDLLKLVKSYHWMGLVH IPTNGSWQWEDGSILSPNLLTIIEMQKGDCALYASSFKGYI ENCSTPNTYICMQRTVGGGGSENLYFQGGGGSEPKSCDKTH TCPPCPAPELLGGPSVFLFPPKPKDTLMISRTPEVTCVVVD VSHEDPEVKFNWYVDGVEVHNAKTKPREEQYNSTYRVVSVL TVLHQDWLNGKEYKCKVSNKALPAPIEKTISKAKGQ PREPQVYTLPPSRDELTKNQVSLTCLVKGFYPSDIAVEWES NGQPENNYKTTPPVLDSDGSFFLYSKLTVDKSRWQQGNVFS CSVMHEALHNHYTQKSLSLSPGKDYKDDDDK |
| cNKG2D (Uniprot ID: P61252) with C-terminal short huFc-FLAG tag | 78-216 | 13 | FLNSLFNQEVQIPLTESYCGPCPKNWICYKNNCYQFFNESK NWYESQASCMSQNASLLKVYSKEDQDLLKLVKSYHWMGLVH IPTNGSWQWEDGSILSPNLLTIIEMQKGDCALYASSFKGYI ENCSIPNTYICMQRTVGGGGSENLYFQGGGGAPELLGGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSRDELTKNQV SLTCLVKGFYPSDIAVEWESNGQPENNYKTTPPVLDSDGSF FLYSKLTVDKSRWQQGNVFSCSVMHEALHNHYTQKSLSLSP GKDYKDDDDK |
| long huFc-Flag tag(Uniprot: P01857) | 99-330 | 14 | EPKSCDKTHTCPPCPAPELLGGPSVFLFPPKPKDTLMISRT PEVTCVVVDVSHEDPEVKFNWYVDGVEVHNAKTKPREEQYN STYRVVSVLTVLHQDWLNGKEYKCKVSNKALPAPIEKTISK AKGQPREPQVYTLPPSRDELTKNQVSLTCLVKGFYPSDIAV EWESNGQPENNYKTTPPVLDSDGSFFLYSKLTVDKSRWQQG NVFSCSVMHEALHNHYTQKSLSLSPGKDYKDDDDK |
| shorthuFc-Flag tag(Uniprot: P01857) | 114-330 | 15 | APELLGGPSVFLFPPKPKDTLMISRTPEVTCVVVDVSHEDP EVKFNWYVDGVEVHNAKTKPREEQYNSTYRVVSVLTVLHQD WLNGKEYKCKVSNKALPAPIEKTISKAKGQPREPQVYTLPP SRDELTKNQVSLTCLVKGFYPSDIAVEWESNGQPENNYKTT PPVLDSDGSFFLYSKLTVDKSRWQQGNVFSCSVMHEALHNH YTQKSLSLSPGKDYKDDDDK |

Example 5: Generation and Selection of Anti-ULBP6 Antibodies

This example illustrates the generation of anti-ULBP6 antibodies using mouse hybridoma technology.

Immunization

Multi strain mice were immunized with hULBP6-01 (SEQ ID NO:6) and hULBP6-02 (SEQ ID NO:7) which were produced in-house. The SIGMA adjuvant system (MILLIPORE SIGMA St. Louis, MO), Freund's Adjuvant, Complete (MILLIPORE SIGMA St. Louis, MO), TITER-MAX Gold Adjuvant (MILLIPORE SIGMA St. Louis, MO), GERBU Adjuvant (V-Biognostics), TLR cocktail (IN-VIVOGEN) was used for the immunizations. Antibody titers were determined by ELISA. Mice which showed sufficient antibody titers were given a final boost without an adjuvant. Fusion was performed 3 days after the final boost. Hybridomas were generated, selected for mouse antibody expression and cloned.

Example 6: Screening and Characterization of Anti-ULBP6 Antibodies

This example demonstrates the methods used to screen and select for anti-ULBP6 antibodies which effectively block the interaction between soluble ULBP6 and NKG2D.

A. Enzyme-Linked Immunosorbent Assay (ELISA)

To detect single hybridoma clones which secrete ULBP6-specific antibodies a direct ELISA was performed 7 days after culturing the picked hybridoma clones.

Materials and Methods

Briefly, 96-well MAXISORP flat bottom plates (THERMO SCIENTIFIC, catalogue number 439454) were coated with 1 pg/mL sULBP6_01, sULBP6_02 and sULBP2 in PBS (50 µL/well) overnight at 4° C. The wells were washed twice with tap water and blocked with blocking solution containing 1% bovine serum albumin (BSA) in phosphate buffered saline (PBS), pH 7.4, 200 µL/well for 1 hr at RT. Next, the wells were washed again and 50 µL/well of culture supernatant from selected hybridomas was added and incubated for 1 hr at RT. After the wash a secondary anti-mouse IgG antibody conjugated to horseradish peroxidase (HRP; Jackson Immuno 115-035-164) was used for detection. The plates were incubated for 45 min at RT. Tetramethylbenzidine (TMB) solution (0.12 mg/mL TMB with 0.04% hydrogen peroxide in 25 mM $NaH_2PO_4$) was used as substrate. The reaction was stopped after 5 min with 2N $H_2SO_4$. Optical density (OD) was measured at 450 nm.

Results

From the primary direct ELISA, 191 clones (binders) were selected, and a confirmatory indirect ELISA was performed that yielded a total of 90 binders which were further tested using FACS binding and a single point blocking ELISA assay as described below.

B. Flow Cytometry Cell Binding Assay

To determine whether the 90 ULBP6-specific binder antibody clones identified in the primary indirect ELISA assay also bound to cell surface-expressed NKG2DLs, a flow cytometry cell binding assay was performed.

Materials and Methods

CHO-S cells were transiently transfected to over-express full-length membrane bound human ULBP6_01, ULBP6_02, ULBP1, ULBP2, ULBP3 and ULBP5. CHO-S cells were harvested by centrifugation at 1200 RPM for 15 mins. Cell pellets were resuspended into 10 mL of FACS buffer (1× PBS containing 1% BSA) and counted. The cells were then plated at 1×10$^6$ cells/well into 96 well plates (Corning 3365). A 96 head liquid handler was used to transfer 50 µL of supernatant from the 96 well plates used to culture the hybridoma cells to the 96 well plates containing the target expression cells. Supernatants were incubated with the cells for 1 h at 4° C. Cells were then washed twice with FACS buffer, incubated with secondary anti-mouse IgG antibody conjugated to APC (5 µg/mL, Jackson Immuno., 115-136-146), for 45 min at 4° C., and then washed twice with FACS buffer. Following washing, the cells were resuspended in 100 µl of FACS buffer for flow cytometric analysis.

Results

Of the 90 clones tested in the flow cytometry binding assay, 7/90 showed binding to CHO-S-ULBP1, 89/90 to CHO-S-ULBP2, 2/90 to CHO-S-ULBP3, 34/90 to CHO-S-ULBP5, 88/90 to CHO-S-ULBP6_01 and 87/90 to CHO-S-ULBP6_02. All 90 clones were then tested in a single point biochemical blocking assay.

C. Single Point Biochemical Blocking Assay

A biochemical blocking assay was performed to detect antibody clones which block binding of human soluble ULBP6 to human NKG2D. For these experiments the ULBP6 haplotype with the highest affinity for NKG2D, sULBP6_02, was used.

Materials and Methods 96-well MAXISORP flat bottom plates (THERMO SCIENTIFIC, catalogue number 439454) were coated with NEUTRAVIDIN (1 µg/mL) in PBS, 100 µL/well overnight at 4° C. The wells were washed two times with tap water and blocked with blocking solution containing 1% bovine serum albumin (BSA) in phosphate buffered saline (PBS) pH 7.4, using 200 µL/well for 1 hr at RT. The wells were washed twice again and biotinlyated-sULBP6_02 was added at 1 µg/ml and the plate was incubated for 1 hr at room temperature. 60 µl of neat hybridoma supernatant and 60 µl of NKG2D-Fc (10 nM) were pre-incubated and the mixed solution was added to the plate for 1 hr at RT. After washing, a secondary anti-human IgG Fc antibody conjugated to horseradish peroxidase (HRP; Jackson Immuno. 109-035-098) was used for detection. The secondary antibody solution was incubated for 45 min at RT. Tetramethylbenzidine (TMB) solution (0.12 mg/mL TMB with 0.04% hydrogen peroxide in 25 mM $NaH_2PO_4$) was used as substrate. The reaction was stopped after 5 min with 2N $H_2SO_4$. Optical density (OD) was measured at 450 nm. A mouse anti-ULBP2/5/6 Antibody (R&D SYSTEMS, MAB1298-100) was used as a positive control at 5 µg/ml. The medium was used as a negative control. The ELISA signal of the negative control was defined as 0% blocking activity. The mouse anti-hULBP2/5/6 Ab (R&D SYSTEMS, MAB1298-100) showed 72% blocking activity.

Results

Of the 90 clones tested in the single point biochemical blocking ELISA, 68/90 showed blocking of sULBP6_02 binding to NKG2D. The 7B3 and 8E11 clones showed 100% blocking activity. The 25 antibodies with the highest blocking activity were then tested for cynomolgus cross-reactivity using cULBP2/6 from Ensembl v99.

D. Cynomolgus Cross-Reactivity

To determine cross-reactivity to cULBP2/6 protein, binding to both human and cynomolgus sULBP6 proteins was tested by assessing binding of mouse hybridoma supernatants in an OCTET R-8 BLI Label-Free Detection System.

Material and Methods

300 µl of each hybridoma supernatant along with 300 nM of both human ULBP6 and cULBP2/6 proteins in 1× PBST (1× PBS, 0.05% Tween-20) were pipetted in the Octet 96 well. A stable baseline for 60 seconds was measured using Anti-Mouse Fc Capture (AMC) biosensor in 1×PBST buffer followed by capturing of mouse antibodies from hybridoma supernatants for 150-300 seconds. After recording another stable baseline for 60 seconds, a biosensor was immersed in either human soluble ULBP6 or cynomolgus ULBP2/6 to measure the interaction/association between the captured mouse antibody from hybridoma supernatant and sULBP6, followed by a dissociation step of 300 seconds in 1×PBST.

Results

Twenty-five blocking antibodies from the single point blocking ELISA were selected for the cross-reactivity study. Of these 25 antibodies, 10 antibodies showed good cross-reactivity against cyno ULBP6. 7B3 showed the strongest binding to cULBP2/6. Since 2/10 blocking antibodies (7B3 and 8E11) showed very strong blocking in the single point blocking assay and good cross-reactivity, they were directly selected to be tested in functional assays, whereas the remaining 8/10 blocking antibodies were further tested in a three point biochemical blocking assay.

E. Three Point Biochemical Blocking Assay

Eight hybridoma clones were selected based on clonal type, blocking activity using one-point neat supernatant, human/cynomolgus cross-reactivity, and binding affinity. These 8 clones were tested in a three point blocking assay for further ranking.

Materials and Methods 96-well MAXISORP flat bottom plates (THERMO SCIENTIFIC, catalogue number 439454) were coated with hNKG2D-Fc (2 µg/mL) in PBS, 100 µL/well overnight at 4° C. The wells were washed two times with tap water and blocked with blocking solution containing 1% bovine serum albumin (BSA) in phosphate buffered saline (PBS) pH 7.4, using 200 µL/well for 1 hr at room temperature. The murine IgG concentration of supernatant was normalized at 1 nM, 0.1 nM and 0.01 nM. 60 µl of normalized hybridoma supernatant and 60 µl of biotinylated-ULBP6_02 (1 nM) were pre-incubated together for 1 hr at RT, and the mixed solution was added to the coated plate for 15 minutes. After washing, a secondary streptavidin poly-HRP (THERMO SCIENTIFIC, N200) was added to the wells and incubated for 45 min at RT. Tetramethylbenzidine (TMB) solution (0.12 mg/mL TMB with 0.04% hydrogen peroxide in 25 mM $NaH_2PO_4$) was used as substrate. The reaction was stopped after 5 min with 2N $H_2SO_4$. Optical density (OD) was measured at 450 nm. The purified strong blocking mAb 7B3 was used as a positive control and blank medium was used as a negative control in the assay.

Results

Of the 8 clones tested in the three point biochemical blocking assay, 4 clones (6E1, 1 D4, 4B1, and 5B8) showed >50% blocking activity.

F. Down-Selection of Clones

Based on ELISA/FACS binding, cyno-cross reactivity, blocking efficiency in the blocking ELISAs, and clonotype information, 4 clones were selected (7B3, 8E11, 6E1, 1 D4) for cloning, expression and purification as recombinant humanized antibodies. One non-blocking antibody (8E8) was chosen as a negative control.

These clones were subsequently humanized to yield four functional blocking human antibody clones (h7B3, h8E11, h6E1, and h1D4) and one strong binding but non-blocking human antibody clone (h8E8). The germline sequences (HC/LC) used for humanisation were: h7B3 (HC: IGHV3-48, LC: IGKV1-33), h8E11 (HC: IGHV3-48, LC: IGKV3-11), h1D4 (HC: IGHV7-4-1, LC: IGKV1-33), h6E1 (HC: IGHV1-2, LC: IGKV1-16). These blocking antibodies were cloned in a pRK vector (both in hIgG1 and mIgG2a backbones), expressed in Expi293 cells, purified, and characterized. The variable heavy (VH) and variable light (VL) sequences for the heavy chain (HC) and light chain (LC, Kappa light chain, KC)) of non-humanized and humanized antibody clones herein are provided in Table 8. The complementarity determining region (CDR) sequences of the VH and VL sequences for the HC and LC of selected murine and humanized anti-ULBP6 antibody clones herein are provided in Table 9 (according to Kabat numbering). Sequences of the CH1 domain with fragment crystallizable (Fc) regions comprising the heavy chain domains CH2 and CH3 (Table 10) that can be modularly combined with VH sequences (Table 8) of clones herein are provided. Fc sequences provided include (a) an effector positive sequence (E+), which can be considered the wild type (WT) Fc sequence, and is fucosylated unless stated otherwise; (b) an effector negative sequence (E−) which comprises a N297G mutation (EU numbering) which eliminates effector function (mutation in bold typeface); and (c) an effector enhanced sequence (referred to herein as "E++" or "E++DE" or "E++(DE)") which comprises S239D and I332E mutations (abbreviated herein as DE) which enhances effector function (mutation in bold typeface), and is fucosylated unless stated otherwise. In some examples, a wild type Fc sequence (e.g., E+) can be afucosylated (Afu), such that the oligosaccharides in the Fc chain comprise no fucose sugar units. Such afucosylation in a wild-type Fc (e.g., E+ Afu) results in enhancement of the effector function substantially similar to that of an E++Fc sequence. A constant light chain domain (CL) sequence (Table 11) that can be modularly combined with VL sequences (Table 8) of clones herein is provided. The full-length sequences for the HC and LC of non-humanized and humanized clones contemplated and/or produced herein are provided in Table 12, wherein the variable chains are underlined and the CDR sequences are indicated in bold typeface. However, in some embodiments, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. For example, an antibody lacking the C-terminal lysine can have a sequence of SEQ ID NO: 160 or SEQ ID NO: 161. Full-length nucleic acid sequences for the HC and LC of humanized clones contemplated and/or produced herein are provided in Table 13.

TABLE 8

Variable chain sequences of selected non-humanized and humanized anti-ULBP6 antibodies

| Antibody Chain | SEQ ID NO: | VH sequence |
| --- | --- | --- |
| 7B3_HC_VH | 16 | DVQLVESGGGLVKPGGSRKLSCAASGFTFSTYGFHWVRQVPEKGLEW VAYISSNSGTIDYADTVKGRFTISRDNAKNTLFLQMTSLRSEDTAMY YCARQGYGFDNWGQGTTLTVSS |
| 8E11_HC_VH | 17 | DVQLVESGGGLVQPGGSRKLSCAASGFTFRTYGMHWVRQAPEKGLEW VAYISSGSGTIDYADTVKGRFTISRDNAKNTLFLQMTSLRSEDTAMY YCTRQTGAMDYWGQGTSVTVSS |
| 6E1_HC_VH | 18 | QVQLQQPGAELVKPGASVKVSCKASGYTFTNYWMHWMKQRPGQGLEW LGRIHPSDSDTNYNQKFKGKATLTVDKSSNIAFMQLSSLTSEDSAVY YCAIEGTGKGYFDVWGTGTTVTVSS |
| 1D4_HC_VH | 19 | QIQLVQSGPELKKPGETVKISCKASGYTFTEYPIHWVKQAPGKGFKW MGMIYTDTGEPTHAEEFKGRFAFSLETSASTAYLQINNLKNEDTATY FCVRWYDGSSYIMDYWGQGTSVTVSS |

TABLE 8-continued

Variable chain sequences of selected non-humanized and humanized anti-ULBP6 antibodies

| | | |
|---|---|---|
| 8E8_HC_VH | 20 | QVQLQQSGAELARPGTSVRLSCKASGYTFTTYGITWVKQRPGQGLEW<br>IGEIYPGTATSYSNERFKGKATLTADRSSSTAYMQLSSLTSEDSAVY<br>FCARRGTYGTYEWYFDVWGAGTTVTSS |
| h7B3_HC_VH | 21 | EVQLVESGGGLVQPGGSLRLSCAASGFTFSTYGFHWVRQAPGKGLEW<br>VAYISSNSGTIDYADTVKGRFTISRDNAKNSLYLQMNSLRAEDTAVY<br>YCARQGYGFDNWGQGTTVTVSS |
| h8E11_HC_VH | 22 | EVQLVESGGGLVQPGGSLRLSCAASGFTFRTYGMHWVRQAPGKGLEW<br>VAYISSGSGTIDYADTVKGRFTISRDNAKNSLYLQMNSLRAEDTAVY<br>YCTRQTGAMDYWGQGTLVTVSS |
| h6E1_HC_VH | 23 | EVQLVQSGAEVKKPGASVKVSCKASGYTFTNYWMHWMRQAPGQGLEW<br>LGRIHPSDSDTNYNQKFKGRATLTVDKSISTAYMELSRLRSDDTAVY<br>YCAIEGTGKYFDVWGRGTLVTVSS |
| h1D4_HC_VH | 24 | EIQLVQSGSELKKPGASVKVSCKASGYTFTEYPIHWVRQAPGQGFEW<br>MGMIYTDTGEPTHAEEFKGRFVFSLDTSVSTAYLQISSLKAEDTAVY<br>FCVRWYDGSSYIMDYWGQGTTVTVSS |
| h8E8_HC_VH | 25 | QVQLVQSGAEVKKPGSSVKVSCKASGYTFTTYGITWVRQAPGQGLEW<br>IGEIYPGTATSYSNERFKGRATLTADRSTSTAYMELSSLRSEDTAVY<br>FCARRGTYGTYEWYFDVWGRGTLVTVSS |

| Antibody | SEQ ID NO: | VL sequence |
|---|---|---|
| 7B3_KC_VL | 26 | EILLTQSPAIIAASPGEKVTITCSASSRVSYMNWYQQKPGSSPKIWV<br>YGISNLASGVPARFSGSGSGTSFSFTINSMEAEDVATYYCQQRSSHP<br>LTFGAGTKLELK |
| 8E11_KC_VL | 27 | EILLTQSPAIIAASPGEKVTITCSASSSVSYMNWYQQKPGSSPKLWI<br>YGISNLASGVPARFSGSGSGTSFSFTINSMEAEDVATYYCQQRSSHP<br>LTFGAGTKLELK |
| 6E1_KC_VL | 28 | DIKMTQSPSSMYASLGERVTITCKASQDIYSYLSWFQQKPGRSPKTL<br>IYRANRLVDGVPSRFSGSGSGQDFSLTISSLDYEDMGIYYCLHYDEF<br>PLTFGTGTKLELK |
| 1D4_KC_VL | 29 | DIKMTQSPSSMYASLGERVTITCKASQDINSYLSWFQQKPGKSPKTL<br>IYRANRLVDGVPSRFSGSGSGQDYSLTISSLEYEDVGIYYCLQYDEF<br>PLTFGAGTKLELK |
| 8E8_KC_VL | 30 | DIQMTQSPASLSVSVGETATITCRASENIYSHLAWYQQKQGKSPQLL<br>VYAATNLADGVPSRFSGSGSGTQYSLKINSLQSEDFGSYYCQHFWGT<br>PWTFGGGTKLEIK |
| h7B3_KC_VL | 31 | DIQLTQSPSSLSASVGDRVTITCSASSRVSYMNWYQQKPGKSPKIWV<br>YGISNLASGVPARFSGSGSGTDFTFTISSLQPEDIATYYCQQRSSHP<br>LTFGGGTKVEIK |
| h8E11_KC_VL | 32 | EIVLTQSPATLSLSPGERATLSCSASSSVSYMNWYQQKPGQSPRLWI<br>YGISNLASGVPARFSGSGSGTDFTLTISSLEPEDFAVYYCQQRSSHP<br>LTFGGGTKVEIK |
| h6E1_KC_VL | 33 | DIQMTQSPSSLSASVGDRVTITCKASQDIYSYLSWFQQKPGKSPKTL<br>IYRANRLVDGVPSRFSGSGSGQDFTLTISSLQPEDFATYYCLHYDEF<br>PLTFGGGTKVEIK |
| h1D4_KC_VL | 34 | DIQMTQSPSSLSASVGDRVTITCKASQDINSYLSWFQQKPGKSPKTL<br>IYRANRLVDGVPSRFSGSGSGQDYTFTISSLQPEDIATYYCLQYDEF<br>PLTFGGGTKVEIK |
| h8E8_KC_VL | 35 | DIQMTQSPSSLSASVGDRVTITCRASENIYSHLAWYQQKPGKSPKLL<br>VYAATNLADGVPSRFSGSGSGTDYTLTISSLQPEDFATYYCQHFWGT<br>PWTFGGGTKVEIK |

TABLE 9

CDR and HVR sequences of selected non-humanized and humanized anti-ULBP6 antibodies

| Antibody Chain | CDRH1 | SEQ ID NO: | CDRH2 | SEQ ID NO: | CDRH3 | SEQ ID NO: |
|---|---|---|---|---|---|---|
| 7B3_HC_VH;<br>h7B3_HC_VH | TYGFH | 36 | YISSNSGTIDYA<br>DTVKG | 37 | QGYGFDN | 38 |
| 8E11_HC_VH;<br>h8E11_HC_VH | TYGMH | 39 | YISSGSGTIDYA<br>DTVKG | 40 | QTGAMDY | 41 |
| 6E1_HC_VH;<br>h6E1_HC_VH | NYWMH | 42 | RIHPSDSDTNYN<br>QKFKG | 43 | EGTGKGYFDV | 44 |
| 1D4_HC_VH;<br>h1D4_HC_VH | EYPIH | 45 | MIYTDTGEPTHA<br>EEFKG | 46 | WYDGSSYIMDY | 47 |

TABLE 9-continued

CDR and HVR sequences of selected non-humanized and humanized anti-ULBP6 antibodies

| Antibody Chain | | SEQ ID NO: | | SEQ ID NO: | | SEQ ID NO: |
|---|---|---|---|---|---|---|
| 8E8_HC_VH; h8E8_HC_VH | TYGIT | 48 | EIYPGTATSYSNERFKG | 49 | RGTYGTYEWYFDV | 50 |

| Antibody Chain | CDRL1 | SEQ ID NO: | CDRL2 | SEQ ID NO: | CDRL3 | SEQ ID NO: |
|---|---|---|---|---|---|---|
| 7B3_KC_VL; h7B3_KC_VL | SASSRVSYMN | 51 | GISNLAS | 52 | QQRSSHPLT | 53 |
| 8E11_KC_VL; h8E11_KC_VL | SASSSVSYMN | 54 | GISNLAS | 55 | QQRSSHPLT | 56 |
| 6E1_KC_VL; h6E1_KC_VL | KASQDIYSYLS | 57 | RANRLVD | 58 | LHYDEFPLT | 59 |
| 1D4_KC_VL; h1D4_KC_VL | KASQDINSYLS | 60 | RANRLVD | 61 | LQYDEFPLT | 62 |
| 8E8_KC_VL; h8E8_KC_VL | RASENIYSHLA | 63 | AATNLAD | 64 | QHFWGTPWT | 65 |

| Antibody Chain | HVRH1 | SEQ ID NO: | HVRH2 | SEQ ID NO: | HVRH3 | SEQ ID NO: |
|---|---|---|---|---|---|---|
| h7B3_HC_VH | GFTFSTYGFH | 130 | AYISSNSGTIDYADTVKG | 131 | ARQGYGFDN | 132 |
| h8E11_HC_VH | GFTFRTYGMH | 133 | AYISSGSGTIDYADTVKG | 134 | TRQTGAMDY | 135 |
| h6E1_HC_VH | GYTFTNYWMH | 136 | GRIHPSDSDTNYNQKFKG | 137 | AIEGTGKGYFDV | 138 |
| h1D4_HC_VH | GYTFTEYPIH | 139 | GMIYTDTGEPTHAEEFKG | 140 | VRWYDGSSYIMDY | 141 |
| h8E8_HC_VH | GYTFTTYGIT | 142 | GEIYPGTATSYSNERFKG | 143 | ARRGTYGTYEWYFDV | 144 |

| Antibody Chain | HVRL1 | SEQ ID NO: | HVRL2 | SEQ ID NO: | HVRL3 | SEQ ID NO: |
|---|---|---|---|---|---|---|
| h7B3_KC_VL | SASSRVSYMN | 145 | GISNLAS | 146 | QQRSSHPLT | 147 |
| h8E11_KC_VL | SASSSVSYMN | 148 | GISNLAS | 149 | QQRSSHPLT | 150 |
| h6E1_KC_VL | KASQDIYSYLS | 151 | RANRLVD | 152 | LHYDEFPLT | 153 |
| h1D4_KC_VL | KASQDINSYLS | 154 | RANRLVD | 155 | LQYDEFPLT | 156 |
| h8E8_KC_VL | RASENIYSHLA | 157 | AATNLAD | 158 | QHFWGTPWT | 159 |

TABLE 10

Fc domain sequences of selected anti-ULBP6 antibodies

| Fc Domain | SEQ ID NO: | Sequence |
|---|---|---|
| hIgG1_E+ (N297) and Afucosylated (WT Fc) | 66 | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK |
| hIgG1_E- (N297G) | 67 | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYGSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK |
| hIgG1_E++ (DE_S239D/I 332E) | 68 | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPDVFLFPPKPKDTLMISRTPEVTCVVVDVS HEDPEVKFNWYVDGVEVHNAKTKPREEQYNSTYRVVSVLTVLHQDWLNGK EYKCKVSNKALPAPEEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK |

Note: The mutations in the E- and E++ sequences are indicated in bold typeface.

TABLE 11

CL domain sequence of selected anti-ULBP6 antibodies

| CL Domain | SEQ ID NO: | Sequence |
|---|---|---|
| CL | 69 | RTVAAPSVFIFPPSDEQLKSGTASVVCLLNNFYPRE AKVQWKVDNALQSGNSQESVTEQDSKDSTYSLSSTL TLSKADYEKHKVYACEVTHQGLSSPVTKSENRGEC |

TABLE 12

Full length sequences of selected non-humanized and humanized anti-ULBP6 antibodies

| Antibody Chain | SEQ ID NO: | Full length sequence |
|---|---|---|
| 7B3 (E+) FL HC (WT Fc) | 70 | DVQLVESGGGLVKPGGSRKLSCAASGFTFSTYGFHWVRQVPEKGLEWVAYI SSNSGTIDYADTVKGRFTISRDNAKNTLFLQMTSLRSEDTAMYYCARQYG FDNWGQGTTLTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| 8E11 (E+) FL HC (WT Fc) | 71 | DVQLVESGGGLVQPGGSRKLSCAASGFTFRTYGMHWVRQAPEKGLEWVAYI SSGSGTIDYADTVKGRFTISRDNAKNTLFLQMTSLRSEDTAMYYCTRQTGA MDYWGQGTSVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |

TABLE 12-continued

Full length sequences of selected non-humanized and humanized anti-ULBP6 antibodies

| Antibody Chain | SEQ ID NO: | Full length sequence |
|---|---|---|
| 6E1(E+) FL HC (WT Fc) | 72 | QVQLQQPGAELVKPGASVKVSCKASGYTFTNYWMHWMKQRPGQGLEWLGRI HPSDSDTNYNQKFKGKATLTVDKSSNIAFMQLSSLTSEDSAVYYCAIEGTG KGYFDVWGTGTTVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK |
| 1D4 (E+) FL HC (WT Fc) | 73 | QIQLVQSGPELKKPGETVKISCKASGYTFTEYPIHWVKQAPGKGFKWMGMI YTDTGEPTHAEEFKGRFAFSLETSASTAYLQINNLKNEDTATYFCVRWYDG SSYIMDYWGQGTSVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 8E8 (E+) FL HC (WT Fc) | 74 | QVQLQQSGAELARPGTSVRLSCKASGYTFTTYGITWVKQRPGQGLEWIGEI YPGTATSYSNERFKGKATLTADRSSSTAYMQLSSLTSEDSAVYFCARRGTY GTYEWYFDVWGAGTTVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| h7B3 (E+) FL HC (WT FC) | 75 | EVQLVESGGGLVQPGGSLRLSCAASGFTFSTYGFHWVRQAPGKGLEWVAYI SSNSGTIDYADTVKGRFTISRDNAKNSLYLQMNSLRAEDTAVYYCARQGYG FDNWGQGTTVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| h8E11 (E+) FL HC (WT FC) | 76 | EVQLVESGGGLVQPGGSLRLSCAASGFTFRTYGMHWVRQAPGKGLEWVAYI SSGSGTIDYADTVKGRFTISRDNAKNSLYLQMNSLRAEDTAVYYCTRQTGA MDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| h6E1 (E+) FL HC (WT FC) | 77 | EVQLVQSGAEVKKPGASVKVSCKASGYTFTNYWMHWMRQAPGQGLEWLGRI HPSDSDTNYNQKFKGRATLTVDKSISTAYMELSRLRSDDTAVYYCAIEGTG KGYFDVWGRGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK |
| h1D4 (E+) FL HC (WT FC) | 78 | EIQLVQSGSELKKPGASVKVSCKASGYTFTEYPIHWVRQAPGQGFEWMGMI YTDTGEPTHAEEFKGRFVFSLDTSVSTAYLQISSLKAEDTAVYFCVRWYDG SSYIMDYWGQGTTVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK |

TABLE 12-continued

Full length sequences of selected non-humanized and humanized anti-ULBP6 antibodies

| Antibody Chain | SEQ ID NO: | Full length sequence |
|---|---|---|
| h8E8 (E+) FL HC (WT FC) | 79 | QVQLVQSGAEVKKPGSSVKVSCKASGYTFTTYGITWVRQAPGQGLEWIGEI YPGTATSYSNERFKGRATLTADRSTSTAYMELSSLRSEDTAVYFCARRGTY GTYEWYFDVWGRGTLVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 7B3 FL HC (E-) | 80 | DVQLVESGGGLVKPGGSRKLSCAASGFTFSTYGFHWVRQVPEKGLEWVAYI SSNSGTIDYADTVKGRFTISRDNAKNTLFLQMTSLRSEDTAMYYCARQGYG FDNWGQGTTLTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYGSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| 8E11 FL HC (E-) | 81 | DVQLVESGGGLVQPGGSRKLSCAASGFTFRTYGMHWVRQAPEKGLEWVAYI SSGSGTIDYADTVKGRFTISRDNAKNTLFLQMTSLRSEDTAMYYCTRQTGA MDYWGQGTSVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYGSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| 6E1 FL HC (E-) | 82 | QVQLQQPGAELVKPGASVKVSCKASGYTFTNYWMHWMKQRPGQGLEWLGRI HPSDSDTNYNQKFKGKATLTVDKSSNIAFMQLSSLTSEDSAVYFCAIEGTG KGYFDVWGTGTTVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYGSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK |
| 1D4 FL HC (E-) | 83 | QIQLVQSGPELKKPGETVKISCKASGYTFTEYPIHWVQAPGKGFKWMGMI YTDTGEPTHAEEFKGRFAFSLETSASTAYLQINNLKNEDTATYFCVRWYDG SSYIMDYWGQGTSVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYGSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 8E8 FL HC (E-) | 84 | QVQLQQSGAELARPGTSVRLSCKASGYTFTTYGITWVKQRPGQGLEWIGEI YPGTATSYSNERFKGKATLTADRSSSTAYMQLSSLTSEDSAVYFCARRGTY GTYEWYFDVWGAGTTVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYGSTYR VVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| h7B3 FL HC (E-) | 85 | EVQLVESGGGLVQPGGSLRLSCAASGFTFSTYGFHWVRQAPGKGLEWVAYI SSNSGTIDYADTVKGRFTISRDNAKNSLYLQMNSLRAEDTAVYYCARQGYG FDNWGQGTTVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYGSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |

TABLE 12-continued

Full length sequences of selected non-humanized and humanized anti-ULBP6 antibodies

| Antibody Chain | SEQ ID NO: | Full length sequence |
|---|---|---|
| h8E11 FL HC (E-) | 86 | EVQLVESGGGLVQPGGSLRLSCAASGFTFRTYGMHWVRQAPGKGLEWVAYI SSGSGTIDYADTVKGRFTISRDNAKNSLYLQMNSLRAEDTAVYYCTRQTGA MDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYGSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| h6E1 FL HC (E- FC) | 87 | EVQLVQSGAEVKKPGASVKVSCKASGYTFTNYWMHWMRQAPGQGLEWLGRI HPSDSDTNYNQKFKGRATLTVDKSISTAYMELSRLRSDDTAVYYCAIEGTG KGYFDVWGRGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYGSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK |
| h1 D4 FL HC (E- FC) | 88 | EIQLVQSGSELKKPGASVKVSCKASGYTFTEYPIHWVRQAPGQGFEWMGMI YTDTGEPTHAEEFKGRFVFSLDTSVSTAYLQISSLKAEDTAVYYCVRWYDG SSYIMDYWGQGTTVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYGSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| h8E8 FL HC (E- FC) | 89 | QVQLVQSGAEVKKPGSSVKVSCKASGYTFTTYGITWVRQAPGQGLEWIGEI YPGTATSYSNERFKGRATLTADRSTSTAYMELSSLRSEDTAVYYCARRGTY GTYEWYFDVWGRGTLVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYGSTYR VVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 7B3 FL HC (E++ FC) | 90 | DVQLVESGGGLVKPGGSRKLSCAASGFTFSTYGFHWVRQVPEKGLEWVAYI SSNSGTIDYADTVKGRFTISRDNAKNTLFLQMTSLRSEDTAMYYCARQGYG FDNWGQGTTLTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPDVFLFPPKPKDTLMISRT PEVTCVVVDVSHEDPEVKFNWYVDGVEVHNAKTKPREEQYNSTYRVVSVLT VLHQDWLNGKEYKCKVSNKALPAPEEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| 8E11 FL HC (E++ FC) | 91 | DVQLVESGGGLVQPGGSRKLSCAASGFTFRTYGMHWVRQAPEKGLEWVAYI SSGSGTIDYADTVKGRFTISRDNAKNTLFLQMTSLRSEDTAMYYCTRQTGA MDYWGQGTSVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPDVFLFPPKPKDTLMISRT PEVTCVVVDVSHEDPEVKFNWYVDGVEVHNAKTKPREEQYNSTYRVVSVLT VLHQDWLNGKEYKCKVSNKALPAPEEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| 6E1 FL HC (E++ FC) | 92 | QVQLQQPGAELVKPGASVKVSCKASGYTFTNYWMHWMKQRPGQGLEWLGRI HPSDSDTNYNQKFKGKATLTVDKSSNIAFMQLSSLTSEDSAVYYCAIEGTG KGYFDVWGTGTTVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPDVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPEEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK |

TABLE 12-continued

Full length sequences of selected non-humanized and humanized anti-ULBP6 antibodies

| Antibody Chain | SEQ ID NO: | Full length sequence |
|---|---|---|
| 1D4 FL HC (E++ FC) | 93 | QIQLVQSGPELKKPGETVKISCKASGYTFTEYPIHWVKQAPGKGFKWMGMI YTDTGEPTHAEEFKGRFAFSLETSASTAYLQINNLKNEDTATYFCVRWYDG SSYIMDYWGQGTSVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPDVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPEEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 8E8 FL HC (E++ FC) | 94 | QVQLQQSGAELARPGTSVRLSCKASGYTFTTYGITWVKQRPGQGLEWIGEI YPGTATSYSNERFKGKATLTADRSSSTAYMQLSSLTSEDSAVYFCARRGTY GTYEWYFDVWGAGTTVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPDVFLFPPKPKDT LMISRTPEVTCVVVDVSHEDPEVKFNWYVDGVEVHNAKTKPREEQYNSTYR VVSVLTVLHQDWLNGKEYKCKVSNKALPAPEEKTISKAKGQPREPQVYTLP PSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| h7B3 FL HC (E++ FC) | 95 | EVQLVESGGGLVQPGGSLRLSCAASGFTFSTYGFHWVRQAPGKGLEWVAYI SSNSGTIDYADTVKGRFTISRDNAKNSLYLQMNSLRAEDTAVYYCQGYG FDNWGQGTTVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPDVFLFPPKPKDTLMISRT PEVTCVVVDVSHEDPEVKFNWYVDGVEVHNAKTKPREEQYNSTYRVVSVLT VLHQDWLNGKEYKCKVSNKALPAPEEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| h8E11 FL HC (E++ FC) | 96 | EVQLVESGGGLVQPGGSLRLSCAASGFTFRTYGMHWVRQAPGKGLEWVAYI SSGSGTIDYADTVKGRFTISRDNAKNSLYLQMNSLRAEDTAVYYCTRQTGA MDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPDVFLFPPKPKDTLMISRT PEVTCVVVDVSHEDPEVKFNWYVDGVEVHNAKTKPREEQYNSTYRVVSVLT VLHQDWLNGKEYKCKVSNKALPAPEEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPGK |
| h6E1 FL HC (E++ FC) | 97 | EVQLVQSGAEVKKPGASVKVSCKASGYTFTNYWMHWMRQAPGQGLEWLGRI HPSDSDTNYNQKFKGRATLTVDKSISTAYMELSRLRSDDTAVYYCAIEGTG KGYFDVWGRGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPDVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPEEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK |
| h1D4 FL HC (E++ FC) | 98 | EIQLVQSGSELKKPGASVKVSCKASGYTFTEYPIHWVRQAPGQGFEWMGMI YTDTGEPTHAEEFKGRFVFSLDTSVSTAYLQISSLKAEDTAVYFCVRWYDG SSYIMDYWGQGTTVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPDVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPEEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| h8E8 FL HC (E++ FC) | 99 | QVQLVQSGAEVKKPGSSVKVSCKASGYTFTTYGITWVRQAPGQGLEWIGEI YPGTATSYSNERFKGRATLTADRSTSTAYMELSSLRSEDTAVYFCARRGTY GTYEWYFDVWGRGTLVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPDVFLFPPKPKDT LMISRTPEVTCVVVDVSHEDPEVKFNWYVDGVEVHNAKTKPREEQYNSTYR VVSVLTVLHQDWLNGKEYKCKVSNKALPAPEEKTISKAKGQPREPQVYTLP PSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |

TABLE 12-continued

Full length sequences of selected non-humanized and humanized anti-ULBP6 antibodies

| Antibody Chain | SEQ ID NO: | Full length sequence |
|---|---|---|
| 7B3 FL LC | 100 | EILLTQSPAIIAASPGEKVTITCSASSRVSYMNWYQQKPGSSPKIWVYGIS NLASGVPARFSGSGSGTSFSFTINSMEAEDVATYYCQQRSSHPLTFGAGTK LELKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| 8E11 FL LC | 101 | EILLTQSPAIIAASPGEKVTITCSASSSVSYMNWYQQKPGSSPKLWIYGIS NLASGVPARFSGSGSGTSFSFTINSMEAEDVATYYCQQRSSHPLTFGAGTK LELKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| 6E1 FL LC | 102 | DIKMTQSPSSMYASLGERVTITCKASQDIYSYLSWFQQKPGRSPKTLIYRA NRLVDGVPSRFSGSGSGQDFSLTISSLDYEDMGIYYCLHYDEFPLTFGTGT KLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSENRGEC |
| 1D4 FL LC | 103 | DIKMTQSPSSMYASLGERVTITCKASQDINSYLSWFQQKPGKSPKTLIYRA NRLVDGVPSRFSGSGSGQDYSLTISSLEYEDVGIYYCLQYDEFPLTFGAGT KLELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| 8E8 FL LC | 104 | DIQMTQSPASLSVSVGETATITCRASENIYSHLAWYQQKQGKSPQLLVYAA TNLADGVPSRFSGSGSGTQYSLKINSLQSEDFGSYYCQHFWGTPWTFGGGT KLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| h7B3 FL LC | 105 | DIQLTQSPSSLSASVGDRVTITCSASSRVSYMNWYQQKPGKSPKIWVYGIS NLASGVPSRFSGSGSGTDFTFTISSLQPEDIATYYCQQRSSHPLTFGGGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| h8E11 FL LC | 106 | EIVLTQSPATLSLSPGERATLSCSASSSVSYMNWYQQKPGQSPRLWIYGIS NLASGVPARFSGSGSGTDFTLTISSLEPEDFAVYYCQQRSSHPLTFGGGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| h6E1 FL LC | 107 | DIQMTQSPSSLSASVGDRVTITCKASQDIYSYLSWFQQKPGKSPKTLIYRA NRLVDGVPSRFSGSGSGQDFTLTISSLQPEDFATYYCLHYDEFPLTFGGGT KVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| h1D4 FL LC | 108 | DIQMTQSPSSLSASVGDRVTITCKASQDINSYLSWFQQKPGKSPKTLIYRA NRLVDGVPSRFSGSGSGQDYTFTISSLQPEDIATYYCLQYDEFPLTFGGGT KVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| h8E8 FL LC | 109 | DIQMTQSPSSLSASVGDRVTITCRASENIYSHLAWYQQKPGKSPKLLVYAA TNLADGVPSRFSGSGSGTDYTLTISSLQPEDFATYYCQHFWGTPWTFGGGT KVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| h7B3 (E+) FL HC (WT FC) K- | 160 | EVQLVESGGGLVQPGGSLRLSCAASGFTFSTYGFHWVRQAPGKGLEWVAYI SSNSGTIDYADTVKGRFTISRDNAKNSLYLQMNSLRAEDTAVYYCARQGYG FDNWGQGTTVTVSSASTKGPSVFPLAPSSKSTSGGTAALGCLVKDYFPEPV TVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSK LTVDKSRWQQGNVFSCSVMHEALHNHYTQKSLSLSPG |

TABLE 12-continued

Full length sequences of selected non-humanized and humanized anti-ULBP6 antibodies

| Antibody Chain | SEQ ID NO: | Full length sequence |
|---|---|---|
| h8E11 (E+) FL HC (WT FC) K- | 161 | EVQLVESGGGLVQPGGSLRLSCAASGFTFRTYGMHWVRQAPGKGLEWVAYI<br>SSGSGTIDYADTVKGRFTISRDNAKNSLYLQMNSLRAEDTAVYYCTRQTGA<br>MDYWGQGTLVTVSSASTKGPSVFPLAPSSKSTSGGTAALGCLVKDYFPEPV<br>TVSWNSGALTSGVHTFPAVLQSSGLYSLSSVVTVPSSSLGTQTYICNVNHK<br>PSNTKVDKKVEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSK<br>LTVDKSRWQQGNVFSCSVMHEALHNHYTQKSLSLSPG |

NOTE: Variable domains are underlined; CDRs are in bold.

TABLE 13

Full length nucleic acid sequences of selected humanized anti-ULBP6 antibodies

| Antibody Chain | SEQ ID NO: | Full length nucleic acid sequence |
|---|---|---|
| h7B3 (E+) FL HC (WT FC) | 110 | GAGGTGCAGCTGGTGGAGTCTGGGGGAGGCTTGGTACAGCCTGGAGGGTCC<br>CTGAGACTCTCCTGTGCAGCCTCTGGATTCACCTTCAGTACCTATGGCTTC<br>CACTGGGTCCGCCAGGCCCCAGGCAAGGGGCTGGAGTGGGTTGCCTACATT<br>AGTAGTAACAGCGGCACCATAGACTACGCAGACACCGTGAAGGGCCGATTC<br>ACCATCTCCAGAGACAACGCCAAGAACAGCCTGTACCTGCAAATGAACAGC<br>CTGAGAGCCGAGGACACGGCTGTGTATTACTGTGCGAGACAGGGCTACGGT<br>TTCGACAACTGGGGCCAAGGGACCACGGTGACCGTCTCCTCAgcctccacc<br>aagggcccatcggtcttccccctggcaccctcctccaagagcacctctggg<br>ggcacagcggccctgggctgcctggtcaaggactacttccccgaaccagtg<br>acggtgtcgtggaactcaggcgccctgaccagcggcgtgcacaccttcccg<br>gctgtcctacagtcctcaggactctactccctcagcagcgtggtgactgtg<br>ccctctagcagcttgggcacccagacctacatctgcaacgtgaatcacaag<br>cccagcaacaccaaggggacaagaaagttgagcccaaatcttgtgacaaa<br>actcacacatgcccaccgtgcccagcacctgaactcctggggggaccgtca<br>gtcttcctcttccccccaaaacccaaggacaccctcatgatctcccggacc<br>cctgaggtcacatgcgtggtggtggacgtgagccacgaagaccctgaggtc<br>aagttcaactggtacgtggacggcgtggaggtgcataatgccaagacaaag<br>ccgcgggaggagcagtacaatagcacgtaccgggtggtcagcgtcctcacc<br>gtcctgcaccaggactggctgaatggcaaggagtacaagtgcaaggtctcc<br>aacaaagccctcccagcccccatcgagaaaaccatctccaaagccaaaggg<br>cagccccgagaaccacaggtgtacaccctgcccccatcccgggatgagctg<br>accaagaaccaggtcagcctgacttgcctggtcaaaggcttctatccagc<br>gacatcgccgtggagtgggagagcaatgggcagccggagaacaactacaag<br>accacgcctcccgtgctggactccgacggctccttcttcctctacagcaag<br>ctcaccgtggacaagagcaggtggcagcaggggaacgtcttctcatgctcc<br>gtgatgcatgaggctctgcacaaccactacacgcagaagagcctctccctg<br>tctccgggtaagtaa |
| h8E11 (E+) FL HC (WT FC) | 111 | GAGGTGCAGCTGGTGGAGTCTGGGGGAGGCTTGGTACAGCCTGGAGGGTCC<br>CTGAGACTCTCCTGTGCAGCCTCTGGATTCACCTTCAGAACCTATGGCATG<br>CACTGGGTCCGCCAGGCTCCAGGCAAGGGGCTGGAGTGGGTTGCCTACATT<br>AGTAGTGGCAGCGGCACCATAGACTACGCAGACACCGTGAAGGGCCGATTC<br>ACCATCTCCAGAGACAACGCCAAGAACAGCCTGTACCTGCAAATGAACAGC<br>CTGAGAGCCGAGGACACGGCTGTGTATTACTGTACCAGACAGACCGGCGCC<br>ATGGACTACTGGGGCCAAGGGACCCTGGTCACCGTCTCCTCAgcctccacc<br>aagggcccatcggtcttccccctggcaccctcctccaagagcacctctggg<br>ggcacagcggccctgggctgcctggtcaaggactacttccccgaaccagtg<br>acggtgtcgtggaactcaggcgccctgaccagcggcgtgcacaccttcccg<br>gctgtcctacagtcctcaggactctactccctcagcagcgtggtgactgtg<br>ccctctagcagcttgggcacccagacctacatctgcaacgtgaatcacaag<br>cccagcaacaccaaggtggacaagaaagttgagcccaaatcttgtgacaaa<br>actcacacatgcccaccgtgcccagcacctgaactcctggggggaccgtca<br>gtcttcctcttccccccaaaacccaaggacaccctcatgatctcccggacc<br>cctgaggtcacatgcgtggtggtggacgtgagccacgaagaccctgaggtc<br>aagttcaactggtacgtggacggcgtggaggtgcataatgccaagacaaag<br>ccgcgggaggagcagtacaatagcacgtaccgggtggtcagcgtcctcacc<br>gtcctgcaccaggactggctgaatggcaaggagtacaagtgcaaggtctcc<br>aacaaagccctcccagcccccatcgagaaaaccatctccaaagccaaaggg<br>cagccccgagaaccacaggtgtacaccctgcccccatcccgggatgagctg |

TABLE 13-continued

Full length nucleic acid sequences of selected humanized anti-ULBP6 antibodies

| Antibody Chain | SEQ ID NO: | Full length nucleic acid sequence |
|---|---|---|
| | | accaagaaccaggtcagcctgacttgcctggtcaaaggcttctatcccagc gacatcgccgtggagtgggagagcaatgggcagccggagaacaactacaag accacgcctcccgtgctggactccgacggctccttcttcctctacagcaag ctcaccgtggacaagagcaggtggcagcaggggaacgtcttctcatgctcc gtgatgcatgaggctctgcacaaccactacacgcagaagagcctctccctg tctccgggtaagtaa |
| h1D4 (E+) FL HC (WT FC) | 112 | GAGATCCAGCTGGTGCAATCTGGGAGCGAGTTGAAGAAGCCTGGGGCCAGC GTGAAGGTGTCCTGCAAGGCTTCTGGATACACCTTCACTGAGTATCCCATC CACTGGGTGAGACAGGCCCCTGGACAGGGGTTCGAGTGGATGGGAATGATC TACACCGACACTGGGGAGCCAACGCACGCCGAGGAGTTCAAGGGACGGTTT GTGTTCTCCTTGGACACCTCTGTGAGCACGGCATATCTGCAGATCAGCAGC CTAAAGGCCGAGGACACTGCCGTGTATTTCTGTGTGAGATGGTACGACGGC AGCAGCTACATCATGGACTACTGGGGCCAAGGGACCACCGTCACCGTCTCC TCAgcctccaccaagggcccatcggtcttccccctggcaccctcctccaag agcacctctgggggcacagcggccctgggctgcctggtcaaggactacttc cccgaaccagtgacggtgtcgtggaactcaggcgccctgaccagcggcgtg cacaccttcccggctgtcctacagtcctcaggactctactccctcagcagc gtggtgactgtgccctctagcagcttgggcacccagacctacatctgcaac gtgaatcacaagcccagcaacaccaaggtggacaagaaagttgagcccaaa tcttgtgacaaaactcacacatgcccaccgtgcccagcacctgaactcctg ggggg accgtcagtcttcctcttccccccaaaacccaaggacaccctcatg atctcccggacccctgaggtcacatgcgtggtggtggacgtgagccacgaa gaccctgaggtcaagttcaactggtacgtggacggcgtggaggtgcataat gccaagacaaagccgcgggaggagcagtacaatagcacgtaccgggtggtc agcgtcctcaccgtcctgcaccaggactggctgaatggcaaggagtacaag tgcaaggtctccaacaaagcccctcccagccccatcgagaaaaccatctcc aaagccaaagggcagccccgagaaccacaggtgtacaccctgcccccatcc cgggatgagctgaccaagaaccaggtcagcctgacttgcctggtcaaaggc ttctatcccagcgacatcgccgtggagtgggagagcaatgggcagccggag aacaactacaagaccacgcctcccgtgctggactccgacggctccttcttc ctctacagcaagctcaccgtggacaagagcaggtggcagcaggggaacgtc ttctcatgctccgtgatgcatgaggctctgcacaaccactacacgcagaag agcctctccctgtctccgggtaagtaa |
| h6E1 (E+) FL HC (WT FC) | 113 | GAGGTGCAGCTGGTGCAGAGCGGGGCTGAGGTGAAGAAGCCTGGGGCCTCA GTGAAGGTCTCCTGCAAGGCTTCTGGATACACCTTCACCAACTACTGGATG CACTGGATGAGACAGGCCCCTGGACAAGGGCTTGAGTGGCTGGGACGGATC CACCCTAGCGACAGCGACACAAACTATAACCAGAAGTTTAAGGGCAGAGCC ACCCTGACCGTGGACAAGTCCATCAGCACCGCCTACATGGAGCTGAGCAGA CTGAGATCTGACGACACCGCCGTGTATTACTGTGCGATCGAGGGCACCGGC AAGGGCTACTTCGATGTGTGGGGCAGAGGCACCCTGGTCACTGTCTCCTCA gcctccaccaagggcccatcggtcttccccctggcaccctcctccaagagc acctctgggggcacagcggccctgggctgcctggtcaaggactacttcccc gaaccagtgacggtgtcgtggaactcaggcgccctgaccagcggcgtgcac accttcccggctgtcctacagtcctcaggactctactccctcagcagcgtg gtgactgtgccctctagcagcttgggcacccagacctacatctgcaacgtg aatcacaagcccagcaacaccaaggtggacaagaaagttgagcccaaatct tgtgacaaaactcacacatgcccaccgtgcccagcacctgaactcctgggg ggaccgtcagtcttcctcttccccccaaaacccaaggacaccctcatgatc tcccggacccctgaggtcacatgcgtggtggtggacgtgagccacgaagac cctgaggtcaagttcaactggtacgtggacggcgtggaggtgcataatgcc aagacaaagccgcgggaggagcagtacaatagcacgtaccgggtggtcagc gtcctcaccgtcctgcaccaggactggctgaatggcaaggagtacaagtgc aaggtctccaacaaagcccctcccagccccatcgagaaaaccatctccaaa gccaaagggcagccccgagaaccacaggtgtacaccctgcccccatccgg gatgagctgaccaagaaccaggtcagcctgacttgcctggtcaaaggcttc tatcccagcgacatcgccgtggagtgggagagcaatgggcagccggagaac aactacaagaccacgcctcccgtgctggactccgacggctccttcttcctc tacagcaagctcaccgtggacaagagcaggtggcagcaggggaacgtcttc tcatgctccgtgatgcatgaggctctgcacaaccactacacgcagaagagc ctctccctgtctccgggtaagtaa |
| h7B3 FL LC | 114 | GACATCCAGCTGACCCAGTCTCCAAGCAGCCTGAGCGCATCTGTGGGAGAC AGAGTCACCATCACTTGCAGCGCGAGTAGCAGAGTGAGCTATATGAATTGG TATCAGCAGAAACCAGGGAAGAGCCCTAAGATCTGGGTGTACGGCATCTCC AATTTGGCCAGCGGGGTCCCAAGCAGGTTCAGTGGAAGTGGATCTGGGACA GACTTTACCTTCACCATCAGCAGCCTGCAGCCCGAAGATATCGCAACATAT TACTGTCAACAGAGAAGCAGCCACCCTCTCACGTTCGGCGGCGGGACCAAG GTGGAGATCAAAcgaactgtggctgcaccatctgtcttcatcttcccgcca tctgatgagcagttgaaatctggaactgcttctgttgtgtgcctgctgaat aacttctatcccagagaggccaaagtacagtggaaggtggataacgccctc caatcgggtaactcccaggagagtgtcacagagcaggacagcaaggacagc |

TABLE 13-continued

Full length nucleic acid sequences of selected humanized anti-ULBP6 antibodies

| Antibody Chain | SEQ ID NO: | Full length nucleic acid sequence |
|---|---|---|
| | | acctacagcctcagcagcaccctgacgctgagcaaagcagactacgagaaa<br>cacaaagtctacgcctgcgaagtcacccatcagggcctgagctcgcccgtc<br>acaaagagcttcaacaggggagagtgttaa |
| h8E11 FL LC | 115 | GAAATTGTGTTGACACAGTCTCCAGCCACCCTGAGCCTGTCTCCAGGGGAA<br>AGAGCCACCCTGAGCTGCAGCGCCAGTAGCAGTGTTAGCTACATGAACTGG<br>TACCAACAGAAACCTGGCCAGAGCCCCAGACTCTGGATCTATGGCATCTCC<br>AACCTGGCCAGCGGCGTGCCAGCCAGGTTCAGTGGCAGTGGGTCTGGGACA<br>GACTTCACCCTGACCATCAGCAGCCTGGAGCCCGAAGATTTCGCAGTGTAT<br>TACTGTCAGCAGCGTAGCAGCCACCCTCTCACGTTCGGCGGCGGGACCAAG<br>GTGGAGATCAAAcgaactgtggctgcaccatctgtcttcatcttcccgcca<br>tctgatgagcagttgaaatctggaactgcttctgttgtgtgcctgctgaat<br>aacttctatcccagagaggccaaagtacagtggaaggtggataacgccctc<br>caatcgggtaactcccaggagagtgtcacagagcaggacagcaaggacagc<br>acctacagcctcagcagcaccctgacgctgagcaaagcagactacgagaaa<br>cacaaagtctacgcctgcgaagtcacccatcagggcctgagctcgcccgtc<br>acaaagagcttcaacaggggagagtgttaa |
| h1D4 FL LC | 116 | GACATCCAGATGACCCAGTCTCCATCCTCCCTGAGCGCATCTGTGGGAGAC<br>AGAGTCACCATCACTTGCAAGGCGAGTCAGGACATTAACAGCTATTTAAGC<br>TGGTTCCAGCAGAAACCAGGGAAAAGCCCTAAGACCCTGATCTACAGAGCA<br>AACAGATTGGTGGACGGGGTCCCATCAAGGTTCAGTGGAAGTGGATCTGGG<br>CAGGATTACACCTTCACCATCAGCAGCCTGCAGCCCGAAGATATCGCCACC<br>TATTACTGTCTGCAGTATGATGAGTTCCCTCTCACGTTCGGCGGCGGTACC<br>AAGGTGGAGATCAAAcgaactgtggctgcaccatctgtcttcatcttcccg<br>ccatctgatgagcagttgaaatctggaactgcttctgttgtgtgcctgctg<br>aataacttctatcccagagaggccaaagtacagtggaaggtggataacgcc<br>ctccaatcgggtaactcccaggagagtgtcacagagcaggacagcaaggac<br>agcacctacagcctcagcagcaccctgacgctgagcaaagcagactacgag<br>aaacacaaagtctacgcctgcgaagtcacccatcagggcctgagctcgccc<br>gtcacaaagagcttcaacaggggagagtgttaa |
| h6E1 FL LC | 117 | GACATCCAGATGACCCAGTCTCCATCCTCACTGAGCGCATCTGTGGGAGAC<br>AGAGTCACCATCACTTGTAAGGCGAGTCAGGACATTTACAGCTATTTAAGC<br>TGGTTTCAGCAGAAACCAGGGAAGAGCCCTAAGACCCTGATCTATAGAGCA<br>AACAGATTGGTGGACGGGGTCCCATCAAGGTTCAGCGGCAGTGGATCTGGG<br>CAGGATTTCACCCTCACCATCAGCAGCCTGCAGCCCGAAGATTTCGCCACC<br>TATTACTGCCTGCACTATGACGAGTTCCCTCTCACGTTCGGCGGCGGTACC<br>AAGGTGGAGATCAAGcgaactgtggctgcaccatctgtcttcatcttcccg<br>ccatctgatgagcagttgaaatctggaactgcttctgttgtgcctgctg<br>aataacttctatcccagagaggccaaagtacagtggaaggtggataacgcc<br>ctccaatcgggtaactcccaggagagtgtcacagagcaggacagcaaggac<br>agcacctacagcctcagcagcaccctgacgctgagcaaagcagactacgag<br>aaacacaaagtctacgcctgcgaagtcacccatcagggcctgagctcgccc<br>gtcacaaagagcttcaacaggggagagtgttaa |

Note: Variable regions are in uppercase; constant regions are in lowercase.

Example 7: Characterization of Humanized Candidate Antibodies

A. SPR Analysis of Humanized Antibodies

To determine the binding affinity of recombinant humanized h7B3, h8E11, h1D4 and h6E1 (blocking antibodies) and h8E8 (non-blocking antibodies) to human and cynomolgus soluble ULBPs, SPR measurements with a BIACORE 8K instrument was performed as described below.

Materials and Methods

BIACORE was performed at 37° C. with various human and Cyno NKG2D ligands, including soluble hULBP2, hULBP6_01, hULBP6_02, cULBP5, and cULBP2/6 (ENSEMBL v99). Briefly, 0.5 µg/ml of recombinant h7B3, h8E11, h1D4, and h6E1 in HBS-P buffer (0.01 M HEPES, pH 7.4, 0.15M NaCl, 0.005% surfactant P20) was applied to a CYTIVA sensor chip Protein A at 30 µL/min flow rate to achieve ~50 response units in a second flow cell (FC2). A first flow cell (FC1) was kept as a reference. For kinetics measurements, 3-fold serial dilutions of hNKG2D and cNKG2Ds ligands in HBS-P buffer (0.01M HEPES pH 7.4, 0.15M NaCl, 0.005% surfactant P20) from high (10 nM or 50 nM) to low (0.01 nM or 0.07 nM) were injected (flow rate: 30 µL/min) at 37° C. The sensorgram was recorded and subject to reference and buffer subtraction before evaluation using BIACORE 8K Evaluation Software (version 1.1.1.7442). Association rates ($k_{on}$) and dissociation rates ($k_{off}$) were calculated using a simple one-to-one Langmuir binding model. The equilibrium dissociation constant (KD) was calculated as the ratio of $k_{off}/k_{on}$ summarized in Table 14.

Results

Humanized h7B3, h8E11, h1D4 and h6E1 showed tight binding to both the human and cynomolgus ULBPs (Table 14). h7B3 showed the greatest strength of binding, followed by h8E11, h1D4 then h6E1.

TABLE 14

Binding characteristics of humanized antibodies to human (h) and cyno (c) soluble ULBP proteins

| Clone | Analyte | Ka (1/Ms) | Kd (1/s) | KD (M) |
|---|---|---|---|---|
| h7B3 | cULBP2/6 | 1.44E+06 | 5.42E−04 | 3.77E−10 |
|  | cULBP5 | 5.54E+05 | 3.40E−03 | 6.13E−09 |
|  | hULBP2 | 7.53E+05 | 5.07E−04 | 6.73E−10 |
|  | hULBP6_01 | 1.45E+06 | 3.82E−04 | 2.63E−10 |
|  | hULBP6_02 | 1.48E+06 | 3.79E−04 | 2.55E−10 |
| h8E11 | cULBP2/6 | 3.96E+05 | 4.50E−03 | 1.14E−08 |
|  | cULBP5 | 1.39E+05 | 3.33E−03 | 2.39E−08 |
|  | hULBP2 | 8.19E+05 | 5.42E−04 | 6.62E−10 |
|  | hULBP6_01 | 1.48E+06 | 4.92E−04 | 3.31E−10 |
|  | hULBP6_02 | 1.20E+06 | 4.59E−04 | 3.83E−10 |
| h1D4 | cULBP2/6 | 8.84E+06 | 1.33E−03 | 1.51E−10 |
|  | cULBP5 | 1.43E+06 | 1.05E−03 | 7.35E−10 |
|  | hULBP2 | 2.31E+06 | 1.48E−03 | 6.42E−10 |
|  | hULBP6_01 | 2.69E+06 | 1.14E−03 | 4.22E−10 |
|  | hULBP6_02 | 1.64E+06 | 2.15E−03 | 1.31E−09 |
| h6E1 | cULBP2/6 | 2.77E+07 | 1.15E−02 | 4.15E−10 |
|  | cULBP5 | 6.10E+06 | 9.22E−03 | 1.51E−09 |
|  | hULBP2 | 3.62E+06 | 3.86E−02 | 1.07E−08 |
|  | hULBP6_01 | 4.70E+06 | 2.46E−02 | 5.24E−09 |
|  | hULBP6_02 | 7.07E+06 | 6.64E−03 | 9.39E−10 |

B. Blocking ELISA of Humanized Clones

To determine and compare the blocking efficacy of humanized h7B3, h8E11, h1D4 and h6E1 between human sULBP6 and hNKG2D, a blocking ELISA was performed.

Materials and Methods

A 96 well plate was coated with 100 μl 1 ug/ml of hNKG2D per well and incubated at 400 overnight. The plate was then blocked using a 300 μl/well blocking buffer (1× PBS, 1% BSA, and 0.05% Tween-20) at room temperature for 1 h. Plate was then washed with a washing buffer (1× PBS and 0.05% Tween-20). Next, each antibody was titrated 3-fold from the initial concentration of 300 nM to a final concentration of 0.005 nM and each titration was mixed with 1 μg/ml (precalculated EC80) of biotinylated human sULBP6 for 1 h at room temperature. The mixture was incubated on the coated hNKG2D plate for 15 min at room temperature. The plate was washed and the binding of biotinylated human sULBP6 to hNKG2D was detected using 100 μl/well of streptavidin-HRP (1:10,000 dilution) for 1 h at room temperature followed by washing and addition of 100 μl of TMB per well for 15 min at room temperature. The absorbance was measured at 450 nm.

Results h7B3 and h8E11 were shown to be the strongest blocking antibodies of the hNKG2D-hULBP6_01 interaction, with $IC_{50}$ values of 4.47 nM and 4.32 nM, respectfully and the hNKG2D-hULBP6_02 interaction, with $D_{50}$ values of 1.52 nM and 1.59 nM, respectfully (Table 15).

TABLE 15

Binding affinity of humanized anti-ULBP6 antibodies

| | BIACORE Binding to human proteins | | | | BIACORE Binding to Cyno proteins | |
|---|---|---|---|---|---|---|
| Antibody clone | hULBP6_01 $K_D$ (nM) | hULBP6_02 $K_D$ (nM) | hULBP2 $K_D$ (nM) | hULBP5 $K_D$ (nM) | Cyno-cULBP2/6 $K_D$ (nM) | Cyno-cULBP5 $K_D$ (nM) |
| Humanized 7B3 (h7B3) (E-) | 0.22 ± 0.02 | 0.2 ± 0.03 | 0.54 ± 0.08 | 2.39 ± 0.16 | 0.48 ± 0.03 | 7.67 ± 1.68 |
| Humanized 8E11 (h8E11) (E-) | 0.27 ± 0.03 | 0.28 ± 0.05 | 0.5 ± 0.09 | 1.76 ± 0.23 | 2.06 ± 0.11 | 23.13 ± 3.83 |
| Humanized 1D4 (h1D4) (E-) | 0.41 ± 0.04 | 1.06 ± 0.14 | 0.47 ± 0.09 | 8.88 ± 0.38 | 0.99 ± 0.03 | 0.63 ± 0.09 |
| Humanized 6E1 (h6E1) (E-) | 4.38 ± 0.43 | 0.68 ± 0.14 | 8.91 ± 0.9 | 8.70 ± 0.68 | 1.76 ± 0.06 | 1.03 ± 0.26 |

| | Epitope bins | Octet Blocking | Blocking ELISA $IC_{50}$ (nM), hNKG2D/ hULBP6_01 | Blocking ELISA $IC_{50}$ (nM), hNKG2D/ hULBP6_02 |
|---|---|---|---|---|
| Humanized 7B3 (h7B3) (E-) | A | Yes | 4.48 | 0.028 |
| Humanized 8E11 (h8E11) (E-) | A | Yes | 5.06 | 0.035 |
| Humanized 1D4 (h1D4) (E-) | B | Yes | 7.70 | 0.265 |
| Humanized 6E1 (h6E1) (E-) | B | Yes | 10.25 | 0.103 |

C. Epitope Binning

To determine whether the humanized antibodies bind to the same or different epitopes on human sULBP6, an epitope binning experiment was done using Octet.

Materials and Methods

100 μM of each antibody was diluted in 300 μl of 1×PBST buffer (1× PBS and 0.05% Tween-20) and pipetted in different wells of the Octet plate. An anti-Human IgG Fc Capture (AHC) biosensor in 1× PBST was immersed in a first humanized antibody (e.g., h7B3) to capture it for 150-300 seconds. The biosensor was then immersed in 1× PBST buffer for 60 seconds to reach a stable baseline, followed by immersion of the same biosensor in human sULBP6 for another 150-300 seconds to facilitate the interaction between the first humanized antibody and sULBP6. The biosensor was then immersed in a second antibody (e.g., h8E11) to determine blocking of the second antibody to sULBP6 by the first antibody. This was repeated for each combination of two antibodies selected from h7B3, h8E8, h8E11, h1D4, and h6E1.

Results

The four blocking antibodies can be grouped into two distinct epitope bins (Table 16). h7B3 shares an overlapping epitope with h8E11, and h1D4 shares an overlapping epitope with h6E1. h8E8 does not share an overlapping epitope with any other tested antibody.

TABLE 16

Summary of epitope binning of humanized anti-ULBP6 antibodies

| Humanized Ab | h7B3 | h8E8 | h8E11 | h1D4 | h6E1 |
|---|---|---|---|---|---|
| h7B3 | O | N | O | N | N |
| h8E8 | N | O | N | N | N |
| h8E11 | O | N | O | N | N |
| h1D4 | N | N | N | O | O |
| h6E1 | N | N | N | O | O |

*O = Overlapping Epitopes; N = No Overlapping Epitopes

D. Characterization of Humanized Anti-ULBP6 Antibodies

To determine binding of h7B3, h8E11, h1D4, and h6E1 to surface ULBP6 expressed on tumor cells, flow cytometry analysis was performed. Binding of humanized antibodies to cell surface ULBP6 in PANC02.13 cells (which express ULPB6_02) and COV644 cells (which express ULPB6_01) was determined as summarized in Table 16. Blocking of NKG2D-Fc binding to cell surface ULBP6 on COV644 cells (which express ULBP6_01) by the humanized antibodies was determined as summarized in Table 17.

Materials/Methods

Binding of humanized anti-ULBP6 antibodies to cell surface ULBP6 on cancer cells with endogenous target expression was compared using a FACS assay. Cells were detached from the surface of culture flask using ACCUTASE cell detachment solution, stained with LIVE/DEAD staining dye and incubated with serially diluted antibodies h7B3, h8E11, h1M4 and h6E1 at a range of concentrations from 83.2 μM to 65 nM for 25 min at 4° C. Bound antibodies were detected with anti-hFc-APC antibody (BIOLEGEND Cat #40936) at 1:100 dilution. Binding of humanized anti-ULBP6 antibodies to cell surface ULBP6 was analyzed by FACS using the Cytoflex LX instrument. Geometric mean was determined and used for $EC_{50}$ calculations.

To determine the blocking of NKG2D-mFc binding to ULBP6, COV644 cells were incubated with hNKG2D-mFc either alone or with serially diluted anti-ULBP6 blocking antibodies selected from h7B3, h8E11, h1D4, and h6E1. Human NKG2D-mFc binding to surface ULBP6 was detected by a flow cytometry assay using an anti-mFc-APC antibody. The geometric mean was determined and $IC_{50}$ values were calculated respectively.

Results

Binding to cell surface ULBP6: h7B3, h8E11, h1D4, and h6E1 displayed $EC_{50}$ values of 1.97 nM (PANC02.13) and 1.93 nM (COV644), 1.28 nM (PANC02.13) and 1.29 nM (COV644), 0.72 nM (PANC02.13) and 1.4 nM (COV644), 0.44 nM (PANC02.13) and 0.36 nM (COV644), respectively, calculated as the average of two technical replicates, as described in Table 17.

Blocking NKG2D-Fc binding to COV644 cell surface ULBP6: h7B3, h8E11, h1D4, and h6E1 displayed $IC_{50}$ values of 0.17 nM, 0.11 nM, 0.22 nM, and 0.2 nM, respectively, as calculated as the average of two technical replicates as described in Table 17.

In conclusion, this example demonstrated the biochemical characterization of 4 humanized anti-ULBP6 antibodies that a) inhibit the interaction between soluble ULBP6 and NKG2D and b) bind to cell surface expressed ULBP6 on tumor cell lines.

TABLE 17

Binding of humanized anti-ULBP6 antibodies to cell surface ULBP6

| Antibody clone | Binding to cell surface ULBP6 | | Blocking NKG2D-Fc binding to COV644 cell surface ULBP6 Blocking $IC_{50}$ (nM) Average of 2 replicates |
|---|---|---|---|
| | PANC02.13 FACS binding $EC_{50}$ (nM) Average of 2 replicates | COV644 FACS binding $EC_{50}$ (nM) Average of 2 replicates | |
| Humanized 7B3 (h7B3) | 1.97 | 1.93 | 0.17 |
| Humanized 8E11 (h8E11) | 1.28 | 1.29 | 0.11 |
| Humanized 1D4 (h1D4) | 0.72 | 1.4 | 0.22 |
| Humanized 6E1 (h6E1) | 0.44 | 0.36 | 0.2 |

Example 8: Reversal of sULBP6-Induced NKG2D Blocking/Internalization by Anti-ULBP6 Antibodies Initial data (not shown) demonstrated that soluble ULBP6 competes with anti-NKG2D mAb for binding to NKG2D expressed by NKG2D expressing cells. In particular, the haplotype sULBP6_02 competed with the anti-NKG2D mAb for NKG2D binding more potently than sULBP6_01. These data suggested that soluble ULBP6 may a) impede the interaction of NKG2D and other NKG2DLs and/or b) induce the internalization of NKG2D on NKG2D-expressing cells.

To determine the effect of anti-ULBP6 antibodies on soluble ULBP6-suppressed NKG2D blocking/internalization, an NKG2D detection assay was performed on primed PBMCs from healthy donors. Soluble ULBP6_02 was used in the assay because it was shown to bind with the highest affinity to NKG2D (see Example 2) and more potently suppressed binding of anti-NKG2D mAb compared to ULBP6_01.

Materials and Methods

In this assay, primed PBMCs (36 hours with 20 ng/ml of IL-2 and IL-15 in X-VIVO 15 media) were incubated as follows: (a) without soluble ULBP6_02, (b) with soluble ULBP6_02 (50 nM) or (c) with soluble ULBP6_02 (50 nM) and anti-ULBP6 antibodies (h7B3(E–), h1D4(E–), h6E1 (E–), h8E11(E–) or isotype control antibody (isotype (E–)); each in assay media of RPMI with 10% FBS. After one hour of incubation, cells were collected and stained with anti-NKG2D-APC antibody to quantify surface expression of NKG2D on various PBMC populations. 69D.12_315 is a tool antibody that weakly binds to ULBP6. 8E8 is a control antibody that binds to but does not block the NKG2D ULBP6 interaction.

Results

Figure 2:
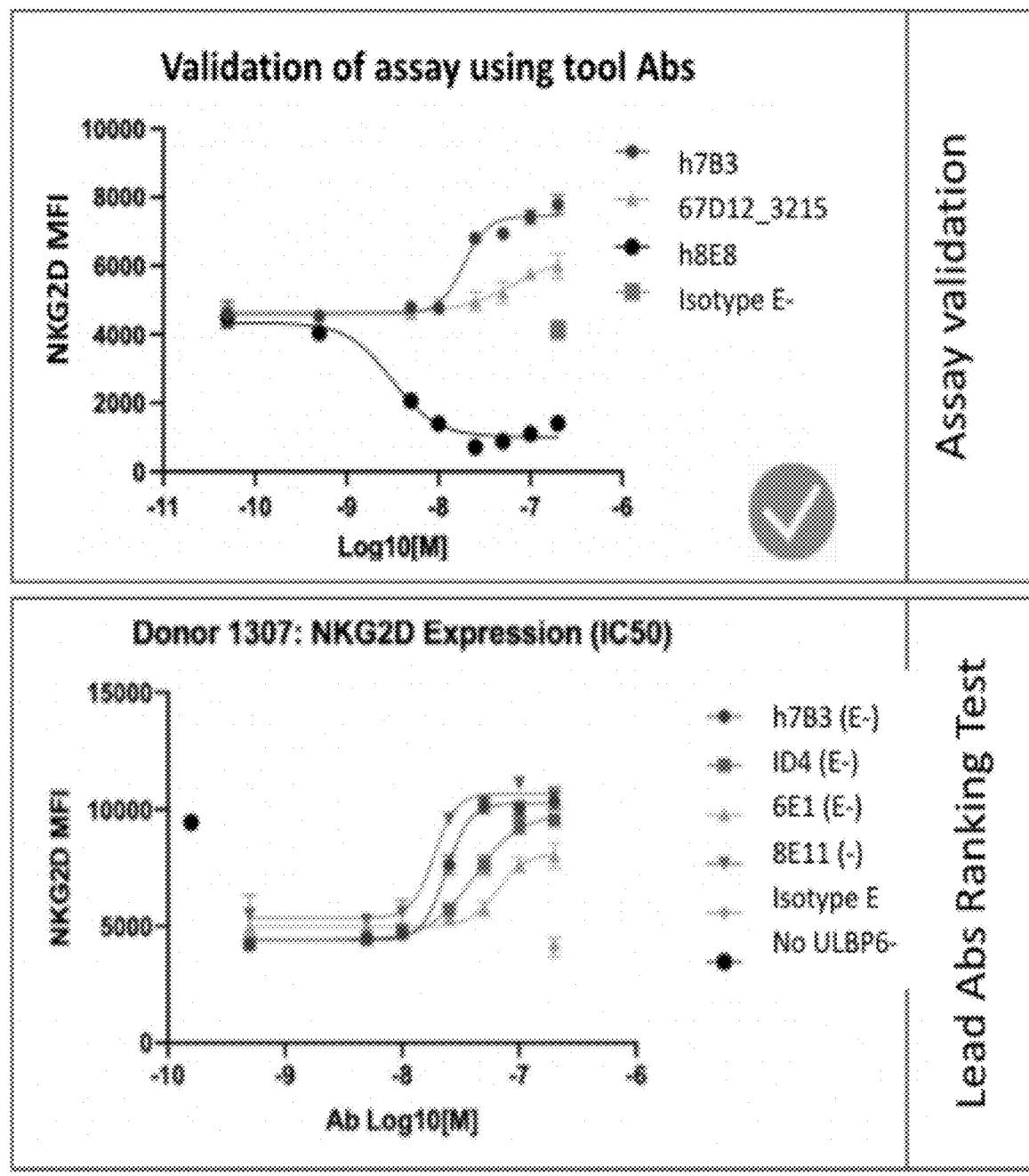
FIG. 2 depicts validation of the NKG2D detection assay with tool antibodies (top panel) and the ability of anti-ULBP6 antibodies (h7B3 (E−) and h8E11 (E−)) to reverse sULBP6_02-induced NKG2D blocking/internalization/downregulation in a NKG2D detection assay on primed PBMCs from a representative healthy donor compared to tool antibodies (1 D4 and 6E1) and isotype controls (bottom panel).

The assay was first validated with tool antibodies (FIG. 2, top panel). At high concentration, the isotype antibody did not change the NKG2D MFI in the presence of sULBP6. The weak binding 69D.12_315 control antibody showed modest reversal of sULBP6-induced NKG2D blocking/downregulation in a dose-dependent manner, whilst the higher affinity 7B3 antibody showed a stronger increase in NKG2D MFI. The non-blocking 8E8 antibody decreased detectable NKG2D MFI relative to the isotype control by stabilizing the interaction between ULBP6 and NKG2D.

The anti-ULBP6 antibodies tested reversed sULBP6-induced NKG2D blocking/downregulation in a dose dependent manner (FIG. 2, bottom panel). h7B3 (E–) and h8E11 (E–) showed reinvigoration of NKG2D at lower doses (left shift of curves) compared with other antibodies tested. These results are representative of data from PBMCs from 3 different healthy donors.

These data indicate that the humanized anti-ULBP6 antibodies, 7B3 and 8E11 in particular, neutralize the suppressive effects of soluble ULBP6, therefore allowing NKG2D to interact with other NKG2DLs.

Example 9: MICA-Mediated Immune Activation of PBMCs

The previous example showed that the humanized anti-ULBP6 antibodies reduced the suppressive effects of sULBP6 on cell surface NKG2D. By neutralizing sULBP6, the anti-ULBP6 antibodies may allow NKG2D activation through alternative NKG2DLs such as MICA.

A PBMC Interferon gamma (IFNg) secretion assay was performed to determine the effect of anti-ULBP6 antibodies on reinvigoration of MICA-mediated immune activation via neutralization of soluble ULBP6.

Materials and Methods

In this assay, primed PBMCs from healthy donors (36 hours in with 20 ng/ml of IL-2 and IL-15 in X-VIVO 15 media) were incubated on MICA-coated plate surface in the presence of soluble ULBP6_02 (50 nM) with anti-ULBP6 antibodies (h7B3(E–), h1D4(E–), h6E1(E–), and h8E11 (E–)) at a range of concentrations from 0.39 nM to 200 nM or with an isotype control antibody (Iso (E–)) added at 200 nM in assay media of RPMI with 10% FBS. After 24 hours of incubation, cell-free assay medium was collected and analyzed for IFNg levels using Luminex technology. 69D.12_315 is a tool antibody that weakly binds to ULBP6, and h8E8 is a control antibody that binds to ULBP6 but does not block its interaction with NKG2D.

Results

Figure 3A:
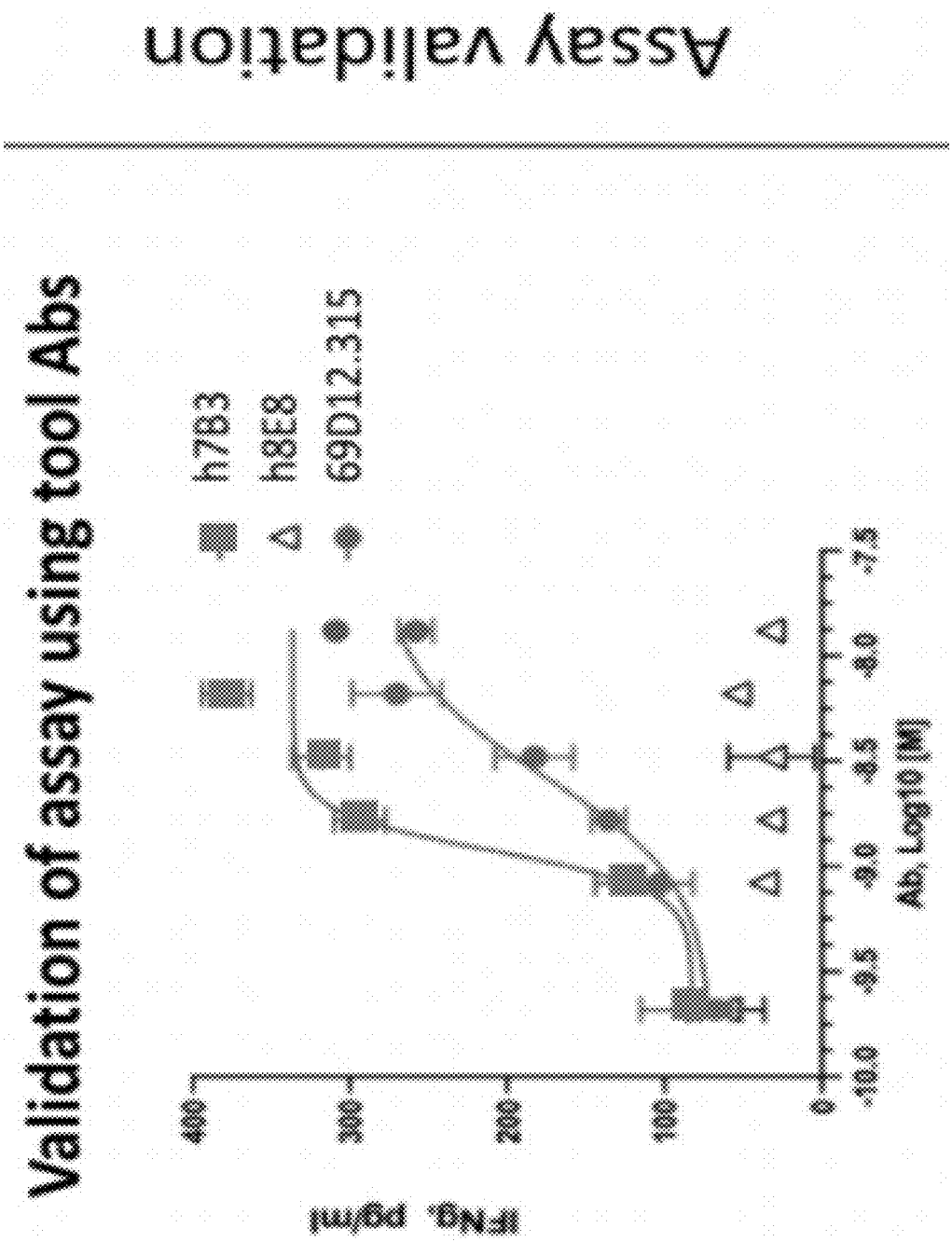
FIG. 3A depicts a plot of the validation of tool antibodies used (top two panels).
Figure 3C:
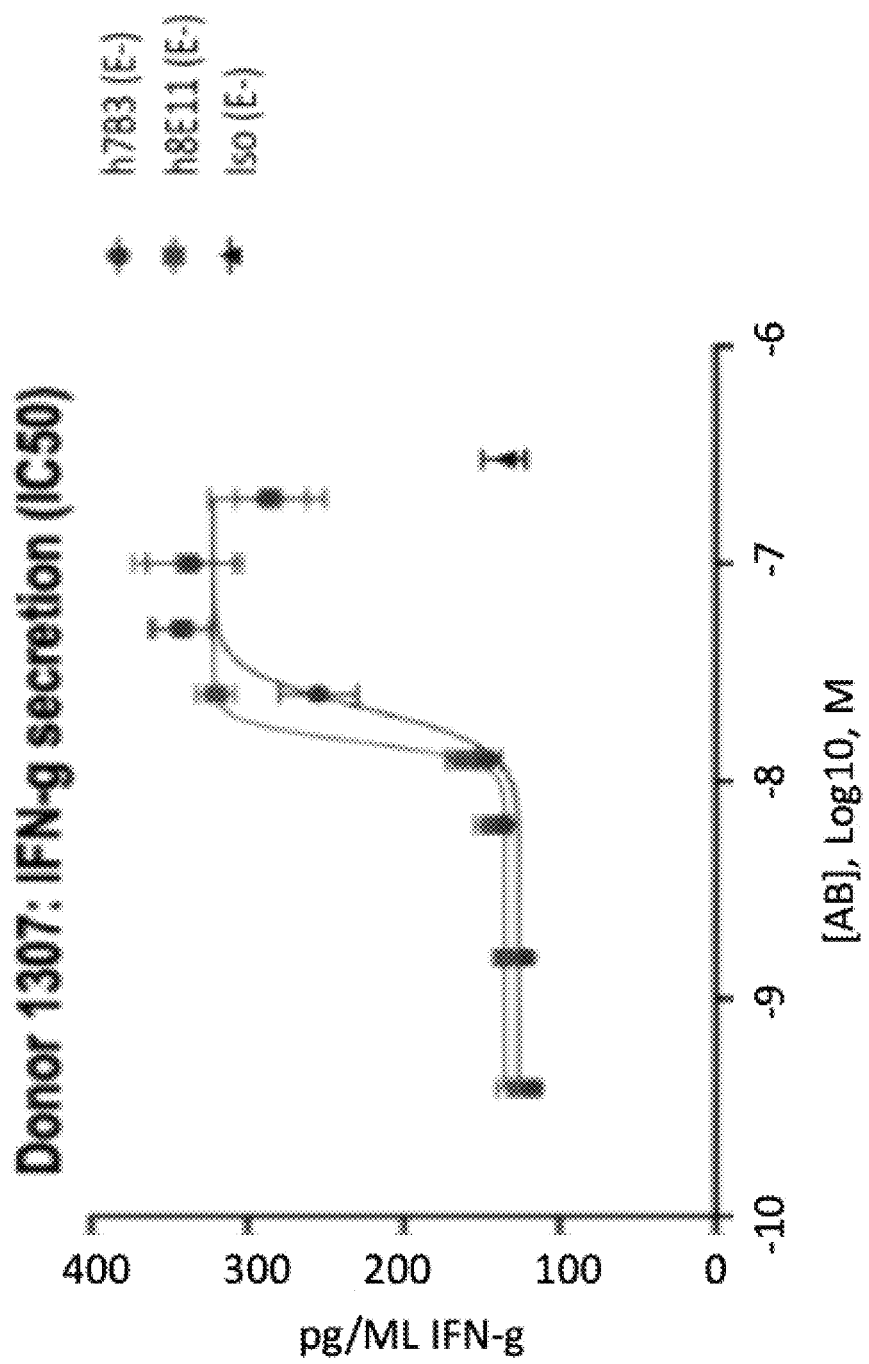
FIG. 3C depict the ability of anti-ULBP6 antibodies (h7B3, h8E11, and an isotype control) to block immune suppression conferred by sULBP6_02, as measured by levels of IFNg secretion in a plate-bound MICA assay.
Figure 3D:
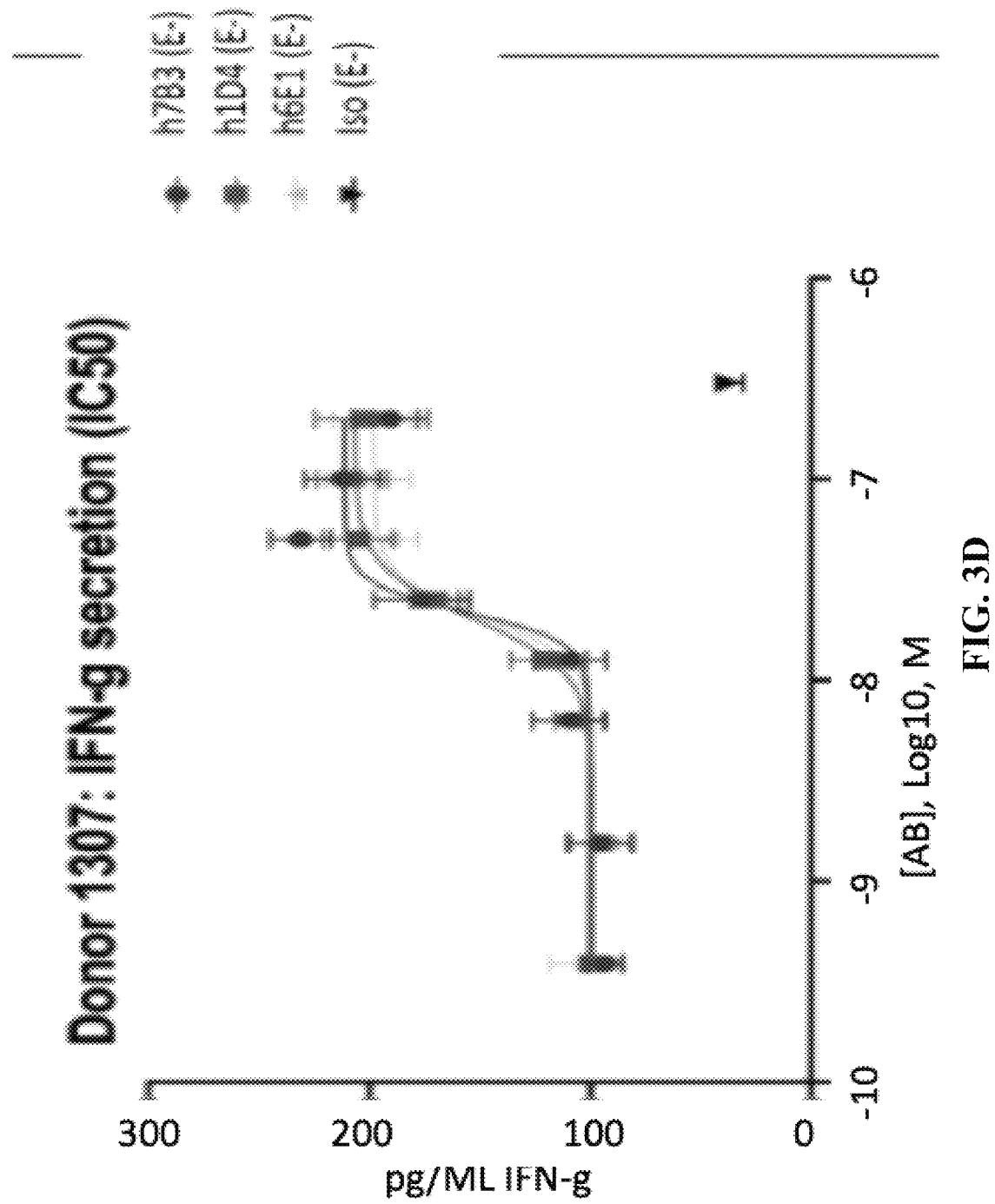
FIG. 3D depicts the ability of anti-ULBP6 antibodies (h7B3, h1D4, h6E1, and an isotype control) to block immune suppression conferred by sULBP6_02, as measured by levels of IFNg secretion in a plate-bound MICA assay.

The activation of PBMCs was measured via IFNg secretion. The assay was first validated with tool antibodies (FIG. 3A and FIG. 3B). The h8E8 antibody was not able to reverse the inhibitory effect of sULBP6 at all tested concentrations as expected. The h7B3 antibody reversed sULBP6-induced blocking of MICA-mediated activation of PBMC in a dose-dependent manner. The 69D.12_315 tool antibody showed a very modest contrast of sULBP6-induced blocking of MICA mediated activation of PBMC, which was well correlated with its weak blocking of and binding to ULBP6 (FIG. 3A and FIG. 3B). In summary, the sensitivity of the assay was able to distinguish between the non-blocking antibody h8E8 which had no effect, and the weakly ULBP6 binding antibody 69D12.315 which showed partial activity and the strongly ULBP6 binding and blocking antibody h7B3 which had the greatest effect (FIG. 3A and FIG. 3B). h7B3(E–), h1D4(E–), h6E1(E–), and h8E11(E–) showed comparable effects on blocking sULBP6 in the assay (FIG. 3C and FIG. 3D). These results from donor 1307 are representative of data from PBMC from 3 independent healthy donors.

Thus, anti-ULBP6 antibodies described herein may reinvigorate immune cell responses by neutralizing the suppressive effect of soluble ULBP6 on NKG2D responses to NKG2DLs.

Example 10: Synergy of NKG2D and FcgRIIIa Activation

In addition to the ULBP6-blocking effect to enhance NKG2D activation described herein, the anti-ULBP6 antibodies may also engage immune cells expressing Fc receptors, for example by binding to surface ULBP6. An IFNg secretion assay was performed to determine if NKG2D activation is synergistic with FcgRIIIa activation by measuring IFNg secretion from PBMCs.

Materials and Methods

For the IFNg secretion assay, PBMCs were pre-primed for 36 hours with IL-2 and IL-15 (20 ng/ml each) in X-VIVO 15. 96 well plates were coated overnight at 4° C. with anti-Lysozyme Fc +("Ab E+") or anti-Lysozyme Fc E– ("Ab E–") antibody with or without 2 copies of ULBP6_02 (referred to as ULBP6 in FIG. 4) fused to the molecule. These were plated in PBS to plate coat them to assay wells at concentrations ranging from 25 nM to 400 nM coating. This artificial fusion molecule in a plate-bound format. Can model cell surface NKG2D ligand(s), and can lead to activation of NKG2D. On the day of the assay, plates were washed, blocked with BSA and the pre-primed PBMCs were added to the plate for 24 h incubation at 37° C. and 5% $CO_2$. This assay was run in the absence of. sULBP6. Cell-free assay medium was collected and IFNg levels were determined using either a Luminex IFNg kit or an Invitrogen ELISA kit (Catalog #88-7316-88).

Results

Figure 4:
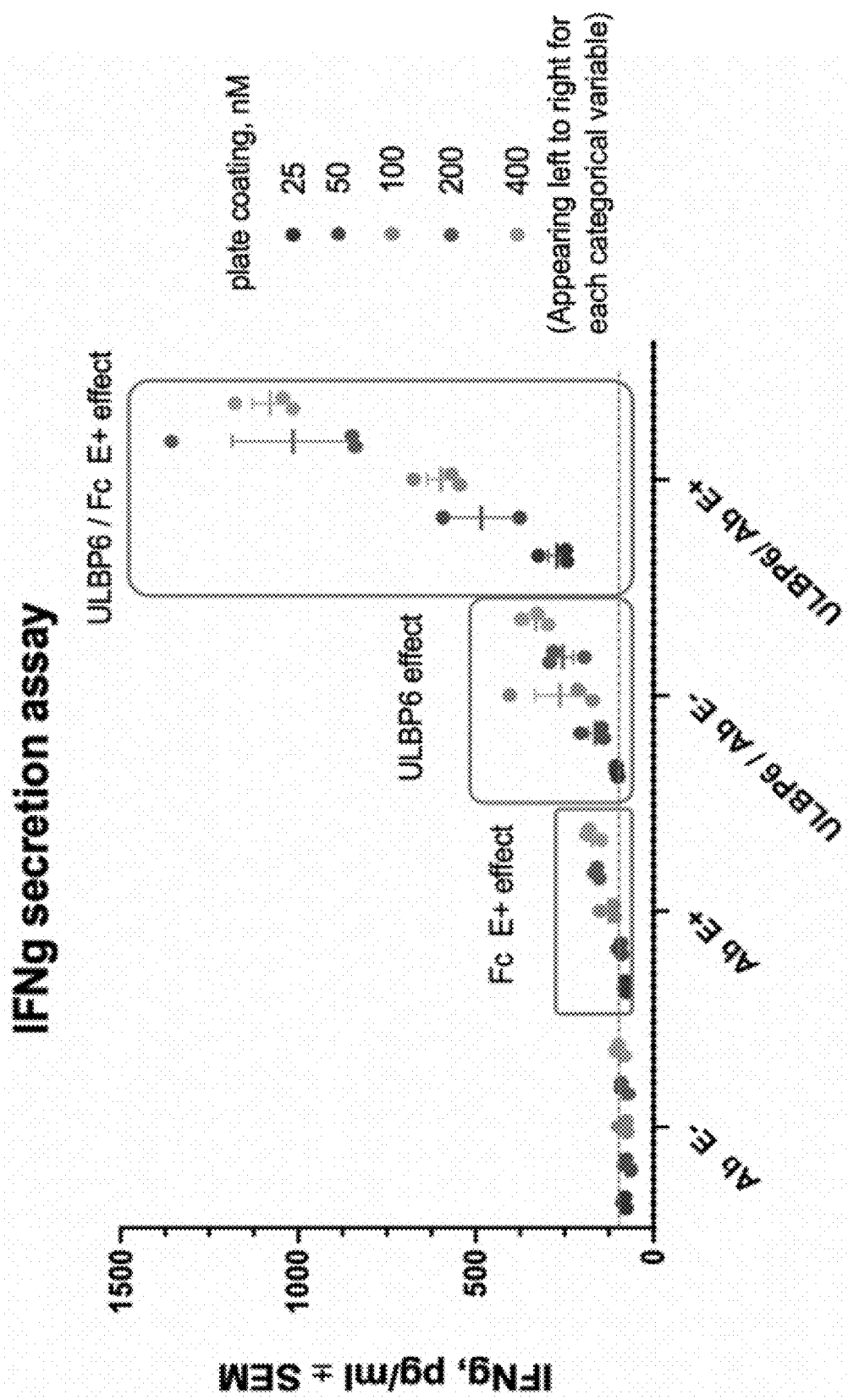
FIG. 4 depicts synergy of NKG2D stimulation and activation of FcgRIIIa assay through IFNg release from PBMCs through activation of NKG2D alone, FcgRIIIa alone, or both simultaneously.

Plate bound anti-Lysozyme antibody effectorless (E–) ("Ab E–") had no effect in regulating IFNg secretion at any concentration and was therefore considered as background (FIG. 4). Plate bound anti-Lysozyme antibody (E+) ("Ab E+") increased IFNg secretion over the background level in a dose-dependent manner (FIG. 4). NKG2D activation via ULBP6 fused to anti-Lysozyme antibody effectorless (E−) (in the graph ULBP6/Ab E−) increased IFNg secretion over the background level in a dose-dependent manner (FIG. 4). Combination of ULBP6 and Fc effector positive anti-Lysozyme antibody (E+) (ULBP6/Ab E+) resulted in a notably higher IFNg secretion compared to the effect of ULBP6/Ab E− or to anti-lysozyme antibody E+("Ab E+") separately. Synergy of NKG2D and FcgRIIIa activation was observed, as the simultaneous co-activation induced an IFNg release that was greater than the sum of the activation of NKG2D alone and the activation of FcgRIIIa alone. This mechanistic insight supports the use of anti-ULBP6 antibodies with an active Fc function if such synergy is desired.

Example 11: Immune Activation in Tumor Cell and PBMC Mixed Assay

To determine the ability of anti-ULBP6 antibodies to block soluble ULBP6-mediated inhibition of IFNg secretion, a tumor cell and PBMC mixed cell assay was performed. A comparison between the effect of E+ and E− versions of the antibodies was also determined.
A. Antibodies Neutralize sULBP6-Mediated Inhibition of IFNg Secretion in Tumor Cell & PBMC Mixed Cell Assay Materials and Methods For the mixed cell assay using COV644 cancer cells (expressing shed and surface ULBP6), PBMCs from healthy donors were pre-primed for 36 hours with IL-2 and IL-15 (20 ng/ml each) in X-VIVO 15 media. 24 hours before the experiment 60,000 COV644 cells were plated into 96 well plate format. On the day of the assay, floating primed PBMCs were collected, counted and added to COV644 cells at a 2:1 ratio. Additionally, antibodies (dose titrations of h7B3, h8E11, h1D4, and h6E1 from 200 nM to 0.5 nM) and 50 nM soluble recombinant sULBP6_02 were added to the plate. The assay was run in RPMI media with 10% FBS. 24 hours after co-incubation, the supernatant was collected and measured using LUMINEX for levels of IFNg. Dose titration curves and max potency values were established for each antibody.

Results

Figure 5A:
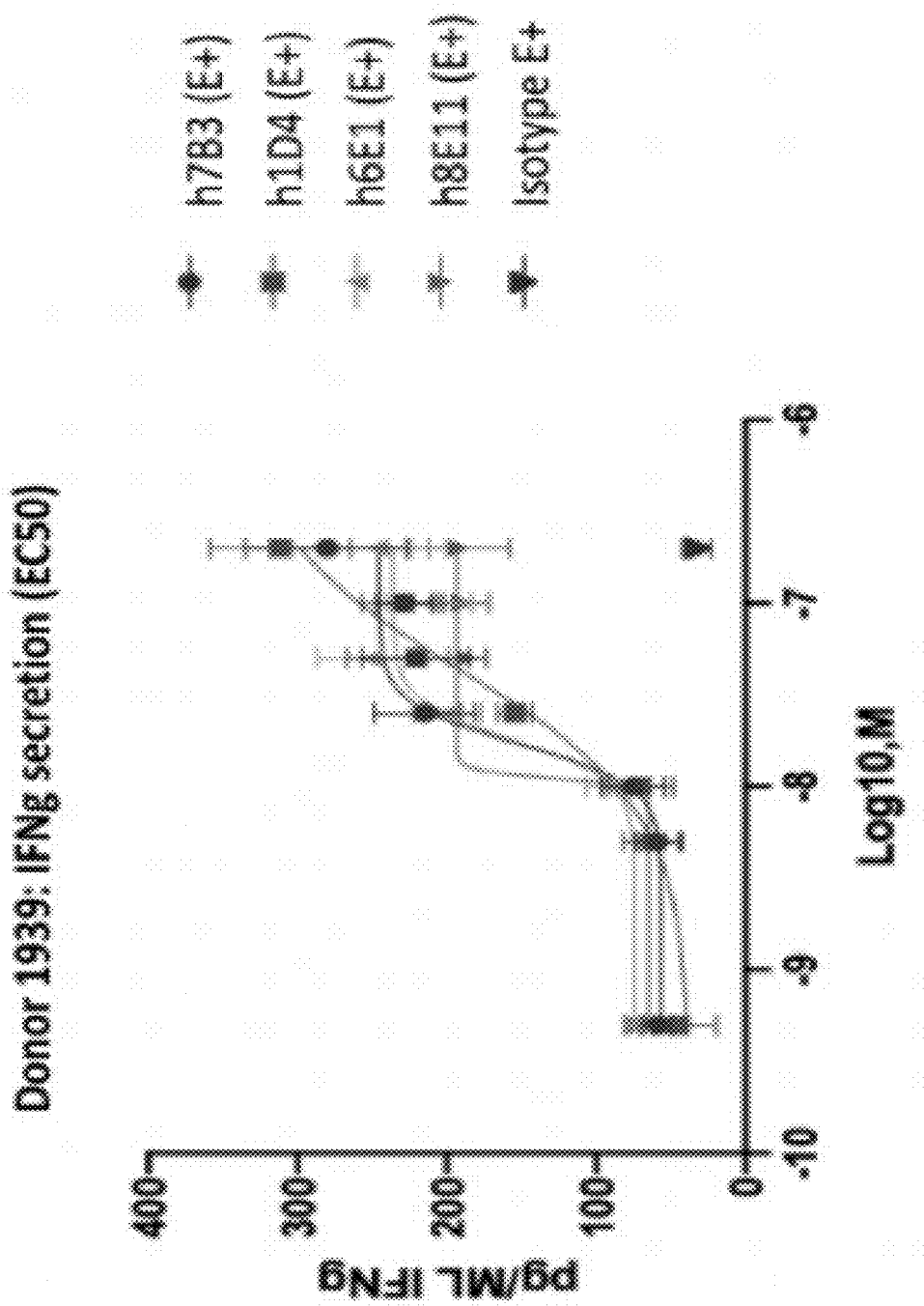
FIG. 5A depicts a mixed cell assay (PBMCs and tumor cells) wherein primed PBMCs were placed on COV644 tumor cells in the presence of 50 nM sULBP6_02 and IFNg release is measured to determine immune cell activation and depicts the ability of effector active (E+) anti-ULBP6 antibodies to increase IFNg secretion in a dose dependent manner by both neutralizing soluble ULBP6-mediated inhibition as well as drive ADCC from surface ULBP6 surface expression on tumors.
Figure 5B:
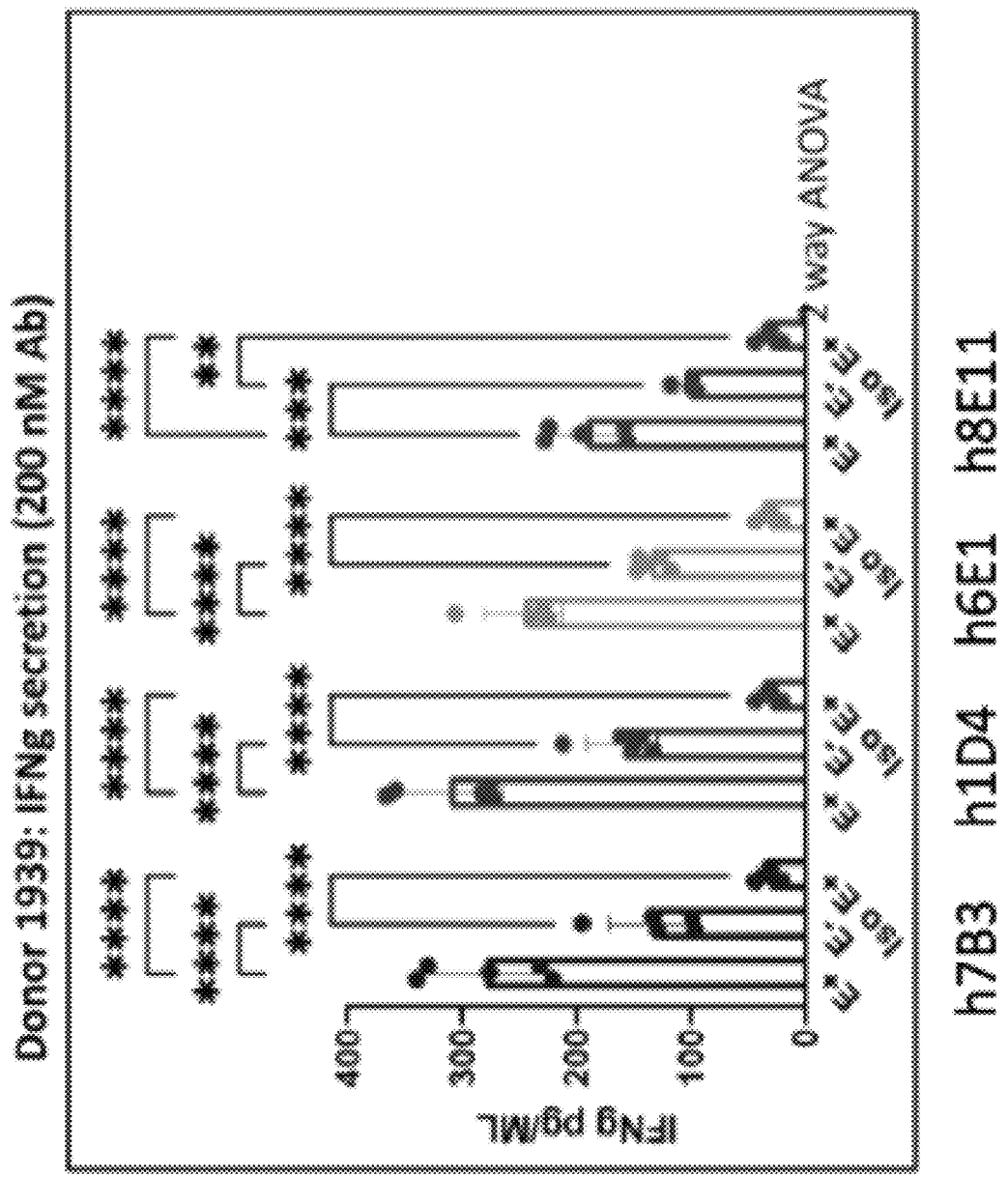
FIG. 5B depicts a mixed cell assay (PBMCs and tumor cells) wherein primed PBMCs were placed on COV644 tumor cells in the presence of 50 nM sULBP6_02 and IFNg release is measured to determine immune cell activation, depicts the comparison of E+, E−, and isotype control antibodies for max potency of IFNg release from 200 nM of antibody treatment.

All of the anti-ULBP6 antibodies neutralized sULBP6-mediated inhibition of IFNg secretion in tumor cell and PBMC mixed cell assays, as provided in FIG. 5A. There were differences in the abilities of these antibodies to increase IFNg in the assay, however all responded in a dose-dependent manner. The E+ molecule was determined to be superior to the E− and isotype control based on the highest dose of antibody used (200 nM) (max potency) (FIG. 5B).
B. Full Titration of Antibodies (E+ Vs E−) Revealed Similar $EC_{50}$, but Greater Max Activity for the E+ Molecules Compared to the E−

A second PBMC mixed cell assay was performed as described in part A of the present example to determine the $EC_{50}$ and maximum activity for the h7B3 molecules.

Materials and Methods

For the mixed cell assay using COV644 cancer cells (expressing shed and surface ULBP6), PBMCs from healthy donors were pre-primed for 36 hours with IL-2 and IL-15 (20 ng/ml each) in X-VIVO 15 media. 24 hours before the experiment 60,000 COV644 cells were plated into 96 well plate format. On the day of the assay, floating primed PBMCs were collected, counted and added to COV644 cells at a 2:1 ratio. Additionally, antibodies (dose titrations of h7B3 (E+ and E−), h8E11(E+ and E−) from 0.05 nM to 200 nM) and 50 nM recombinant sULBP6_02 were added to the plate. The assay was run in RPMI media with 10% FBS. 24 hours after co-incubation, the supernatant was collected and measured using LUMINEX for levels of IFNg. $EC_{50}$ curves were established for h7B3 (E−) and h7B3 (E+).

Results

Figure 6:
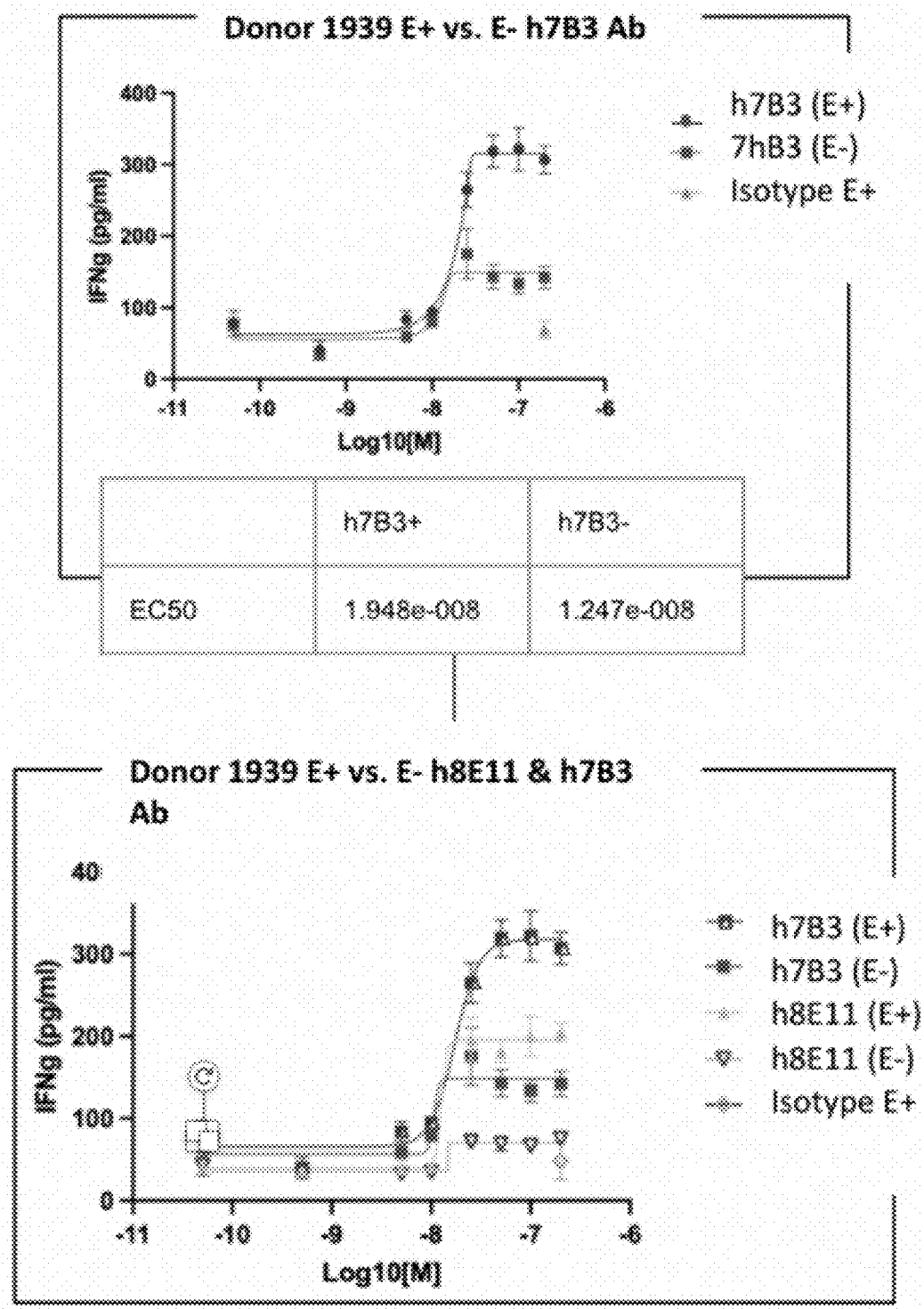
FIG. 6 depicts IFNg release in a mixed cell assay (PBMC and tumor cell) with pre-primed PBMCs on COV644 tumor cells with 50 nM of soluble ULBP6, wherein increased IFNg release can be driven by blocking the inhibitory effect of sULBP6_02 or through ADCC mediated activation from E+ molecules bound to tumor cell surface; presented are data for (top panel) h7B3 E+ and h7B3 E− and (bottom panel) h7B3 E+, h7B3 E−, h8E11 E+ and h8E11 E−. The top graph depicts dose titrations of h7B3 E− vs. E+ wherein the antibodies show similar $EC_{50}$ but E+ shows a higher max potency. An isotype control is included at the maximum dose of the antibodies for comparison. The bottom graph shows a comparison of four anti-ULBP6 antibodies (h7B3 E− and E+ and h8E11 E− and E+) in the same assay, wherein the antibodies all show similar E050 but the E+ antibodies show a greater maximum potency. Isotype control is included at the maximum dose of the antibodies for comparison.
Figure 7A:
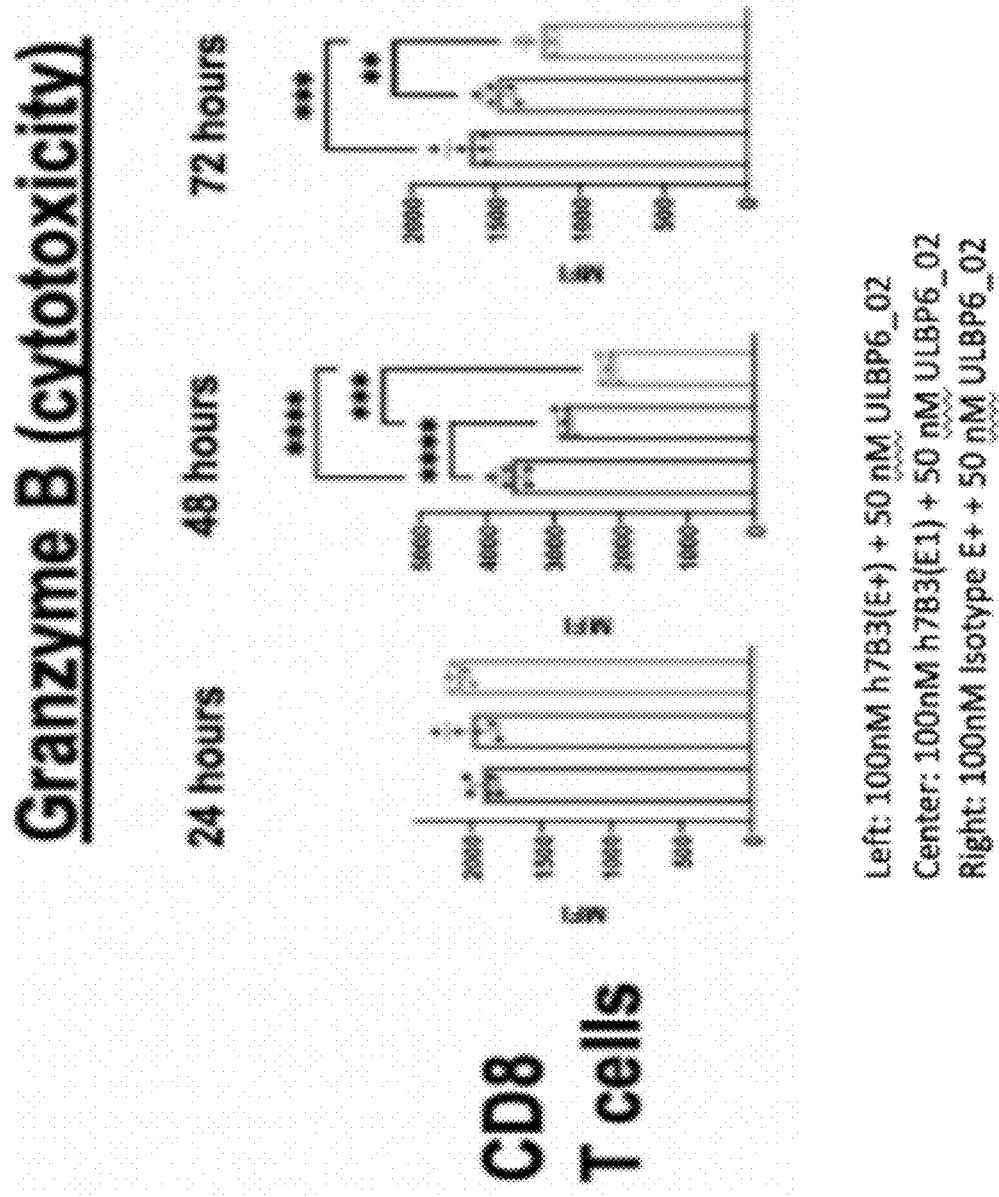
FIG. 7A demonstrates the ability of anti-ULBP6 antibodies (h7B3 (E+) and h7B3 (E−)) to rescue the decrease of granzyme B in CD8 T cells (bottom two panels) (as measured using FACS from total PBMCs) by soluble ULBP6 in a mixed cell assay of primed PBMCs on COOV644 tumor cells with 50 nM of sULBP6_02, wherein PBMC levels of granzyme B and Ki-67 were measured by FACS following co-incubation.
Figure 7B:
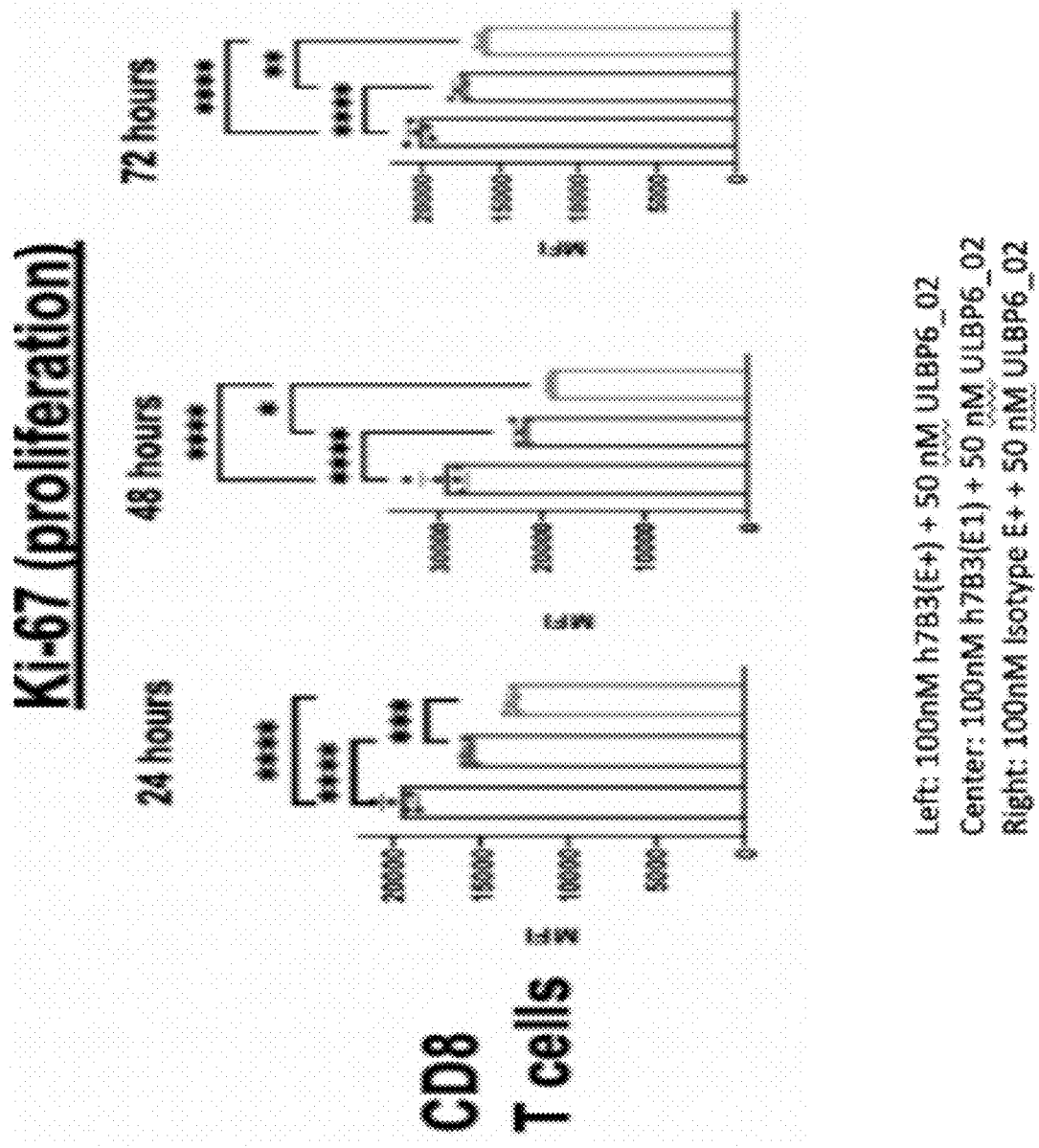
FIG. 7B demonstrates the ability of anti-ULBP6 antibodies (h7B3 (E+) and h7B3 (E−)) to rescue the decrease of Ki-67 in CD8 T cells (as measured using FACS from total PBMCs) by soluble ULBP6 in a mixed cell assay of primed PBMCs on COOV644 tumor cells with 50 nM of sULBP6_02, wherein PBMC levels of granzyme B and Ki-67 were measured by FACS following co-incubation.
Figure 7C:
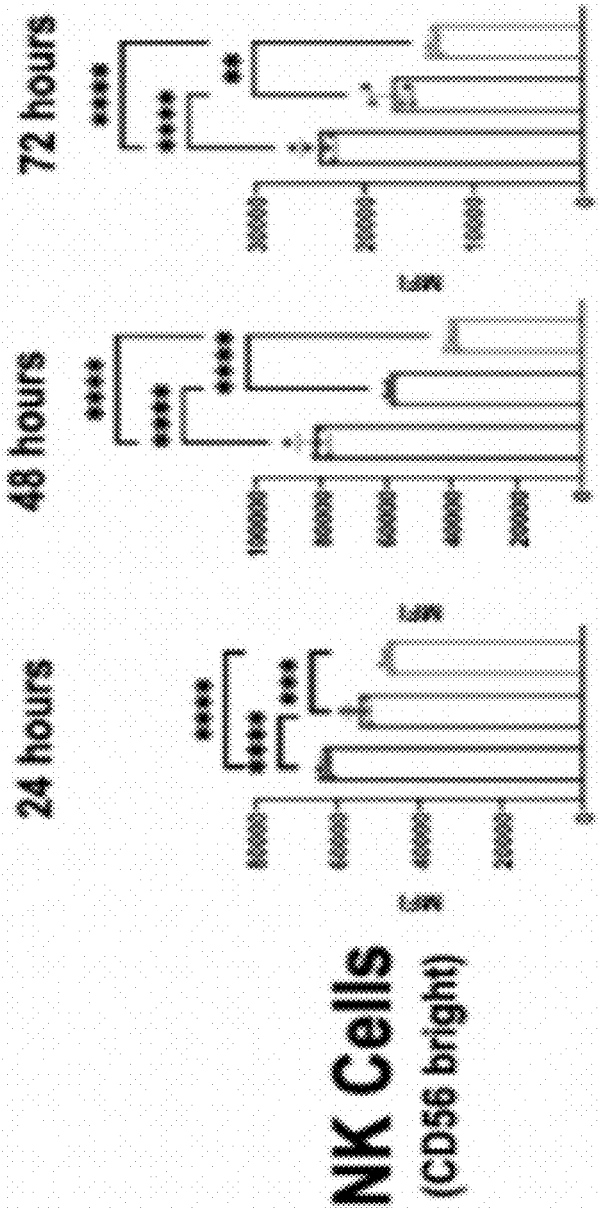
FIG. 7C demonstrates the ability of anti-ULBP6 antibodies (h7B3 (E+) and h7B3 (E−)) to rescue the decrease of granzyme B in NKcells (as measured using FACS from total PBMCs) by soluble ULBP6 in a mixed cell assay of primed PBMCs on COOV644 tumor cells with 50 nM of sULBP6_02, wherein PBMC levels of granzyme B and Ki-67 were measured by FACS following co-incubation.
Figure 7D:
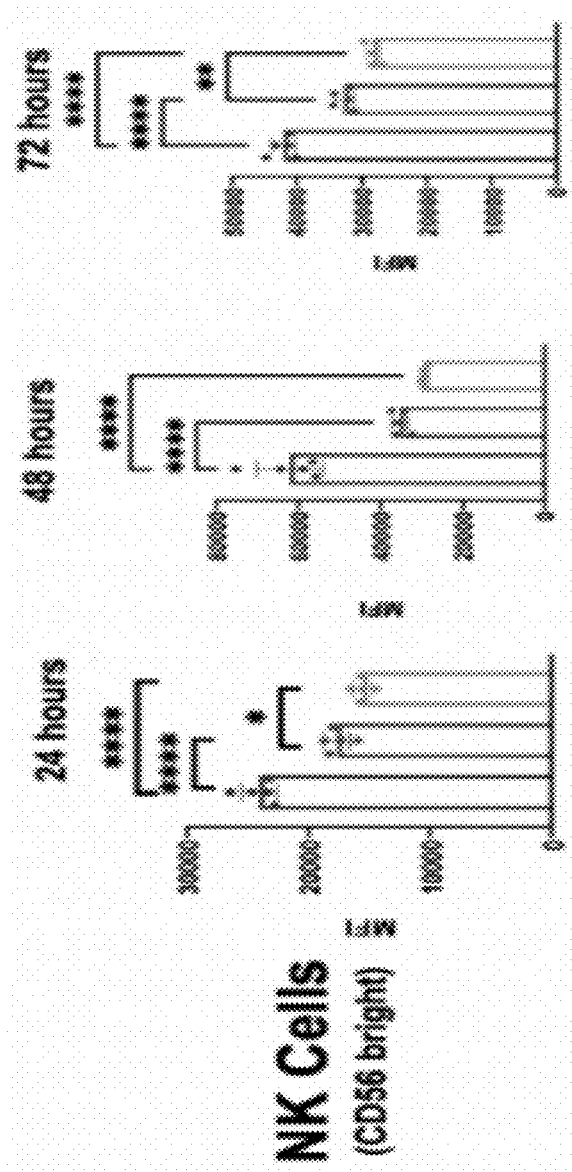
FIG. 7D demonstrates the ability of anti-ULBP6 antibodies (h7B3 (E+) and h7B3 (E−) to rescue the decrease of Ki-67 in NK cells (as measured using FACS from total PBMCs) by soluble ULBP6 in a mixed cell assay of primed PBMCs on COOV644 tumor cells with 50 nM of sULBP6_02, wherein PBMC levels of granzyme B and Ki-67 were measured by FACS following co-incubation.

Both h7B3 E− and h8E11 E− antibodies showed dose dependent increased levels of IFNg compared to isotype control (FIG. 6, top panel) due to neutralization of the inhibitory effects of soluble ULBP6. Both E+ antibodies showed higher max potency, potentially likely due to ADCC from tumor surface binding of E+ antibodies compared to E− versions of the same antibodies. h7B3 showed greater max potency than h8E11 for comparisons of E− antibodies and E+ antibodies. IFNg max potency levels were further increased with E+ versions of these antibodies (FIG. 6, bottom panel). H7B3 E− had a similar $EC_{50}$ value to h7B3 E+.

Example 12: Cytotoxicity and Proliferation in Tumor-Immune Mixed Cell Assay

In addition to IFNg secretion, the level of immune cell activation in the presence of tumor cells and the anti-ULBP6 antibodies described herein can also be determined by measuring immune cell surface expression of markers of cytotoxicity and proliferation. A tumor-immune mixed cell assay was performed using PBMCs from healthy donors. The PBMCs were incubated with tumor cells and 500 nM sULBP6_02 with or without anti-ULBP6 antibodies, and staining of Granzyme B and Ki-67 was measured by flow cytometry. The results show the effects of the anti-ULBP6 antibodies on the cytotoxicity and proliferation of NK cells and T cells in the presence of soluble ULBP6.

Materials and Methods

PBMCs from healthy donors were primed for 36 hours in IL-2 and IL-15 (20 ng/ml each) containing X-VIVO 15 media. Floating cells were collected and replated (100,000 cells per well) on COV644 cancer cells (60,000 cells per well). 50 nM of sULBP6-02 was added to each well along with 100 nM of one of 7B3(E−), 7B3(E+) or Isotype (E+) (isotype control) antibody. The assay was run in RPMI media with 10% FBS. Cells were collected from wells either 24, 48 or 72 hours post incubation and stained with anti-granzyme B or anti-Ki-67 antibodies and gated on CD8 T cell and NK cell populations (as defined by FACS antibodies CD3, CD8, and CD56).

Results

Granzyme B and Ki-67 were generally decreased over time in both CD8 and NK cell populations when 50 nM sULBP6_02 (Isotype antibody) was present. The anti-ULBP6 antibodies (h7B3 (E+) and h7B3 (E−)) were able to rescue these decreases, with the E+ antibody generally showing stronger efficacy than the E− antibody (FIG. 7A, FIG. 7B, FIG. 7C, and FIG. 7D).

Example 13: Blocking Activity of Effector Positive Antibodies

To increase ADCC, anti-ULBP6 antibodies with ADCC-enhancing mutations S239D/I332E were prepared. In this example, the ULBP6 blocking activity and FcG receptor activation of E−, E+ and E++ candidate anti-ULBP6 antibodies was compared in a mixed cell assay using COV644 cancer cells and PBMCs.

Materials and Methods

For the mixed cell assay using COV644 cancer cells, PBMCs from healthy donors were pre-primed for 36 hours with IL-2 and IL-15 (20 ng/ml each) in X-VIVO 15 media. 24 hours before the experiment 60,000 COV644 cells were plated into 96 well plate format. On the day of the assay, floating primed PBMCs were collected, counted and added to COV644 cells at a 2:1 ratio. Additionally, antibodies (various concentrations of h7B3(E−), h7B3(E+) and h7B3 (E++) (DE)) and 50 nM soluble recombinant sULBP6_02 were added to the plate. The assay was run in RPMI media with 10% FBS. 24 hours after co-incubation, the assay supernatant was collected and measured using luminex for levels of IFNg.

Figure 8A:
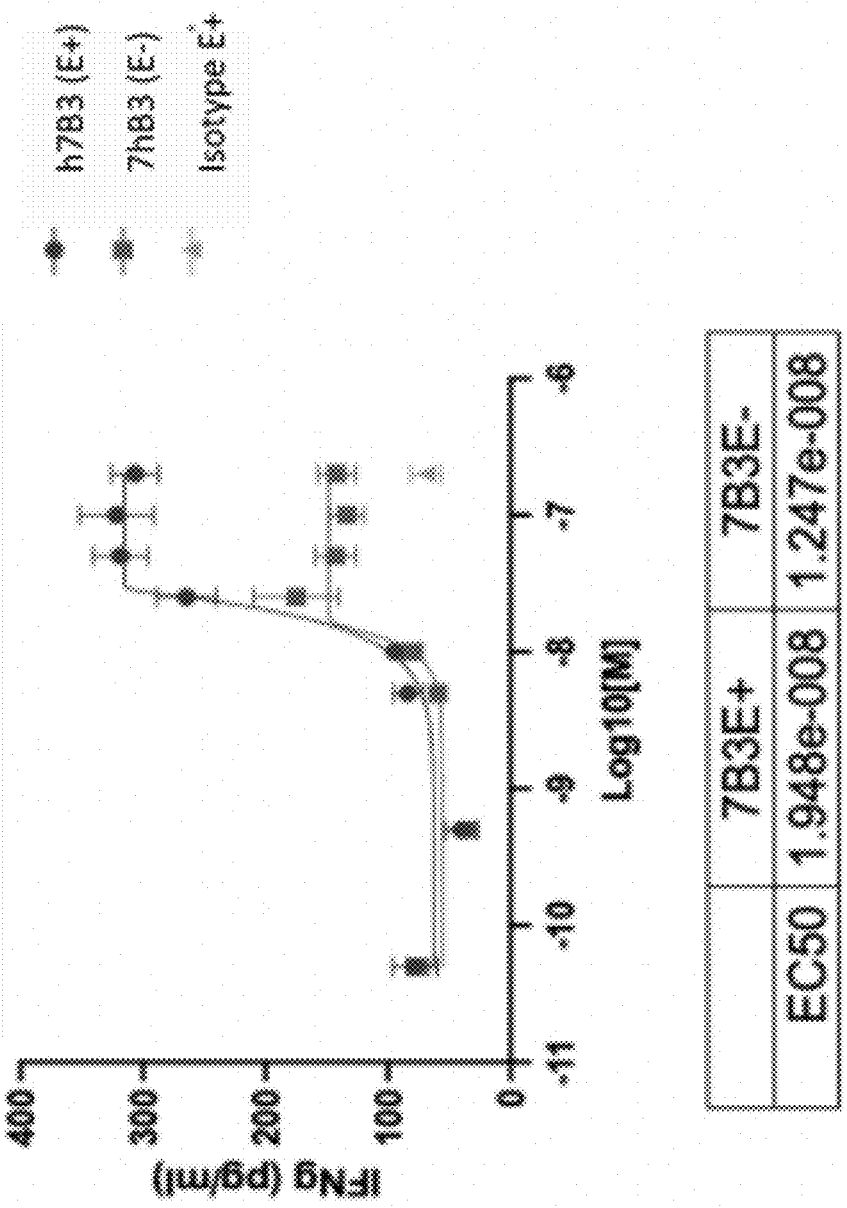
FIG. 8A shows a mixed cell assay (PBMCs and tumor cells) with pre-primed PBMCs and COV644 tumor cells that have been treated with 50 nM of sULBP6_02, wherein the assay looks for IFNg release as a measure of immune cell activation (which can be driven by blocking soluble ULBP6 by h7B3 E− or E+, or by ADCC for h7B3 E+). Depicted are dose titrations of h7B3E+vs E− antibodies which show similar $EC_{50}$ but higher max potency for E+ antibody. The maximum dose of the antibodies is also shown for an isotype control.
Figure 8B:
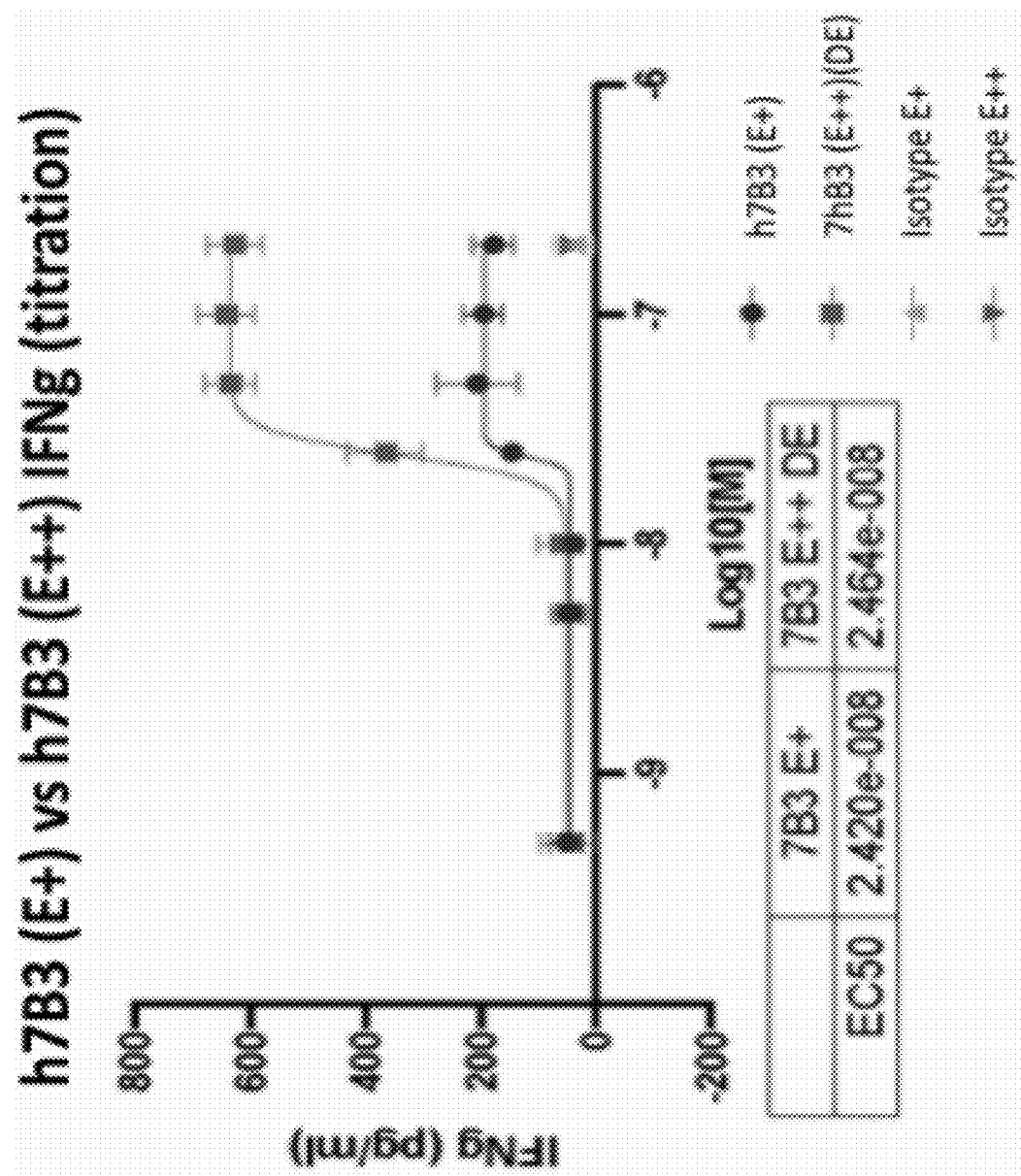
FIG. 8B shows a mixed cell assay (PBMCs and tumor cells) with pre-primed PBMCs and COV644 tumor cells that have been treated with 50 nM of sULBP6_02, wherein the assay looks for IFNg release as a measure of immune cell activation (which can be driven by blocking soluble ULBP6 by h7B3 E− or E+, or by ADCC for h7B3 E+). Depicted are dose titration of h7B3E+vs. E++DE antibodies which show similar $EC_{50}$ but increased max potency for E++DE. The maximum dose of the antibodies is also shown for Isotype control.
Figure 8C:
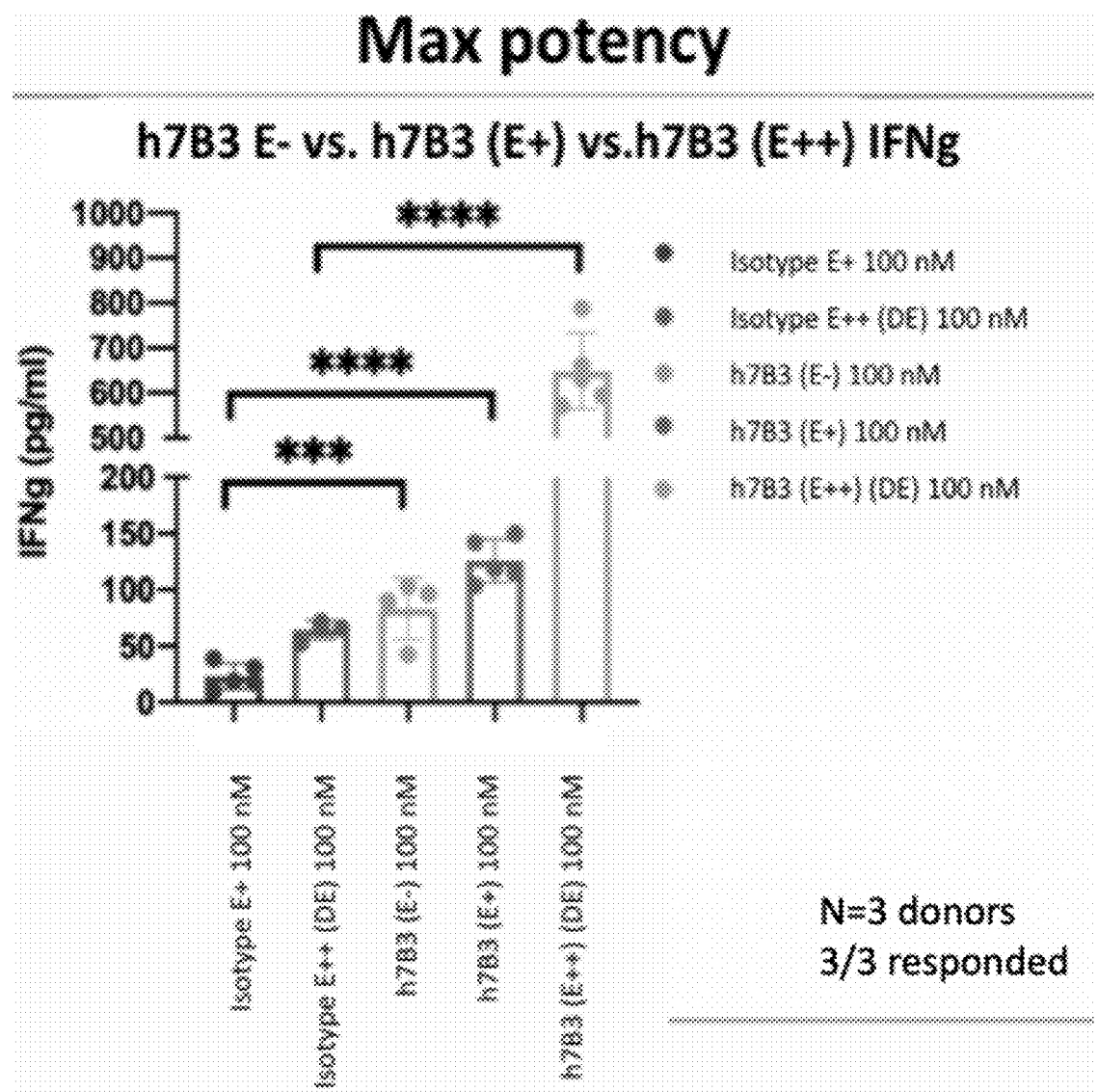
FIG. 8C shows a mixed cell assay (PBMCs and tumor cells) with pre-primed PBMCs and COV644 tumor cells that have been treated with 50 nM of sULBP6_02, wherein the assay looks for IFNg release as a measure of immune cell activation (which can be driven by blocking soluble ULBP6 by h7B3 E− or E+, or by ADCC for h7B3 E+). Depicted are maximum doses (100 nM) for all three h7B3 antibodies (E−, E+, E++DE) compared to isotype controls.

Results h7B3(E−), h7B3(E+), and h7B3(E++) DE each showed a dose-dependent increase of IFNg in this assay due to inhibition of soluble ULBP6 (FIG. 8A and FIG. 8B). The max potency of IFNg in this assay was increased with h7B3(E++) (DE) compared with h7B3(E−) and h7B3(E+) (FIG. 8C).

Example 14: Immune Cell Killing Assay (E−, E+, E++ Antibodies)

To test whether the anti-ULBP6 antibodies described herein could enhance killing of tumor cells, INCUCYTE immune cell killing assays were performed using PBMC from 8 healthy donors to detect immune cell-mediated killing of tumor cells.

Materials and Methods

PBMCs from 8 healthy donors were primed for 36 hours in IL-2 and IL-15 (20 ng/ml) in X-VIVO 15 media. One day before the assay setup, 3,000 COV644-GFP cancer cells (COV644 cancer cell line engineered to express GFP) were plated in 96 well plates suitable for the INCUCYTE assay. On the day of the assay PBMCs were plated on top of COV644 cells at a 25:1 ratio in the presence of 50 nM human sULBP6_02 protein. Additionally, isotype or anti-ULBP6 antibodies (100 nM) were also included in this experiment. The humanized antibodies tested in this assay included h7B3 (E−) (ULBP6 neutralizer with no FcgR engagement), h7B3 (E+) (ULBP6 neutralizer with FcgR engagement) and h7B3 (E++) (ULBP6 neutralizer with enhanced FcgR engagement). The assay was run in RPMI media with 10% FBS. Assay plates were placed in the INCUCYTE machine and GFP levels (per well) were measured over 5 days of the assay. A lower GFP signal between conditions was interpreted to indicate less presence of tumor cells, perhaps in part due to tumor cell killing via CD8 T cells and NK cells that had been activated by ULBP6 antibodies.

Figure 9A:
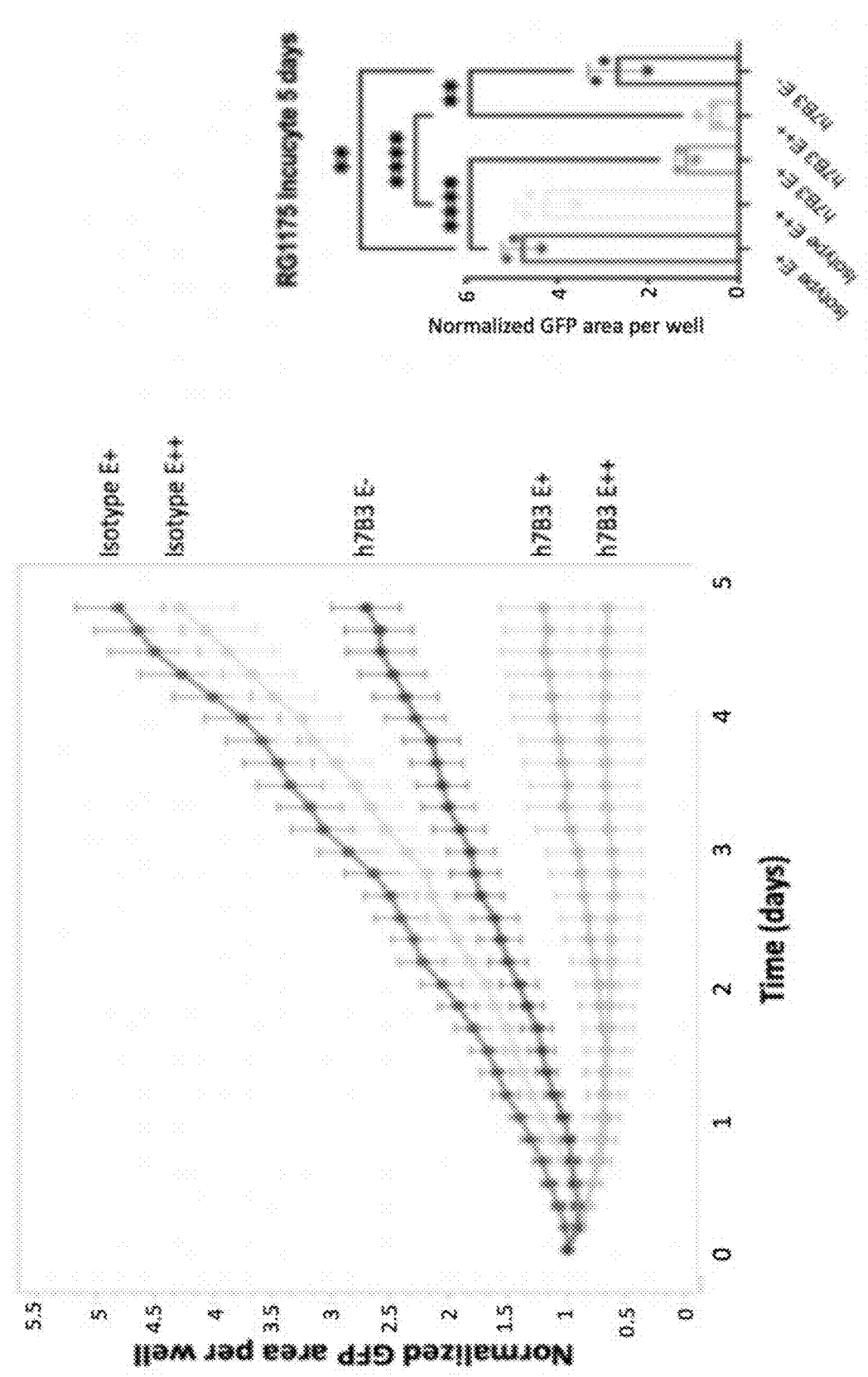
FIG. 9A depicts a strong responding donor in the INCUCYTE tumor killing assay setup. Shown is a decrease in GFP tumor cells with h7B3 E−, which is further decreased with h7B3 E+ and even more so with h7B3 E++ compared to isotype controls. The right panel provides measurement of GFP at the final time point.
Figure 9B:
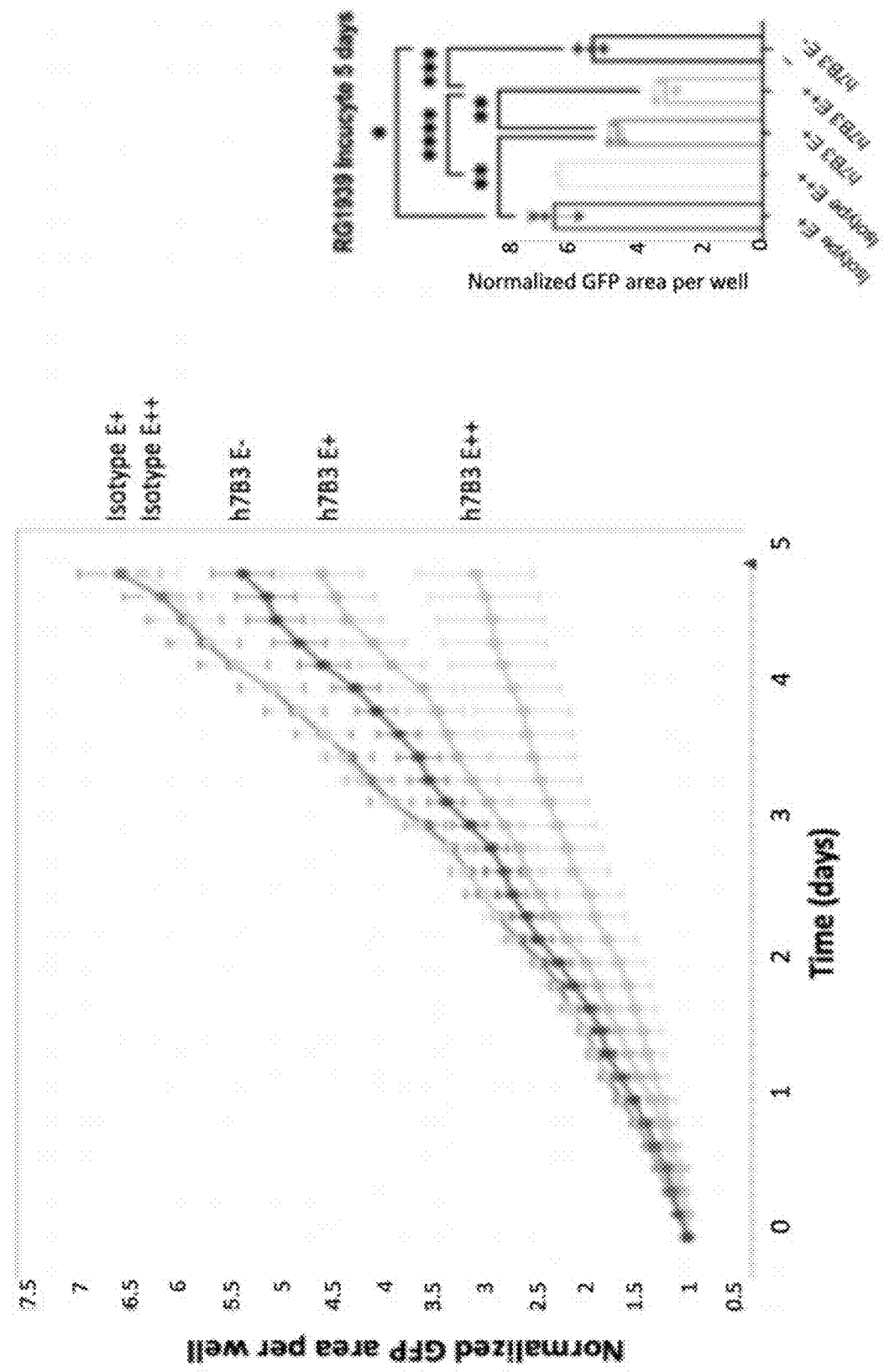
FIG. 9B depicts a moderate responding donor in the INCUCYTE assay setup. Shown is a moderate GFP decrease with the h7B3 E− antibody, which is further decreased with both E+("h7B3 E+") and E++DE h7B3 ("h7B3 E++") antibodies compared to isotype controls. The right panel provides measurement of GFP at the final time point.
Figure 9C:
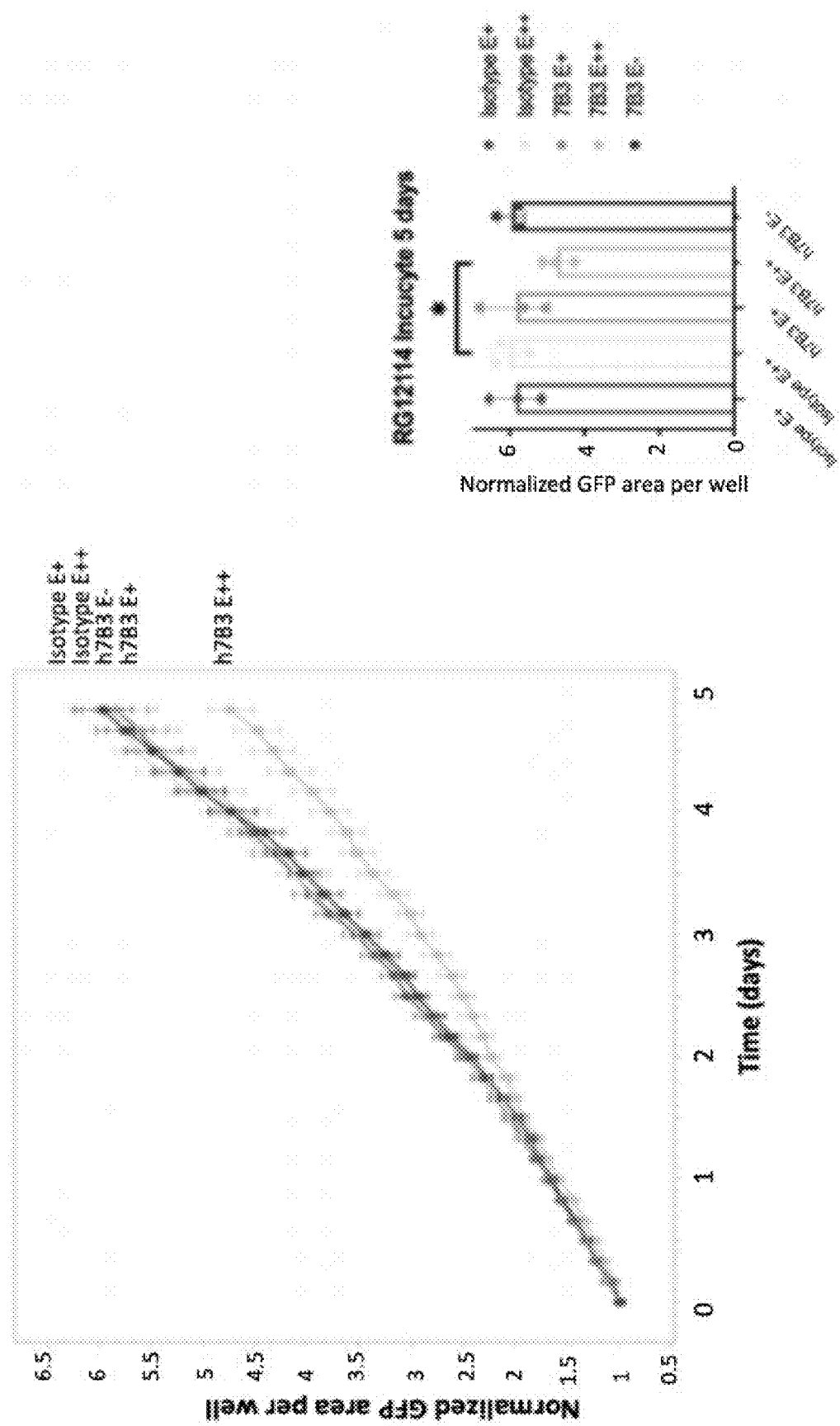
FIG. 9C depicts a weak responding donor in the INCUCYTE assay setup. Only the h7B3 E++DE ("h7B3 E++") molecule shows a decrease of GFP compared to isotype controls. The right panel provides measurement of GFP at the final time point.

Results h7B3 antibody efficiently blocked the immunosuppressive activity of soluble ULBP6 and thereby increased immune cell activation and killing of tumor cells. h7B3 E+ further enhanced tumor cell killing efficacy compared to h7B3 E−. h7B3 E++(DE) further enhanced tumor cell killing efficacy compared to h7B3 E+. A total of 8 healthy donors were screened in this assay. 4 out of 8 responded strongly to h7B3 as shown in FIG. 9A. 3 out of 8 donors were defined as moderate responders to h7B3 as shown in FIG. 9B. 1 out of 8 low responders to h7B3 were identified as shown in FIG. 9C. Table 18 summarizes the strength of the response from each donor and shows all 8 donors assessed in this INCUCYTE assay and how well they responded to each anti-ULBP6 antibody in their ability to kill tumor cells.

TABLE 18

Response to anti-ULBP6 antibody treatment of healthy donor PBMCs in INCUCYTE immune cell killing assay.

| Donor | Response | | | |
|---|---|---|---|---|
| | 7B3 E− | 7B3E+ | 7B3E++ | |
| 1175 | O | OO | OOO | strong |
| 2114 | X | X | O | low |
| 1939 | O | OO | OOO | moderate |
| 3788 | O | OOO | OOO | strong |
| 3864 | X | OO | OOO | moderate |
| 1565 | O | OO | OOO | moderate |
| 3761 | OO | OOO | OOO | strong |
| 46812 | OOO | OO | OOO | strong |

O = low response of donor to the treatment;
OO = moderate response of donor to the treatment;
OOO = strong response of the donor to the treatment;
X = The donor did not respond to the treatment Example 15: Effector Enhanced and Afucosylated Antibodies This example shows the testing of afucosylated anti-ULBP6 antibodies in the immune cell-tumor cell mixed assay and INCUCYTE killing assay described above.
A. IFNg Expression in Mixed Cell Assay
To compare the effects on IFNg expression in our previously described mixed cell assay between h7B3(E+), h7B3 (E++) (DE) and h7B3(E+) (afucosylated, Afu; "h7B3 E+ Afu") antibodies.

Materials and Methods

PBMCs were primed for 36 hours in X-VIVO 15 media containing IL-2 and IL-15 (20 ng/ml each). Floating cells were collected and replated (100,000 cells per well) on COV644 cancer cells (60,000 cells per well). 50 nM of sULBP6-02 was added to each well with either h7B3 (E+), h7B3(E++) (DE mutation), or h7B3(E+) (Afu) ("h7B3 E+ Afu") or isotype E+(isotype control) antibody at various doses from 0.05 nM to 200 nM. The assay was run in RPMI media with 10% FBS. Assay supernatant was collected after 24 hours and assessed for IFNg levels.

Results

Figure 10:
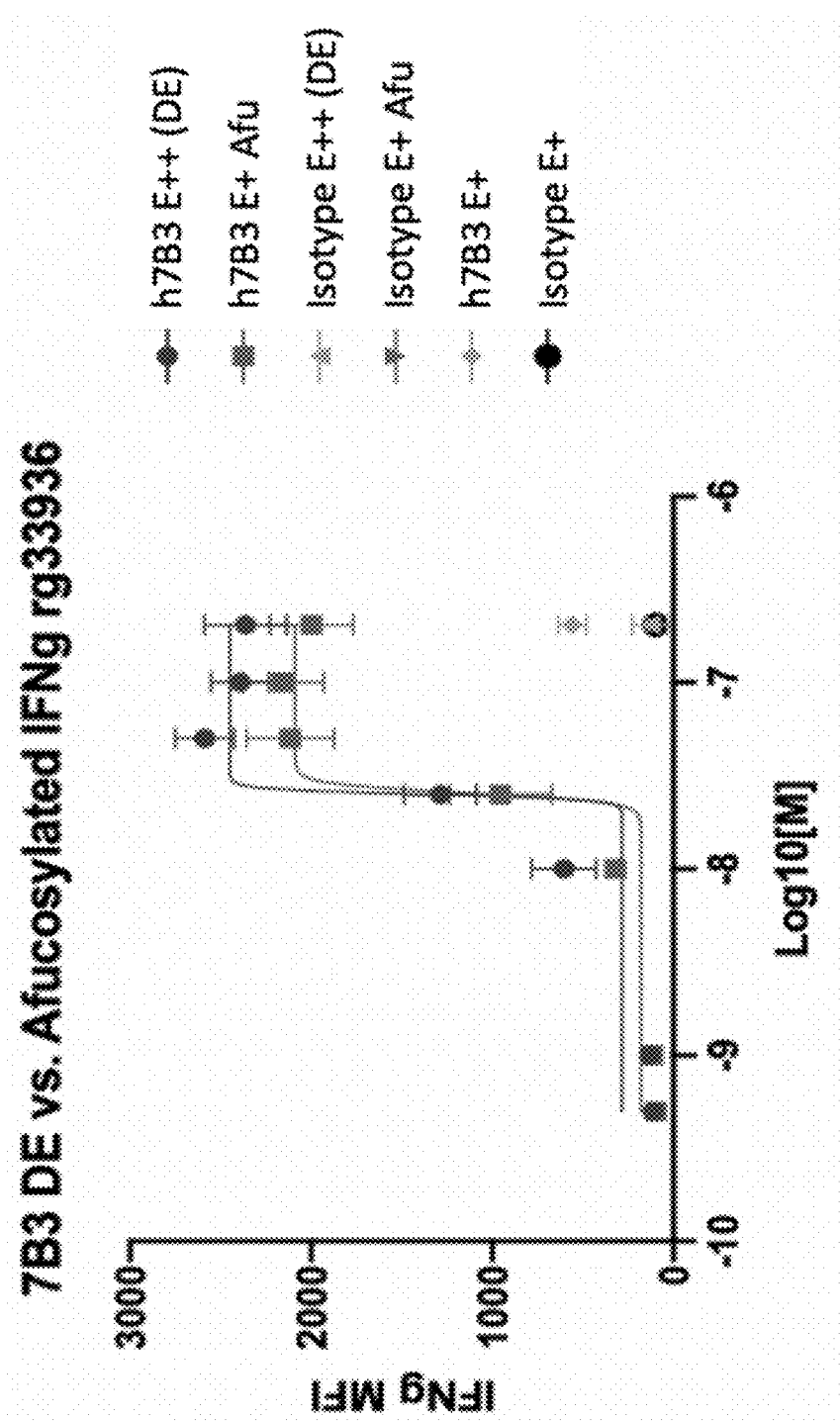
FIG. 10 depicts the IFNg levels from a mixed cell assay in which primed PBMCs are incubated on top of COV644 cells for 24 hours in the presence of 50 nM sULBP6_02 and isotype or anti-ULBP6 antibodies (h7B3 E++DE or h7B3 E+ Afu in dose titrations). Both antibodies show a similar $EC_{50}$ curve with similar max potencies of IFNg release.

The 7B3(E+) antibody showed significant increases of IFNg compared to isotype controls which was further increased by both h7B3(E++) DE and h7B3(E+) afucosylated ("h7B3 E+ Afu") molecules (FIG. 10). There was little to no difference in both max potency and the curve shapes between the h7B3(E++) DE and the h7B3(E+) afucosylated ("h7B3 E+ Afu") molecules in this assay. The h7B3(E+) afucosylated ("h7B3 E+ Afu") molecule is equivalent to the 7B3(E++) DE molecule in promoting IFNg secretion.

B. Tumor Cell Killing

An INCUCYTE killing assay was performed on 4 healthy donors comparing h7B3 E+, h7B3E++(DE) and h7B3 E+ Afu for their ability to increase tumor cell killing.

Materials and Methods

PBMCs from 4 healthy donors were primed for 36 hours in IL-2 and IL-15 (20 ng/ml each) in X_VIVO 15 media. One day before the assay setup, 3,000 COV644-GFP cancer cells (COV644 cancer cell line engineered to express GFP) were plated in 96 well plates suitable for the INCUCYTE assay. On the day of the assay PBMCs were plated on top of COV644 cells at a 25:1 ratio in the presence of 50 nM sULBP6_02 protein. Additionally, isotype or anti-ULBP6 antibodies were also included in this experiment. The assay was run in RPMI media with 10% FBS. The humanized antibodies tested in this assay included h7B3 (E+) (ULBP6 neutralizer with no FcgR engagement), h7B3E++(DE) (ULBP6 neutralizer with FcgR enhanced engagement) and h7B3 Afu (E+) (ULBP6 neutralizer with enhanced FcgR engagement by afucosylation). Assay plates were placed in the INCUCYTE machine and GFP levels were measured over 5 days of the assay. A lower GFP signal between conditions can be due to less tumor cell presence, due in part to increased tumor cell killing via CD8 T cells and NK cells because of increased immune activity driven by ULBP6 antibodies.

Figure 11A:
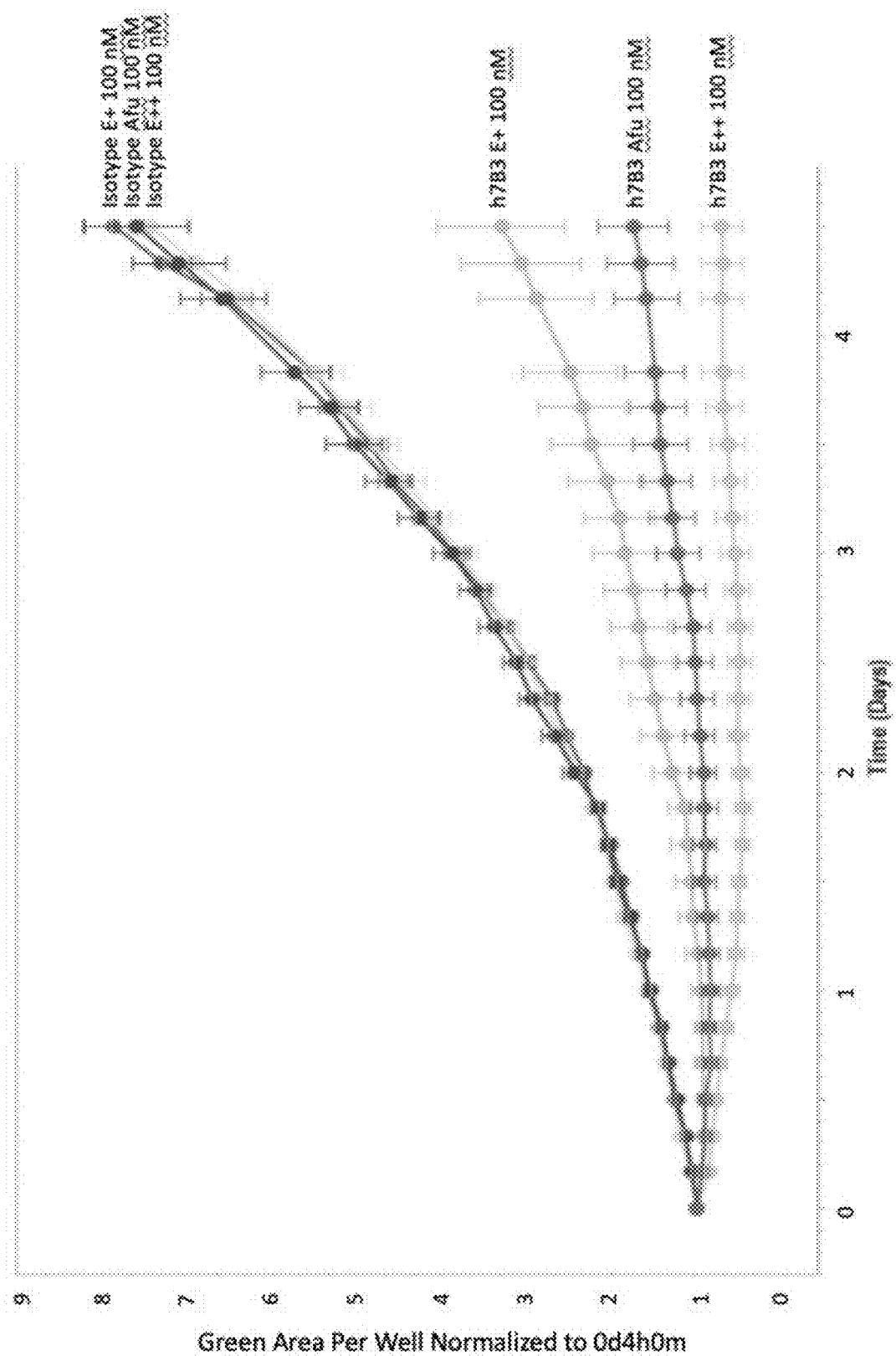
FIG. 11A depicts a strong responding donor in the INCUCYTE assay setup, and an observed decrease in GFP tumor cells with h7B3 E+, which was further decreased comparably with h7B3 E++DE ("h7B3 E++") and h7B3 E+ Afu ("h7B3 Afu").
Figure 11B:
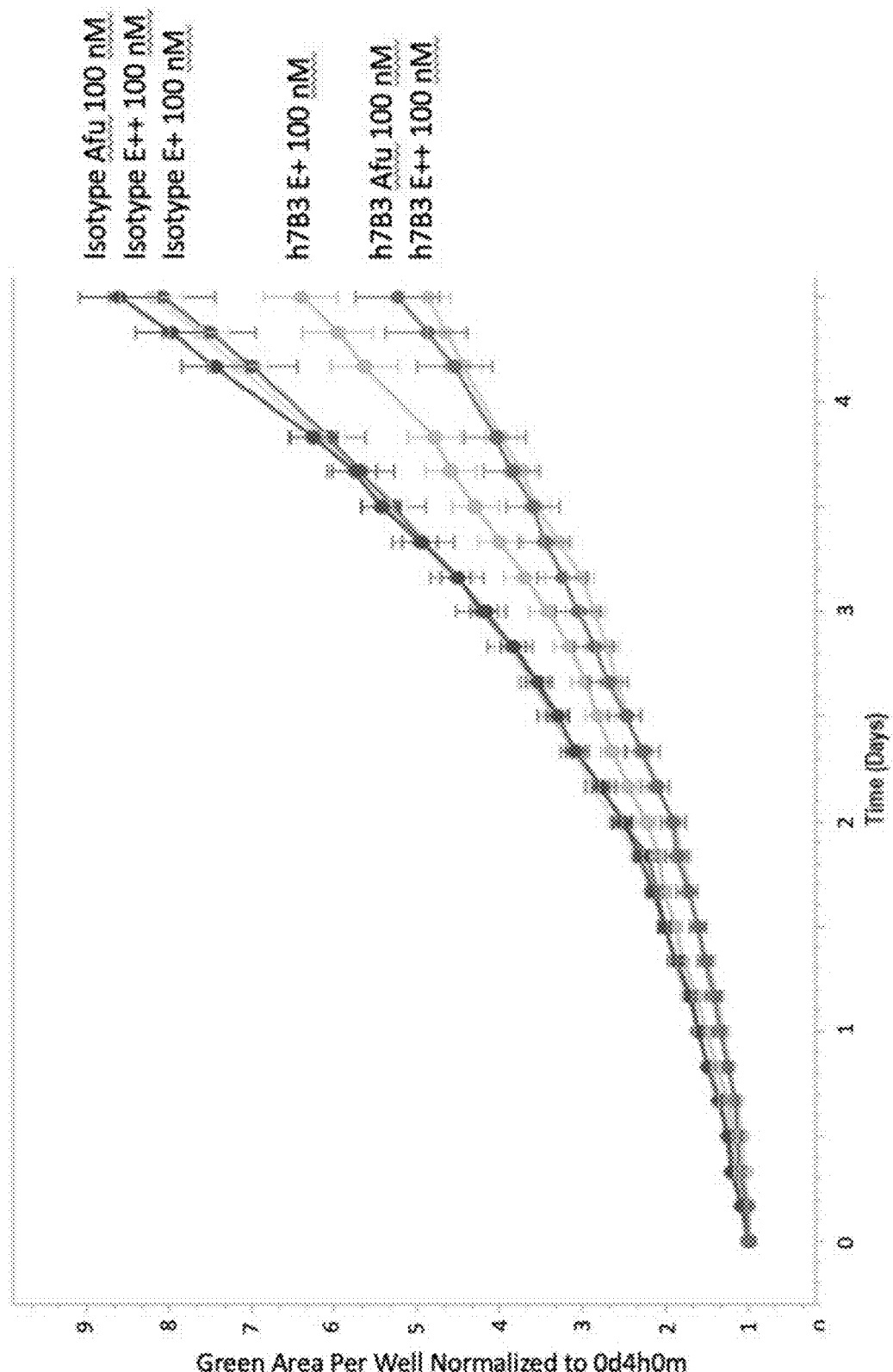
FIG. 11B depicts a moderate responding donor in the INCUCYTE assay setup, and an observed moderate GFP decrease with the h7B3 E+ antibody, which was expanded with both h7B3 E++DE ("h7B3 E++") and h7B3 E+ Afu ("h7B3 Afu") antibodies compared to isotype controls.

Results h7B3 E+ afucosylated (Afu) antibody was comparable to h7B3 E++(DE) in a tumor killing assay with some variability between donors. The h7B3 E++(DE) and h7B3E+ Afu ("h7B3 Afu") molecules showed less average GFP per well, which can be suggestive of less tumor per well, which can be likely due to increased tumor cell killing compared to the h7B3 E+ as well as isotype controls. Two out of four donors showed a strong response for the h7B3 E+_Afu ("h7B3 Afu") and h7B3 E++DE antibodies (FIG. 11A) and two showed a moderate response (FIG. 11B).

Example 16: Pharmacokinetic Properties of Anti-ULBP6 Antibodies in Cynomolgus Monkeys The objective of this experiment was to determine the pharmacokinetic properties of anti-ULBP6 antibodies in a pharmacologically relevant species, the cynomolgus monkey (*Macaca fascicularis*, Mf), and to screen the variable regions of h7B3 (E+) and h8E11 (E+) for sequence liabilities with potential for eliciting poor pharmacokinetic behavior.

Materials and Methods

Male (M) cynomolgus monkeys (naive, 3-4 years old, 3.0 to 3.3 kg, Chinese origin) were administered a single 3 mg/kg dose of h7B3 (E+) (PUR4377) or h8E11 (E+) (PUR4379) by slow iv bolus (5 min infusion). Approximately 12 samples of whole blood, later processed to serum, were collected from each animal beginning before the dose (pre-dose) and ending 28 day after the dose (post-dose). The serum samples were analyzed for the amount h7B3 (E+) or h8E11 (E+) using a qualified ELISA with a lower limit of quantitation (LLOQ) of 0.015 μg/mL. The group mean (N=3) concentration-time profiles for h7B3 (E+) and h8E11 (E+) are shown on a semilog plot (GraphPad PRISM 9.0). Mean PK parameters estimated by non-compartmental analysis (NCA) are also listed (Phoenix WinNonlin 8.2).

Results

Figure 12:
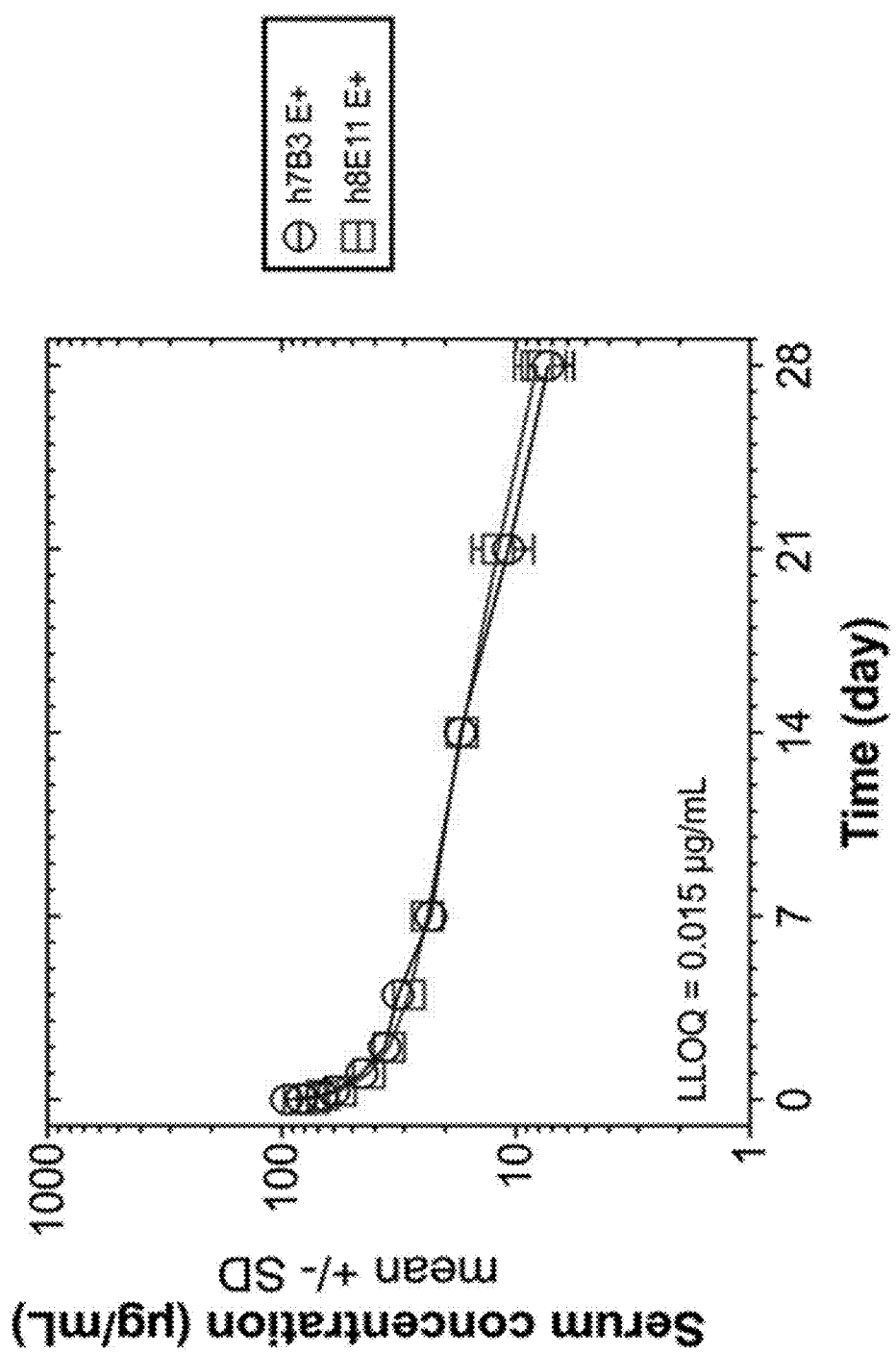
FIG. 12 depicts the concentration-time profiles for h7B3 (E+) and h8E11 (E+) in cynomolgus monkeys following a 3 mg/kg intravenous dose administered by slow bolus. Data are plotted as mean and standard deviation (N=3M/group) on a semilog plot using GraphPad PRISM 9.0. LLOQ=lower limit of quantitation and SD=standard deviation.

Anti-ULBP6 antibodies h7B3 (E+) and h8E11 (E+) had PK profiles of a typical IgG with linear elimination (FIG. 12). The mean half-life was long, from 11.8 to 13.3 days for h7B3 (E+) and h8E11 (E+) (Table 19), respectively, consistent with other IgG therapeutics with linear PK in monkeys (Betts et al, 2018, mAbs, 10(5); 751-764). Other PK properties, including clearance and volume of distribution, were within typical ranges for a therapeutic IgG in monkeys (Table 19). There was no difference in exposure among h7B3 (E+) and h8E11 (E+), as assessed by Cmax and AUClast, confirming no apparent sequence liability among the two clones (Table 19). There was no evidence of target-mediated drug disposition (TMDD) at the dose level tested, suggesting 3 mg/kg may be a target-saturating dose in healthy monkeys (FIG. 12).

TABLE 19

Mean PK Parameters for h7B3 (E+) and h8E11 (E+) in cynomolgus monkeys estimated by non-compartmental analysis (NCA)

| Antibody, Dose, Route | Cmax μg/mL (CV, %) | AUClast day*μg/mL (CV, %) | T1/2 day (CV, %) | CL mL/day/kg (CV, %) | Vz mL/kg (CV, %) |
|---|---|---|---|---|---|
| h7B3 (E+) 3 mg/kg, IV | 95.4 (9.9) | 552 (2.4) | 11.8 (26.9) | 4.42 (8.3) | 74.1 (20.5) |
| h8E11 (E+) 3 mg/kg, IV | 84.2 (4.5) | 551 (13.1) | 13.3 (19.4) | 4.32 (18.7) | 81.0 (5.6) |

N = 3M for all data;
Mean AUCextra was ≤ 22% and individual AUCextra was ≤ 28%;
M = male;
CV = coefficient of variation;
Cmax = maximum observed concentration;
AUClast = area under the curve (AUC) from the start of dose administration until the last whole blood sample was collected;
T1/2 = terminal elimination half-life;
CL = clearance;
Vz = volume of distribution;
AUCextra = percentage of AUCinf due to extrapolation from Tlast to infinity, where AUCinf = AUC from time of dosing extrapolated to infinity and Tlast is the last time point in the sample collection period with detectable drug Example 17: Structural Mapping of the h7B3 Binding Site on ULBP602

Materials and Methods

For crystallization a human ULBP602 construct covering the residue positions 26 to 218 was generated. The construct included a penta-His tag at the protein's C-terminus for purification purposes. Subsequent complex formation, crystallization, data collection, model solving and model building and refinement was performed by Proteros Biostructures GmbH, Germany. The complex between ULBP6 and h7B3 Fab was formed by mixing both proteins at a ratio of 1.2:1 and incubation for 2.5 hours at room temperature. The complex was purified via size exclusion chromatography using a HiLoad 16/60 Superdex 75 prep grade column pre-equilibrated in 20 mM HEPES pH7.0, 100 mM NaCl.

h7B3-Fab ULBP602 co-crystals were obtained under the following crystal conditions: 0.1 µl of h7B3-Fab ULBP602 complex at 26.72 mg/ml in 20 mM HEPES pH7.0, 100 mM NaCl was mixed with a buffer containing 0.1 µl 10% glycerol (v/v), 0.1M MES pH 6.9, 5% PEG 1000 w/v, 30% PEG600 w/v. The resulting drop was incubated at 4° C.

The obtained co-crystals were flash-frozen in liquid nitrogen. Diffraction data of the h7B3-Fab and ULBP602 co-crystal were obtained at the Swiss Light Source (SLS, Villigen, Switzerland) at beamline PXII-X10SA. The diffraction data collection was performed at 100 Kelvin using a wavelength of 0.9998 Å and a Dectris EIGNER2 Si 16M detector. Data were processed using the autoROC XDS and autoPROC AIMLESS programs (Table 20).

TABLE 20

| Data Collection statistics | |
|---|---|
| Space group | C2 |
| Cell: a; b; c; [Å] | 106.55; 95.8; 97.2 |
| α; β; γ [°] | 90.0; 117.7; 90.0 |
| Resolution [Å] | 86.03-2.31 (2.66-2.31) |
| Unique reflections | 19970 (999) |
| Multiplicity | 4.0 (3.6) |
| Spherical completeness [%] | 52.4 (7.6) |
| Ellipsoidal completeness [%] | 92.3 (71.1) |
| $R_{pim}$ [%]$^3$ | 8.8 (50.8) |
| $R_{sym}$ [%]$^1$ | 15.3 (82.8) |
| $R_{meas}$ [%]$^2$ | 17.7 (97.6) |
| CC1/2 [%] | 99.10 (58.10) |
| Mean(I)/sd | 7.2 (1.6) |

Values in the parentheses refer to the highest resolution bin $$Rsym = \frac{\left(\sum_h \sum_i^{n_h} |\hat{I}_h - I_{h,i}|\right)}{\left(\sum_h \sum_i^{n_h} |I_{h,i}|\right)} \text{ with } \hat{I}_h = (1/n_h) \sum_i^{n_h} I_{h,i}$$

Where $I_{h,i}$ is the intensity value of the $i^{th}$ measurement of h;

Rmeas =

$$\frac{\sum_h \sqrt{n_h/(n_h - 1)} \sum_i^{n_h} |\hat{I}_h - I_{h,i}|}{\sum_h \sum_i^{n_h} I_{hi}} \text{ with } \hat{I}_h = (1/n_h) \sum_i^{n_h} I_{h,i}$$

Where $I_{h,i}$ is the intensity value of the $i^{th}$ measurement of h; and

Precision indicating $Rpim = \frac{\sum_h \sqrt{1/(N-1)} |I_{h,i} - <I_h>|}{\sum_h <I_h>}$ Phase information to determine the structure was obtained by molecular replacement using phaser from the CCP4 (https://www.ccp4.ac.uk/) software package and ULBP6 (4S0U) as template. Subsequent model building and refinement was performed according to standard protocols with COOT (https://www2.mrc-lmb.cam.ac.uk/personal/pemsley/coot/) and the software package CCP4, respectively (Table 21).

TABLE 21

| Refinement and model statistics | |
|---|---|
| Resolution | 86.03-2.31 |
| Number of reflections (working/test) | 18964/1006 |
| Rcryst [%]/Rfree [%] | 21.7/28.3 |
| Total number of atoms - Protein | 4663 |
| Total number of atoms - Water | 119 |
| Average B-factor-Protein | 46.3 |
| Average B-factor-Water | 26.8 |
| bond length deviation [Å] | 0.004 |
| bond angle deviation [°] | 1.42 |
| Ramachandran plot - favored [%] | 95.63 |

TABLE 21-continued

| Refinement and model statistics | |
|---|---|
| Ramachandran plot - allowed [%] | 4.2 |
| Ramachandran plot - outliers [%] | 0.17 |

$$Rcryst = \frac{\sum_h |F_{o,h} - F_{c,h}|}{\sum_h F_{o,h}}$$

where $F_{o,h}$ and $F_{c,h}$ are the observed and calculated structure factor amplitude for reflection h.

For free R-factor calculation about 5.0% of measured reflections were excluded from the refinement procedure.

Results

Figure 13:
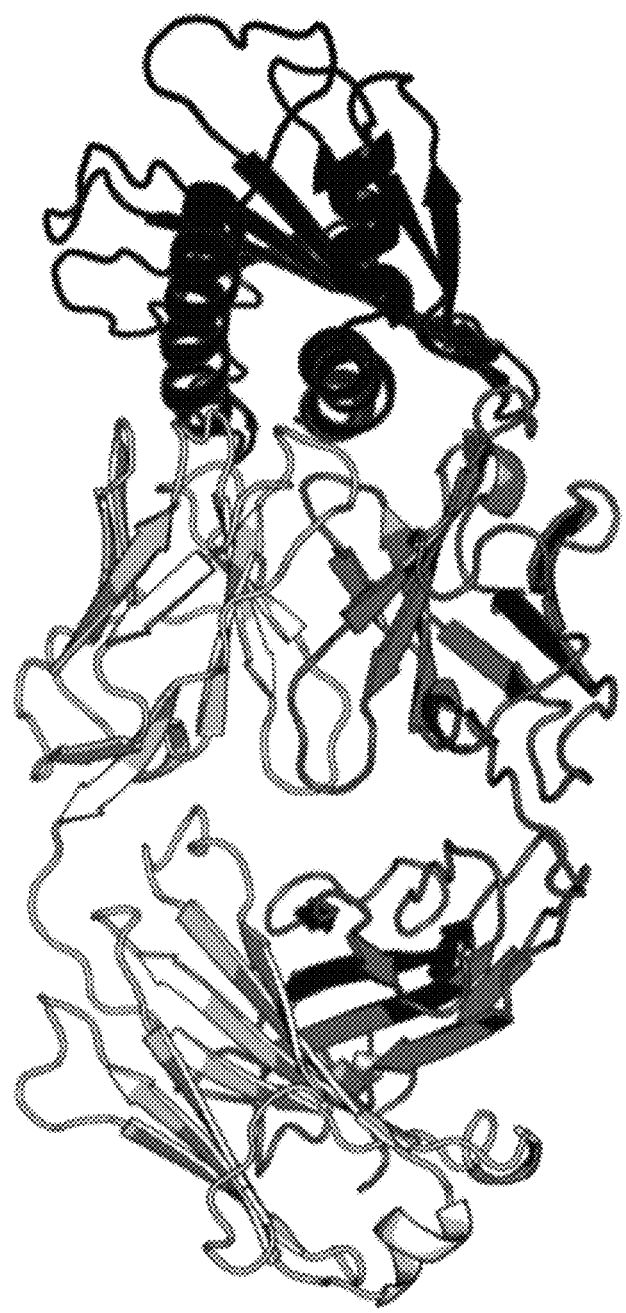
FIG. 13 depicts a cartoon representation of the crystal structure of h7B3 Fab in complex with ULBP602. ULBP6 is colored in black (toward the top of the structure), the h7B3 Fab light chain is colored in light gray (toward the left hand side of the structure), the heavy is colored in dark gray (toward the right hand side of the structure).
Figure 14:
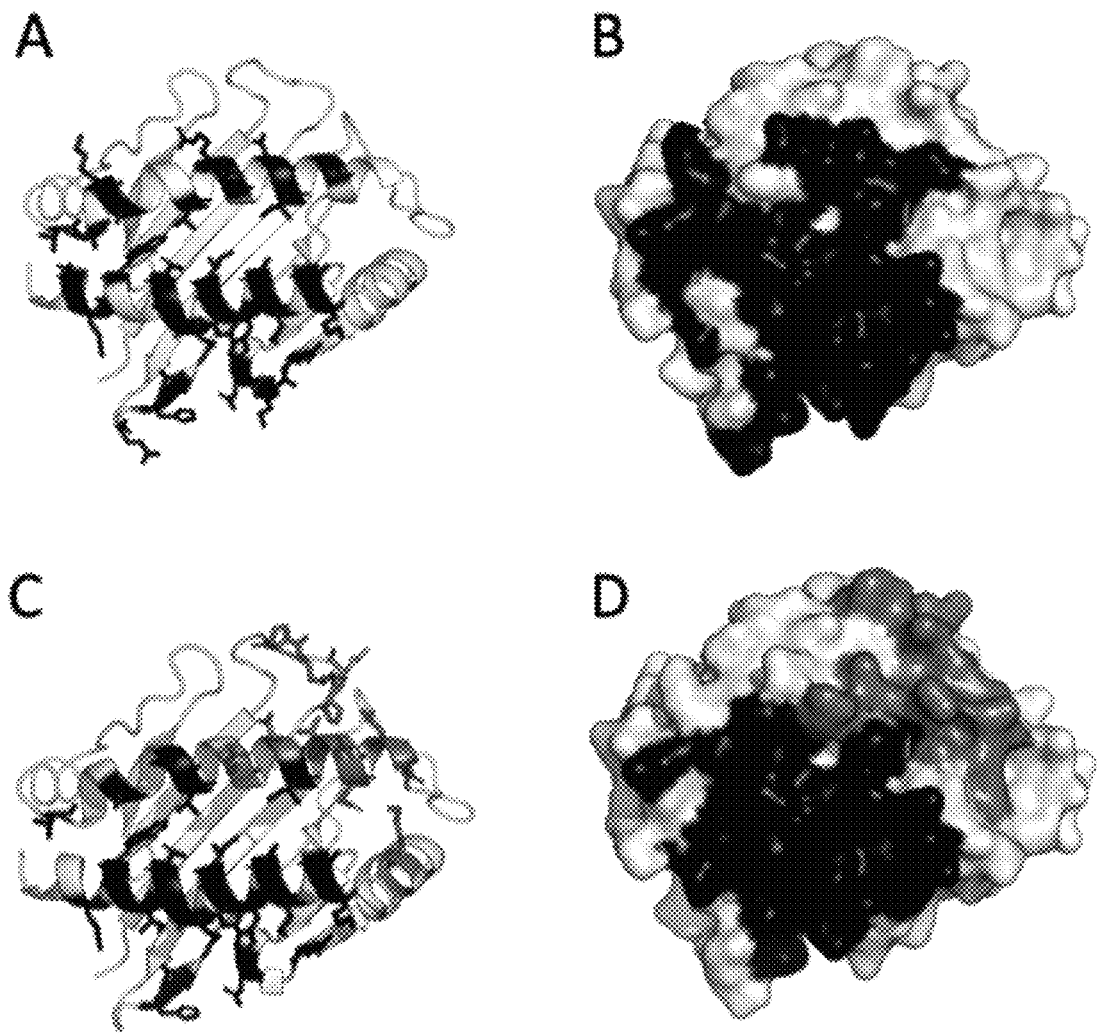
FIG. 14 depicts (panel A) the structural epitope of h7B3 on huULBP602 is determined by changes in solvent accessible surface area of ULBP602 residues between free and bound state. The epitope residues are colored in black and shown in stick representation on the cartoon representation structure of UBLP602. (panel B) Surface representation of ULBP6 with residues comprising the epitope h7B3 epitope colored in black. (panel C) The structural binding site of NKG2D on ULBP6 determined from the crystal structure of ULBP6 in complex with NKG2D (PDB ID: 4s0u). Residues (in stick representation) which interact with the NKG2D protomer A are colored black, residues interacting with the NKG2D protomer B are shown in gray on the cartoon representation structure of UBLP602. (panel D) Surface representation of ULBP6 with residues comprising the NKG2D protomer A binding side colored in black and residues forming the NKG2D protomer B binding site in gray.

The crystal structure of h7B33 Fab was solved at 2.31 Å resolution (FIG. 13). The structure of ULBP602 is highly similar to the previously solved crystal structure of UBLP6 in complex with NKG21D (PDB entry: 4s0u) with an r.m.s.d of 0.580 Å$^2$ over 1098 atoms. h7B33 Fab binding of ULBP6 buries a solvent accessible surface area of 1267 Å$^2$ on ULBP6. Using changes in solvent accessible surface area (SASA) between the free ULBP6 structure and the one bound in the complex we identified 32 residues which comprise the structural epitope (Table 22). NKG21D is a dimeric protein composed of two protomers (A and B) (Zuo et al., 2017). The h7B33 epitope on ULBP602 overlaps with most of the binding site of the NKG21D A protomer and with some of the binding site of the NKG21D B protomer (FIG. 14).

In addition to the SASA based epitope we also determined an extended structural epitope, defined by all residues in ULBP602 which are within 4 Å of any residue of h7B3. This epitope is composed of 54 residues (Table 22).

TABLE 22

| Structural epitope of h7B3 for binding to ULBP602 | | | |
|---|---|---|---|
| ULBP6 position | Amino acid | ≤4 Å | SASA difference between free and bound ULBP602 Å2 |
| 85 | THR | no | −10.54 |
| 86 | ALA | no | −5.42 |
| 87 | TRP | yes | 0 |
| 88 | LYS | yes | −6.56 |
| 89 | ALA | yes | −44.88 |
| 90 | GLN | yes | 0 |
| 91 | ASN | yes | 0 |
| 92 | PRO | yes | 0 |
| 93 | VAL | yes | −53.94 |
| 94 | LEU | yes | 0 |
| 95 | ARG | yes | −18.93 |
| 96 | GLU | yes | −90.23 |
| 97 | VAL | yes | 0 |
| 98 | VAL | yes | 0 |
| 99 | ASP | yes | −29.8 |
| 100 | ILE | yes | −22.21 |
| 101 | LEU | yes | 0 |
| 103 | GLU | yes | −13.54 |
| 104 | GLN | yes | 0 |
| 129 | GLN | no | −5.57 |
| 130 | LYS | yes | 0 |
| 132 | GLU | yes | −5.95 |
| 133 | GLY | yes | −52.37 |
| 134 | HIS | yes | −30.83 |
| 135 | SER | yes | −42.07 |
| 136 | SER | yes | 0 |
| 137 | GLY | yes | 0 |
| 138 | SER | yes | 0 |
| 152 | ASP | yes | 0 |
| 153 | SER | yes | 0 |

TABLE 22-continued

Structural epitope of h7B3 for binding to ULBP602

| ULBP6 position | Amino acid | ≤4 Å | SASA difference between free and bound ULBP602 Å2 |
|---|---|---|---|
| 154 | GLU | yes | −82.75 |
| 155 | LYS | yes | −21.28 |
| 156 | ARG | yes | −36.27 |
| 157 | MET | yes | 0 |
| 175 | ASP | yes | 0 |
| 176 | LYS | yes | −59.98 |
| 177 | ASP | yes | −54.07 |
| 178 | VAL | yes | 0 |
| 179 | ALA | yes | 0 |
| 180 | MET | yes | −44.54 |
| 181 | SER | yes | −35.12 |
| 182 | PHE | yes | 0 |
| 183 | HIS | yes | −35.43 |
| 184 | TYR | yes | −138.79 |
| 185 | ILE | yes | −9.71 |
| 186 | SER | yes | 0 |
| 187 | MET | yes | −24.34 |
| 188 | GLY | yes | −36.71 |
| 189 | ASP | yes | −51.46 |
| 190 | CYS | yes | 0 |
| 191 | ILE | yes | 0 |
| 192 | GLY | yes | −21.57 |
| 193 | TRP | yes | −24.01 |
| 194 | LEU | yes | −10.94 |
| 195 | GLU | yes | −40.41 |
| 196 | ASP | yes | −5.79 |
| 197 | PHE | yes | 0 |

All residue numbering is according to the uniprot entry of human ULBP6 (Q5VY80)

Example 18: Identification of hULBP6 Epitope Residues Involved in Binding of h7B3, h8E11 and h6E1

To identify epitope residues involved in binding of the fully human clones h7B3, h8E11 and h6E1 to hULBP6, functional epitope mapping with phage display was employed. Briefly, human ULBP602 (residue R26-G218) carrying a mouse IgG signal peptide and C-terminal His-tag was produced followed by functional epitope mapping with phage display comprising displaying ULBP6 on phage, Generation of a ULBP6 phage mutagenesis library, sorting the ULBP6 phage mutagenesis library, and NGS sequencing and data analysis.

Materials and Methods

Human ULBP602 (residue R26-G218) carrying a mouse IgG signal peptide and C-terminal His-tag were transiently expressed in 293 cells. The secreted proteins were purified from the cell culture supernatant by Ni-NTA chromatography, A Ni Excel, 10 mL, XK16/5 column was equilibrated with PBS pH 7.4 as a loading buffer. A step gradient of 4%, 50%, 100% PBS pH 7.4, 500 mM Imidazole was used for elution. The eluted protein was further purified by a size exclusion chromatography (Superdex, 60L XK15/30 using PBSk pH 7.4 as buffer). The heavy chain with C-terminal His-tag and light chain of Fab 7B3 were cloned into two separate vectors and were co-transfected into ExpiCHO cell. The Fabs were formed by heavy- and light-chain and were purified from cell culture supernatant by Ni-NTA chromatography. For the purification, clarified supernatant media from the expression culture was loaded on a Ni-NTA column equilibrated with PBS. After loading, the column was washed with PBS and 20 mM Imidazole. The eluted protein was further purified by a size exclusion chromatography (16/600 HiLoad Superdex200, using 2× PBS, pH6.5). To make ULBP6-Fab h7B3 complex, a molar excess of ULBP6 (molar ratio 1.2:1) was incubated with Fab h7B3 for 2.5 hours in PBS, pH 7.4, followed by a size exclusion chromatography on a HiLoad 16/60 Superdex 75 pre grade column pre-equilibrated in 20 mM HEPES pH 7.0, 100 nM NaCl.

For display ULBP6 on phage, ULBP6 phage production was followed by purification of the phage, an ELISA assay, ULBP6 display on the phage, and ULBP6 folding on the phage, as described below.

Phagemid encoding human ULBP6-HA-plll was designed to display ULBP6 protein on the phage surface. The vector was constructed by fusing the ULBP6 gene to the N-terminal domain of M13 minor coating protein (glll). An epitope tag (HA tag, amino acid sequence: YPYDVPDYA) was added between the ULBP6 and plll genes. The phagemid was chemically transformed to XL-1 blue competent cells (Agilent Technologies, cat #200249) and spread on a Carbenicillin-50 agar plate with overnight incubation at 37° C. One colony was then inoculated in 5 mL 2YT broth (TEKNOVA, cat #Y0167) for expansion. The culture was incubated at 37° C. with shaking until O.D. 600 reached 0.3/mL. 50 µL M13K07 helper phage (New England Biolabs, cat #N0315S) was added to the culture. After shaking at 37° C. for 1 hour, the 5 mL culture was expanded to 50 mL 2YT broth supplemented with 50 µg/mL carbenicilin and 50 µg/mL kanamycin. The expanded culture was incubated at 37° C. for 4 hours, followed by overnight incubation at 30° C.

Phage culture was harvested by spinning at 8000 g for 10 minutes at 4° C. The supernatant was collected for phage purification. Phage was precipitated from supernatant by 2.5M NaCl, 20% PEG solution (TEKNOVA, cat #P4137) and was resuspended by 1×PBS buffer (137 mM NaCl, 2.7 mM KCl, 4.3 mM $Na_2HPO_4$, 1.47 mM $KH_2PO_4$, pH 7.4). The PEG precipitation treatment was repeated to increase purity. The final phage pellet was resuspended in 1×PBS buffer to a concentration of 10.0 O.D./mL. O.D. was read on Nanodrop (ThermoFisher Scientific) at 268 nm. Purified phage was stored at 4° C.

MaxiSorp plates (ThermoFisher Scientific, cat #437915) were coated overnight with 2 µg/mL antibody or recombinant protein receptor (e.g., anti-HA antibody, anti-ULBP6 antibodies, and ULBP6 receptor) and then blocked with 1% bovine serum albumin (BSA, ThermoFisher Scientific, cat #P137520) in 1×PBS buffer for 30 minutes. Phage was diluted to 1.0 O.D./mL in 120 µL ELISA buffer (0.5% BSA, 0.05% Tween-20 in 1×PBS) in the 96-well plate (ThermoFisher Scientific, cat #156545). A 3-fold serial dilution was performed. 65 µL diluted phage solution was loaded to each corresponding well in the blocked MaxiSorp plate and incubated at room temperature for 15 minutes with shaking. Horseradish peroxidase (HRP)-labeled anti-M13 antibody (Sino Biological, cat #11973-MM05T-H) at 1:2500 dilution in the ELISA buffer was then added at 100 µL/well as the secondary reagent. The ELISA plates were developed using a TMB solution (ThermoFisher Scientific, cat #34022), and the reaction was stopped by addition of 50 µL of 2 M $H_2SO_4$(VWR, cat #BDH7259-1). Absorbance was read at 450 nm on a VersaMax microplate reader (Molecular Devices).

Figure 15:
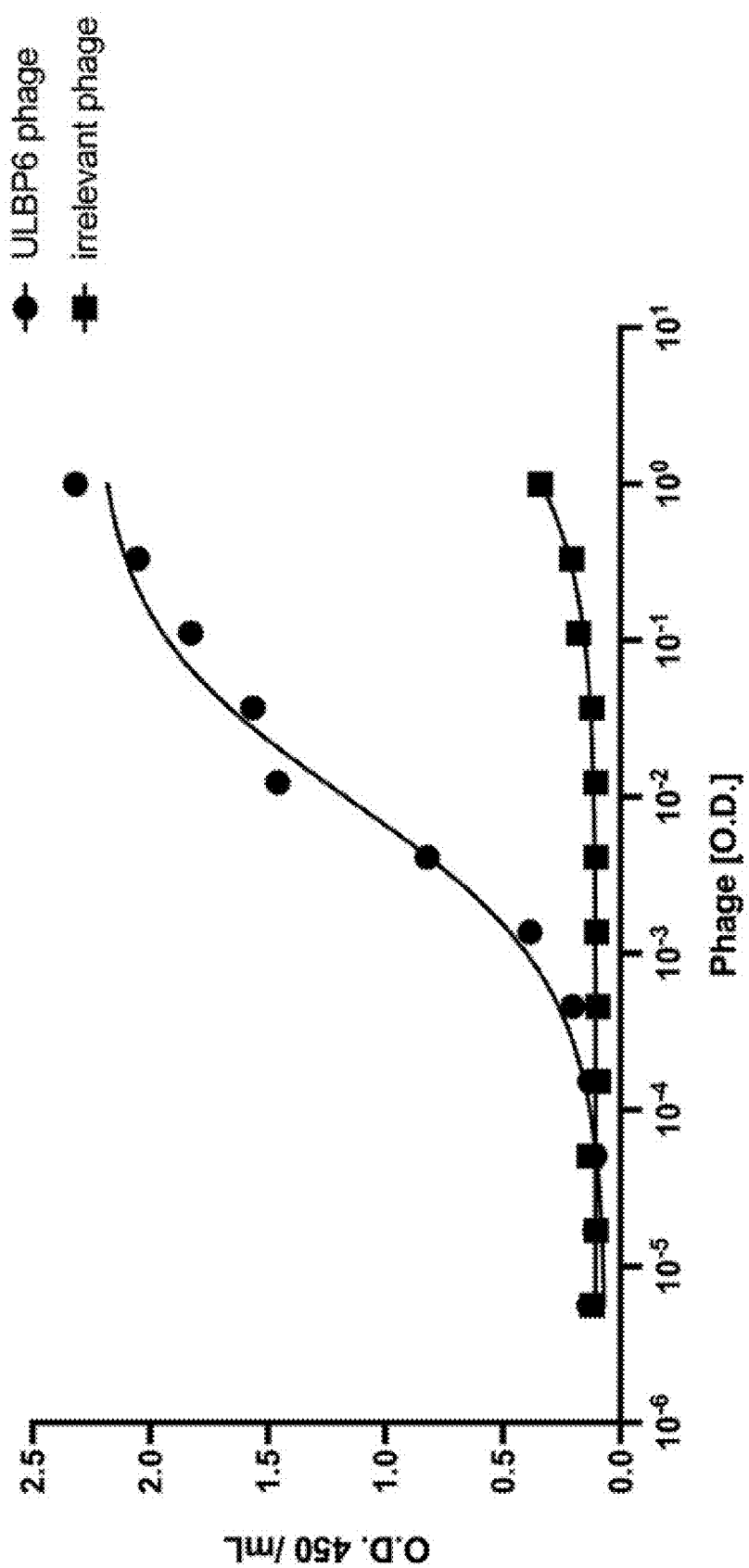
FIG. 15 depicts ULBP6 phage binding to an anti-HA antibody.

The display of ULBP6 on phage was validated by investigating HA tag expression with ELISA assay. ULBP6 phage binding to anti-HA antibody, shown in FIG. 15, demonstrated the expression of HA tag and display of ULBP6 on phage. Negative control with irrelevant phage further excluded non-specific phage binding to anti-HA antibody.

Figure 16:
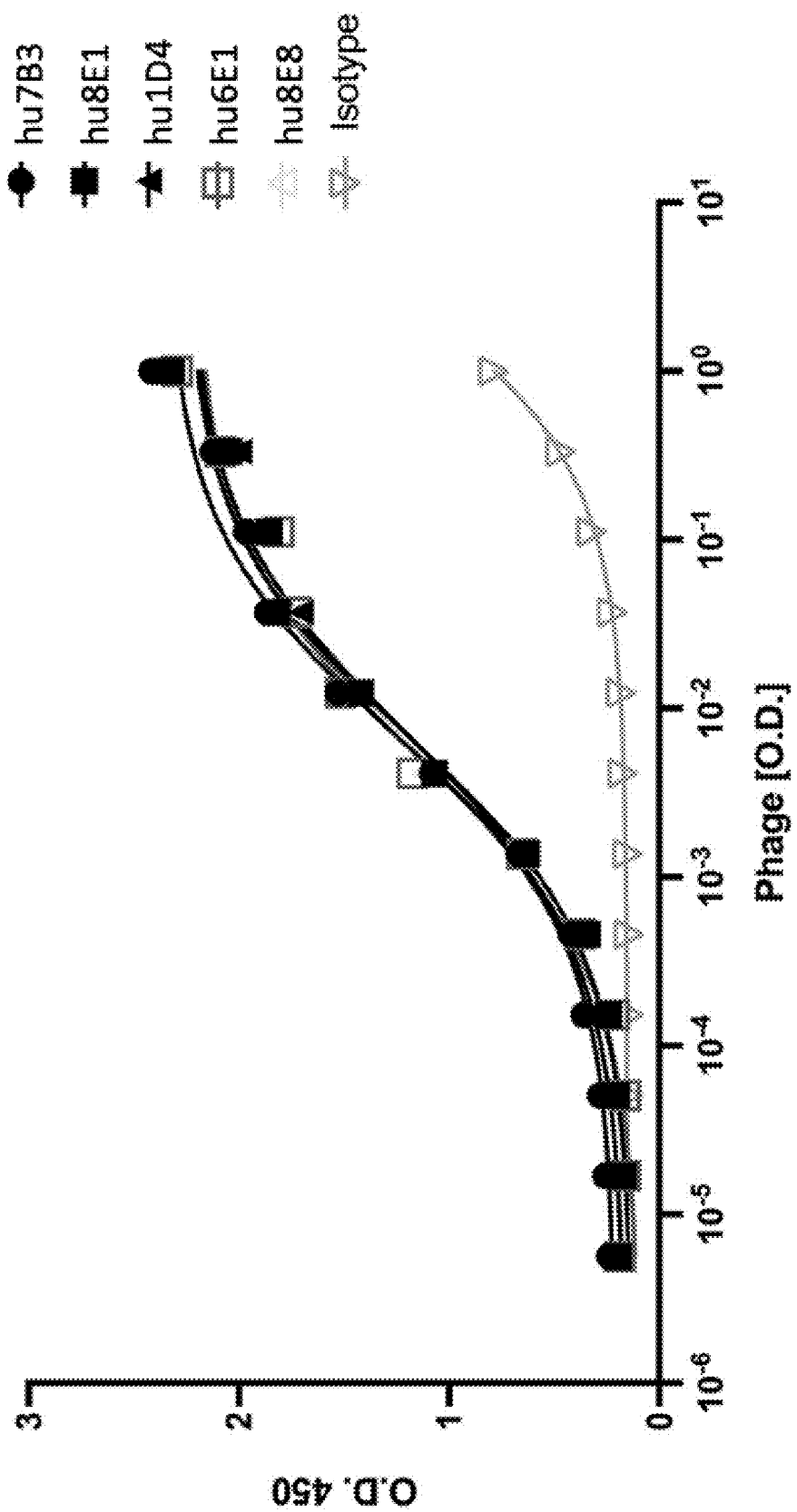
FIG. 16 depicts binding affinity to ULBP6 to hu7B3, hu8E1, hu1D4, hu6E1, and hu8E8.
Figure 17:
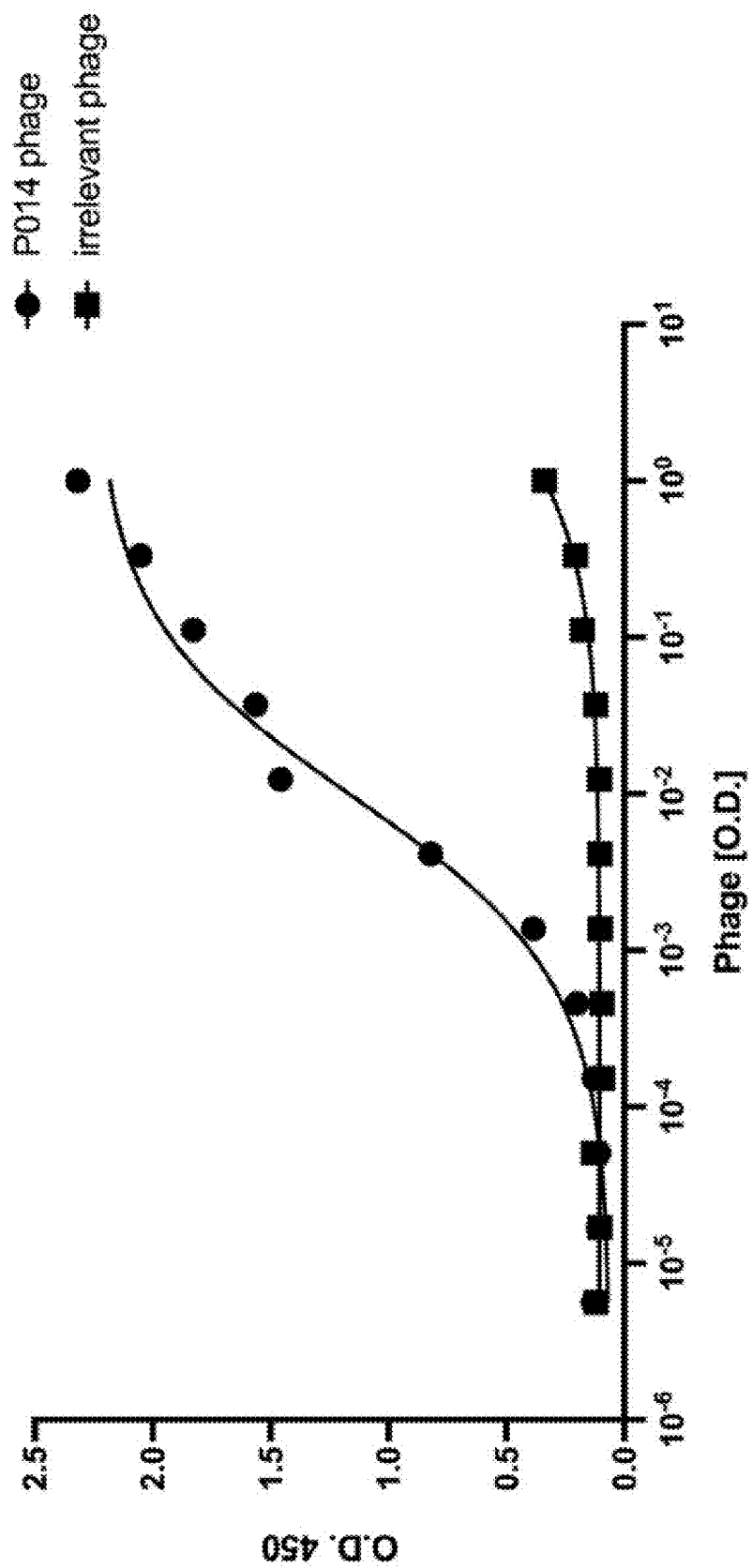
FIG. 17 depicts binding affinity to ULBP6 receptors.

The folding of ULBP6 on phage was validated by investigating phage binding to ULBP6 lead antibodies discovered with recombinant ULBP6 or ULBP6 receptor NKG2D (Table 23) with ELISA assay. ULBP6 phage showed binding affinity to hu7B3, hu8E1, hu1D4, hu6E1, and hu8E8 as well as ULBP6 receptors (FIG. 16 and FIG. 17). The result demonstrated ULBP6 was properly folded on phage.

TABLE 23 anti-ULBP6 antibodies and ULBP6 receptor

| Anti-ULBP6 antibodies | PUR # |
|---|---|
| h7B3 | PUR3922 |
| h8E11 | PUR3926 |
| h1D4 | PUR3987 |
| h6E1 | PUR3993 |
| h8E8 | PUR3924 |
| NKG2D | PUR4928 |
| Isotype antibody control | PUR3678 |

A ULBP6 phage library was engineered for functional epitope mapping by generating random mutagenesis across genes encoding ULBP6. Mutagenesis was implemented with error-prone PCR. The error-prone PCR product was subcloned into phagemids and transformed into XL-1 blue cells to create the mutagenized ULBP6 phage library.

Error-prone PCR was implemented with a GeneMorph II Random Mutagenesis Kit (Aglient, cat #200550). The mutation frequency was controlled by adjusting the initial target DNA amounts and the number of PCR cycles. For determining the functional residues in antibody binding, the desired mutation frequency was one amino acid change (1-2 nucleotide changes) per gene. To achieve the desired mutation frequency, the error-prone PCR mixture was set up as in Table 24. The forward and reverse primers used were as provided in Table 25.

TABLE 24

Error-Prone PCR Reaction Setup

| Component | Total 50 µL reaction |
|---|---|
| Mutazyme II reaction buffer | 5 µL |
| 40 mM dNTP mix | 1 µL (200M final concentration) |
| 100 ng/µL primer | 1.25 µL |
| Mutazyme II DNA polymerase (2.5 U/µL) | 1 µL |
| Template 100 ng/µL | 5 µL |
| Water | 35.5 µL |

TABLE 25

Primers utilized in Error-prone PCR

| Primer | Sequence | SEQ ID NO |
|---|---|---|
| Forward | GCATCTATGTTCGTTTTTTCTATTGCTACAA ACGCGTATGCA | 118 |
| Reverse | CACATCATACGGATAAGAACCACCACCACCC | 119 |

To amplify DNA in a thermal cycler, the program was set up as Table 26.

TABLE 26

Error Prone PCR Thermocycling Setup

| Step | Temperature | Time |
|---|---|---|
| Initial Denaturation | 95° C. | 2 minutes |
| 24 cycles | 95° C. | 30 seconds |
| | 61° C. | 30 seconds |
| | 72° C. | 60 seconds |
| Final extension | 72° C. | 10 minutes |
| Hold | 4° C. | — |

The error prone-PCR product was purified with QIAquick Gel Extraction kit (Qiagen, cat #28706X4). The purified PCR product and phagemid vector were digested by restriction enzymes MluI (New England Biolabs, cat #R3198) and XhoI (New England Biolabs, cat #r0146S), followed by a ligation reaction. The ligation product was transformed to XL-1 Blue competent cells. After transformation, XL-1 Blue cells were plated on the Carbenicillin-50 agar plates and incubated at 37° C. overnight. 20-30 colonies were picked for Sanger sequencing (ELIM Biopharmaceuticals) and analyzing the mutation frequency. Unbiased mutations are randomly generated across the amplified region with above-described error-prone PCR protocol. The mutation frequency was 1.2 bp/gene.

To produce the mutagenized phage library, the error-prone PCR product was transformed to XL-1 blue competent cells by electroporation. Cells were recovered in 25 mL SoC media (ThermoFisher Scientific, cat #15544034) at 37° C. for 40 minutes. 250 µL M13K07 helper phage was added to the culture. After incubation at 37° C. for 1 hour, the 25 mL culture was expanded to 60 mL 2YT broth with 50 µg/mL Carbenicilin and 50 µg/mL Kanamycin. The expanded culture was incubated at 37° C. for 4 hours, followed by overnight incubation at 30° C. Phage library was harvested by spinning the culture at 8000 g for 10 minutes at 4° C., and purified following the phage purification method described above. Purified ULBP6 phage library was stored at 4° C. Cell pellets were saved for NGS sequencing.

ULBP6 phage library was sorted twice with lead antibodies (7B3, 6E1 and 8E11) by plate panning for the first round and solution panning for the second round. Enrichment was determined by phage titration to evaluate the panning performance.

The MaxiSorp plate was coated with 5 µg/mL lead antibodies (7B3, 6E1 and 8E11) in 1×PBS, 100 µL/well, for 8 wells for each antibody, at 4° C. overnight. Two wells were coated with 1×PBS buffer as background. The next day, the plate was washed 6 times using 1×PBST (1×PBS, 0.1% Tween 20 detergent) and blocked with 1% BSA in 1×PBS buffer, 65 µL/well, for 30 minutes at room temperature. Then, 40 µL 1×PBS with 1% Tween-20 was added to each well and incubated for another 30 minutes at room temperature. The plate was washed 6 times with 1×PBST. The mutagenized phage library was diluted to 2.5 O.D./mL and blocked with 1×PBS buffer with 1% BSA and 0.05% Tween-20 for 30 minutes, shaking at room temperature. The blocked phage library was added to the blocked plate, 100 µL/well, and incubated for 2 hours at room temperature with shaking. The plate was mildly washed with 1×PBST buffer 10 times. The bound phage was eluted from the plate using 0.1 M HCl, 100 µL/well, and neutralized with 1 M Tris base and 1% BSA. The eluted phage was titered to determine the enrichment (Table 27) and amplified using XL-1 Blue cells. The sorted phage library was purified and stored at 4° C. Cell pellets were saved for NGS sequencing.

TABLE 27

Plate Panning Enrichment

| Antibody | Phage enrichment |
| --- | --- |
| h7B3 | 75x |
| h6E1 | 220x |
| h8E11 | 145x |

The MaxiSorp plate was coated with 5 µg/mL Neutravidin (ThermoFisher Scientific, cat #31000) in 1×PBS, 100 µL/well, at 4° C. overnight. The next day, lead antibodies (7B3, 6E1 and 8E11) were first biotinylated using EZ-Link™ Sulfo-NHS-LC-Biotinylation Kit (ThermoFisher Scientific, cat #21435). Phage library was diluted in 600 µL SuperBlock (ThermoFisher Scientific, cat #37515) supplemented with 0.05% Tween-20 and incubated at room temperature for 30 minutes. Blocked phage library was then incubated with biotinylated lead antibodies at 100 nM, 20 nM, or 0 nM (background), followed by incubation at room temperature for 2 hours with shaking. The MaxiSorp plate was washed 6 times using 1×PBST and blocked with SuperBlock, 65 µL/well, for 30 minutes at room temperature. Then, 40 µL 1×PBS with 1% Tween-20 was added to each well and incubated for another 30 minutes at room temperature. The plate was washed 6 times with 1×PBST. Phage/antigen solutions were diluted 6-fold with Superblock, loaded to the Maxisorp plate, 100 µL/mL, and incubated at room temperature for 15 minutes with shaking. The plate was mildly washed with 1×PBST buffer 10 times. The bound phage was eluted from the plate using 0.1 M HCl, 100 µL/well, and neutralized with 1 M Tris base and 1% BSA. The eluted phage was titered to determine the enrichment (Table 28) and amplified using XL-1 Blue cells. The sorted phage library was purified and stored at 4° C. Cell pellets were saved for NGS sequencing.

TABLE 28

Solution Panning Enrichment

| Antibody | Phage enrichment, 100 nM | Phage enrichment, 20 nM |
| --- | --- | --- |
| h7B3 | 176x | 222x |
| h6E1 | 286x | 77x |
| h8E11 | 48x | 234x |

For sequencing, the ULBP6 mutagenized phagemid library was divided into two amplicons: Amplicon 1 spans over the N-terminus of the protein from position 29 to 142, while amplicon 2 covers the C-terminus of the protein, inclusive of amino acids 101 through 218. All amino acid positions are numbered according to uniport entry Q5VY80 ULBP6_HUMAN. Phagemid libraries were extracted from phage pellets with Monarch® Plasmid Miniprep Kit (New England Biolabs, cat #T1010S). For each amplicon, NGS samples were prepared by two PCR cycles to adapters and barcodes. The amplicon PCR was performed with Q5® High-Fidelity 2× Master Mix (New England Biolabs, cat #M0492S) using primers as provided in Table 29.

TABLE 29

Amplicon PCR Primers

| Amplicon | Primer | Sequence | SEQ ID NO. |
| --- | --- | --- | --- |
| 1 | Forward | TCGTCGGCAGCGTCAGATGTGTATAAGA GACAGcgtcgtgacgacccg | 120 |
|   | Reverse | GTCTCGTGGGCTCGGAGATGTGTATAAG AGACAGgagaactgccaagaaccagaa | 121 |
| 2 | Forward | TCGTCGGCAGCGTCAGATGTGTATAAGA GACAGccgaacagctgctggaca | 122 |
|   | Reverse | GTCTCGTGGGCTCGGAGATGTGTATAAG AGACAGaccagaagacatcgccag | 123 |

Amplicon PCR reaction setup is shown as Table 30, and thermocycling setup as Table 31. Amplicon PCR products were purified with 2% E-Gel EX Size Select (Invitrogen, cat #G661012). Sequencing adapters were further added with Nextera XT DNA Library Preparation kit (Illumina, cat #FC-131-1024), and reaction products were purified with AMPure XP beads (ThermoFisher Scientific, cat #NC9933872). Prepared samples were pulled with 25% PhiX control (Illumina, FC-110-3001) and sequenced with an Illumina MiSeq NGS sequencer.

TABLE 30

Amplicon PCR Reaction Setup

| Component | Total 50 µL reaction |
| --- | --- |
| 2x Q5 master mix | 25 µL |
| Forward primer (10 µM) | 2.5 µL |
| Reverse primer (10 µM) | 2.5 µL |
| Template (10 ng/µL) | 1 µL |
| PCR grade water | 19 µL |

TABLE 31

Thermocycling Setup

| Step | Temperature (C.) | Time |
| --- | --- | --- |
| Initial Denaturation | 98 | 3 minutes |
| 18 cycles | 98 | 10 seconds |
|  | 66 | 20 seconds |
|  | 72 | 30 seconds |
| Final extension | 72 | 3 minutes |
| Hold | 4 | — |

The sequencing results obtained from panning of each of 6E1, 7B3 and 8E11 were first analyzed separately (see Table 4 for sample details). In the first step the paired reads were pairwise aligned using flash pairwise aligner. Samples which were sequenced in sequencing run 1 (Table 4) were aligned, restricting alignments to reads where the read overlap was 100% identical in order to minimize the impact of sequencing error in the subsequent analysis. Due to slightly lower read quality in sequencing run 2 a 1% mismatch in the overlapping region was allowed. Sequencing samples and statistics thereof are provided in Table 32.

TABLE 32

Sequencing Samples and Statistics

| Sample info | Sequencing run | Antibody | Sort condition | Total # reads | Flash output (# combined reads) | Reads with correct length |
|---|---|---|---|---|---|---|
| Presort Amp1 | 1 | — | — | 2831472 | 991159 | 961317 |
| Presort Amp2 | 1 | — | — | 3106688 | 670291 | 648295 |
| 7B3 R2 Amp1 | 1 | 7B3 | 20 nM 7B3, round 2 | 2713073 | 786047 | 779924 |
| 7B3 R2 Amp2 | 1 | 7B3 | 20 nM 7B3, round 2 | 2372727 | 414673 | 411501 |
| Presort Amp1 | 2 | — | — | 6511300 | 1176933 | 974388 |
| Presort Amp2 | 2 | — | — | 5521519 | 581228 | 537202 |
| 8E11 R2 Amp1 | 2 | 8E11 | 20 nM 8E11, round 2 | 629523 | 68374 | 67507 |
| 8E11 R2 Amp2 | 2 | 8E11 | 20 nM 8E11, round 2 | 552622 | 37182 | 36275 |
| 6E1 R2 Amp1 | 2 | 6E1 | 20 nM 6E1, round 2 | 548468 | 173760 | 166036 |
| 6E1 R2 Amp2 | 2 | 6E1 | 20 nM 6E1, round 2 | 642494 | 53044 | 51922 |

Next, position weight matrices (PWM) for each amino acid sample were generated, which contain the frequency of each of the 20 amino acids at every position analyzed. The assembled paired end reads were translated into amino acid sequence. Then for each protein position across all reads the occurrence of all 20 amino acids was counted. The analysis was restricted to sections of each amplicon which was covered by both R1 and R2. The analysis strategy was chosen to minimize the impact of sequencing errors on position weight matrix generation. Therefore, the PWMs cover the following regions of ULBP6: Amplicon 1: 43-122, Amplicon 2: 118-202. Using the PWMs the mutation frequency of each position in the PWMs was calculated by dividing the sum of all mutation counts at a given position by the total read counts covering the position:

$$F^x = m_i^x/r^x$$

wherein $F^x$ is the mutation frequency for position x, $m_i^x$ is the mutation count for mutation i at position x, and $r^x$ is the total number of reads at position x. The mutation frequencies were then used to calculated the log 2 enrichment ratios (ER):

$$ER = \log 2(S^x/P^x)$$

wherein $S^x$ is frequency of mutations in sorted library at amino acid position x, and $P^x$ is frequency of mutations in presorted library at amino acid position x.

To identify residues of the functional epitope a linear regression analysis between ERs from different epitope bins was performed comparing the ER values obtained for h7B3 with ER obtained for h6E1 as well as comparing the ER of h8E11 with the ones obtained for h6E1. The idea is that positions where mutations have no impact or an indirect impact on antibody binding (for example because they destabilize the antigen fold in general) should have a small residual while mutations which directly impact binding of one of the antibodies will have a large residual. Positions which have a residual larger than 0.5 were considered being part of the functional epitope.

Results

For h7B3 the 4 ULBP6 positions were identified to have residuals larger than 0.5 when comparing the ERs with h6E1 (Table 33):

TABLE 33 positions in the functional epitope of h7B3

| ULBP6 position[#] | residual | regression analysis with | Residue is part of the NKG2D binding site* |
|---|---|---|---|
| 54G | 1.26828589 | 6E1 | No |
| 189D | 1.13618383 | 6E1 | NKGD2-protomer A |
| 184Y | 0.62179682 | 6E1 | NKGD2-protomer A |
| 183H | 0.56607195 | 6E1 | NKGD2-protomer A |

[#]ULBP6 position numbering according to Uniprot entry Q5VY80
*NKG2D binding site identified using solvent accessible surface area (SASA) using the crystal structure of the ULBP6/NKG2D complex (PDB:4S0U).

For h8E11 two ULBP6 positions were identified to have residuals larger than 0.5 when comparing the ERs with h6E1 (Table 34)

TABLE 34 positions in the functional epitope of h8E11

| ULBP6 position[#] | residual | regression analysis with | Residue is part of the NKG2D binding site* |
|---|---|---|---|
| 188G | 0.80841862 | 8E11 | NKGD2-protomer A |
| 189D | 0.54850412 | 8E11 | NKGD2-protomer A |

[#]ULBP6 position numbering according to Uniprot entry Q5VY80
*NKG2D binding site identified using solvent accessible surface area (SASA) using the crystal structure of the ULBP6/NKG2D complex (PDB:4S0U).

For h6E1, seven ULBP6 positions were identified to have residuals larger than 0.5 when comparing the ERs with h7B3 and h8E11 (Table 35).

TABLE 35 positions in the functional epitope of 6E1

| ULBP6 position[#] | residual | regression analysis with | Residue is part of the NKG2D binding site* |
|---|---|---|---|
| 69K | 0.98829148 | 7B3 | No |
| 44R | 0.91474334 | 7B3 | NKGD2-protomer B |
| 58E | 0.85419714 | 7B3 | No |
| 103E | 0.80537266 | 7B3 | NKGD2-protomer B |
| 128E | 0.55804883 | 7B3 | No |
| 182F | 0.54240776 | 7B3 | No, but neighbor to 181 and 182 which are in NKGD2-protomer A binding site |
| 44R | 0.84193897 | 8E11 | NKGD2-protomer B |
| 120T | 0.51989906 | 8E11 | No |

[#]ULBP6 position numbering according to Uniprot entry Q5VY80
*NKG2D binding site identified using solvent accessible surface area (SASA) using the crystal structure of the ULBP6/NKG2D complex (PDB:4S0U).

Figure 18:
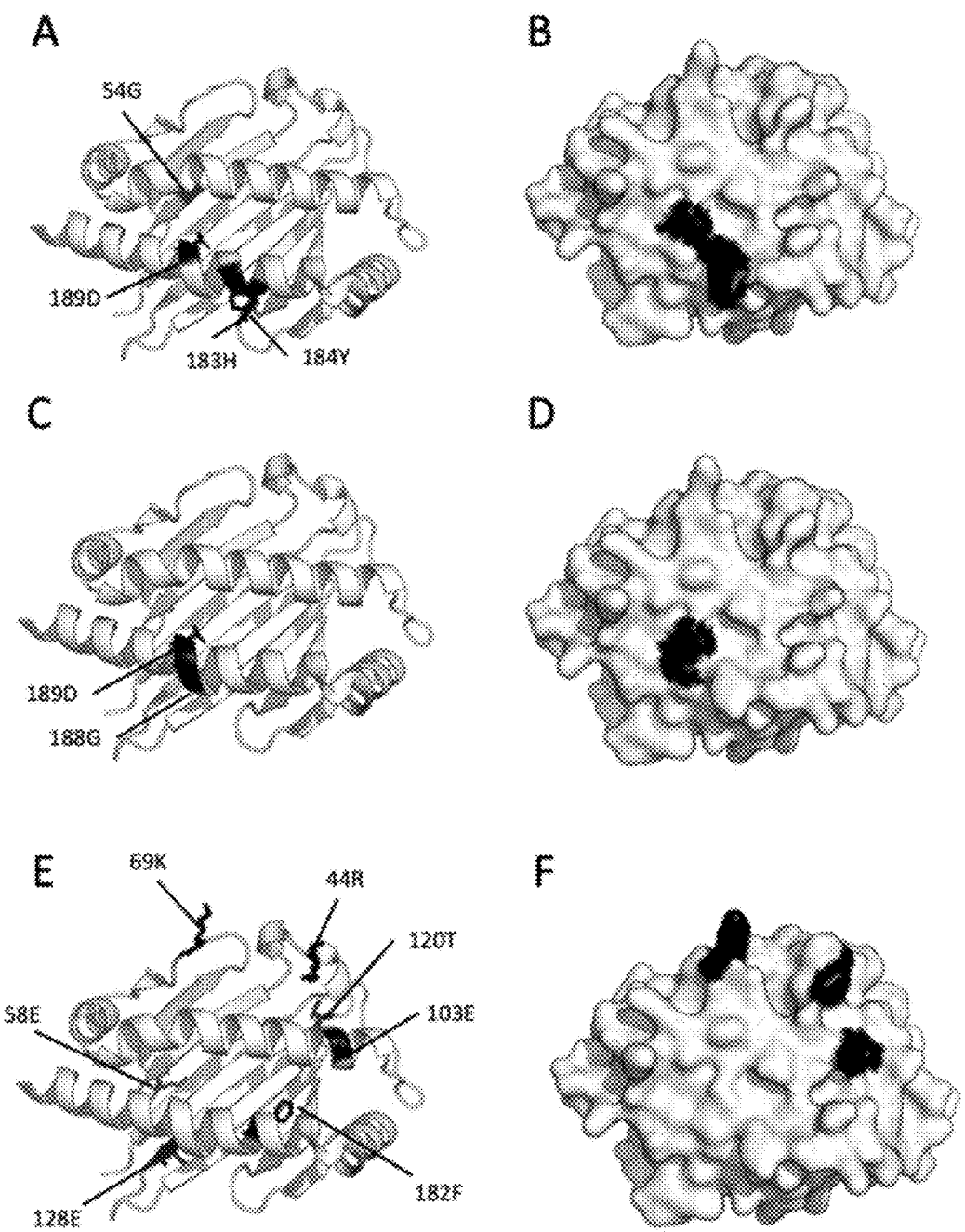
FIG. 18 depicts the functional epitope of 7B3, (panel A and panel B), the functional epitope of (panel C and panel D), and the functional epitope of 6E11 (panel E and panel F), as determined herein.

Three of the four residues which were identified as a 7B3 functional epitope—183H, 184Y and 189D are surface exposed and located in the NKG2D protomer A binding site, as depicted in panels A and B of FIG. 18. These three residues are also located within the structural epitope identified by the crystal structure of 7B3 in complex with ULBP6.

The two residues identified as a functional epitope of 8E11 are also located within the NKG2D protomer A binding site on ULBP6, as depicted in panels C and D of FIG. 18. The functional epitope of 8E11 overlaps with the one of 7B3 as they share both residue 189D in the epitope.

In contrast to functional epitopes of 7B3 and 8E1, the residues of the 6E11 functional epitope are distinct. Two of the seven residues are located in the NKG2D protomer B binding site, as depicted in panels E and F of FIG. 18.

Example 19: ULBP6—Antibody Interactions by HDX

The interactions between human ULBP6 and 6 different monoclonal antibodies (mAbs), were assessed using hydrogen-deuterium exchange mass spectrometry (HDX).

Materials and Methods

The ULBP6 protein used in this example had the following sequence before processing, as provided in Table 36.

TABLE 36

| ULBP6 amino acid sequence for HDX experiments | |
|---|---|
| Protein | Sequence | SEQ ID NO |
| ULBP6 | MGWSCIILFLVATATGVHSRRDDPHSLCYDITV IPKFRPGPRWCAVQGQVDEKTFLHYDCGNKTVT PVSPLGKKLNVTTAWKAQNPVLREVVDILTEQL LDIQLENYTPKEPLTLQARMSCEQKAEGHSSGS WQFSIDGQTFLLEDSEKRMWTTVHPGARKMKEK WENDKDVAMSFHYISMGDCIGWLEDFLMGMDST LEPSAGAPLAMSSGHHHHHHHH | 124 |

Figure 22:
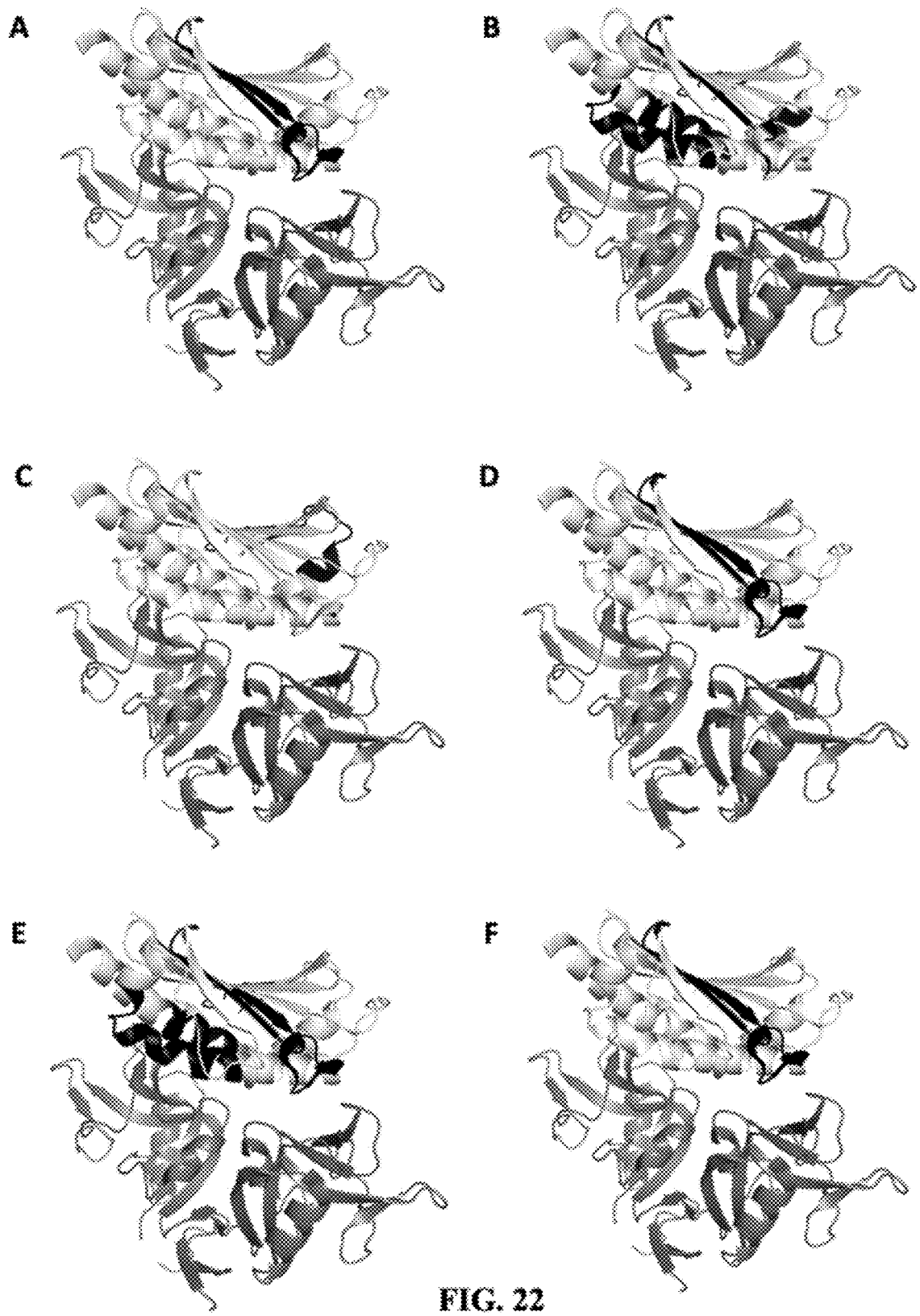
FIG. 22 depicts, on a crystal structure of the NKG2D-ULBP6 complex, residues of ULBP6 peptides having significant protection by mAb1298 (panel A), h7B3 (E+ Afu) (panel B), h8E8 (E+) (panel C), h1D4 (E+) (panel D), h8E11 (E+) (panel E), and h6E1 (E+) (panel F), as determined by HDX and indicated in black.

Residues 20-212 of SEQ ID 123 correspond with residues 26-218 of the native human ULBP6_02 sequence provided herein as SEQ ID NO: 7 (Uniprot: Q5VY80).

h7B3 (E+ Afu), h8E11 (E+), h1D4 (E+), h6E1 (E+), h8E8 (E+), and mab1298 (mIgG2a, R&D SYSTEMS, clone #165903) were tested, and are referred to as 7B3, 8E11, 1D4, 6E1, 8E8 and 1298, respectively, in FIG. 21A, FIG. 21B and FIG. 22.

Buffers and solvents used for HDX experiments described herein were as provided in Table 36.

TABLE 36

| HDX Buffers and Solvents | |
|---|---|
| Reagent | Composition |
| MOPS-H2O Sample buffer | 50 mM MOPS, 150 mM NaCl, 20 mg/l sodium azide, pH 7.2 |
| MOPS-D2O Labelling buffer | 50 mM MOPS, 150 mM NaCl, dissolved in D2O and adjusted to pD 6.8 (uncorrected) |
| Quench buffer | 3M GnHCl, 500M TCEP, 1% Formic acid, adjusted to pH 2.2 with NaOH |
| Solvent A | 0.2% Formic acid + 0.03% TFA |
| Solvent B | Acetonitrile + 0.2% formic acid |

Liquid handling, deuterium labelling, online digest and LCMS analysis were performed on an automated HDX-MS system comprising a LEAP H/D-X PAL™ robot (LEAP-TRAJAN), an ACQUITY M-Class UPLC (WATERS), an HDX Manager (WATERS), and a CYCLIC mass spectrometer (WATERS). Software packages used for data acquisition and interpretation include MASSLYNX, v4.2 (WATERS), Chronos, V4.11.0-beta.24 (AXELSEMRAU), ProteinLynxGlobal SERVER (PLGS), v3.0.2 (WATERS), and HDEXAMINER, v3.3.0 (LEAP-TRAJAN).

Prior to HDX analysis, all samples were kept at 0° C. An automated LEAP-TRAJAN liquid handling workstation was used to prepare samples for HDX. Samples were prepared for peptide mapping as 40 pmol of ULBP6 protein stock in 5 µl MOPS-H2O buffer, diluted with 55 µl MOPS-H2O to a final volume of 60 µl. Prepared samples were labeled as 40 pmol of ULBP6 protein (apo reference), or 40 pmol of ULBP6 protein+0.75 molar equivalents of mAb (complexes of ULBP6 with each of mAb1298, h7B3, h8E8, h1D4, h8E11, and h6E1) in 5 µl MOPS-H2O buffer, diluted with 55 µl MOPS-D2O to a final volume of 60 µl and incubated at 20° C. for a period of 20, 200, 2000 or 20000 seconds.

For the peptide mapping, 55 µl of the reaction mixture was quenched 1:1 with pre-cooled quench buffer for 1 minute (labelling experiments) or for between 1 and 20 minutes (peptide mapping) at 0° C. $10^5$ µl of the reaction mixture was then injected onto an immobilised digestion column (Nepenthesin2, Affipro Part no AP-PC-004), and maintained at 15° C.

During digestion, the released peptides were trapped on a guard column (2.1×5 mm WATERS VANGUARD BEH C18 1.8 µm 130 Å guard column, Part no: 186003975) maintained at 0.5° C. The digestion/trapping was performed over 4 minutes in solvent A, with flow rates as shown in Table 37.

TABLE 37

| Flow rates of solvent A during sample digestion/trapping | | |
|---|---|---|
| # | Time (min) | Flow rate (µl/min) |
| 1 | Initial | 100.000 |
| 3 | 3.00 | 100.000 |
| 4 | 3.20 | 200.000 |
| 5 | 3.90 | 200.000 |
| 6 | 4.00 | 100.000 |

Trapped peptides were then eluted from the guard column onto an analytical column (1.0×50 mm ULP BEH C18, Part no: 186002344) at 0.5° C. in solvent A according to the initial conditions and analytical gradient provided in Table 38.

TABLE 38

| Elution gradient for peptide mapping and labelling experiments | | | |
|---|---|---|---|
| # | Time (min) | Flow Rate (µl/min) | % B |
| 1 | Initial | 20.000 | 11.0 |
| 2 | 0.80 | 20.000 | 16.0 |
| 3 | 10.00 | 20.000 | 34.0 |
| 4 | 12.00 | 20.000 | 46.0 |
| 5 | 12.50 | 20.000 | 98.0 |
| 6 | 14.90 | 20.000 | 98.0 |
| 7 | 15.00 | 20.000 | 11.0 |

During elution, mass spectra were recorded from 2.0 to 15.0 minutes, either in HDMSE ion mobility acquisition mode (for peptide mapping experiments) or in HDMS ion mobility mode (for labelling experiments). Four replicates were recorded for each of the peptide mapping and labelling time courses.

Peptide mapping raw data were processed with PLGS. PLGS output from multiple replicates was further optimized for sequence coverage, data quality, and reproducibility with an in-house implementation of the selection algorithm LARS (Sorensen & Salbo, 2018). The LARS procedure was applied after hard filter conditions comprising a PLGS peptide score>6.5, a peptide length≥25, and a mass error≥7 ppm.

Raw data from each labelling time course were analyzed against the LARS peptide map using HDEXAMINER to determine update (AFU) values for all peptides. Peptides that on visual inspection showed potential error (e.g.: overlap, poor signal to noise ratio, bimodal isotope distributions, or high carry-over) were eliminated. Final HDEXAMINER states files were uploaded to an in-house HDX database and visualization tool for interpretation.

Results

Figure 19:
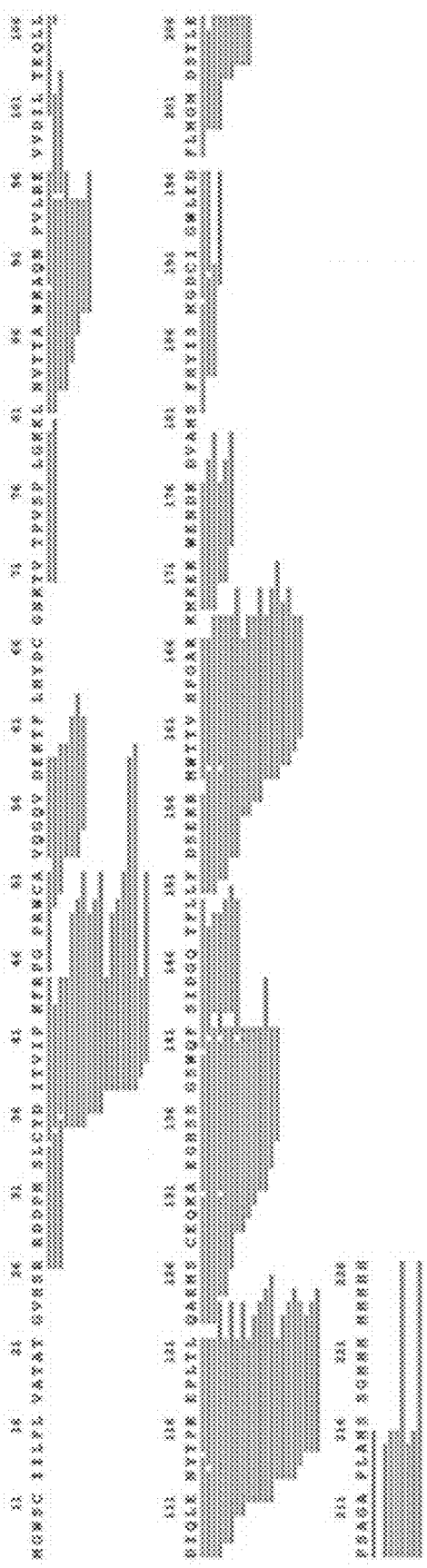
FIG. 19 depicts 131 peptides covering 87.7% of a ULBP6 construct sequence which were included in evaluation of data from HDX experiments.

A final set of 131 peptides covering 87.7% of the total ULBP6 construct sequence provided herein as SEQ ID NO: 123 (96.3% of the native part of the ULBP6_02 sequence provided herein as SEQ ID NO: 7) were included in the evaluation, as depicted in FIG. 19.

Figure 20A:
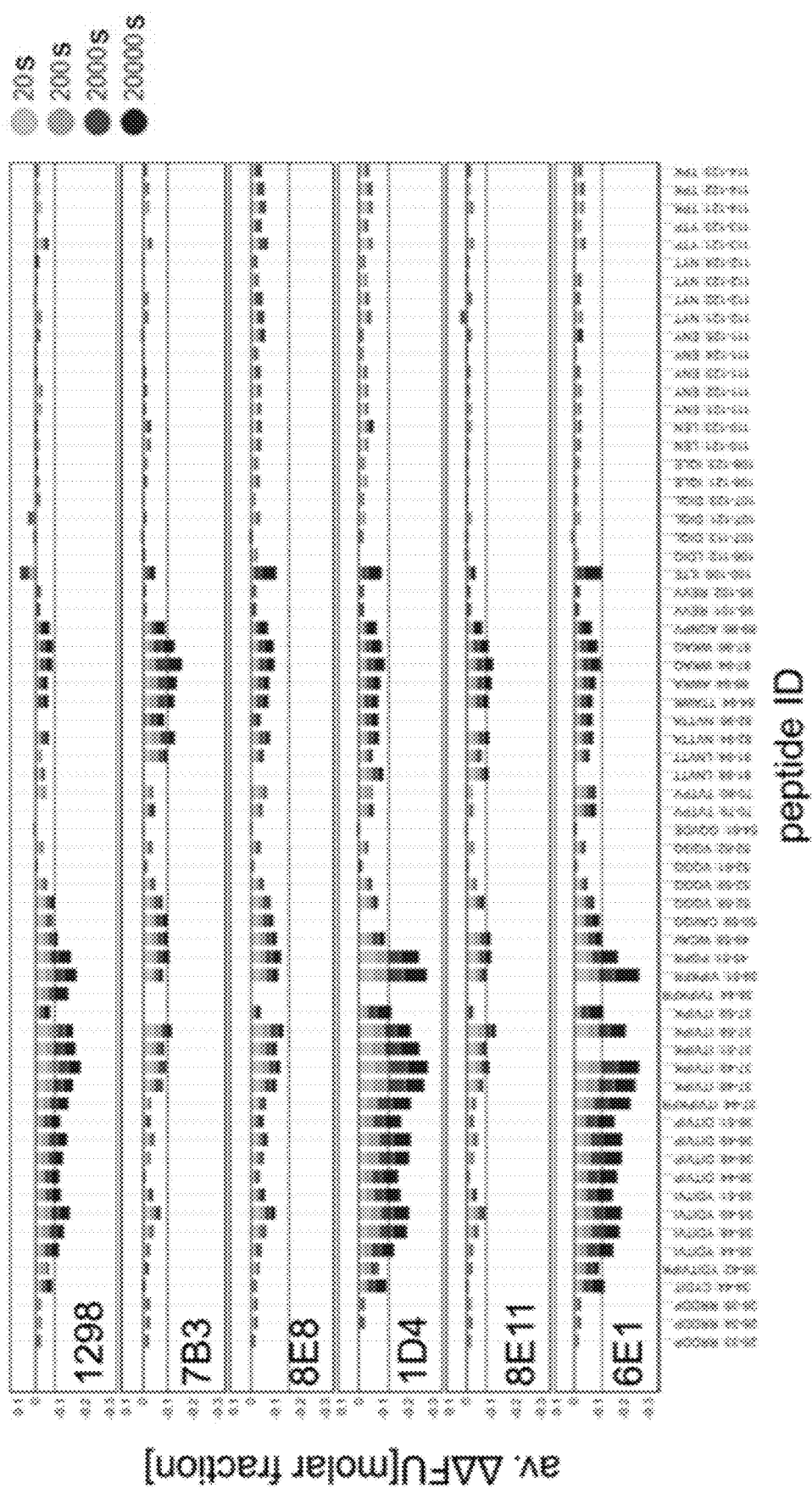
FIG. 20A depicts differential fractional uptake for each detected peptide of amino acids 26 through 123 of ULBP6 from HDX experiments.
Figure 20B:
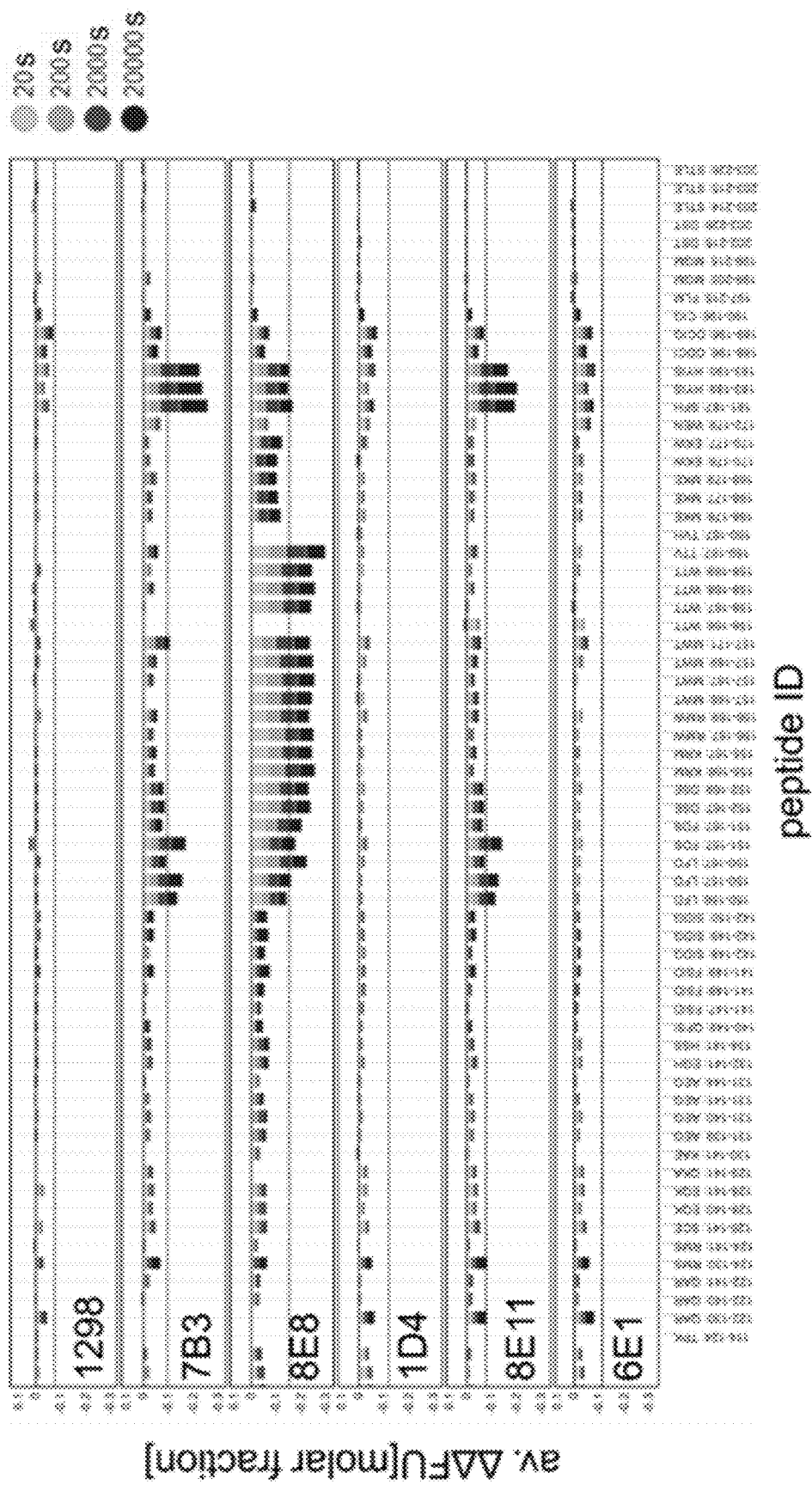
FIG. 20B depicts differential fractional uptake for each detected peptide of amino acids 114 through 226 of ULBP6 from HDX experiments.

A cut-off of 1 standard deviation was applied to differentiate mAb-induced site-specific protection from the global protection at the peptide level. All residues of any peptide that exceeded this threshold were considered significantly protected. Differential fractional uptake for each detected peptide are depicted in FIG. 20A (amino acids 26 through 123 of ULBP6) and FIG. 20B (Amino acids 114 through 226 of ULBP6). In FIG. 21, ULBP6 peptides determined to be significantly protected by mAb1298, h7B3, h8E8, h1D4, h8E11, and h6E1 are identified as underlined bold text. The crystal structure of the NKG2D-ULBP6 complex is provided in panels A through F of FIG. 22, whereby residues of ULBP6 peptides having significant protection by mAb1298 (panel A), h7B3 (E+ Afu) (panel B), h8E8 (E+) (panel C), h1D4 (E+) (panel D), h8E11 (E+) (panel E), and h6E1 (E+) (panel F), as determined by HDX are indicated in black.

Antibodies were determined to be of three classes of HDX protection patterns according to the residues that were significantly protected, as provided in Table 39.

TABLE 39

Classes of patterns of protection of ULBP6 residues by antibodies as determined by HDX

| Class | Antibodies |
|---|---|
| 1 | mAb1298, h1D4 (E+), h6E1 (E+) |
| 2 | H7B3 (E+ Afu), h8E11 (E+) |
| 3 | H8E8 (E+) |

Significant protection of residues 35/36 through 58/59 of ULBP6 was provided by antibodies in Class 1. Protection of residues 35/36 through 58/59 of ULBP6 at a low but significant level, accompanied by stronger protection of residues 81/82 through 96, 150 through 157, and 181 through 190 of ULBP6, was provided by antibodies in Class 2. Significant protection of residues 150 through 169 of ULBP6 was provided by the antibody of Class 3.

Considering the location of the abovementioned patterns in the crystal structure of the NKG3D/ULBP6 complex, the HDX data were compatible with the following binding sites.

The HDX protection pattern of the Class 1 antibodies was restricted to β-strands 1 and 2, including the intervening connecting loop, as depicted in FIG. 22, panel A (mAb1298), panel D (h1D4 (E+)), and Panel F (h6E1 (E+)). This is consistent with those mAbs targeting the β-sheet away from the NKG2D binding site without disrupting the NDG2D/ULBP6 complex.

Amino acid segments having strong protection patterns as described herein are provided in Table 40.

TABLE 40

Protected amino acids of hULBP6 as determined by HDX

| Residues (ULBP6) | Sequence | SEQ ID NO |
|---|---|---|
| 77-106 | LGKKLNVTMAWKAQNPVLREVVDILTEQLL | 125 |
| 166-202 | RKMKEKWENDKDVAMSFHYISMGDCIGWLE DFLMGMD | 126 |
| 150-157 | LFDSEKRM | 127 |
| 81-96 | LNVTMAWKAQNPVLRE | 128 |
| 181-190 | SFHYISMGDC | 129 |

Strong protection patterns of class 2 antibodies were observed on a first α-helix (SEQ ID NO: 126 and/or SEQ ID NO: 127), a second α-helix (SEQ ID NO: 127), and an intervening loop (SEQ ID NO: 128). An additional weak protection pattern on β-strand 2 (residues 36-58 of ULBP6) opposite the aforementioned α-helices was of borderline significance. As observed in FIG. 20A and FIG. 20B, peptides covering residues 35/36 to 58/59 may be allosteric, and not necessarily indicative of direct contact by the antibody on these residues. Overall, the protection pattern of the Class 2 antibodies was consistent with binding to the α-helices located in the NKG2D-ULBP6 complex interface, suggesting that Class 2 can antibodies disrupt interactions between NKG2D and ULBP6.

The Class 3 antibody showed a very strong HDX protection pattern for residues 150 through 169. Because the dominate protection feature was located to the side of the NKG2D-ULBP6 complex, it was not predicted whether this antibody would disrupt this complex.

Example 20: In Vivo Tumor Models to Evaluate Activity of Anti-ULBP6 Antibodies

This example illustrates select in vivo tumor model studies of the functional activity of one or more anti-ULBP6 antibodies provided herein and may not be inclusive of all in vivo studies and/or results that can inform the functional activity or another property of ULBP6 binding proteins provided herein.

Materials and Methods

An anti-ULBP6 antibody provided herein can be prepared for administration to a subject. For example, the anti-ULBP6 antibody can be prepared as about or exactly 0.1 mg/kg, 1 mg/kg, 10 mg/kg, 100 mg/kg, or 1000 mg/kg, or a dose within a range between any of the two foregoing doses. In some embodiments, the anti-ULBP6 antibody can be prepared such that a predetermined volume (e.g., at least about 1 mL/kg, not more than about 40 mL/kg, or between 1 mL/kg and 40 mL/kg) can be administered at one or more a doses, such as a dose provided herein or another dose determined to be effective. In some embodiments, a dose of unknown effectiveness can be administered. A control preparation can be prepared that can substantially match the buffer and concentration of the test article, or the effects thereof. In some embodiments, a control preparation can be identical to a preparation comprising an anti-ULBP6 antibody, with the addition of an antibody whose properties comprise no physiologically significant binding to ULBP6, no physiologically significant binding to FcγR, or no physiologically significant binding to both ULBP6 and FcγR, or the absence of any antibody.

A murine tumor model can be employed to probe the functional activity of one or more anti-ULBP6 antibodies. Briefly, the murine tumor model can be engineered to express human ULBP6, or injected with murine or human hULBP6 expressing tumor cells. The murine tumor model can host a human immune cell, or retain its own immune system An anti-ULBP6 antibody preparation or control preparation can be administered to the murine tumor model. For example, an anti-ULBP6 can be administered at a one or more doses, for example as provided above. Animals can be administered a preparation, for example as several doses once or more per week. Animals can be sacrificed at different time points, for example with different tumor sizes, at which time tumor, lymphoid tissue, blood, and/or other samples can be collected. In some embodiments, tumor size can be monitored, for example using a caliper or via one or more appropriate imaging-based technologies.

Blood and/or tissue samples collected can be processed to isolate phenotypic readouts informative of biomarkers to prepare slides for IHC or other pathological assessment, for example of DNA and/or RNA.

Processed samples can be assessed to determine the presence, absence, or level of immune cells, and their relative status (e.g., activation, proliferation and/or cytotoxicity).

Results

Upon anti-ULBP6 treatment in vivo we are expecting to reinvigorate CD8 T cells and NK cells cytotoxicity against tumor cells. As a result, CD8 T cells and NK cells phenotypic changes should be detectable and/or tumor growth inhibition.

Results are described in this section for mice as provided herein, but are envisioned for other subjects (e.g. rat, rabbit, monkey, cat, dog, hamster, human) having a ULBP6-expressing tumor burden and/or metastasis and receiving a preparation comprising an anti-ULBP6 antibody.

Tumor growth (measured, for example, as a change in tumor volume over time by an acceptable method) in a mouse or group of mice receiving a preparation comprising an anti-ULBP6 antibody can at least about 25% slower, at least about 50% slower, at least about 60% slower, at least about 70% slower, at least about 80% slower, at least about 90% slower, at least about 95% slower, or at least about 99% slower, or a range between any two foregoing values, compared with tumor growth in a mouse or group of mice receiving a preparation comprising a control antibody. Slowing of tumor growth can be dose-dependent for a range of doses, such as provided herein.

Tumor size can be reduced by at least about 25%, at least about 50%, at least about 60%, at least about 70%, at least about 80%, at least about 90%, at least about 95%, or at least about 99%, or a range between any two foregoing values, compared with the beginning of treatment in a mouse or group of mice receiving a preparation comprising an anti-ULBP6 antibody. Reduction of tumor size can be dose-dependent for a range of doses, such as provided herein.

Metastases can be reduced by at least about 20%, at least about 50%, at least about 60%, at least about 70%, at least about 80%, at least about 90%, at least about 95%, at least about 99%, or a range between any two foregoing values, in a mouse or group of mice receiving a preparation comprising an anti-ULBP6 antibody compared with the metastases in the same mice or group of mice before receiving the preparation.

Activation of one or more types of immune cells in a mouse receiving a preparation comprising an anti-ULBP6 antibody can be increased by at least about 20%, at least about 50%, at least about 60%, at least about 70%, at least about 80%, at least about 90%, at least about 95%, at least about 99%, or a range between any two foregoing values, in a mouse or group of mice receiving a preparation comprising an anti-ULBP6 antibody compared with a control mouse or group of mice.

The invention claimed is:

1. An anti-ULBP6 antibody comprising 6 CDRs selected from the following:
   CDRH1 of SEQ ID NO: 36, CDRH2 of SEQ ID NO: 37, CDRH3 of SEQ ID NO: 38, CDRL1 of SEQ ID NO: 51, CDRL2 of SEQ ID NO: 52 and CDRL3 of SEQ ID NO: 53;
   CDRH1 of SEQ ID NO: 39, CDRH2 of SEQ ID NO: 40, CDRH3 of SEQ ID NO: 41, CDRL1 of SEQ ID NO: 54, CDRL2 of SEQ ID NO: 55 and CDRL3 of SEQ ID NO: 56;
   CDRH1 of SEQ ID NO: 42, CDRH2 of SEQ ID NO: 43, CDRH3 of SEQ ID NO: 44, CDRL1 of SEQ ID NO: 57, CDRL2 of SEQ ID NO: 58 and CDRL3 of SEQ ID NO: 59; or
   CDRH1 of SEQ ID NO: 45, CDRH2 of SEQ ID NO: 46, CDRH3 of SEQ ID NO: 47, CDRL1 of SEQ ID NO: 60, CDRL2 of SEQ ID NO: 61 and CDRL3 of SEQ ID NO: 62.

2. The anti-ULBP6 antibody according to claim 1, wherein the antibody comprises:
   a VH region that is at least 80% identical to SEQ ID NO: 21 and a VL region that is at least 80% identical to SEQ ID NO: 31;
   a VH region that is at least 80% identical to SEQ ID NO: 22 and a VL region that is at least 80% identical to SEQ ID NO: 32;
   a VH region that is at least 80% identical to SEQ ID NO: 23 and a VL region that is at least 80% identical to SEQ ID NO: 33; or
   a VH region that is at least 80% identical to SEQ ID NO: 24 and a VL region that is at least 80% identical to SEQ ID NO: 34.

3. The anti-ULBP6 antibody according to claim 1, wherein the antibody comprises:
   a) a Heavy Chain (HC) sequence at least 80% identical to any one of SEQ ID NOs: 75-78, 85-88 or 95-98; and/or
   b) a Light Chain (LC) sequence at least 80% identical to any one of SEQ ID NOs: 105-108.

4. The anti-ULBP6 antibody according to claim 1, wherein the antibody inhibits the interaction of human ULBP6 and human NKG2D.

5. The anti-ULBP6 antibody according to claim 1, wherein the antibody inhibits the binding of soluble ULBP6 to NKG2D.

6. The anti-ULBP6 antibody according to claim 1, wherein the antibody comprises a modified Fc region.

7. The anti-ULBP6 antibody according to claim 6, wherein the modified Fc region comprises the amino acid substitutions S239D and 1332E (as numbered according to the EU index).

8. The anti-ULBP6 antibody according to claim 1, wherein the antibody is afucosylated.

9. The anti-ULBP6 antibody according to claim 6, wherein the modified Fc region comprises amino acid substitutions selected from S239D/A330L/1332E, G236A/S239D/A330L/1332E, L235V/F243L/R292P/Y300L/P396L or F243L/R292P/Y300L/V305l/P396L (as numbered according to the EU index).

10. An isolated nucleic acid which encodes an amino acid sequence of the anti-ULBP6 antibody of claim 1.

11. An expression vector comprising the isolated nucleic acid of claim 10.

12. A recombinant host cell comprising the isolated nucleic acid of claim 10.

13. A recombinant host cell comprising the expression vector of claim 11.

14. A method for the production of an anti-ULBP6 antibody comprising culturing a recombinant host cell of claim 12 under suitable conditions whereby the anti-ULBP6 antibody is produced.

15. A cell line that expresses the anti-ULBP6 antibody of claim 1.

16. A pharmaceutical composition comprising the anti-ULBP6 antibody of claim 1 and a pharmaceutically acceptable excipient.

17. A method for the treatment of cancer in a subject in need thereof comprising administering to said subject a therapeutically effective amount of the anti-ULBP6 antibody of claim 1.

* * * * *

SEQUENCE LISTING

```
Sequence total quantity: 161
SEQ ID NO: 1            moltype = AA  length = 190
FEATURE                 Location/Qualifiers
source                  1..190
                        mol_type = protein
                        organism = synthetic construct
SEQUENCE: 1
GWVDTHCLCY DFIITPKSRP EPQWCEVQGL VDERPFLHYD CVNHKAKAFA SLGKKVNVTK  60
TWEEQTETLR DVVDFLKGQL LDIQVENLIP IEPLTLQARM SCEHEAHGHG RGSWQFLFNG 120
QKFLLFDSNN RKWTALHPGA KKMTEKWEKN RDVTMFFQKI SLGDCKMWLE EFLMYWEQML 180
DPTKPPSLAP                                                       190

SEQ ID NO: 2            moltype = AA  length = 191
FEATURE                 Location/Qualifiers
source                  1..191
                        mol_type = protein
                        organism = synthetic construct
SEQUENCE: 2
GRADPHSLCY DITVIPKFRP GPRWCAVQGQ VDEKTFLHYD CGNKTVTPVS PLGKKLNVTT  60
```

```
AWKAQNPVLR EVVDILTEQL RDIQLENYTP KEPLTLQARM SCEQKAEGHS SGSWQFSFDG    120
QIFLLFDSEK RMWTTVHPGA RKMKEKWEND KVVAMSFHYF SMGDCIGWLE DFLMGMDSTL    180
EPSAGAPLAM S                                                        191

SEQ ID NO: 3                moltype = AA   length = 187
FEATURE                     Location/Qualifiers
source                      1..187
                            mol_type = protein
                            organism = synthetic construct
SEQUENCE: 3
DAHSLWYNFT IIHLPRHGQQ WCEVQSQVDQ KNFLSYDCGS DKVLSMGHLE EQLYATDAWG    60
KQLEMLREVG QRLRLELADT ELEDFTPSGP LTLQVRMSCE CEADGYIRGS WQFSFDGRKF    120
LLFDSNNRKW TVVHAGARRM KEKWEKDSGL TTFFKMVSMR DCKSWLRDFL MHRKKRLEPT    180
APPTMAP                                                              187

SEQ ID NO: 4                moltype = AA   length = 195
FEATURE                     Location/Qualifiers
source                      1..195
                            mol_type = protein
                            organism = synthetic construct
SEQUENCE: 4
HSLCFNFTIK SLSRPGQPWC EAQVFLNKNL FLQYNSDNNM VKPLGLLGKK VYATSTWGEL    60
TQTLGEVGRD LRMLLCDIKP QIKTSDPSTL QVEMFCQREA ERCTGASWQF ATNGEKSLLF    120
DAMNMTWTVI NHEASKIKET WKKDRGLEKY FRKLSKGDCD HWLREFLGHW EAMPEPTVSP    180
VNASDIHWSS SSLPD                                                     195

SEQ ID NO: 5                moltype = AA   length = 193
FEATURE                     Location/Qualifiers
source                      1..193
                            mol_type = protein
                            organism = synthetic construct
SEQUENCE: 5
GLADPHSLCY DITVIPKFRP GPRWCAVQGQ VDEKTFLHYD CGSKTVTPVS PLGKKLNVTT    60
AWKAQNPVLR EVVDILTEQL LDIQLENYIP KEPLTLQARM SCEQKAEGHG SGSWQLSFDG    120
QIFLLFDSEN RMWTTVHPGA RKMKEKWEND KDMTMSFHYI SMGDCTGWLE DFLMGMDSTL    180
EPSAGAPPTM SSG                                                       193

SEQ ID NO: 6                moltype = AA   length = 193
FEATURE                     Location/Qualifiers
source                      1..193
                            mol_type = protein
                            organism = synthetic construct
SEQUENCE: 6
GRDDPHSLCY DITVIPKFRP GPRWCAVQGQ VDEKTFLHYD CGNKTVTPVS PLGKKLNVTT    60
AWKAQNPVLR EVVDILTEQL RDIQLENYTP KEPLTLQARM SCEQKAEGHS SGSWQFSIDG    120
QIFLLFDSEK RMWTTVHPGA RKMKEKWEND KDVAMSFHYI SMGDCIGWLE DFLMGMDSTL    180
EPSAGAPLAM SSG                                                       193

SEQ ID NO: 7                moltype = AA   length = 193
FEATURE                     Location/Qualifiers
source                      1..193
                            mol_type = protein
                            organism = synthetic construct
SEQUENCE: 7
RRDDPHSLCY DITVIPKFRP GPRWCAVQGQ VDEKTFLHYD CGNKTVTPVS PLGKKLNVTT    60
AWKAQNPVLR EVVDILTEQL LDIQLENYTP KEPLTLQARM SCEQKAEGHS SGSWQFSIDG    120
QTFLLFDSEK RMWTTVHPGA RKMKEKWEND KDVAMSFHYI SMGDCIGWLE DFLMGMDSTL    180
EPSAGAPLAM SSG                                                       193

SEQ ID NO: 8                moltype = AA   length = 190
FEATURE                     Location/Qualifiers
source                      1..190
                            mol_type = protein
                            organism = synthetic construct
SEQUENCE: 8
ADPHSLCYDI TIIPKFRPGP RWCAVQGQVD KKTFLHYDCG NKTVTPVSTL GKKLNVTKAW    60
KAQNPVLREV VDMLTEQLLD IELENYTPRE PLTLQTRMSC EQKAEGHSSG SWQLGFDGQV    120
FLLFDSENRM WATVHPGARK MKEKWQNDKD VTMSFHYISM GDCTKWLKDF LTGMDSTLEP    180
SAGAPLTMSS                                                           190

SEQ ID NO: 9                moltype = AA   length = 190
FEATURE                     Location/Qualifiers
source                      1..190
                            mol_type = protein
                            organism = synthetic construct
SEQUENCE: 9
DDLHSLCYDI TIIPKFRPGP RWCAVQGQVD KKTFLHYDCG NKTVTSVSTL GKKLNVTKAW    60
KAQNPVLREV VDMLTEQLLD IQLENYTPRE PLTLQARMSC EQKAEGHSSG SWQFGFDGQV    120
FLLFDSENRM WTTVHPGARK MKEKWENDKD VTMSFHYISM GDCTRWLGDF LMDMDSTLEP    180
```

```
SAGAPLTMSS                                                                   190

SEQ ID NO: 10           moltype = AA   length = 321
FEATURE                 Location/Qualifiers
source                  1..321
                        mol_type = protein
                        organism = synthetic construct
SEQUENCE: 10
MGLGPVFLLL AGIFPFAPPG AAAEPHSLRY NLTVLSWDGS VQSGFLTEVH LDGQPFLRCD             60
RQKCRAKPQG QWAEDVLGNK TWDRETRDLT GNGKDLRMTL AHIKDQKEGL HSLQEIRVCE            120
IHEDNSTRSS QHFYYDGELF LSQNLETKEW TMPQSSRAQT LAMNVRNFLK EDAMKTKTHY            180
HAMHADCLQE LRRYLKSGVV LRRTVPPMVN VTRSEASEGN ITVTCRASGF YPWNITLSWR            240
QDGVSLSHDT QQWGDVLPDG NGTYQTWVAT RICQGEEQRF TCYMEHSGNH STHPVPSGKV            300
LVLQSHWQGG GSGLNDIFEA Q                                                     321

SEQ ID NO: 11           moltype = AA   length = 395
FEATURE                 Location/Qualifiers
source                  1..395
                        mol_type = protein
                        organism = synthetic construct
SEQUENCE: 11
MGLGRVLLFL AVAFPPFAPPA AAAEPHSLRY NLMVLSQDES VQSGFLAEGH LDGQPFLRYD            60
RQKRRAKPQG QWAEDVLGAK TWDTETEDLT ENGQDLRRTL THIKDQKGGL HSLQEIRVCE            120
IHEDSSTRGS RHFYYDGELF LSQNLETQES TVPQSSRAQT LAMNVTNFWK EDAMKTKTHY            180
RAMQADCLQK LQRYLKSGVA IRRTVPPMVN VTCSEVSEGN ITVTCRASSF YPRNITLTWR            240
QDGVSLSHNT QQWGDVLPDG NGTYQTWVAT RIRQGEEQRF TCYMEHSGNH GTHPVPSGKV            300
LVLQSQRTDF PYVSAAMPCF VIIIILCVPC CKKKTSAAEG PELVSLQVLD QHPVGTGDHR            360
DAAQLGFQPL MSATGSTGST EGAGGGSGLN DIFEA                                      395

SEQ ID NO: 12           moltype = AA   length = 395
FEATURE                 Location/Qualifiers
source                  1..395
                        mol_type = protein
                        organism = synthetic construct
SEQUENCE: 12
FLNSLFNQEV QIPLTESYCG PCPKNWICYK NNCYQFFDES KNWYESQASC MSQNASLLKV             60
YSKEDQDLLK LVKSYHWMGL VHIPTNGSWQ WEDGSILSPN LLTIIEMQKG DCALYASSFK            120
GYIENCSTPN TYICMQRTVG GGGSENLYFQ GGGGSEPKSC DKTHTCPPCP APELLGGPSV            180
FLFPPKPKDT LMISRTPEVT CVVVDVSHED PEVKFNWYVD GVEVHNAKTK PREEQYNSTY            240
RVVSVLTVLH QDWLNGKEYK CKVSNKALPA PIEKTISKAK GQPREPQVYT LPPSRDELTK            300
NQVSLTCLVK GFYPSDIAVE WESNGQPENN YKTTPPVLDS DGSFFLYSKL TVDKSRWQQG            360
NVFSCSVMHE ALHNHYTQKS LSLSPGKDYK DDDDK                                      395

SEQ ID NO: 13           moltype = AA   length = 379
FEATURE                 Location/Qualifiers
source                  1..379
                        mol_type = protein
                        organism = synthetic construct
SEQUENCE: 13
FLNSLFNQEV QIPLTESYCG PCPKNWICYK NNCYQFFNES KNWYESQASC MSQNASLLKV             60
YSKEDQDLLK LVKSYHWMGL VHIPTNGSWQ WEDGSILSPN LLTIIEMQKG DCALYASSFK            120
GYIENCSIPN TYICMQRTVG GGGSENLYFQ GGGGAPELLG GPSVFLFPPK PKDTLMISRT            180
PEVTCVVVDV SHEDPEVKFN WYVDGVEVHN AKTKPREEQY NSTYRVVSVL TVLHQDWLNG            240
KEYKCKVSNK ALPAPIEKTI SKAKGQPREP QVYTLPPSRD ELTKNQVSLT CLVKGFYPSD            300
IAVEWESNGQ PENNYKTTPP VLDSDGSFFL YSKLTVDKSR WQQGNVFSCS VMHEALHNHY            360
TQKSLSLSPG KDYKDDDDK                                                        379

SEQ ID NO: 14           moltype = AA   length = 240
FEATURE                 Location/Qualifiers
source                  1..240
                        mol_type = protein
                        organism = synthetic construct
SEQUENCE: 14
EPKSCDKTHT CPPCPAPELL GGPSVFLFPP KPKDTLMISR TPEVTCVVVD VSHEDPEVKF             60
NWYVDGVEVH NAKTKPREEQ YNSTYRVVSV LTVLHQDWLN GKEYKCKVSN KALPAPIEKT            120
ISKAKGQPRE PQVYTLPPSR DELTKNQVSL TCLVKGFYPS DIAVEWESNG QPENNYKTTP            180
PVLDSDGSFF LYSKLTVDKS RWQQGNVFSC SVMHEALHNH YTQKSLSLSP GKDYKDDDDK            240

SEQ ID NO: 15           moltype = AA   length = 225
FEATURE                 Location/Qualifiers
source                  1..225
                        mol_type = protein
                        organism = synthetic construct
SEQUENCE: 15
APELLGGPSV FLFPPKPKDT LMISRTPEVT CVVVDVSHED PEVKFNWYVD GVEVHNAKTK             60
PREEQYNSTY RVVSVLTVLH QDWLNGKEYK CKVSNKALPA PIEKTISKAK GQPREPQVYT            120
LPPSRDELTK NQVSLTCLVK GFYPSDIAVE WESNGQPENN YKTTPPVLDS DGSFFLYSKL            180
TVDKSRWQQG NVFSCSVMHE ALHNHYTQKS LSLSPGKDYK DDDDK                           225
```

```
SEQ ID NO: 16              moltype = AA   length = 116
FEATURE                    Location/Qualifiers
source                     1..116
                           mol_type = protein
                           organism = synthetic construct
SEQUENCE: 16
DVQLVESGGG LVKPGGSRKL SCAASGFTFS TYGFHWVRQV PEKGLEWVAY ISSNSGTIDY    60
ADTVKGRFTI SRDNAKNTLF LQMTSLRSED TAMYYCARQG YGFDNWGQGT TLTVSS       116

SEQ ID NO: 17              moltype = AA   length = 116
FEATURE                    Location/Qualifiers
source                     1..116
                           mol_type = protein
                           organism = synthetic construct
SEQUENCE: 17
DVQLVESGGG LVQPGGSRKL SCAASGFTFR TYGMHWVRQA PEKGLEWVAY ISSGSGTIDY    60
ADTVKGRFTI SRDNAKNTLF LQMTSLRSED TAMYYCTRQT GAMDYWGQGT SVTVSS       116

SEQ ID NO: 18              moltype = AA   length = 119
FEATURE                    Location/Qualifiers
source                     1..119
                           mol_type = protein
                           organism = synthetic construct
SEQUENCE: 18
QVQLQQPGAE LVKPGASVKV SCKASGYTFT NYWMHWMKQR PGQGLEWLGR IHPSDSDTNY    60
NQKFKGKATL TVDKSSNIAF MQLSSLTSED SAVYYCAIEG TKGYFDVWG TGTTVTVSS     119

SEQ ID NO: 19              moltype = AA   length = 120
FEATURE                    Location/Qualifiers
source                     1..120
                           mol_type = protein
                           organism = synthetic construct
SEQUENCE: 19
QIQLVQSGPE LKKPGETVKI SCKASGYTFT EYPIHWVKQA PGKGFKWMGM IYTDTGEPTH    60
AEEFKGRFAF SLETSASTAY LQINNLKNED TATYFCVRWY DGSSYIMDYW GQGTSVTVSS   120

SEQ ID NO: 20              moltype = AA   length = 122
FEATURE                    Location/Qualifiers
source                     1..122
                           mol_type = protein
                           organism = synthetic construct
SEQUENCE: 20
QVQLQQSGAE LARPGTSVRL SCKASGYTFT TYGITWVKQR PGQGLEWIGE IYPGTATSYS    60
NERFKGKATL TADRSSSTAY MQLSSLTSED SAVYFCARRG TYGTYEWYFD VWGAGTTVTV   120
SS                                                                 122

SEQ ID NO: 21              moltype = AA   length = 116
FEATURE                    Location/Qualifiers
source                     1..116
                           mol_type = protein
                           organism = synthetic construct
SEQUENCE: 21
EVQLVESGGG LVQPGGSLRL SCAASGFTFS TYGFHWVRQA PGKGLEWVAY ISSNSGTIDY    60
ADTVKGRFTI SRDNAKNSLY LQMNSLRAED TAVYYCARQG YGFDNWGQGT TVTVSS       116

SEQ ID NO: 22              moltype = AA   length = 116
FEATURE                    Location/Qualifiers
source                     1..116
                           mol_type = protein
                           organism = synthetic construct
SEQUENCE: 22
EVQLVESGGG LVQPGGSLRL SCAASGFTFR TYGMHWVRQA PGKGLEWVAY ISSGSGTIDY    60
ADTVKGRFTI SRDNAKNSLY LQMNSLRAED TAVYYCTRQT GAMDYWGQGT LVTVSS       116

SEQ ID NO: 23              moltype = AA   length = 119
FEATURE                    Location/Qualifiers
source                     1..119
                           mol_type = protein
                           organism = synthetic construct
SEQUENCE: 23
EVQLVQSGAE VKKPGASVKV SCKASGYTFT NYWMHWMRQA PGQGLEWLGR IHPSDSDTNY    60
NQKFKGRATL TVDKSISTAY MELSRLRSDD TAVYYCAIEG TKGYFDVWG RGTLVTVSS     119

SEQ ID NO: 24              moltype = AA   length = 120
FEATURE                    Location/Qualifiers
source                     1..120
                           mol_type = protein
                           organism = synthetic construct
SEQUENCE: 24
```

```
EIQLVQSGSE LKKPGASVKV SCKASGYTFT EYPIHWVRQA PGQGFEWMGM IYTDTGEPTH    60
AEEFKGRFVF SLDTSVSTAY LQISSLKAED TAVYFCVRWY DGSSYIMDYW GQGTTVTVSS   120

SEQ ID NO: 25          moltype = AA  length = 122
FEATURE                Location/Qualifiers
source                 1..122
                       mol_type = protein
                       organism = synthetic construct
SEQUENCE: 25
QVQLVQSGAE VKKPGSSVKV SCKASGYTFT TYGITWVRQA PGQGLEWIGE IYPGTATSYS    60
NERFKGRATL TADRSTSTAY MELSSLRSED TAVYFCARRG TYGTYEWYFD VWGRGTLVTV   120
SS                                                                 122

SEQ ID NO: 26          moltype = AA  length = 106
FEATURE                Location/Qualifiers
source                 1..106
                       mol_type = protein
                       organism = synthetic construct
SEQUENCE: 26
EILLTQSPAI IAASPGEKVT ITCSASSRVS YMNWYQQKPG SSPKIWVYGI SNLASGVPAR    60
FSGSGSGTSF SFTINSMEAE DVATYYCQQR SSHPLTFGAG TKLELK                 106

SEQ ID NO: 27          moltype = AA  length = 106
FEATURE                Location/Qualifiers
source                 1..106
                       mol_type = protein
                       organism = synthetic construct
SEQUENCE: 27
EILLTQSPAI IAASPGEKVT ITCSASSSVS YMNWYQQKPG SSPKLWIYGI SNLASGVPAR    60
FSGSGSGTSF SFTINSMEAE DVATYYCQQR SSHPLTFGAG TKLELK                 106

SEQ ID NO: 28          moltype = AA  length = 107
FEATURE                Location/Qualifiers
source                 1..107
                       mol_type = protein
                       organism = synthetic construct
SEQUENCE: 28
DIKMTQSPSS MYASLGERVT ITCKASQDIY SYLSWFQQKP GRSPKTLIYR ANRLVDGVPS    60
RFSGSGSGQD FSLTISSLDY EDMGIYYCLH YDEFPLTFGT GTKLELK                107

SEQ ID NO: 29          moltype = AA  length = 107
FEATURE                Location/Qualifiers
source                 1..107
                       mol_type = protein
                       organism = synthetic construct
SEQUENCE: 29
DIKMTQSPSS MYASLGERVT ITCKASQDIN SYLSWFQQKP GKSPKTLIYR ANRLVDGVPS    60
RFSGSGSGQD YSLTISSLEY EDVGIYYCLQ YDEFPLTFGA GTKLELK                107

SEQ ID NO: 30          moltype = AA  length = 107
FEATURE                Location/Qualifiers
source                 1..107
                       mol_type = protein
                       organism = synthetic construct
SEQUENCE: 30
DIQMTQSPAS LSVSVGETAT ITCRASENIY SHLAWYQQKQ GKSPQLLVYA ATNLADGVPS    60
RFSGSGSGTQ YSLKINSLQS EDFGSYYCQH FWGTPWTFGG GTKLEIK                107

SEQ ID NO: 31          moltype = AA  length = 106
FEATURE                Location/Qualifiers
source                 1..106
                       mol_type = protein
                       organism = synthetic construct
SEQUENCE: 31
DIQLTQSPSS LSASVGDRVT ITCSASSRVS YMNWYQQKPG KSPKIWVYGI SNLASGVPSR    60
FSGSGSGTDF TFTISSLQPE DIATYYCQQR SSHPLTFGGG TKVEIK                 106

SEQ ID NO: 32          moltype = AA  length = 106
FEATURE                Location/Qualifiers
source                 1..106
                       mol_type = protein
                       organism = synthetic construct
SEQUENCE: 32
EIVLTQSPAT LSLSPGERAT LSCSASSSVS YMNWYQQKPG QSPRLWIYGI SNLASGVPAR    60
FSGSGSGTDF TLTISSLEPE DFAVYYCQQR SSHPLTFGGG TKVEIK                 106

SEQ ID NO: 33          moltype = AA  length = 107
FEATURE                Location/Qualifiers
source                 1..107
```

```
                            mol_type = protein
                            organism = synthetic construct
SEQUENCE: 33
DIQMTQSPSS LSASVGDRVT ITCKASQDIY SYLSWFQQKP GKSPKTLIYR ANRLVDGVPS    60
RFSGSGSGQD FTLTISSLQP EDFATYYCLH YDEFPLTFGG GTKVEIK                  107

SEQ ID NO: 34               moltype = AA   length = 107
FEATURE                     Location/Qualifiers
source                      1..107
                            mol_type = protein
                            organism = synthetic construct
SEQUENCE: 34
DIQMTQSPSS LSASVGDRVT ITCKASQDIN SYLSWFQQKP GKSPKTLIYR ANRLVDGVPS    60
RFSGSGSGQD YTFTISSLQP EDIATYYCLQ YDEFPLTFGG GTKVEIK                  107

SEQ ID NO: 35               moltype = AA   length = 107
FEATURE                     Location/Qualifiers
source                      1..107
                            mol_type = protein
                            organism = synthetic construct
SEQUENCE: 35
DIQMTQSPSS LSASVGDRVT ITCRASENIY SHLAWYQQKP GKSPKLLVYA ATNLADGVPS    60
RFSGSGSGTD YTLTISSLQP EDFATYYCQH FWGTPWTFGG GTKVEIK                  107

SEQ ID NO: 36               moltype = AA   length = 5
FEATURE                     Location/Qualifiers
source                      1..5
                            mol_type = protein
                            organism = synthetic construct
SEQUENCE: 36
TYGFH                                                                5

SEQ ID NO: 37               moltype = AA   length = 17
FEATURE                     Location/Qualifiers
source                      1..17
                            mol_type = protein
                            organism = synthetic construct
SEQUENCE: 37
YISSNSGTID YADTVKG                                                   17

SEQ ID NO: 38               moltype = AA   length = 7
FEATURE                     Location/Qualifiers
source                      1..7
                            mol_type = protein
                            organism = synthetic construct
SEQUENCE: 38
QGYGFDN                                                              7

SEQ ID NO: 39               moltype = AA   length = 5
FEATURE                     Location/Qualifiers
source                      1..5
                            mol_type = protein
                            organism = synthetic construct
SEQUENCE: 39
TYGMH                                                                5

SEQ ID NO: 40               moltype = AA   length = 17
FEATURE                     Location/Qualifiers
source                      1..17
                            mol_type = protein
                            organism = synthetic construct
SEQUENCE: 40
YISSGSGTID YADTVKG                                                   17

SEQ ID NO: 41               moltype = AA   length = 7
FEATURE                     Location/Qualifiers
source                      1..7
                            mol_type = protein
                            organism = synthetic construct
SEQUENCE: 41
QTGAMDY                                                              7

SEQ ID NO: 42               moltype = AA   length = 5
FEATURE                     Location/Qualifiers
source                      1..5
                            mol_type = protein
                            organism = synthetic construct
SEQUENCE: 42
NYWMH                                                                5
```

-continued

```
SEQ ID NO: 43              moltype = AA   length = 17
FEATURE                    Location/Qualifiers
source                     1..17
                           mol_type = protein
                           organism = synthetic construct
SEQUENCE: 43
RIHPSDSDTN YNQKFKG                                                    17

SEQ ID NO: 44              moltype = AA   length = 10
FEATURE                    Location/Qualifiers
source                     1..10
                           mol_type = protein
                           organism = synthetic construct
SEQUENCE: 44
EGTGKGYFDV                                                            10

SEQ ID NO: 45              moltype = AA   length = 5
FEATURE                    Location/Qualifiers
source                     1..5
                           mol_type = protein
                           organism = synthetic construct
SEQUENCE: 45
EYPIH                                                                  5

SEQ ID NO: 46              moltype = AA   length = 17
FEATURE                    Location/Qualifiers
source                     1..17
                           mol_type = protein
                           organism = synthetic construct
SEQUENCE: 46
MIYTDTGEPT HAEEFKG                                                    17

SEQ ID NO: 47              moltype = AA   length = 11
FEATURE                    Location/Qualifiers
source                     1..11
                           mol_type = protein
                           organism = synthetic construct
SEQUENCE: 47
WYDGSSYIMD Y                                                          11

SEQ ID NO: 48              moltype = AA   length = 5
FEATURE                    Location/Qualifiers
source                     1..5
                           mol_type = protein
                           organism = synthetic construct
SEQUENCE: 48
TYGIT                                                                  5

SEQ ID NO: 49              moltype = AA   length = 17
FEATURE                    Location/Qualifiers
source                     1..17
                           mol_type = protein
                           organism = synthetic construct
SEQUENCE: 49
EIYPGTATSY SNERFKG                                                    17

SEQ ID NO: 50              moltype = AA   length = 13
FEATURE                    Location/Qualifiers
source                     1..13
                           mol_type = protein
                           organism = synthetic construct
SEQUENCE: 50
RGTYGTYEWY FDV                                                        13

SEQ ID NO: 51              moltype = AA   length = 10
FEATURE                    Location/Qualifiers
source                     1..10
                           mol_type = protein
                           organism = synthetic construct
SEQUENCE: 51
SASSRVSYMN                                                            10

SEQ ID NO: 52              moltype = AA   length = 7
FEATURE                    Location/Qualifiers
source                     1..7
                           mol_type = protein
                           organism = synthetic construct
SEQUENCE: 52
```

```
GISNLAS                                                                      7

SEQ ID NO: 53            moltype = AA   length = 9
FEATURE                  Location/Qualifiers
source                   1..9
                         mol_type = protein
                         organism = synthetic construct
SEQUENCE: 53
QQRSSHPLT                                                                    9

SEQ ID NO: 54            moltype = AA   length = 10
FEATURE                  Location/Qualifiers
source                   1..10
                         mol_type = protein
                         organism = synthetic construct
SEQUENCE: 54
SASSSVSYMN                                                                  10

SEQ ID NO: 55            moltype = AA   length = 7
FEATURE                  Location/Qualifiers
source                   1..7
                         mol_type = protein
                         organism = synthetic construct
SEQUENCE: 55
GISNLAS                                                                      7

SEQ ID NO: 56            moltype = AA   length = 9
FEATURE                  Location/Qualifiers
source                   1..9
                         mol_type = protein
                         organism = synthetic construct
SEQUENCE: 56
QQRSSHPLT                                                                    9

SEQ ID NO: 57            moltype = AA   length = 11
FEATURE                  Location/Qualifiers
source                   1..11
                         mol_type = protein
                         organism = synthetic construct
SEQUENCE: 57
KASQDIYSYL S                                                                11

SEQ ID NO: 58            moltype = AA   length = 7
FEATURE                  Location/Qualifiers
source                   1..7
                         mol_type = protein
                         organism = synthetic construct
SEQUENCE: 58
RANRLVD                                                                      7

SEQ ID NO: 59            moltype = AA   length = 9
FEATURE                  Location/Qualifiers
source                   1..9
                         mol_type = protein
                         organism = synthetic construct
SEQUENCE: 59
LHYDEFPLT                                                                    9

SEQ ID NO: 60            moltype = AA   length = 11
FEATURE                  Location/Qualifiers
source                   1..11
                         mol_type = protein
                         organism = synthetic construct
SEQUENCE: 60
KASQDINSYL S                                                                11

SEQ ID NO: 61            moltype = AA   length = 7
FEATURE                  Location/Qualifiers
source                   1..7
                         mol_type = protein
                         organism = synthetic construct
SEQUENCE: 61
RANRLVD                                                                      7

SEQ ID NO: 62            moltype = AA   length = 9
FEATURE                  Location/Qualifiers
source                   1..9
                         mol_type = protein
                         organism = synthetic construct
```

```
SEQUENCE: 62
LQYDEFPLT                                                                                         9

SEQ ID NO: 63           moltype = AA  length = 11
FEATURE                 Location/Qualifiers
source                  1..11
                        mol_type = protein
                        organism = synthetic construct
SEQUENCE: 63
RASENIYSHL A                                                                                     11

SEQ ID NO: 64           moltype = AA  length = 7
FEATURE                 Location/Qualifiers
source                  1..7
                        mol_type = protein
                        organism = synthetic construct
SEQUENCE: 64
AATNLAD                                                                                           7

SEQ ID NO: 65           moltype = AA  length = 9
FEATURE                 Location/Qualifiers
source                  1..9
                        mol_type = protein
                        organism = synthetic construct
SEQUENCE: 65
QHFWGTPWT                                                                                         9

SEQ ID NO: 66           moltype = AA  length = 330
FEATURE                 Location/Qualifiers
source                  1..330
                        mol_type = protein
                        organism = synthetic construct
SEQUENCE: 66
ASTKGPSVFP LAPSSKSTSG GTAALGCLVK DYFPEPVTVS WNSGALTSGV HTFPAVLQSS                                 60
GLYSLSSVVT VPSSSLGTQT YICNVNHKPS NTKVDKKVEP KSCDKTHTCP PCPAPELLGG                                120
PSVFLFPPKP KDTLMISRTP EVTCVVVDVS HEDPEVKFNW YVDGVEVHNA KTKPREEQYN                                180
STYRVVSVLT VLHQDWLNGK EYKCKVSNKA LPAPIEKTIS KAKGQPREPQ VYTLPPSRDE                                240
LTKNQVSLTC LVKGFYPSDI AVEWESNGQP ENNYKTTPPV LDSDGSFFLY SKLTVDKSRW                                300
QQGNVFSCSV MHEALHNHYT QKSLSLSPGK                                                                330

SEQ ID NO: 67           moltype = AA  length = 330
FEATURE                 Location/Qualifiers
source                  1..330
                        mol_type = protein
                        organism = synthetic construct
SEQUENCE: 67
ASTKGPSVFP LAPSSKSTSG GTAALGCLVK DYFPEPVTVS WNSGALTSGV HTFPAVLQSS                                 60
GLYSLSSVVT VPSSSLGTQT YICNVNHKPS NTKVDKKVEP KSCDKTHTCP PCPAPELLGG                                120
PSVFLFPPKP KDTLMISRTP EVTCVVVDVS HEDPEVKFNW YVDGVEVHNA KTKPREEQYG                                180
STYRVVSVLT VLHQDWLNGK EYKCKVSNKA LPAPIEKTIS KAKGQPREPQ VYTLPPSRDE                                240
LTKNQVSLTC LVKGFYPSDI AVEWESNGQP ENNYKTTPPV LDSDGSFFLY SKLTVDKSRW                                300
QQGNVFSCSV MHEALHNHYT QKSLSLSPGK                                                                330

SEQ ID NO: 68           moltype = AA  length = 330
FEATURE                 Location/Qualifiers
source                  1..330
                        mol_type = protein
                        organism = synthetic construct
SEQUENCE: 68
ASTKGPSVFP LAPSSKSTSG GTAALGCLVK DYFPEPVTVS WNSGALTSGV HTFPAVLQSS                                 60
GLYSLSSVVT VPSSSLGTQT YICNVNHKPS NTKVDKKVEP KSCDKTHTCP PCPAPELLGG                                120
PDVFLFPPKP KDTLMISRTP EVTCVVVDVS HEDPEVKFNW YVDGVEVHNA KTKPREEQYN                                180
STYRVVSVLT VLHQDWLNGK EYKCKVSNKA LPAPEEKTIS KAKGQPREPQ VYTLPPSRDE                                240
LTKNQVSLTC LVKGFYPSDI AVEWESNGQP ENNYKTTPPV LDSDGSFFLY SKLTVDKSRW                                300
QQGNVFSCSV MHEALHNHYT QKSLSLSPGK                                                                330

SEQ ID NO: 69           moltype = AA  length = 107
FEATURE                 Location/Qualifiers
source                  1..107
                        mol_type = protein
                        organism = synthetic construct
SEQUENCE: 69
RTVAAPSVFI FPPSDEQLKS GTASVVCLLN NFYPREAKVQ WKVDNALQSG NSQESVTEQD                                 60
SKDSTYSLSS TLTLSKADYE KHKVYACEVT HQGLSSPVTK SFNRGEC                                             107

SEQ ID NO: 70           moltype = AA  length = 446
FEATURE                 Location/Qualifiers
source                  1..446
                        mol_type = protein
```

```
                                organism = Mus musculus
SEQUENCE: 70
DVQLVESGGG LVKPGGSRKL SCAASGFTFS TYGFHWVRQV PEKGLEWVAY ISSNSGTIDY      60
ADTVKGRFTI SRDNAKNTLF LQMTSLRSED TAMYYCARQG YGFDNWGQGT TLTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKKVEPKSCD KTHTCPPCPA PELLGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKALPAP IEKTISKAKG QPREPQVYTL PPSRDELTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPGK                                         446

SEQ ID NO: 71              moltype = AA  length = 446
FEATURE                    Location/Qualifiers
source                     1..446
                           mol_type = protein
                           organism = Mus musculus
SEQUENCE: 71
DVQLVESGGG LVQPGGSRKL SCAASGFTFR TYGMHWVRQA PEKGLEWVAY ISSGSGTIDY      60
ADTVKGRFTI SRDNAKNTLF LQMTSLRSED TAMYYCTRQT GAMDYWGQGT SVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKKVEPKSCD KTHTCPPCPA PELLGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKALPAP IEKTISKAKG QPREPQVYTL PPSRDELTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPGK                                         446

SEQ ID NO: 72              moltype = AA  length = 449
FEATURE                    Location/Qualifiers
source                     1..449
                           mol_type = protein
                           organism = Mus musculus
SEQUENCE: 72
QVQLQQPGAE LVKPGASVKV SCKASGYTFT NYWMHWMKQR PGQGLEWLGR IHPSDSDTNY      60
NQKFKGKATL TVDKSSNIAF MQLSSLTSED SAVYYCAIEG TGKGYFDVWG TGTTVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSRDEL     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                      449

SEQ ID NO: 73              moltype = AA  length = 450
FEATURE                    Location/Qualifiers
source                     1..450
                           mol_type = protein
                           organism = Mus musculus
SEQUENCE: 73
QIQLVQSGPE LKKPGETVKI SCKASGYTFT EYPIHWVKQA PGKGFKWMGM IYTDTGEPTH      60
AEEFKGRFAF SLETSASTAY LQINNLKNED TATYFCVRWY DGSSYIMDYW GQGTSVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKKVEP KSCDKTHTCP CPAPELLGGP     240
PSVFLFPPKP KDTLMISRTP EVTCVVVDVS HEDPEVKFNW YVDGVEVHNA KTKPREEQYN     300
STYRVVSVLT VLHQDWLNGK EYKCKVSNKA LPAPIEKTIS KAKGQPREPQ VYTLPPSRDE     360
LTKNQVSLTC LVKGFYPSDI AVEWESNGQP ENNYKTTPPV LDSDGSFFLY SKLTVDKSRW     420
QQGNVFSCSV MHEALHNHYT QKSLSLSPGK                                     450

SEQ ID NO: 74              moltype = AA  length = 452
FEATURE                    Location/Qualifiers
source                     1..452
                           mol_type = protein
                           organism = Mus musculus
SEQUENCE: 74
QVQLQQSGAE LARPGTSVRL SCKASGYTFT TYGITWVKQR PGQGLEWIGE IYPGTATSYS      60
NERFKGKATL TADRSSSTAY MQLSSLTSED SAVYFCARRG TYGTYEWYFD VWGAGTTVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                  452

SEQ ID NO: 75              moltype = AA  length = 446
FEATURE                    Location/Qualifiers
source                     1..446
                           mol_type = protein
                           organism = synthetic construct
SEQUENCE: 75
EVQLVESGGG LVQPGGSLRL SCAASGFTFS TYGFHWVRQA PGKGLEWVAY ISSNSGTIDY      60
ADTVKGRFTI SRDNAKNSLY LQMNSLRAED TAVYYCARQG YGFDNWGQGT TVTVSSASTK     120
```

```
GPSVFPPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 76           moltype = AA  length = 446
FEATURE                 Location/Qualifiers
source                  1..446
                        mol_type = protein
                        organism = synthetic construct
SEQUENCE: 76
EVQLVESGGG LVQPGGSLRL SCAASGFTFR TYGMHWVRQA PGKGLEWVAY ISSGSGTIDY     60
ADTVKGRFTI SRDNAKNSLY LQMNSLRAED TAVYYCTRQT GAMDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 77           moltype = AA  length = 449
FEATURE                 Location/Qualifiers
source                  1..449
                        mol_type = protein
                        organism = synthetic construct
SEQUENCE: 77
EVQLVQSGAE VKKPGASVKV SCKASGYTFT NYWMHWMRQA PGQGLEWLGR IHPSDSDTNY     60
NQKFKGRATL TVDKSISTAY MELSRLRSDD TAVYYCAIEG TGKGYFDVWG RGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 78           moltype = AA  length = 450
FEATURE                 Location/Qualifiers
source                  1..450
                        mol_type = protein
                        organism = synthetic construct
SEQUENCE: 78
EIQLVQSGSE LKKPGASVKV SCKASGYTFT EYPIHWVRQA PGQGFEWMGM IYTDTGEPTH     60
AEEFKGRFVF SLDTSVSTAY LQISSLKAED TAVYFCVRWY DGSSYIMDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 79           moltype = AA  length = 452
FEATURE                 Location/Qualifiers
source                  1..452
                        mol_type = protein
                        organism = synthetic construct
SEQUENCE: 79
QVQLVQSGAE VKKPGSSVKV SCKASGYTFT TYGITWVRQA PGQGLEWIGE IYPGTATSYS     60
NERFKGRATL TADRSTSTAY MELSSLRSED TAVYFCARRG TYGTYEWYFD VWGRGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                 452

SEQ ID NO: 80           moltype = AA  length = 446
FEATURE                 Location/Qualifiers
source                  1..446
                        mol_type = protein
                        organism = synthetic construct
SEQUENCE: 80
DVQLVESGGG LVKPGGSRKL SCAASGFTFS TYGFHWVRQV PEKGLEWVAY ISSNSGTIDY     60
ADTVKGRFTI SRDNAKNTLF LQMTSLRSED TAMYYCARQG YGFDNWGQGT TLTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYGSTYR    300
VVSVLTVLHQ DWLNGKEYKC KVSNKALPAP IEKTISKAKG QPREPQVYTL PPSRDELTKN    360
```

```
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                         446

SEQ ID NO: 81              moltype = AA   length = 446
FEATURE                    Location/Qualifiers
source                     1..446
                           mol_type = protein
                           organism = synthetic construct
SEQUENCE: 81
DVQLVESGGG LVQPGGSRKL SCAASGFTFR TYGMHWVRQA PEKGLEWVAY ISSGSGTIDY     60
ADTVKGRFTI SRDNAKNTLF LQMTSLRSED TAMYYCTRQT GAMDYWGQGT SVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYGSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                         446

SEQ ID NO: 82              moltype = AA   length = 449
FEATURE                    Location/Qualifiers
source                     1..449
                           mol_type = protein
                           organism = synthetic construct
SEQUENCE: 82
QVQLQQPGAE LVKPGASVKV SCKASGYTFT NYWMHWMKQR PGQGLEWLGR IHPSDSDTNY     60
NQKFKGKATL TVDKSSNIAF MQLSSLTSED SAVYYCAIEG TGKGYFDVWG TGTTVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYGS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 83              moltype = AA   length = 450
FEATURE                    Location/Qualifiers
source                     1..450
                           mol_type = protein
                           organism = synthetic construct
SEQUENCE: 83
QIQLVQSGPE LKKPGETVKI SCKASGYTFT EYPIHWVKQA PGKGFKWMGM IYTDTGEPTH     60
AEEFKGRFAF SLETSASTAY LQINNLKNED TATYFCVRWY DGSSYIMDYW GQGTSVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYG    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 84              moltype = AA   length = 452
FEATURE                    Location/Qualifiers
source                     1..452
                           mol_type = protein
                           organism = synthetic construct
SEQUENCE: 84
QVQLQQSGAE LARPGTSVRL SCKASGYTFT TYGITWVKQR PGQGLEWIGE IYPGTATSYS     60
NERFKGKATL TADRSSSTAY MQLSSLTSED SAVYFCARRG TYGTYEWYFD VWGAGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YGSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 85              moltype = AA   length = 446
FEATURE                    Location/Qualifiers
source                     1..446
                           mol_type = protein
                           organism = synthetic construct
SEQUENCE: 85
EVQLVESGGG LVQPGGSLRL SCAASGFTFS TYGFHWVRQA PGKGLEWVAY ISSNSGTIDY     60
ADTVKGRFTI SRDNAKNSLY LQMNSLRAED TAVYYCARQG YGFDNWGQGT TVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYGSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                         446

SEQ ID NO: 86              moltype = AA   length = 446
```

| FEATURE | Location/Qualifiers |
|---|---|
| source | 1..446<br>mol_type = protein<br>organism = synthetic construct |

SEQUENCE: 86
```
EVQLVESGGG LVQPGGSLRL SCAASGFTFR TYGMHWVRQA PGKGLEWVAY ISSGSGTIDY   60
ADTVKGRFTI SRDNAKNSLY LQMNSLRAED TAVYYCTRQT GAMDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYGSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446
```

| SEQ ID NO: 87 | moltype = AA length = 449 |
|---|---|
| FEATURE | Location/Qualifiers |
| source | 1..449<br>mol_type = protein<br>organism = synthetic construct |

SEQUENCE: 87
```
EVQLVQSGAE VKKPGASVKV SCKASGYTFT NYWMHWMRQA PGQGLEWLGR IHPSDSDTNY   60
NQKFKGRATL TVDKSISTAY MELSRLRSDD TAVYYCAIEG TGKGYFDVWG RGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYGS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449
```

| SEQ ID NO: 88 | moltype = AA length = 450 |
|---|---|
| FEATURE | Location/Qualifiers |
| source | 1..450<br>mol_type = protein<br>organism = synthetic construct |

SEQUENCE: 88
```
EIQLVQSGSE LKKPGASVKV SCKASGYTFT EYPIHWVRQA PGQGFEWMGM IYTDTGEPTH   60
AEEFKGRFVF SLDTSVSTAY LQISSLKAED TAVYFCVRWY DGSSYIMDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYG  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450
```

| SEQ ID NO: 89 | moltype = AA length = 452 |
|---|---|
| FEATURE | Location/Qualifiers |
| source | 1..452<br>mol_type = protein<br>organism = synthetic construct |

SEQUENCE: 89
```
QVQLVQSGAE VKKPGSSVKV SCKASGYTFT TYGITWVRQA PGQGLEWIGE IYPGTATSYS   60
NERFKGRATL TADRSTSTAY MELSSLRSED TAVYFCARRG TYGTYEWYFD VWGRGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YGSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452
```

| SEQ ID NO: 90 | moltype = AA length = 446 |
|---|---|
| FEATURE | Location/Qualifiers |
| source | 1..446<br>mol_type = protein<br>organism = synthetic construct |

SEQUENCE: 90
```
DVQLVESGGG LVKPGGSRKL SCAASGFTFS TYGFHWVRQV PEKGLEWVAY ISSNSGTIDY   60
ADTVKGRFTI SRDNAKNTLF LQMTSLRSED TAMYYCARQG YGFDNWGQGT TLTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPDVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP EEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446
```

| SEQ ID NO: 91 | moltype = AA length = 446 |
|---|---|
| FEATURE | Location/Qualifiers |
| source | 1..446<br>mol_type = protein<br>organism = synthetic construct |

```
SEQUENCE: 91
DVQLVESGGG LVQPGGSRKL SCAASGFTFR TYGMHWVRQA PEKGLEWVAY ISSGSGTIDY    60
ADTVKGRFTI SRDNAKNTLF LQMTSLRSED TAMYYCTRQT GAMDYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPDVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP EEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 92           moltype = AA   length = 449
FEATURE                 Location/Qualifiers
source                  1..449
                        mol_type = protein
                        organism = synthetic construct
SEQUENCE: 92
QVQLQQPGAE LVKPGASVKV SCKASGYTFT NYWMHWMKQR PGQGLEWLGR IHPSDSDTNY    60
NQKFKGKATL TVDKSSNIAF MQLSSLTSED SAVYYCAIEG TGKGYFDVWG TGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
DVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPEEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 93           moltype = AA   length = 450
FEATURE                 Location/Qualifiers
source                  1..450
                        mol_type = protein
                        organism = synthetic construct
SEQUENCE: 93
QIQLVQSGPE LKKPGETVKI SCKASGYTFT EYPIHWVKQA PGKGFKWMGM IYTDTGEPTH    60
AEEFKGRFAF SLETSASTAY LQINNLKNED TATYFCVRWY DGSSYIMDYW GQGTSVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP CPAPELLGG   240
PDVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPEEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 94           moltype = AA   length = 452
FEATURE                 Location/Qualifiers
source                  1..452
                        mol_type = protein
                        organism = synthetic construct
SEQUENCE: 94
QVQLQQSGAE LARPGTSVRL SCKASGYTFT TYGITWVKQR PGQGLEWIGE IYPGTATSYS    60
NERFKGKATL TADRSSSTAY MQLSSLTSED SAVYFCARRG TYGTYEWYFD VWGAGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPDVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPEEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 95           moltype = AA   length = 446
FEATURE                 Location/Qualifiers
source                  1..446
                        mol_type = protein
                        organism = synthetic construct
SEQUENCE: 95
EVQLVESGGG LVQPGGSLRL SCAASGFTFS TYGFHWVRQA PGKGLEWVAY ISSNSGTIDY    60
ADTVKGRFTI SRDNAKNSLY LQMNSLRAED TAVYYCARQG YGFDNWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPDVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP EEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 96           moltype = AA   length = 446
FEATURE                 Location/Qualifiers
source                  1..446
                        mol_type = protein
                        organism = synthetic construct
SEQUENCE: 96
EVQLVESGGG LVQPGGSLRL SCAASGFTFR TYGMHWVRQA PGKGLEWVAY ISSGSGTIDY    60
ADTVKGRFTI SRDNAKNSLY LQMNSLRAED TAVYYCTRQT GAMDYWGQGT LVTVSSASTK   120
GPSVFPLAPS SKSTSGGTAA LGCLVKDYFP EPVTVSWNSG ALTSGVHTFP AVLQSSGLYS   180
```

```
LSSVVTVPSS SLGTQTYICN VNHKPSNTKV DKKVEPKSCD KTHTCPPCPA PELLGGPDVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP EEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 97            moltype = AA  length = 449
FEATURE                  Location/Qualifiers
source                   1..449
                         mol_type = protein
                         organism = synthetic construct
SEQUENCE: 97
EVQLVQSGAE VKKPGASVKV SCKASGYTFT NYWMHWMRQA PGQGLEWLGR IHPSDSDTNY     60
NQKFKGRATL TVDKSISTAY MELSRLRSDD TAVYYCAIEG TGKGYFDVWG RGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
DVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPEEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 98            moltype = AA  length = 450
FEATURE                  Location/Qualifiers
source                   1..450
                         mol_type = protein
                         organism = synthetic construct
SEQUENCE: 98
EIQLVQSGSE LKKPGASVKV SCKASGYTFT EYPIHWVRQA PGQGFEWMGM IYTDTGEPTH     60
AEEFKGRFVF SLDTSVSTAY LQISSLKAED TAVYFCVRWY DGSSYIMDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PDVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPEEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 99            moltype = AA  length = 452
FEATURE                  Location/Qualifiers
source                   1..452
                         mol_type = protein
                         organism = synthetic construct
SEQUENCE: 99
QVQLVQSGAE VKKPGSSVKV SCKASGYTFT TYGITWVRQA PGQGLEWIGE IYPGTATSYS     60
NERFKGRATL TADRSTSTAY MELSSLRSED TAVYFCARRG TYGTYEWYFD VWGRGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPDVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPEEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                 452

SEQ ID NO: 100           moltype = AA  length = 213
FEATURE                  Location/Qualifiers
source                   1..213
                         mol_type = protein
                         organism = Mus musculus
SEQUENCE: 100
EILLTQSPAI IAASPGEKVT ITCSASSRVS YMNWYQQKPG SSPKIWVYGI SNLASGVPAR     60
FSGSGSGTSF SFTINSMEAE DVATYYCQQR SSHPLTFGSG TKLELKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                213

SEQ ID NO: 101           moltype = AA  length = 213
FEATURE                  Location/Qualifiers
source                   1..213
                         mol_type = protein
                         organism = Mus musculus
SEQUENCE: 101
EILLTQSPAI IAASPGEKVT ITCSASSSVS YMNWYQQKPG SSPKLWIYGI SNLASGVPAR     60
FSGSGSGTSF SFTINSMEAE DVATYYCQQR SSHPLTFGAG TKLELKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                213

SEQ ID NO: 102           moltype = AA  length = 214
FEATURE                  Location/Qualifiers
source                   1..214
                         mol_type = protein
                         organism = Mus musculus
SEQUENCE: 102
```

```
DIKMTQSPSS MYASLGERVT ITCKASQDIY SYLSWFQQKP GRSPKTLIYR ANRLVDGVPS    60
RFSGSGSGQD FSLTISSLDY EDMGIYYCLH YDEFPLTFGT GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 103          moltype = AA   length = 214
FEATURE                 Location/Qualifiers
source                  1..214
                        mol_type = protein
                        organism = Mus musculus
SEQUENCE: 103
DIKMTQSPSS MYASLGERVT ITCKASQDIN SYLSWFQQKP GKSPKTLIYR ANRLVDGVPS    60
RFSGSGSGQD YSLTISSLEY EDVGIYYCLQ YDEFPLTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 104          moltype = AA   length = 214
FEATURE                 Location/Qualifiers
source                  1..214
                        mol_type = protein
                        organism = Mus musculus
SEQUENCE: 104
DIQMTQSPAS LSVSVGETAT ITCRASENIY SHLAWYQQKQ GKSPQLLVYA ATNLADGVPS    60
RFSGSGSGTQ YSLKINSLQS EDFGSYYCQH FWGTPWTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 105          moltype = AA   length = 213
FEATURE                 Location/Qualifiers
source                  1..213
                        mol_type = protein
                        organism = synthetic construct
SEQUENCE: 105
DIQLTQSPSS LSASVGDRVT ITCSASSRVS YMNWYQQKPG KSPKIWVYGI SNLASGVPSR    60
FSGSGSGTDF TFTISSLQPE DIATYYCQQR SSHPLTFGGG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                               213

SEQ ID NO: 106          moltype = AA   length = 213
FEATURE                 Location/Qualifiers
source                  1..213
                        mol_type = protein
                        organism = synthetic construct
SEQUENCE: 106
EIVLTQSPAT LSLSPGERAT LSCSASSSVS YMNWYQQKPG QSPRLWIYGI SNLASGVPAR    60
FSGSGSGTDF TLTISSLEPE DFAVYYCQQR SSHPLTFGGG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                               213

SEQ ID NO: 107          moltype = AA   length = 214
FEATURE                 Location/Qualifiers
source                  1..214
                        mol_type = protein
                        organism = synthetic construct
SEQUENCE: 107
DIQMTQSPSS LSASVGDRVT ITCKASQDIY SYLSWFQQKP GKSPKTLIYR ANRLVDGVPS    60
RFSGSGSGQD FTLTISSLQP EDFATYYCLH YDEFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 108          moltype = AA   length = 214
FEATURE                 Location/Qualifiers
source                  1..214
                        mol_type = protein
                        organism = synthetic construct
SEQUENCE: 108
DIQMTQSPSS LSASVGDRVT ITCKASQDIN SYLSWFQQKP GKSPKTLIYR ANRLVDGVPS    60
RFSGSGSGQD YTFTISSLQP EDIATYYCLQ YDEFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 109          moltype = AA   length = 214
FEATURE                 Location/Qualifiers
source                  1..214
                        mol_type = protein
                        organism = synthetic construct
SEQUENCE: 109
DIQMTQSPSS LSASVGDRVT ITCRASENIY SHLAWYQQKP GKSPKLLVYA ATNLADGVPS    60
RFSGSGSGTD YTLTISSLQP EDFATYYCQH FWGTPWTFGG GTKVEIKRTV AAPSVFIFPP   120
```

SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC 214

SEQ ID NO: 110           moltype = DNA   length = 1341
FEATURE                  Location/Qualifiers
source                   1..1341
                         mol_type = other DNA
                         organism = synthetic construct
SEQUENCE: 110
gaggtgcagc tggtggagtc tgggggaggc ttggtacagc ctggagggtc cctgagactc    60
tcctgtgcag cctctggatt caccttcagt acctatggct tccactgggt ccgccaggcc   120
ccaggcaagg ggctggagtg ggttgcctac attagtagta acagcggcac catagactac   180
gcagacaccg tgaagggccg attcaccatc tccagagaca acgccaagaa cagcctgtac   240
ctgcaaatga acagcctgag agccgaggac acggctgtgt attactgtgc gagacagggc   300
tacggtttcg acaactgggg ccaagggacc acggtgaccg tctcctcagc ctccaccaag   360
ggcccatcgg tcttcccc ct ggcaccctcc tccaagagca cctctggggg cacagcggcc   420
ctgggctgcc tggtcaagga ctacttcccc gaaccagtga cggtgtcgtg gaactcaggc   480
gccctgacca gcggcgtgca caccttcccg gctgtcctac agtcctcagg actctactcc   540
ctcagcagcg tggtgactgt gccctctagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaatag cacgtaccgg   900
gtggtcagcg tcctcaccgt cctgcaccag gactggctga atggcaagga gtacaagtgc   960
aaggtctcca acaaagccct cccagcccccc atcgagaaaa ccatctccaa agccaaaggg  1020
cagccccgag aaccacaggt gtacaccctg cccccatccc gggatgagct gaccaagaac  1080
caggtcagcc tgacttgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaagta a                                            1341

SEQ ID NO: 111           moltype = DNA   length = 1341
FEATURE                  Location/Qualifiers
source                   1..1341
                         mol_type = other DNA
                         organism = synthetic construct
SEQUENCE: 111
gaggtgcagc tggtggagtc tgggggaggc ttggtacagc ctggagggtc cctgagactc    60
tcctgtgcag cctctggatt caccttcaga acctatggca tgcactgggt ccgccaggct   120
ccaggcaagg ggctggagtg ggttgcctac attagtagtg gcagcggcac catagactac   180
gcagacaccg tgaagggccg attcaccatc tccagagaca acgccaagaa cagcctgtac   240
ctgcaaatga acagcctgag agccgaggac acggctgtgt attactgtac cagacagacc   300
ggcgccatgg actactgggg ccaagggacc ctggtcaccg tctcctcagc ctccaccaag   360
ggcccatcgg tcttcccc ct ggcaccctcc tccaagagca cctctggggg cacagcggcc   420
ctgggctgcc tggtcaagga ctacttcccc gaaccagtga cggtgtcgtg gaactcaggc   480
gccctgacca gcggcgtgca caccttcccg gctgtcctac agtcctcagg actctactcc   540
ctcagcagcg tggtgactgt gccctctagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaatag cacgtaccgg   900
gtggtcagcg tcctcaccgt cctgcaccag gactggctga atggcaagga gtacaagtgc   960
aaggtctcca acaaagccct cccagcccccc atcgagaaaa ccatctccaa agccaaaggg  1020
cagccccgag aaccacaggt gtacaccctg cccccatccc gggatgagct gaccaagaac  1080
caggtcagcc tgacttgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaagta a                                            1341

SEQ ID NO: 112           moltype = DNA   length = 1353
FEATURE                  Location/Qualifiers
source                   1..1353
                         mol_type = other DNA
                         organism = synthetic construct
SEQUENCE: 112
gagatccagc tggtgcaatc tgggagcgag ttgaagaagc tggggccag cgtgaaggtg    60
tcctgcaagg cttctggata caccttcact gagtatccca tccactgggt gagacaggcc   120
cctggacagg ggttcgagtg gatgggaatg atctacaccg acactgggga gccaacgcac   180
gccgaggagt tcaagggacg gtttgtgttc tccttggaca cctctgtgag cacggcatat   240
ctgcagatca gcagcctaaa ggccgaggac actgccgtgt atttctgtgt gagatggtac   300
gacggcagca gctacatcat ggactactgg ggccaaggga ccaccgtcac cgtctcctca   360
gcctccacca agggcccatc ggtcttcccc ctggcaccct cctccaagag cacctctggg   420
ggcacagcgg ccctgggctg cctggtcaag gactacttcc ccgaaccagt gacggtgtcg   480
tggaactcag gcgccctgac cagcggcgtg cacaccttcc cggctgtcct acagtcctca   540
ggactctact ccctcagcag cgtggtgact gtgccctcta gcagcttggg cacccagacc   600

```
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaat  900
agcacgtacc gggtggtcag cgtcctcacc gtcctgcacc aggactggct gaatggcaag  960
gagtacaagt gcaaggtctc caacaaagcc ctcccagccc ccatcgagaa aaccatctcc 1020
aaagccaaag ggcagcccc gagaaccacag gtgtacaccc tgcccccatc ccgggatgag 1080
ctgaccaaga accaggtcag cctgacttgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaag taa                              1353

SEQ ID NO: 113          moltype = DNA   length = 1350
FEATURE                 Location/Qualifiers
source                  1..1350
                        mol_type = other DNA
                        organism = synthetic construct
SEQUENCE: 113
gaggtgcagc tggtgcagag cggggctgag gtgaagaagc ctggggcctc agtgaaggtc   60
tcctgcaagg cttctggata caccttcacc aactactgga tgcactggat gagacaggcc  120
cctggacaag ggcttgagtg gctgggacgg atccaccctg cgacagcga cacaaactat  180
aaccagaagt ttaagggcag agccaccctg accgtggaca gtccatcag caccgcctac  240
atggagctga gcagactgag atctgacgac accgccgtgt attactgtgc gatcgagggc  300
accggcaagg gctacttcga tgtgtggggc agaggccccc tggtcactgt ctcctcagcc  360
tccaccaagg gcccatcggt cttccccctg gcaccctcct ccaagagcac ctctgggggc  420
acagcggccc tgggctgcct ggtcaaggac tacttccccg aaccagtgac ggtgtcgtgg  480
aactcaggcg ccctgaccag cggcgtgcac accttcccgg ctgtcctaca gtcctcagga  540
ctctactccc tcagcagcgt ggtgactgtg ccctctagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaatagc  900
acgtaccggg tggtcagcgt cctcaccgtc ctgcaccagg actggctgaa tggcaaggag  960
tacaagtgca aggtctccaa caaagccctc ccagccccca tcgagaaaac catctccaaa 1020
gccaaagggc agcccagaa accacaggtg tacaccctgc ccccatcccg ggatgagctg 1080
accaagaacc aggtcagcct gacttgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagagcctct ccctgtctcc gggtaagtaa                                  1350

SEQ ID NO: 114          moltype = DNA   length = 642
FEATURE                 Location/Qualifiers
source                  1..642
                        mol_type = other DNA
                        organism = synthetic construct
SEQUENCE: 114
gacatccagc tgacccagtc tccaagcagc ctgagcgcat ctgtgggaga cagagtcacc   60
atcacttgca gcgcgagtag cagagtgagc tatatgaatt ggtatcagca gaaaccaggg  120
aagagcccta agatctgggt gtacggcatc tccaatttgg ccagcggggt cccaagcagg  180
ttcagtggaa gtgggatctg ggacagactt taccttcacca tcagcagcct gcagcccgaa  240
gatatcgcaa catattactg tcaacagaga agcagccacc tctcacgtt cggcggcggg  300
accaaggtgg agatcaaacg aactgtggct gcaccatctg tcttcatctt cccgccatct  360
gatgagcagt tgaaatctgg aactgcttct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgtt aa                    642

SEQ ID NO: 115          moltype = DNA   length = 642
FEATURE                 Location/Qualifiers
source                  1..642
                        mol_type = other DNA
                        organism = synthetic construct
SEQUENCE: 115
gaaattgtgt tgacacagtc tccagccacc ctgagcctgt ctccagggga aagagccacc   60
ctgagctgca gcgccagtag cagtgttagc tacatgaact ggtaccaaca gaaacctggc  120
cagagcccca gactctggat ctatggcatc tccaacctgg ccagcggcgt gccagcagg   180
ttcagtggca gtgggtctgg gacagactta accctgacca tcagcagcct ggagcccgaa  240
gatttcgcag tgtattactg tcagcagcgt agcagccacc tctcacgtt cggcggcggg  300
accaaggtgg agatcaaacg aactgtggct gcaccatctg tcttcatctt cccgccatct  360
gatgagcagt tgaaatctgg aactgcttct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgtt aa                    642
```

```
SEQ ID NO: 116         moltype = DNA  length = 645
FEATURE                Location/Qualifiers
source                 1..645
                       mol_type = other DNA
                       organism = synthetic construct
SEQUENCE: 116
gacatccaga tgacccagtc tccatcctcc ctgagcgcat ctgtgggaga cagagtcacc   60
atcacttgca aggcgagtca ggacattaac agctatttaa gctggttcca gcagaaacca  120
gggaaaagcc ctaagaccct gatctacaga gcaaacagat tggtggacgg ggtcccatca  180
aggttcagtg gaagtggatc tgggcaggat tacaccttca ccatcagcag cctgcagccc  240
gaagatatcg ccacctatta ctgtctgcag tatgatgagt tccctctcac gttcggcggc  300
ggtaccaagg tggagatcaa acgaactgtg gctgcaccat ctgtcttcat cttcccgcca  360
tctgatgagc agttgaaatc tggaactgct tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag cacccctgacg  540
ctgagcaaag cagactacga gaaacacaaa gtctacgcct gcgaagtcac ccatcagggc  600
ctgagctcgc ccgtcacaaa gagcttcaac aggggagagt gttaa              645

SEQ ID NO: 117         moltype = DNA  length = 645
FEATURE                Location/Qualifiers
source                 1..645
                       mol_type = other DNA
                       organism = synthetic construct
SEQUENCE: 117
gacatccaga tgacccagtc tccatcctca ctgagcgcat ctgtgggaga cagagtcacc   60
atcacttgta aggcgagtca ggacatttac agctatttaa gctggtttca gcagaaacca  120
gggaagagcc ctaagaccct gatctataga gcaaacagat tggtggacgg ggtcccatca  180
aggttcagcg gcagtggatc tgggcaggat ttcaccctca ccatcagcag cctgcagccc  240
gaagatttcg ccacctatta ctgcctgcac tatgacgagt tccctctcac gttcggcggc  300
ggtaccaagg tggagatcaa gcgaactgtg gctgcaccat ctgtcttcat cttcccgcca  360
tctgatgagc agttgaaatc tggaactgct tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag cacccctgacg  540
ctgagcaaag cagactacga gaaacacaaa gtctacgcct gcgaagtcac ccatcagggc  600
ctgagctcgc ccgtcacaaa gagcttcaac aggggagagt gttaa              645

SEQ ID NO: 118         moltype = DNA  length = 42
FEATURE                Location/Qualifiers
source                 1..42
                       mol_type = other DNA
                       organism = synthetic construct
SEQUENCE: 118
gcatctatgt tcgttttttc tattgctaca aacgcgtatg ca                  42

SEQ ID NO: 119         moltype = DNA  length = 31
FEATURE                Location/Qualifiers
source                 1..31
                       mol_type = other DNA
                       organism = synthetic construct
SEQUENCE: 119
cacatcatac ggataagaac caccaccacc c                              31

SEQ ID NO: 120         moltype = DNA  length = 48
FEATURE                Location/Qualifiers
source                 1..48
                       mol_type = other DNA
                       organism = synthetic construct
SEQUENCE: 120
tcgtcggcag cgtcagatgt gtataagaga cagcgtcgtg acgacccg             48

SEQ ID NO: 121         moltype = DNA  length = 55
FEATURE                Location/Qualifiers
source                 1..55
                       mol_type = other DNA
                       organism = synthetic construct
SEQUENCE: 121
gtctcgtggg ctcggagatg tgtataagag acaggagaac tgccaagaac cagaa     55

SEQ ID NO: 122         moltype = DNA  length = 51
FEATURE                Location/Qualifiers
source                 1..51
                       mol_type = other DNA
                       organism = synthetic construct
SEQUENCE: 122
tcgtcggcag cgtcagatgt gtataagaga cagccgaaca gctgctggac a         51

SEQ ID NO: 123         moltype = DNA  length = 52
FEATURE                Location/Qualifiers
```

```
                              -continued source                    1..52
                          mol_type = other DNA
                          organism = synthetic construct
SEQUENCE: 123
gtctcgtggg ctcggagatg tgtataagag acagaccaga agacatcgcc ag          52

SEQ ID NO: 124            moltype = AA   length = 220
FEATURE                   Location/Qualifiers
source                    1..220
                          mol_type = protein
                          organism = synthetic construct
SEQUENCE: 124
MGWSCIILFL VATATGVHSR RDDPHSLCYD ITVIPKFRPG PRWCAVQGQV DEKTFLHYDC   60
GNKTVTPVSP LGKKLNVTTA WKAQNPVLRE VVDILTEQLL DIQLENYTPK EPLTLQARMS  120
CEQKAEGHSS GSWQFSIDGQ TFLLFDSEKR MWTTVHPGAR KMKEKWENDK DVAMSFHYIS  180
MGDCIGWLED FLMGMDSTLE PSAGAPLAMS SGHHHHHHHH                        220

SEQ ID NO: 125            moltype = AA   length = 30
FEATURE                   Location/Qualifiers
source                    1..30
                          mol_type = protein
                          organism = synthetic construct
SEQUENCE: 125
LGKKLNVTMA WKAQNPVLRE VVDILTEQLL                                   30

SEQ ID NO: 126            moltype = AA   length = 37
FEATURE                   Location/Qualifiers
source                    1..37
                          mol_type = protein
                          organism = synthetic construct
SEQUENCE: 126
RKMKEKWEND KDVAMSFHYI SMGDCIGWLE DFLMGMD                           37

SEQ ID NO: 127            moltype = AA   length = 8
FEATURE                   Location/Qualifiers
source                    1..8
                          mol_type = protein
                          organism = synthetic construct
SEQUENCE: 127
LFDSEKRM                                                            8

SEQ ID NO: 128            moltype = AA   length = 16
FEATURE                   Location/Qualifiers
source                    1..16
                          mol_type = protein
                          organism = synthetic construct
SEQUENCE: 128
LNVTMAWKAQ NPVLRE                                                  16

SEQ ID NO: 129            moltype = AA   length = 10
FEATURE                   Location/Qualifiers
source                    1..10
                          mol_type = protein
                          organism = synthetic construct
SEQUENCE: 129
SFHYISMGDC                                                         10

SEQ ID NO: 130            moltype = AA   length = 10
FEATURE                   Location/Qualifiers
source                    1..10
                          mol_type = protein
                          organism = synthetic construct
SEQUENCE: 130
GFTFSTYGFH                                                         10

SEQ ID NO: 131            moltype = AA   length = 18
FEATURE                   Location/Qualifiers
source                    1..18
                          mol_type = protein
                          organism = synthetic construct
SEQUENCE: 131
AYISSNSGTI DYADTVKG                                                18

SEQ ID NO: 132            moltype = AA   length = 9
FEATURE                   Location/Qualifiers
source                    1..9
                          mol_type = protein
                          organism = synthetic construct
SEQUENCE: 132
```

-continued

```
ARQGYGFDN                                                              9

SEQ ID NO: 133          moltype = AA   length = 10
FEATURE                 Location/Qualifiers
source                  1..10
                        mol_type = protein
                        organism = synthetic construct
SEQUENCE: 133
GFTFRTYGMH                                                             10

SEQ ID NO: 134          moltype = AA   length = 18
FEATURE                 Location/Qualifiers
source                  1..18
                        mol_type = protein
                        organism = synthetic construct
SEQUENCE: 134
AYISSGSGTI DYADTVKG                                                    18

SEQ ID NO: 135          moltype = AA   length = 9
FEATURE                 Location/Qualifiers
source                  1..9
                        mol_type = protein
                        organism = synthetic construct
SEQUENCE: 135
TRQTGAMDY                                                              9

SEQ ID NO: 136          moltype = AA   length = 10
FEATURE                 Location/Qualifiers
source                  1..10
                        mol_type = protein
                        organism = synthetic construct
SEQUENCE: 136
GYTFTNYWMH                                                             10

SEQ ID NO: 137          moltype = AA   length = 18
FEATURE                 Location/Qualifiers
source                  1..18
                        mol_type = protein
                        organism = synthetic construct
SEQUENCE: 137
GRIHPSDSDT NYNQKFKG                                                    18

SEQ ID NO: 138          moltype = AA   length = 12
FEATURE                 Location/Qualifiers
source                  1..12
                        mol_type = protein
                        organism = synthetic construct
SEQUENCE: 138
AIEGTGKGYF DV                                                          12

SEQ ID NO: 139          moltype = AA   length = 10
FEATURE                 Location/Qualifiers
source                  1..10
                        mol_type = protein
                        organism = synthetic construct
SEQUENCE: 139
GYTFTEYPIH                                                             10

SEQ ID NO: 140          moltype = AA   length = 18
FEATURE                 Location/Qualifiers
source                  1..18
                        mol_type = protein
                        organism = synthetic construct
SEQUENCE: 140
GMIYTDTGEP THAEEFKG                                                    18

SEQ ID NO: 141          moltype = AA   length = 13
FEATURE                 Location/Qualifiers
source                  1..13
                        mol_type = protein
                        organism = synthetic construct
SEQUENCE: 141
VRWYDGSSYI MDY                                                         13

SEQ ID NO: 142          moltype = AA   length = 10
FEATURE                 Location/Qualifiers
source                  1..10
                        mol_type = protein
                        organism = synthetic construct
```

```
SEQUENCE: 142
GYTFTTYGIT                                                                      10

SEQ ID NO: 143          moltype = AA  length = 18
FEATURE                 Location/Qualifiers
source                  1..18
                        mol_type = protein
                        organism = synthetic construct
SEQUENCE: 143
GEIYPGTATS YSNERFKG                                                             18

SEQ ID NO: 144          moltype = AA  length = 15
FEATURE                 Location/Qualifiers
source                  1..15
                        mol_type = protein
                        organism = synthetic construct
SEQUENCE: 144
ARRGTYGTYE WYFDV                                                                15

SEQ ID NO: 145          moltype = AA  length = 10
FEATURE                 Location/Qualifiers
source                  1..10
                        mol_type = protein
                        organism = synthetic construct
SEQUENCE: 145
SASSRVSYMN                                                                      10

SEQ ID NO: 146          moltype = AA  length = 7
FEATURE                 Location/Qualifiers
source                  1..7
                        mol_type = protein
                        organism = synthetic construct
SEQUENCE: 146
GISNLAS                                                                         7

SEQ ID NO: 147          moltype = AA  length = 9
FEATURE                 Location/Qualifiers
source                  1..9
                        mol_type = protein
                        organism = synthetic construct
SEQUENCE: 147
QQRSSHPLT                                                                       9

SEQ ID NO: 148          moltype = AA  length = 10
FEATURE                 Location/Qualifiers
source                  1..10
                        mol_type = protein
                        organism = synthetic construct
SEQUENCE: 148
SASSSVSYMN                                                                      10

SEQ ID NO: 149          moltype = AA  length = 7
FEATURE                 Location/Qualifiers
source                  1..7
                        mol_type = protein
                        organism = synthetic construct
SEQUENCE: 149
GISNLAS                                                                         7

SEQ ID NO: 150          moltype = AA  length = 9
FEATURE                 Location/Qualifiers
source                  1..9
                        mol_type = protein
                        organism = synthetic construct
SEQUENCE: 150
QQRSSHPLT                                                                       9

SEQ ID NO: 151          moltype = AA  length = 11
FEATURE                 Location/Qualifiers
source                  1..11
                        mol_type = protein
                        organism = synthetic construct
SEQUENCE: 151
KASQDIYSYL S                                                                    11

SEQ ID NO: 152          moltype = AA  length = 7
FEATURE                 Location/Qualifiers
source                  1..7
                        mol_type = protein
```

```
                               -continued organism = synthetic construct
SEQUENCE: 152
RANRLVD                                                              7

SEQ ID NO: 153       moltype = AA   length = 9
FEATURE              Location/Qualifiers
source               1..9
                     mol_type = protein
                     organism = synthetic construct
SEQUENCE: 153
LHYDEFPLT                                                            9

SEQ ID NO: 154       moltype = AA   length = 11
FEATURE              Location/Qualifiers
source               1..11
                     mol_type = protein
                     organism = synthetic construct
SEQUENCE: 154
KASQDINSYL S                                                         11

SEQ ID NO: 155       moltype = AA   length = 7
FEATURE              Location/Qualifiers
source               1..7
                     mol_type = protein
                     organism = synthetic construct
SEQUENCE: 155
RANRLVD                                                              7

SEQ ID NO: 156       moltype = AA   length = 9
FEATURE              Location/Qualifiers
source               1..9
                     mol_type = protein
                     organism = synthetic construct
SEQUENCE: 156
LQYDEFPLT                                                            9

SEQ ID NO: 157       moltype = AA   length = 11
FEATURE              Location/Qualifiers
source               1..11
                     mol_type = protein
                     organism = synthetic construct
SEQUENCE: 157
RASENIYSHL A                                                         11

SEQ ID NO: 158       moltype = AA   length = 7
FEATURE              Location/Qualifiers
source               1..7
                     mol_type = protein
                     organism = synthetic construct
SEQUENCE: 158
AATNLAD                                                              7

SEQ ID NO: 159       moltype = AA   length = 9
FEATURE              Location/Qualifiers
source               1..9
                     mol_type = protein
                     organism = synthetic construct
SEQUENCE: 159
QHFWGTPWT                                                            9

SEQ ID NO: 160       moltype = AA   length = 445
FEATURE              Location/Qualifiers
source               1..445
                     mol_type = protein
                     organism = synthetic construct
SEQUENCE: 160
EVQLVESGGG LVQPGGSLRL SCAASGFTFS TYGFHWVRQA PGKGLEWVAY ISSNSGTIDY     60
ADTVKGRFTI SRDNAKNSLY LQMNSLRAED TAVYYCARQG YGFDNWGQGT TVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 161       moltype = AA   length = 445
FEATURE              Location/Qualifiers
source               1..445
                     mol_type = protein
```

```
                          organism = synthetic construct
SEQUENCE: 161
EVQLVESGGG  LVQPGGSLRL  SCAASGFTFR  TYGMHWVRQA  PGKGLEWVAY  ISSGSGTIDY   60
ADTVKGRFTI  SRDNAKNSLY  LQMNSLRAED  TAVYYCTRQT  GAMDYWGQGT  LVTVSSASTK  120
GPSVFPLAPS  SKSTSGGTAA  LGCLVKDYFP  EPVTVSWNSG  ALTSGVHTFP  AVLQSSGLYS  180
LSSVVTVPSS  SLGTQTYICN  VNHKPSNTKV  DKKVEPKSCD  KTHTCPPCPA  PELLGGPSVF  240
LFPPKPKDTL  MISRTPEVTC  VVVDVSHEDP  EVKFNWYVDG  VEVHNAKTKP  REEQYNSTYR  300
VVSVLTVLHQ  DWLNGKEYKC  KVSNKALPAP  IEKTISKAKG  QPREPQVYTL  PPSRDELTKN  360
QVSLTCLVKG  FYPSDIAVEW  ESNGQPENNY  KTTPPVLDSD  GSFFLYSKLT  VDKSRWQQGN  420
VFSCSVMHEA  LHNHYTQKSL  SLSPG                                          445
```